United States Patent
Ribelin et al.

(10) Patent No.: US 11,925,779 B2
(45) Date of Patent: Mar. 12, 2024

(54) CATHETER INSERTION DEVICE INCLUDING TOP-MOUNTED ADVANCEMENT COMPONENTS

(71) Applicant: C. R. Bard, Inc., Franklin Lakes, NJ (US)

(72) Inventors: Rex A. Ribelin, West Jordan, UT (US); Daniel B. Blanchard, Bountiful, UT (US); Matthew C. Rich, St. George, UT (US); Jay A. Muse, Salt Lake City, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 154 days.

(21) Appl. No.: 17/493,806

(22) Filed: Oct. 4, 2021

(65) Prior Publication Data
US 2022/0062596 A1   Mar. 3, 2022

Related U.S. Application Data

(60) Division of application No. 16/529,622, filed on Aug. 1, 2019, now Pat. No. 11,135,406, which is a division
(Continued)

(51) Int. Cl.
*A61M 25/09* (2006.01)
*A61M 25/00* (2006.01)
(Continued)

(52) U.S. Cl.
CPC .. *A61M 25/09041* (2013.01); *A61M 25/0097* (2013.01); *A61M 25/0105* (2013.01);
(Continued)

(58) Field of Classification Search
CPC .............. A61M 25/01; A61M 25/0113; A61M 25/09041; A61M 25/0606; A61M 25/065
See application file for complete search history.

(56) References Cited

U.S. PATENT DOCUMENTS

| 2,211,975 A | 8/1940 | Hendrickson |
| 2,259,488 A | 10/1941 | Raiche |

(Continued)

FOREIGN PATENT DOCUMENTS

| AU | 691141 B2 | 5/1998 |
| AU | 710967 B2 | 9/1999 |

(Continued)

OTHER PUBLICATIONS

JP 2016-107046 filed May 30, 2016 Office Action dated Jul. 28, 2016.
(Continued)

*Primary Examiner* — Emily L Schmidt
(74) *Attorney, Agent, or Firm* — Rutan & Tucker LLP

(57) ABSTRACT

An insertion tool for inserting a catheter into a patient's body includes a housing in which at least a portion of the catheter is initially disposed, a hollow needle distally extending from the housing with the catheter pre-disposed over the needle, and a guidewire pre-disposed in the needle. The insertion tool can include a guidewire advancement assembly that can include a first finger pad for selectively advancing the guidewire distally past a distal end of the needle in preparation for distal advancement of the catheter. The insertion tool can further include a catheter advancement assembly that can include a second finger pad for selectively advancing the catheter into the patient. The first and second finger pads can be positioned such that a user can begin to advance the second finger pad after advancing the first finger pad without substantially re-positioning the thumb or finger of the user.

19 Claims, 89 Drawing Sheets

Related U.S. Application Data of application No. 15/154,808, filed on May 13, 2016, now Pat. No. 10,384,039, which is a continuation-in-part of application No. 14/702,580, filed on May 1, 2015, now Pat. No. 9,950,139, which is a continuation-in-part of application No. 14/099,050, filed on Dec. 6, 2013, now Pat. No. 9,872,971, which is a continuation-in-part of application No. 13/107,781, filed on May 13, 2011, now Pat. No. 8,932,258.

(60) Provisional application No. 62/162,580, filed on May 15, 2015, provisional application No. 61/988,114, filed on May 2, 2014, provisional application No. 61/771,703, filed on Mar. 1, 2013, provisional application No. 61/415,248, filed on Nov. 18, 2010, provisional application No. 61/385,844, filed on Sep. 23, 2010, provisional application No. 61/372,050, filed on Aug. 9, 2010, provisional application No. 61/345,022, filed on May 14, 2010, provisional application No. 61/345,005, filed on May 14, 2010.

(51) Int. Cl.
  *A61M 25/01* (2006.01)
  *A61M 25/06* (2006.01)

(52) U.S. Cl.
  CPC ..... *A61M 25/0618* (2013.01); *A61M 25/0606* (2013.01); *A61M 25/065* (2013.01); *A61M 25/0693* (2013.01); *A61M 2025/09083* (2013.01)

(56) References Cited

U.S. PATENT DOCUMENTS

| | | |
|---|---|---|
| 2,330,400 A | 9/1943 | Winder |
| D138,589 S | 8/1944 | Brandenburg |
| 3,185,151 A | 5/1965 | Czorny |
| 3,297,030 A | 1/1967 | Czorny et al. |
| 3,416,567 A | 12/1968 | von Dardel et al. |
| 3,469,579 A | 9/1969 | Hubert |
| 3,500,828 A | 3/1970 | Podhora |
| 3,552,384 A | 1/1971 | Pierie et al. |
| 3,572,334 A | 3/1971 | Petterson |
| 3,585,996 A | 6/1971 | Reynolds et al. |
| 3,589,361 A | 6/1971 | Loper et al. |
| 3,592,192 A | 7/1971 | Harautuneian |
| 3,595,230 A | 7/1971 | Suyeoka et al. |
| 3,610,240 A | 10/1971 | Harautuneian |
| 3,682,173 A | 8/1972 | Center |
| 3,766,916 A | 10/1973 | Moorehead et al. |
| 3,884,242 A | 5/1975 | Bazell et al. |
| 3,921,631 A | 11/1975 | Thompson |
| 3,995,628 A | 12/1976 | Gula et al. |
| 4,027,668 A | 6/1977 | Dunn |
| 4,037,600 A | 7/1977 | Poncy et al. |
| 4,079,738 A | 3/1978 | Dunn et al. |
| 4,106,506 A | 8/1978 | Koehn et al. |
| 4,177,809 A | 12/1979 | Moorehead |
| 4,292,970 A | 10/1981 | Hession, Jr. |
| 4,317,445 A | 3/1982 | Robinson |
| 4,345,602 A | 8/1982 | Yoshimura et al. |
| 4,354,491 A | 10/1982 | Marbry |
| 4,368,730 A | 1/1983 | Sharrock |
| 4,387,879 A | 6/1983 | Tauschinski |
| 4,417,886 A | 11/1983 | Frankhouser et al. |
| 4,449,693 A | 5/1984 | Gereg |
| 4,456,017 A | 6/1984 | Miles |
| 4,464,171 A | 8/1984 | Garwin |
| 4,509,534 A | 4/1985 | Tassin, Jr. |
| 4,509,945 A | 4/1985 | Kramann et al. |
| 4,511,359 A | 4/1985 | Vaillancourt |
| 4,512,766 A | 4/1985 | Vailancourt |
| 4,525,157 A | 6/1985 | Vaillancourt |
| 4,581,019 A | 4/1986 | Curelaru et al. |
| 4,585,440 A | 4/1986 | Tchervenkov et al. |
| D287,877 S | 1/1987 | Holewinski et al. |
| 4,728,322 A | 3/1988 | Walker et al. |
| 4,738,659 A | 4/1988 | Sleiman |
| 4,747,831 A | 5/1988 | Kulli |
| 4,767,407 A | 8/1988 | Foran |
| 4,767,408 A * | 8/1988 | McFarlane ........ A61M 25/0693 604/168.01 |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,798,193 A | 1/1989 | Giesy et al. |
| 4,813,934 A | 3/1989 | Engelson et al. |
| 4,826,070 A | 5/1989 | Kakihana |
| 4,828,547 A | 5/1989 | Sahi et al. |
| 4,834,708 A | 5/1989 | Pillari |
| 4,834,718 A | 5/1989 | McDonald |
| 4,840,613 A | 6/1989 | Balbierz |
| 4,840,622 A | 6/1989 | Hardy |
| 4,842,591 A | 6/1989 | Luther |
| 4,846,812 A | 7/1989 | Walker et al. |
| 4,850,961 A | 7/1989 | Wanderer et al. |
| 4,860,757 A | 8/1989 | Lynch et al. |
| 4,869,259 A | 9/1989 | Elkins |
| D304,079 S | 10/1989 | McFarlane |
| 4,871,358 A | 10/1989 | Gold |
| 4,874,377 A | 10/1989 | Newgard et al. |
| 4,883,461 A | 11/1989 | Sawyer |
| 4,883,699 A | 11/1989 | Aniuk et al. |
| 4,894,052 A | 1/1990 | Crawford |
| 4,895,346 A | 1/1990 | Steigerwald |
| 4,900,307 A | 2/1990 | Kulli |
| 4,906,956 A | 3/1990 | Kakihana |
| 4,908,021 A | 3/1990 | McFarlane |
| 4,909,793 A | 3/1990 | Vining et al. |
| 4,911,691 A | 3/1990 | Aniuk et al. |
| 4,913,704 A | 4/1990 | Kurimoto |
| 4,917,102 A | 4/1990 | Miller et al. |
| 4,917,668 A | 4/1990 | Haindl |
| 4,917,671 A | 4/1990 | Chang |
| 4,929,235 A | 5/1990 | Merry et al. |
| 4,935,010 A | 6/1990 | Cox et al. |
| 4,944,725 A | 7/1990 | McDonald |
| 4,944,728 A | 7/1990 | Carrell et al. |
| 4,955,863 A | 9/1990 | Walker et al. |
| 4,961,729 A | 10/1990 | Vaillancourt |
| 4,966,586 A | 10/1990 | Vaillancourt |
| 4,966,589 A | 10/1990 | Kaufman |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Sahi |
| 5,019,048 A | 5/1991 | Margolin |
| 5,019,049 A | 5/1991 | Haining |
| D318,733 S | 7/1991 | Wyzgala |
| 5,034,347 A | 7/1991 | Kakihana |
| 5,047,013 A | 9/1991 | Rossdeutscher |
| D321,250 S | 10/1991 | Jepson et al. |
| 5,053,014 A | 10/1991 | Van Heugten |
| 5,054,501 A | 10/1991 | Chuttani et al. |
| 5,061,254 A | 10/1991 | Karakelle et al. |
| 5,064,416 A | 11/1991 | Newgard et al. |
| 5,078,694 A | 1/1992 | Wallace |
| 5,078,696 A | 1/1992 | Nedbaluk |
| 5,078,702 A | 1/1992 | Pomeranz |
| 5,084,023 A | 1/1992 | Lemieux |
| 5,085,645 A | 2/1992 | Purdy et al. |
| 5,088,984 A | 2/1992 | Fields |
| 5,093,692 A | 3/1992 | Su et al. |
| 5,098,392 A | 3/1992 | Fleischhacker et al. |
| 5,098,395 A | 3/1992 | Fields |
| 5,098,396 A | 3/1992 | Taylor et al. |
| 5,098,405 A | 3/1992 | Peterson et al. |
| 5,108,375 A | 4/1992 | Harrison et al. |
| 5,108,376 A | 4/1992 | Bonaldo |
| 5,112,312 A | 5/1992 | Luther |

(56) References Cited

U.S. PATENT DOCUMENTS

| | | |
|---|---|---|
| 5,116,323 A | 5/1992 | Kreuzer et al. |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,154,703 A | 10/1992 | Bonaldo |
| 5,156,590 A | 10/1992 | Vilmar |
| 5,156,596 A | 10/1992 | Balbierz et al. |
| 5,158,544 A | 10/1992 | Weinstein |
| 5,167,637 A | 12/1992 | Okada et al. |
| 5,176,650 A | 1/1993 | Haining |
| 5,186,168 A | 2/1993 | Spofford et al. |
| 5,186,712 A | 2/1993 | Kelso et al. |
| 5,188,607 A | 2/1993 | Wu |
| 5,190,528 A | 3/1993 | Fonger et al. |
| 5,192,301 A | 3/1993 | Kamiya et al. |
| 5,195,974 A | 3/1993 | Hardy |
| 5,195,980 A | 3/1993 | Catlin |
| 5,195,985 A | 3/1993 | Hall |
| 5,205,830 A | 4/1993 | Dassa et al. |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,234,410 A | 8/1993 | Graham et al. |
| 5,242,411 A | 9/1993 | Yamamoto et al. |
| 5,246,426 A * | 9/1993 | Lewis ............... A61M 25/0693 604/168.01 |
| 5,246,430 A | 9/1993 | MacFarlane |
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,312,363 A | 5/1994 | Ryan et al. |
| 5,318,541 A | 6/1994 | Viera et al. |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |
| 5,376,094 A | 12/1994 | Kline |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,419,777 A | 5/1995 | Hofling |
| 5,423,760 A | 6/1995 | Yoon |
| 5,425,718 A | 6/1995 | Tay et al. |
| 5,431,506 A | 7/1995 | Masunaga |
| 5,439,449 A | 8/1995 | Mapes et al. |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,671 A | 3/1996 | Rosen et al. |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A | 5/1996 | Sellers et al. |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Werge et al. |
| 5,542,933 A | 8/1996 | Marks |
| 5,554,136 A | 9/1996 | Luther |
| 5,562,629 A | 10/1996 | Haughton et al. |
| 5,562,630 A | 10/1996 | Nichols |
| 5,562,631 A | 10/1996 | Bogert |
| 5,562,633 A | 10/1996 | Wozencroft |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,575,777 A | 11/1996 | Cover et al. |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Hakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,697,914 A | 12/1997 | Brimhall |
| 5,700,250 A | 12/1997 | Erskine |
| 5,702,367 A | 12/1997 | Cover et al. |
| 5,702,369 A | 12/1997 | Mercereau |
| 5,704,914 A * | 1/1998 | Stocking ........... A61M 25/0631 604/195 |
| 5,722,425 A | 3/1998 | Bostrom |
| 5,725,503 A | 3/1998 | Arnett |
| 5,730,150 A | 3/1998 | Peppel et al. |
| 5,730,733 A | 3/1998 | Mortier et al. |
| 5,730,741 A | 3/1998 | Horzewski et al. |
| 5,738,144 A | 4/1998 | Rogers |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |
| 5,749,857 A | 5/1998 | Cuppy |
| 5,749,861 A | 5/1998 | Guala et al. |

(56) References Cited

U.S. PATENT DOCUMENTS

| | | |
|---|---|---|
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,810,780 A | 9/1998 | Brimhall et al. |
| 5,810,835 A | 9/1998 | Ryan et al. |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,830,224 A | 11/1998 | Cohn et al. |
| 5,839,470 A | 11/1998 | Hiejima et al. |
| 5,843,002 A | 12/1998 | Pecor et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |
| 5,865,806 A | 2/1999 | Howell |
| 5,873,864 A | 2/1999 | Luther et al. |
| 5,879,332 A | 3/1999 | Schwemberger et al. |
| 5,879,337 A | 3/1999 | Kuracina et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| D413,382 S | 8/1999 | Maissami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,001,080 A | 12/1999 | Kuracina et al. |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A | 2/2000 | Dehdashtian et al. |
| 6,045,734 A | 4/2000 | Luther et al. |
| 6,056,726 A | 5/2000 | Isaacson |
| 6,059,484 A | 5/2000 | Greive |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,109,264 A | 8/2000 | Sauer |
| 6,117,108 A | 9/2000 | Woehr et al. |
| 6,120,494 A | 9/2000 | Jonkman |
| 6,126,633 A | 10/2000 | Kaji et al. |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Greene et al. |
| 6,221,048 B1 | 4/2001 | Phelps |
| 6,221,049 B1 | 4/2001 | Selmon et al. |
| 6,224,569 B1 * | 5/2001 | Brimhall ............ A61M 25/0618 604/164.08 |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,287,278 B1 | 9/2001 | Woehr et al. |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 * | 8/2002 | Botich ............. A61B 5/150732 604/110 |
| 6,436,112 B2 | 8/2002 | Wensel et al. |
| 6,443,929 B1 | 9/2002 | Kuracina et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |

(56) References Cited

U.S. PATENT DOCUMENTS

| | | |
|---|---|---|
| 6,544,239 B2 | 4/2003 | Kinsey et al. |
| 6,547,762 B1 | 4/2003 | Botich et al. |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |
| 6,589,262 B1 | 7/2003 | Honebrink et al. |
| 6,595,955 B2 | 7/2003 | Ferguson et al. |
| 6,595,959 B1 | 7/2003 | Stratienko |
| 6,599,296 B1 | 7/2003 | Gillick et al. |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,623,456 B1 | 9/2003 | Holdaway et al. |
| 6,626,868 B1 | 9/2003 | Prestidge et al. |
| 6,626,869 B1 | 9/2003 | Bint |
| 6,629,959 B2 | 10/2003 | Kuracina et al. |
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Plat |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,125,397 B2 | 10/2006 | Woehr et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,186,239 B2 | 3/2007 | Woehr |
| 7,191,900 B2 | 3/2007 | Opie et al. |
| 7,192,433 B2 | 3/2007 | Osypka et al. |
| 7,204,813 B2 | 4/2007 | Shue et al. |
| 7,214,211 B2 | 5/2007 | Woehr et al. |
| 7,255,685 B2 | 8/2007 | Pressly, Sr. et al. |
| 7,264,613 B2 | 9/2007 | Woehr et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,374,554 B2 | 5/2008 | Menzi et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,534,231 B2 | 5/2009 | Kuracina et al. |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| 7,608,057 B2 | 10/2009 | Woehr et al. |
| D604,839 S | 11/2009 | Crawford et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |

(56) References Cited

U.S. PATENT DOCUMENTS

| | | |
|---|---|---|
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,687 B2 | 6/2010 | Menzi et al. |
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,833,201 B2 | 11/2010 | Carlyon et al. |
| 7,850,644 B2 | 12/2010 | Gonzalez et al. |
| 7,857,770 B2 | 12/2010 | Raulerson et al. |
| D634,843 S | 3/2011 | Kim et al. |
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tal et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,313 B2 | 7/2011 | Woehr et al. |
| 7,972,324 B2 | 7/2011 | Quint |
| D643,531 S | 8/2011 | van der Weiden |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,062,261 B2 | 11/2011 | Adams |
| 8,075,529 B2 | 12/2011 | Nakajima et al. |
| 8,079,979 B2 | 12/2011 | Moorehead |
| D653,329 S | 1/2012 | Lee-Sepsick |
| 8,100,858 B2 | 1/2012 | Woehr et al. |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,251 B2 | 6/2012 | Bierman et al. |
| 8,202,253 B1 | 6/2012 | Wexler |
| 8,206,343 B2 | 6/2012 | Racz |
| 8,211,070 B2 | 7/2012 | Woehr et al. |
| 8,221,387 B2 | 7/2012 | Shelso et al. |
| 8,226,612 B2 | 7/2012 | Nakajima |
| 8,235,945 B2 | 8/2012 | Baid |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,303,543 B2 | 11/2012 | Abulhaj |
| 8,308,685 B2 | 11/2012 | Botich et al. |
| 8,308,691 B2 | 11/2012 | Woehr et al. |
| D672,456 S | 12/2012 | Lee-Sepsick |
| 8,323,249 B2 | 12/2012 | White et al. |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,361,038 B2 | 1/2013 | McKinnon et al. |
| 8,376,994 B2 | 2/2013 | Woehr et al. |
| 8,377,006 B2 | 2/2013 | Tal et al. |
| 8,382,721 B2 | 2/2013 | Woehr et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,529,515 B2 | 9/2013 | Woehr et al. |
| 8,535,271 B2 | 9/2013 | Fuchs et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,579,881 B2 | 11/2013 | Agro et al. |
| 8,585,651 B2 | 11/2013 | Asai |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,958 B2 | 1/2014 | Jones et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,715,242 B2 | 5/2014 | Helm, Jr. |
| 8,721,546 B2 | 5/2014 | Belson |
| 8,728,030 B2 | 5/2014 | Woehr |
| 8,728,035 B2 | 5/2014 | Warring et al. |
| 8,740,859 B2 | 6/2014 | McKinnon et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,827,965 B2 | 9/2014 | Woehr et al. |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,945,011 B2 | 2/2015 | Sheldon et al. |
| 8,951,230 B2 | 2/2015 | Tanabe et al. |
| 8,956,327 B2 | 2/2015 | Bierman et al. |
| 8,974,426 B2 | 3/2015 | Corcoran et al. |
| 8,979,802 B2 | 3/2015 | Woehr |

(56) References Cited

U.S. PATENT DOCUMENTS

| | | |
|---|---|---|
| 8,986,227 B2 | 3/2015 | Belson |
| D726,908 S | 4/2015 | Yu et al. |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |
| D728,781 S | 5/2015 | Pierson et al. |
| 9,022,979 B2 | 5/2015 | Woehr |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,089,671 B2 | 7/2015 | Stout et al. |
| 9,089,674 B2 | 7/2015 | Ginn et al. |
| 9,095,683 B2 | 8/2015 | Hall et al. |
| 9,101,746 B2 | 8/2015 | Stout et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,126,012 B2 | 9/2015 | McKinnon et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,162,036 B2 | 10/2015 | Caples et al. |
| 9,162,037 B2 | 10/2015 | Belson et al. |
| 9,180,275 B2 | 11/2015 | Helm |
| D746,445 S | 12/2015 | Lazarus |
| 9,205,231 B2 | 12/2015 | Call et al. |
| 9,216,109 B2 | 12/2015 | Badawi et al. |
| 9,220,531 B2 | 12/2015 | Datta et al. |
| 9,220,871 B2 | 12/2015 | Thorne et al. |
| 9,220,882 B2 | 12/2015 | Belley et al. |
| D748,254 S | 1/2016 | Freigang et al. |
| 9,227,038 B2 | 1/2016 | Woehr |
| 9,242,071 B2 | 1/2016 | Morgan et al. |
| 9,242,072 B2 | 1/2016 | Morgan et al. |
| RE45,896 E | 2/2016 | Stout et al. |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| 9,289,237 B2 | 3/2016 | Woehr et al. |
| 9,308,352 B2 | 4/2016 | Teoh et al. |
| 9,308,354 B2 | 4/2016 | Farrell et al. |
| 9,320,870 B2 | 4/2016 | Woehr |
| D755,368 S | 5/2016 | Efinger et al. |
| 9,352,119 B2 | 5/2016 | Burkholz et al. |
| 9,352,127 B2 | 5/2016 | Yeh et al. |
| 9,352,129 B2 | 5/2016 | Nardeo et al. |
| 9,358,364 B2 | 6/2016 | Isaacson et al. |
| 9,370,641 B2 | 6/2016 | Woehr et al. |
| 9,381,324 B2 | 7/2016 | Fuchs et al. |
| 9,399,116 B2 | 7/2016 | Goral et al. |
| 9,408,569 B2 | 8/2016 | Andreae et al. |
| 9,421,345 B2 | 8/2016 | Woehr et al. |
| 9,427,549 B2 | 8/2016 | Woehr et al. |
| D775,330 S | 12/2016 | Blennow et al. |
| 9,522,254 B2 | 12/2016 | Belson |
| D776,259 S | 1/2017 | Eldredge |
| 9,545,495 B2 | 1/2017 | Goral et al. |
| 9,554,817 B2 | 1/2017 | Goldfarb et al. |
| D779,059 S | 2/2017 | Nino et al. |
| D779,661 S | 2/2017 | McKnight et al. |
| 9,579,486 B2 | 2/2017 | Burkholz et al. |
| 9,586,027 B2 | 3/2017 | Tisci et al. |
| 9,592,367 B2 | 3/2017 | Harding et al. |
| 9,616,201 B2 | 4/2017 | Belson |
| 9,623,210 B2 | 4/2017 | Woehr |
| 9,675,784 B2 | 6/2017 | Belson |
| 9,687,633 B2 | 6/2017 | Teoh |
| D791,311 S | 7/2017 | Yantz |
| 9,707,378 B2 | 7/2017 | Leinsing et al. |
| 9,717,523 B2 | 8/2017 | Feng et al. |
| 9,717,887 B2 | 8/2017 | Tan |
| 9,737,252 B2 | 8/2017 | Teoh et al. |
| 9,750,532 B2 | 9/2017 | Toomey et al. |
| 9,750,928 B2 | 9/2017 | Burkholz et al. |
| 9,757,540 B2 | 9/2017 | Belson |
| 9,764,085 B2 | 9/2017 | Teoh |
| 9,764,117 B2 | 9/2017 | Bierman et al. |
| 9,775,972 B2 | 10/2017 | Christensen et al. |
| 9,782,568 B2 | 10/2017 | Belson |
| 9,789,279 B2 | 10/2017 | Burkholz et al. |
| 9,795,766 B2 | 10/2017 | Teoh |
| 9,844,646 B2 | 12/2017 | Knutsson |
| 9,861,792 B2 | 1/2018 | Hall et al. |
| 9,872,971 B2 | 1/2018 | Blanchard |
| D810,282 S | 2/2018 | Ratjen |
| D815,737 S | 4/2018 | Bergstrom et al. |
| 9,950,139 B2 | 4/2018 | Blanchard et al. |
| 9,962,525 B2 | 5/2018 | Woehr |
| 10,004,878 B2 | 6/2018 | Ishida |
| 10,086,171 B2 | 10/2018 | Belson |
| 10,232,146 B2 | 3/2019 | Braithwaite et al. |
| 10,328,239 B2 | 6/2019 | Belson |
| 10,357,635 B2 | 7/2019 | Korkuch et al. |
| 10,384,039 B2 | 8/2019 | Ribelin et al. |
| 10,426,931 B2 | 10/2019 | Blanchard et al. |
| D870,271 S | 12/2019 | Kheradpir et al. |
| D870,883 S | 12/2019 | Harding et al. |
| 10,493,262 B2 | 12/2019 | Tran et al. |
| 10,525,236 B2 | 1/2020 | Belson |
| 10,688,280 B2 | 6/2020 | Blanchard et al. |
| 10,688,281 B2 | 6/2020 | Blanchard et al. |
| 10,722,685 B2 | 7/2020 | Blanchard et al. |
| 10,806,906 B2 | 10/2020 | Warring et al. |
| 11,389,626 B2 | 7/2022 | Tran et al. |
| 11,400,260 B2 | 8/2022 | Huang et al. |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0030291 A1 | 2/2004 | Holdaway et al. |
| 2004/0034383 A1 | 2/2004 | Belson |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0193118 A1 | 9/2004 | Bergeron |
| 2004/0215146 A1 | 10/2004 | Lampropoulos et al. |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0004532 A1 | 1/2005 | Woehr et al. |
| 2005/0010095 A1 | 1/2005 | Stewart et al. |
| 2005/0020940 A1 | 1/2005 | Opie et al. |
| 2005/0021002 A1 | 1/2005 | Deckman et al. |
| 2005/0027256 A1 | 2/2005 | Barker et al. |
| 2005/0033137 A1 | 2/2005 | Oral et al. |

(56) References Cited

U.S. PATENT DOCUMENTS

| | | |
|---|---|---|
| 2005/0040061 A1 | 2/2005 | Opie et al. |
| 2005/0075606 A1 | 4/2005 | Botich et al. |
| 2005/0107769 A1 | 5/2005 | Thommen |
| 2005/0119619 A1 | 6/2005 | Haining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long et al. |
| 2005/0273057 A1 | 12/2005 | Popov |
| 2006/0025721 A1 | 2/2006 | Duffy et al. |
| 2006/0036219 A1 | 2/2006 | Alvin |
| 2006/0079787 A1 | 4/2006 | Whiting et al. |
| 2006/0084964 A1 | 4/2006 | Knudson et al. |
| 2006/0155245 A1 | 7/2006 | Woehr |
| 2006/0161115 A1 | 7/2006 | Fangrow |
| 2006/0167405 A1 | 7/2006 | King et al. |
| 2006/0200080 A1 | 9/2006 | Abulhaj |
| 2006/0229563 A1 | 10/2006 | O'Reagan et al. |
| 2006/0264834 A1 | 11/2006 | Vaillancourt |
| 2006/0264841 A1 | 11/2006 | Cote et al. |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0191786 A1 | 8/2007 | Raines et al. |
| 2007/0193903 A1 | 8/2007 | Opie et al. |
| 2007/0225647 A1 | 9/2007 | Luther et al. |
| 2007/0233007 A1 | 10/2007 | Adams |
| 2007/0244438 A1 | 10/2007 | Perez |
| 2007/0255221 A1 | 11/2007 | Nakajima |
| 2007/0276288 A1 | 11/2007 | Khaw |
| 2008/0039796 A1 | 2/2008 | Nakajima |
| 2008/0065011 A1 | 3/2008 | Marchand et al. |
| 2008/0082082 A1 | 4/2008 | Carlyon et al. |
| 2008/0097330 A1 | 4/2008 | King et al. |
| 2008/0108911 A1 | 5/2008 | Palmer et al. |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0132846 A1 | 6/2008 | Shue et al. |
| 2008/0147010 A1 | 6/2008 | Nakajima et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0018567 A1 | 1/2009 | Escudero et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0227953 A1 | 9/2009 | Tan et al. |
| 2009/0287154 A1 | 11/2009 | Harding et al. |
| 2009/0292243 A1 | 11/2009 | Harding et al. |
| 2009/0299291 A1 | 12/2009 | Baid |
| 2010/0010441 A1 | 1/2010 | Belson |
| 2010/0010447 A1 | 1/2010 | Luther et al. |
| 2010/0016838 A1 | 1/2010 | Butts et al. |
| 2010/0036331 A1 | 2/2010 | Sen |
| 2010/0056910 A1 | 3/2010 | Yanuma |
| 2010/0057183 A1 | 3/2010 | Mangiardi et al. |
| 2010/0087787 A1 | 4/2010 | Woehr et al. |
| 2010/0094116 A1 | 4/2010 | Silverstein |
| 2010/0094310 A1 | 4/2010 | Warring et al. |
| 2010/0137815 A1 | 6/2010 | Kuracina et al. |
| 2010/0168674 A1 | 7/2010 | Shaw et al. |
| 2010/0204654 A1 | 8/2010 | Mulholland et al. |
| 2010/0204660 A1 | 8/2010 | McKinnon et al. |
| 2010/0204675 A1 | 8/2010 | Woehr et al. |
| 2010/0210934 A1* | 8/2010 | Belson ............ A61B 5/150503 600/371 |
| 2010/0238705 A1 | 9/2010 | Kim et al. |
| 2010/0246707 A1 | 9/2010 | Michelitsch |
| 2010/0331732 A1 | 12/2010 | Raulerson et al. |
| 2011/0004162 A1 | 1/2011 | Tal |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0046570 A1 | 2/2011 | Stout et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0071857 A1 | 3/2012 | Goldfarb et al. |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0123354 A1 | 5/2012 | Woehr |
| 2012/0157854 A1 | 6/2012 | Kurrus et al. |
| 2012/0179104 A1 | 7/2012 | Woehr et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0310179 A1 | 12/2012 | Truitt et al. |
| 2012/0316500 A1 | 12/2012 | Bierman et al. |
| 2012/0323181 A1 | 12/2012 | Shaw et al. |
| 2013/0030391 A1 | 1/2013 | Baid |
| 2013/0158506 A1 | 6/2013 | Harris et al. |
| 2013/0184645 A1 | 7/2013 | Baid |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0310764 A1 | 11/2013 | Burkholz et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058329 A1 | 2/2014 | Walker et al. |
| 2014/0058336 A1 | 2/2014 | Burkholz et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0143999 A1 | 5/2014 | Goral et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1 | 8/2014 | Nakagami et al. |
| 2014/0243734 A1 | 8/2014 | Eubanks et al. |
| 2014/0249488 A1 | 9/2014 | Woehr |
| 2014/0257359 A1 | 9/2014 | Tegels et al. |
| 2014/0276224 A1 | 9/2014 | Ranganathan et al. |
| 2014/0276432 A1 | 9/2014 | Bierman et al. |
| 2014/0276434 A1 | 9/2014 | Woehr et al. |

(56) References Cited

U.S. PATENT DOCUMENTS

| | | |
|---|---|---|
| 2014/0303561 A1 | 10/2014 | Li |
| 2014/0323988 A1 | 10/2014 | Magnani et al. |
| 2014/0336582 A1 | 11/2014 | Tisci et al. |
| 2014/0357983 A1 | 12/2014 | Toomey et al. |
| 2014/0358123 A1 | 12/2014 | Ueda et al. |
| 2014/0364809 A1 | 12/2014 | Isaacson et al. |
| 2014/0371715 A1 | 12/2014 | Farrell et al. |
| 2014/0371720 A1 | 12/2014 | Urmey |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0094659 A1 | 4/2015 | Schraga |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0151086 A1 | 6/2015 | Teoh |
| 2015/0151088 A1 | 6/2015 | Lim et al. |
| 2015/0190168 A1 | 7/2015 | Bierman et al. |
| 2015/0190570 A1 | 7/2015 | Teoh |
| 2015/0190617 A1 | 7/2015 | Anderson et al. |
| 2015/0202414 A1 | 7/2015 | Hwang |
| 2015/0202421 A1 | 7/2015 | Ma et al. |
| 2015/0224267 A1 | 8/2015 | Farrell et al. |
| 2015/0231364 A1 | 8/2015 | Blanchard et al. |
| 2015/0238705 A1 | 8/2015 | Gravesen et al. |
| 2015/0290431 A1 | 10/2015 | Hall et al. |
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0335858 A1 | 11/2015 | Woehr et al. |
| 2015/0359473 A1 | 12/2015 | Garrett et al. |
| 2016/0008580 A1 | 1/2016 | Woehr et al. |
| 2016/0015943 A1 | 1/2016 | Belson et al. |
| 2016/0015945 A1 | 1/2016 | Warring et al. |
| 2016/0022312 A1 | 1/2016 | Tang et al. |
| 2016/0022963 A1 | 1/2016 | Belson |
| 2016/0030716 A1 | 2/2016 | Mallin et al. |
| 2016/0045715 A1 | 2/2016 | Galgano et al. |
| 2016/0089513 A1 | 3/2016 | Ishida |
| 2016/0106959 A1 | 4/2016 | Woehr |
| 2016/0114136 A1 | 4/2016 | Woehr |
| 2016/0114137 A1 | 4/2016 | Woehr et al. |
| 2016/0158503 A1 | 6/2016 | Woehr |
| 2016/0158526 A1 | 6/2016 | Woehr |
| 2016/0175563 A1 | 6/2016 | Woehr et al. |
| 2016/0184557 A1 | 6/2016 | Call et al. |
| 2016/0199575 A1 | 7/2016 | Belley et al. |
| 2016/0206852 A1 | 7/2016 | Morgan et al. |
| 2016/0206858 A1 | 7/2016 | Ishida |
| 2016/0220161 A1 | 8/2016 | Goral et al. |
| 2016/0220786 A1 | 8/2016 | Mitchell et al. |
| 2016/0256667 A1 | 9/2016 | Ribelin et al. |
| 2016/0296729 A1 | 10/2016 | Fuchs et al. |
| 2016/0310704 A1 | 10/2016 | Ng et al. |
| 2016/0331937 A1 | 11/2016 | Teoh |
| 2016/0331938 A1 | 11/2016 | Blanchard et al. |
| 2016/0354580 A1 | 12/2016 | Teoh et al. |
| 2016/0361490 A1 | 12/2016 | Phang et al. |
| 2016/0361519 A1 | 12/2016 | Teoh et al. |
| 2017/0000982 A1 | 1/2017 | Ishida |
| 2017/0035992 A1 | 2/2017 | Harding et al. |
| 2017/0043132 A1 | 2/2017 | Ishida |
| 2017/0080205 A1 | 3/2017 | Lauer |
| 2017/0087338 A1 | 3/2017 | Belson |
| 2017/0136217 A1 | 5/2017 | Riesenberger et al. |
| 2017/0203050 A1 | 7/2017 | Bauer et al. |
| 2017/0209668 A1 | 7/2017 | Belson |
| 2017/0246429 A1 | 8/2017 | Tan et al. |
| 2017/0259036 A1 | 9/2017 | Belson |
| 2017/0361071 A1 | 12/2017 | Belson |
| 2018/0028780 A1 | 2/2018 | Blanchard et al. |
| 2018/0071509 A1 | 3/2018 | Tran et al. |
| 2018/0099123 A1 | 4/2018 | Woehr |
| 2018/0126125 A1 | 5/2018 | Hall et al. |
| 2018/0133437 A1 | 5/2018 | Blanchard |
| 2018/0229003 A1 | 8/2018 | Blanchard et al. |
| 2018/0229004 A1 | 8/2018 | Blanchard et al. |
| 2019/0022358 A1 | 1/2019 | Belson |
| 2019/0192829 A1 | 6/2019 | Belson et al. |
| 2019/0201667 A1 | 7/2019 | Braithwaite et al. |
| 2019/0240459 A1 | 8/2019 | Belson |
| 2019/0275303 A1 | 9/2019 | Tran et al. |
| 2019/0307986 A1 | 10/2019 | Belson |
| 2019/0351193 A1 | 11/2019 | Hall |
| 2019/0351196 A1 | 11/2019 | Ribelin et al. |
| 2020/0001051 A1 | 1/2020 | Huang et al. |
| 2020/0094037 A1 | 3/2020 | Tran et al. |
| 2020/0261696 A1 | 8/2020 | Blanchard |
| 2020/0261703 A1 | 8/2020 | Belson et al. |
| 2020/0316347 A1 | 10/2020 | Belson |
| 2021/0052858 A1 | 2/2021 | Isaacson et al. |
| 2021/0308428 A1 | 10/2021 | Blanchard et al. |
| 2021/0402155 A1 | 12/2021 | Hall et al. |
| 2022/0362523 A1 | 11/2022 | Huang et al. |
| 2022/0379093 A1 | 12/2022 | Nielson |

FOREIGN PATENT DOCUMENTS

| | | |
|---|---|---|
| CN | 1178707 A | 4/1998 |
| CN | 1319023 A | 10/2001 |
| CN | 1523970 A | 8/2004 |
| CN | 1871043 A | 11/2006 |
| CN | 101242868 A | 8/2008 |
| CN | 101293122 A | 10/2008 |
| CN | 101417159 A | 4/2009 |
| CN | 101784300 A | 7/2010 |
| CN | 102099075 A | 6/2011 |
| CN | 102939129 A | 2/2013 |
| CN | 104689456 A | 6/2015 |
| CN | 105073174 A | 11/2015 |
| CN | 105188826 A | 12/2015 |
| CN | 105705191 A | 6/2016 |
| DE | 20210394 U1 | 9/2002 |
| EP | 0314470 A2 | 5/1989 |
| EP | 417764 A1 | 3/1991 |
| EP | 475857 A1 | 3/1992 |
| EP | 515710 A1 | 12/1992 |
| EP | 567321 A2 | 10/1993 |
| EP | 652020 A2 | 5/1995 |
| EP | 0730880 A1 | 9/1996 |
| EP | 747075 A2 | 12/1996 |
| EP | 750916 A2 | 1/1997 |
| EP | 778043 A1 | 6/1997 |
| EP | 800790 A2 | 10/1997 |
| EP | 832663 A2 | 4/1998 |
| EP | 910988 A1 | 4/1999 |
| EP | 942761 A1 | 9/1999 |
| EP | 1075850 A2 | 2/2001 |
| EP | 1378263 A2 | 1/2004 |
| EP | 1418971 A2 | 5/2004 |
| EP | 1457229 A1 | 9/2004 |
| EP | 1611916 A1 | 1/2006 |
| EP | 1907042 A2 | 4/2008 |
| EP | 1974765 A1 | 10/2008 |
| EP | 2150304 A2 | 2/2010 |
| EP | 2272432 A1 | 1/2011 |
| EP | 2347785 A1 | 7/2011 |
| EP | 2569046 A1 | 3/2013 |
| GB | 2529270 A | 2/2016 |
| JP | 2003-159334 A | 6/2003 |
| JP | 2004-130074 A | 4/2004 |
| JP | 2004-223252 A | 8/2004 |
| JP | 2005-137888 A | 6/2005 |
| JP | 2009-500129 A | 1/2009 |
| JP | 2010-088521 A | 4/2010 |
| JP | 2013-529111 A | 7/2013 |
| JP | 2018-118079 A | 8/2018 |

(56) References Cited

FOREIGN PATENT DOCUMENTS

| | | |
|---|---|---|
| JP | 6692869 B2 | 5/2020 |
| WO | 83/01575 A1 | 5/1983 |
| WO | 1992013584 A1 | 8/1992 |
| WO | 92/22344 A1 | 12/1992 |
| WO | 1994006681 A2 | 3/1994 |
| WO | 1995011710 A1 | 5/1995 |
| WO | 95/19193 A1 | 7/1995 |
| WO | 95/23003 A1 | 8/1995 |
| WO | 96/32981 A1 | 10/1996 |
| WO | 1996040359 A1 | 12/1996 |
| WO | 97/05912 A2 | 2/1997 |
| WO | 97/21458 A1 | 6/1997 |
| WO | 1997045151 A1 | 12/1997 |
| WO | 98/24494 A1 | 6/1998 |
| WO | 1998030268 A1 | 7/1998 |
| WO | 1998053875 A1 | 12/1998 |
| WO | 1999008742 A1 | 2/1999 |
| WO | 1999026682 A1 | 6/1999 |
| WO | 00/06226 A1 | 2/2000 |
| WO | 00/12160 A1 | 3/2000 |
| WO | 2000012167 A1 | 3/2000 |
| WO | 00/47256 A1 | 8/2000 |
| WO | 00/67829 A1 | 11/2000 |
| WO | 2001007103 A1 | 2/2001 |
| WO | 01/26725 A1 | 4/2001 |
| WO | 02/41932 A2 | 5/2002 |
| WO | 02/066093 A2 | 8/2002 |
| WO | 02/076526 A2 | 10/2002 |
| WO | 03/11381 A1 | 2/2003 |
| WO | 03/043686 A1 | 5/2003 |
| WO | 03/047675 A2 | 6/2003 |
| WO | 2004/018031 A2 | 3/2004 |
| WO | 2005002659 A1 | 1/2005 |
| WO | 2004106203 A3 | 3/2005 |
| WO | 2005/074412 A2 | 8/2005 |
| WO | 2005/087306 A1 | 9/2005 |
| WO | 2006062996 A2 | 6/2006 |
| WO | 2007006055 A2 | 1/2007 |
| WO | 2007/032343 A1 | 3/2007 |
| WO | 2007094841 A1 | 8/2007 |
| WO | 2007098355 A1 | 8/2007 |
| WO | 2007098359 A1 | 8/2007 |
| WO | 2008005618 A2 | 1/2008 |
| WO | 2008030999 A2 | 3/2008 |
| WO | 2008/131300 A2 | 10/2008 |
| WO | 2008/137956 A2 | 11/2008 |
| WO | 2009/001309 A1 | 12/2008 |
| WO | 2008147600 A1 | 12/2008 |
| WO | 2009031161 A1 | 3/2009 |
| WO | 2009114837 A2 | 9/2009 |
| WO | 2009/124990 A1 | 10/2009 |
| WO | 2010015676 A1 | 2/2010 |
| WO | 2010/048449 A2 | 4/2010 |
| WO | 2010/132608 A2 | 11/2010 |
| WO | 2011036574 A1 | 3/2011 |
| WO | 2011/143621 A1 | 11/2011 |
| WO | 2012/037213 A1 | 3/2012 |
| WO | 2012106266 A1 | 8/2012 |
| WO | 2012154277 A1 | 11/2012 |
| WO | 2012166746 A1 | 12/2012 |
| WO | 2012174109 A1 | 12/2012 |
| WO | 2013119557 A1 | 8/2013 |
| WO | 2013126446 A1 | 8/2013 |
| WO | 2013187827 A1 | 12/2013 |
| WO | 2014006403 A1 | 1/2014 |
| WO | 2014029424 A1 | 2/2014 |
| WO | 2014074417 A2 | 5/2014 |
| WO | 2014081942 A1 | 5/2014 |
| WO | 2014/123848 A1 | 8/2014 |
| WO | 2014120741 A1 | 8/2014 |
| WO | 2014133617 A1 | 9/2014 |
| WO | 2014140257 A1 | 9/2014 |
| WO | 2014140265 A1 | 9/2014 |
| WO | 2014/165783 A1 | 10/2014 |
| WO | 2014158908 A1 | 10/2014 |
| WO | 2014182421 A1 | 11/2014 |
| WO | 2014197656 A1 | 12/2014 |
| WO | 2014204593 A1 | 12/2014 |
| WO | 2015017136 A1 | 2/2015 |
| WO | 2015024904 A1 | 2/2015 |
| WO | 2015035393 A1 | 3/2015 |
| WO | 2015058136 A1 | 4/2015 |
| WO | 15108913 A1 | 7/2015 |
| WO | 2015/168655 A2 | 11/2015 |
| WO | 15164912 A1 | 11/2015 |
| WO | 2016/037127 A1 | 3/2016 |
| WO | 16178974 A1 | 11/2016 |
| WO | 2018/049413 A1 | 3/2018 |
| WO | 2018170349 A1 | 9/2018 |
| WO | 2019173641 A1 | 9/2019 |

OTHER PUBLICATIONS

JP 2016-107046 filed May 30, 2016 Office Action dated Nov. 7, 2017.
JP 2016-563441 filed Oct. 19, 2016 Office Action dated Jan. 25, 2019.
JP 2018-039302 filed Mar. 6, 2018 Office Action dated Feb. 20, 2019.
Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Landmark™ Aquavene® Catheters Brochure, 1992.
Menlo Care, Publications on Aquavene® Technology, Aug. 1992.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 2, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.
Office action dated Nov. 4, 2013 for U.S. Appl. No. 12/307,519.
Office action dated Mar. 12, 2015 for U.S. Appl. No. 11/577,491.
PCT/CN2017/075370 filed Mar. 1, 2017 International Search Report and Written Opinion dated Nov. 30, 2017.
PCT/US15/28950 filed May 1, 2015 International Search Report and Written Opinion dated Oct. 19, 2015.
PCT/US2008/062954 filed May 7, 2008 International search report and written opinion dated Jan. 16, 2009.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed Jan. 29, 2014 International search report and written opinion dated Apr. 14, 2014.
PCT/US2015/048676 filed Sep. 4, 2015 International search report and written opinion dated Dec. 4, 2015.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
PCT/US2017/051214 filed Sep. 12, 2017 International Search Report and Written Opinion dated Nov. 13, 2017.
PCT/US2019/021231 filed Mar. 7, 2019 International Search Report and Written Opinion, dated Jun. 27, 2019.
PR Newswire, Luther Medical Products, Inc. Receives Approval to Supply Improved Neonatal Product to Japan, Aug. 20, 1998.

(56) References Cited

OTHER PUBLICATIONS

Rasor, Julia S, Review of Catheter-related infection rates: comparison of conventional catheter materials with Aquavene®, JVAN vol. 1, No. 3, Spring 1991.
RU 2017141812 filed Nov. 30, 2017 Office Action dated Jan. 31, 2018.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 16/296,087, filed Mar. 7, 2019 Final Office Action dated Sep. 10, 2021.
U.S. Appl. No. 16/296,087, filed Mar. 7, 2019 Non-Final Office Action dated Mar. 26, 2021.
U.S. Appl. No. 16/296,087, filed Mar. 7, 2019 Restriction Requirement dated Feb. 8, 2021.
U.S. Appl. No. 16/389,719, filed Apr. 19, 2019 Final Office Action dated Jun. 14, 2021.
U.S. Appl. No. 16/389,719, filed Apr. 19, 2019 Non-Final Office Action dated Mar. 19, 2021.
U.S. Appl. No. 16/450,800, filed Jun. 24, 2019 Non-Final Office Action dated Jul. 9, 2021.
U.S. Appl. No. 16/450,800, filed Jun. 24, 2019 Notice of Allowance dated Nov. 3, 2021.
U.S. Appl. No. 16/490,023, filed Aug. 29, 2019 Non-Final Office Action dated Oct. 4, 2021.
U.S. Appl. No. 16/490,023, filed Aug. 29, 2019 Restriction Requirement dated May 4, 2021.
U.S. Appl. No. 16/529,602, filed Aug. 1, 2019 Notice of Allowance dated Jan. 19, 2021.
U.S. Appl. No. 16/529,622, filed Aug. 1, 2019 Non-Final Office Action dated May 7, 2021.
U.S. Appl. No. 16/529,622, filed Aug. 1, 2019 Notice of Allowance dated Aug. 23, 2021.
U.S. Appl. No. 29/536,043, filed Aug. 12, 2015 Final Office Action dated Mar. 26, 2018.
U.S. Appl. No. 29/536,043, filed Aug. 12, 2015 Non-Final Office Action dated Aug. 31, 2017.
U.S. Appl. No. 29/545,436, filed Nov. 12, 2015 Final Office Action dated Mar. 26, 2018.
U.S. Appl. No. 29/545,436, filed Nov. 12, 2015 Non-Final Office Action dated Sep. 12, 2017.
U.S. Appl. No. 29/654,521, filed Jun. 25, 2018 Notice of Allowability dated Sep. 30, 2020.
U.S. Appl. No. 29/654,521, filed Jun. 25, 2018 Notice of Allowance dated Aug. 17, 2020.
U.S. Appl. No. 29/654,521, filed Jun. 25, 2018 Restriction Requirement dated Apr. 8, 2020.
U.S. Appl. No. 29/654,527, filed Jun. 25, 2018 Notice of Allowability dated Sep. 30, 2020.
U.S. Appl. No. 29/654,527, filed Jun. 25, 2018 Notice of Allowance dated Aug. 18, 2020.
U.S. Appl. No. 29/654,527, filed Jun. 25, 2018 Restriction Requirement dated Mar. 10, 2020.
U.S. Appl. No. 29/658,136, filed Jul. 27, 2018 Non-Final Office Action dated Sep. 9, 2020.
U.S. Appl. No. 29/658,136, filed Jul. 27, 2018 Notice of Allowance dated Mar. 23, 2021.
U.S. Appl. No. 29/658,136, filed Jul. 27, 2018 Restriction Requirement dated May 11, 2020.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
U.S. Appl. No. 14/866,738, filed Sep. 25, 2015 Non-Final Office Action dated Oct. 31, 2016.
U.S. Appl. No. 14/866,738, filed Sep. 25, 2015 Notice of Allowance dated Sep. 24, 2020.
U.S. Appl. No. 14/866,738, filed Sep. 25, 2015 Notice of Panel Decision dated Jun. 23, 2017.
U.S. Appl. No. 14/866,738, filed Sep. 25, 2015 Patent Board Decision dated Jul. 13, 2020.
U.S. Appl. No. 14/876,735, filed Oct. 6, 2015 Non-Final Office Action dated Mar. 30, 2017.
U.S. Appl. No. 15/154,384, filed May 13, 2016 Final Office Action dated Dec. 24, 2020.
U.S. Appl. No. 15/154,384, filed May 13, 2016 Final Office Action dated Nov. 27, 2019.
U.S. Appl. No. 15/154,384, filed May 13, 2016 Non-Final Office Action dated Jun. 26, 2020.
U.S. Appl. No. 15/154,384, filed May 13, 2016 Non-Final Office Action dated Jun. 28, 2019.
U.S. Appl. No. 15/154,384, filed May 13, 2016 Notice of Allowance dated Apr. 29, 2021.
U.S. Appl. No. 15/154,384, filed May 13, 2016 Notice of Allowance dated Mar. 17, 2021.
U.S. Appl. No. 15/154,384, filed May 13, 2016 Restriction Requirement dated Jan. 25, 2019.
U.S. Appl. No. 15/154,808, filed May 13, 2016 Advisory Action dated Oct. 26, 2018.
U.S. Appl. No. 15/154,808, filed May 13, 2016 Final Office Action dated Aug. 16, 2018.
U.S. Appl. No. 15/154,808, filed May 13, 2016 Non-Final Office Action dated Apr. 6, 2018.
U.S. Appl. No. 15/154,808, filed May 13, 2016 Notice of Allowance dated Apr. 16, 2019.
U.S. Appl. No. 15/154,808, filed May 13, 2016 Restriction Requirement dated Jan. 3, 2018.
U.S. Appl. No. 15/377,880, filed Dec. 13, 2016 Final Office Action dated Oct. 19, 2018.
U.S. Appl. No. 15/377,880, filed Dec. 13, 2016 Non-Final Office Action dated May 14, 2018.
U.S. Appl. No. 15/481,773, filed Apr. 7, 2017 Final Office Action dated Jan. 10, 2019.
U.S. Appl. No. 15/481,773, filed Apr. 7, 2017 Non-Final Office Action dated Jun. 29, 2018.
U.S. Appl. No. 15/608,802, filed May 30, 2017 Non-Final Office Action dated Jun. 6, 2019.
U.S. Appl. No. 15/692,915, filed Aug. 31, 2017 Non-Final Office Action dated Jan. 29, 2018.
U.S. Appl. No. 15/702,537, filed Sep. 12, 2017 Final Office Action dated Mar. 8, 2019.
U.S. Appl. No. 15/702,537, filed Sep. 12, 2017 Non-Final Office Action dated Nov. 29, 2018.
U.S. Appl. No. 15/702,537, filed Sep. 12, 2017 Notice of Allowance dated Jul. 31, 2019.
U.S. Appl. No. 15/727,528, filed Oct. 6, 2017 Final Office Action dated Jan. 28, 2020.

(56) References Cited

OTHER PUBLICATIONS

U.S. Appl. No. 15/727,528, filed Oct. 6, 2017 Non-Final Office Action dated Sep. 20, 2019.
U.S. Appl. No. 15/727,528, filed Oct. 6, 2017 Restriction Requirement dated Aug. 7, 2019.
U.S. Appl. No. 15/727,528, filed Oct. 6, 2017 Notice of Allowance dated Mar. 27, 2020.
U.S. Appl. No. 15/862,380, filed Jan. 4, 2018 Final Office Action dated Oct. 26, 2020.
U.S. Appl. No. 15/862,380, filed Jan. 4, 2018 Non-Final Office Action dated Jul. 9, 2020.
U.S. Appl. No. 15/862,380, filed Jan. 4, 2018 Notice of Allowance dated Jun. 16, 2021.
U.S. Appl. No. 15/862,380, filed Jan. 4, 2018 Restriction Requirement dated Dec. 23, 2019.
U.S. Appl. No. 15/869,872, filed Jan. 12, 2018 Advisory Action dated Sep. 23, 2020.
U.S. Appl. No. 15/869,872, filed Jan. 12, 2018 Final Office Action dated Jun. 25, 2020.
U.S. Appl. No. 15/869,872, filed Jan. 12, 2018 Non-Final Office Action dated Apr. 10, 2020.
U.S. Appl. No. 15/951,931, filed Apr. 12, 2018 Non-Final Office Action dated Nov. 19, 2019.
U.S. Appl. No. 15/951,931, filed Apr. 12, 2018 Notice of Allowance dated Feb. 20, 2020.
U.S. Appl. No. 15/951,931, filed Apr. 12, 2018 Notice of Allowability dated Apr. 16, 2020.
U.S. Appl. No. 15/951,954, filed Apr. 12, 2018 Non-Final Office Action dated Nov. 4, 2019.
U.S. Appl. No. 15/951,954, filed Apr. 12, 2018 Notice of Allowance dated Feb. 23, 2020.
U.S. Appl. No. 15/951,954, filed Apr. 12, 2018 Notice of Allowability dated Apr. 7, 2020.
U.S. Appl. No. 16/138,523, filed Sep. 21, 2018 Notice of Allowance dated Mar. 26, 2020.
U.S. Appl. No. 16/292,076, filed Mar. 4, 2019 Corrected Notice of Allowance dated Feb. 25, 2021.
U.S. Appl. No. 16/292,076, filed Mar. 4, 2019 Non-Final Office Action dated Aug. 10, 2020.
U.S. Appl. No. 16/292,076, filed Mar. 4, 2019 Notice of Allowance dated Feb. 4, 2021.
U.S. Appl. No. 16/295,906, filed Mar. 7, 2019 Final Office Action dated Dec. 22, 2020.
U.S. Appl. No. 16/295,906, filed Mar. 7, 2019 Non-Final Office Action dated Sep. 4, 2020.
U.S. Appl. No. 16/295,906, filed Mar. 7, 2019 Notice of Allowance dated Mar. 4, 2021.
EP 22192364.2 filed Aug. 26, 2022 Extended European Search Report dated Nov. 30, 2022.
U.S. Appl. No. 16/867,349, filed May 5, 2020 Final Office Action dated Dec. 28, 2022.
U.S. Appl. No. 16/868,461, filed May 6, 2020 Examiner's Answer dated Jan. 31, 2023.
U.S. Appl. No. 16/902,031, filed Jun. 15, 2020 Non-Final Office Action dated Dec. 21, 2022.
U.S. Appl. No. 17/164,653, filed Feb. 1, 2021, Notice of Allowance dated Nov. 1, 2022.
U.S. Appl. No. 17/164,653, filed Feb. 1, 2021, Restriction Requirement dated Sep. 7, 2022.
U.S. Appl. No. 17/337,273, filed Jun. 2, 2021 Notice of Allowance dated Oct. 5, 2022.
U.S. Appl. No. 17/471,051, filed Sep. 9, 2021 Restriction Requirement dated Dec. 22, 2021.
U.S. Appl. No. 17/863,179, filed Jul. 12, 2022 Non-Final Office Action dated Dec. 7, 2022.
U.S. Appl. No. 15/869,872, filed Jan. 12, 2018 Notice of Allowance dated Dec. 24, 2021.
U.S. Appl. No. 16/868,461, filed May 6, 2020 Non-Final Office Action dated Feb. 15, 2022.

Access Scientific, The PICC Wand® Product Data Sheet, Revision F, May 22, 2012.
Access Scientific, The Powerwand® Extended Dwell Catheter Brochure (http://accessscientific.com/media/4Fr-POWERWAND-Brochure.pdf) last accessed Sep. 25, 2015.
BD Angiocath™ Autoguard™ Shielded IV Catheter Brochure, © 2001.
BD Medical Systems, I.V. Catheter Family Brochure (2006).
BD Saf-T-Intima™ Integrated Safety IV Catheter Brochure, © 2001.
Becton Dickinson, Insyte® AutoGuard™ Shielded I.V. Catheter Brochure, 1998.
CA 2,799,360 filed May 13, 2011 Office Action dated Jun. 7, 2017.
CN 201180029526.7 filed Dec. 14, 2012 First Office Action dated Apr. 21, 2014.
CN 2012800008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
CN 201380073657.4 filed Aug. 21, 2015 Office Action dated Jun. 28, 2017.
CN 201380073657.4 filed Aug. 21, 2015 Office Action dated Mar. 2, 2018.
CN 201480019467.9 filed Sep. 29, 2015 Office Action dated Apr. 6, 2017.
CN 201510079782.7 filed Feb. 13, 2015 Office Action dated Dec. 30, 2016.
CN 201510079782.7 filed Feb. 13, 2015 Office Action dated Feb. 5, 2018.
CN 201510079782.7 filed Feb. 13, 2015 Office Action dated Sep. 19, 2017.
CN 201580022407.7 filed Nov. 2, 2016 Office Action dated Jan. 31, 2019.
CN 201580022407.7 filed Nov. 2, 2016 Office Action dated Sep. 16, 2019.
Cook Medical "Lunderquist Extra-Stiff wire guide" (2012).
Endovascular Today "Coiled Stainless Steel Guidewires" Buyer's Guide pp. 13-20, (2012).
EP 07783404.2 filed Jan. 19, 2009 Office Action dated Apr. 16, 2019.
EP 07783404.2 filed Jan. 19, 2009 Office Action dated Mar. 7, 2018.
EP 10075422.5 filed Jul. 5, 2008 European search report and written opinion dated Dec. 1, 2010.
EP 11781384.0 filed Sep. 21, 2012 Extended European Search Report dated Oct. 31, 2017.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 12782187.4 filed Sep. 10, 2013 Office Action dated Apr. 24, 2018.
EP 12782187.4 filed Sep. 10, 2013 Office Action dated Nov. 28, 2018.
EP 13876666.2 filed Sep. 7, 2015 Extended European Search Report dated Sep. 20, 2016.
EP 15785819.2 filed Dec. 2, 2016 Extended European Search Report dated Dec. 4, 2017.
EP 16797029.2 filed Nov. 21, 2017 Extended European Search Report dated May 3, 2018.
EP 16797029.2 filed Nov. 21, 2017 Office Action dated Mar. 27, 2020.
EP 16797047.4 filed Dec. 6, 2017 Supplemental European Search Report dated Jan. 9, 2019.
EP 19181963.0 filed Jun. 24, 2019 Extended European Search Report dated Jul. 16, 2019.
EP17849786.3 filed Apr. 12, 2019 Extended European Search Report dated May 13, 2020.
European office action dated Apr. 21, 2008 for EP Application No. 06800027.2.
European office action dated Aug. 6, 2012 for EP Application No. 07783404.2.

(56) References Cited

OTHER PUBLICATIONS

European office action dated Oct. 5, 2010 for EP Application No. 07783404.2.

European search report and opinion dated Jul. 10, 2009 for EP Application No. 07783404.2.

Hadaway, Lynn C., A Midline Alternative to Central and Peripheral Venous Access, Caring Magazine, May 1990, pp. 45-50.

International search report and written opinion dated Apr. 2, 2012 for PCT/US2012/023192.

International search report and written opinion dated Jun. 1, 2007 for PCT/US2006/026671.

International search report and written opinion dated Oct. 23, 2008 for PCT/US2007/068393.

JP 2013-510353 filed Oct. 31, 2012 First Office Action dated Feb. 19, 2015.

JP 2013-510353 filed Oct. 31, 2012 Office Action dated Dec. 15, 2016.

JP 2013-510353 filed Oct. 31, 2012 Second Office Action dated Jan. 28, 2016.

JP 2015-560173 filed Aug. 28, 2015 Office Action dated Aug. 2, 2018.

JP 2015-560173 filed Aug. 28, 2015 Office Action dated Sep. 19, 2017.

JP 2016-107046 filed May 30, 2016 Office Action dated Apr. 26, 2017.

EP 22159383.3 filed Mar. 1, 2022 Extended European Search Report dated May 30, 2022.

PCT/US2019/052225 filed Sep. 20, 2019 International Search Report and Written Opinion dated Jun. 25, 2020.

PCT/US2020/046860 filed Aug. 18, 2020 International Search Report and Written Opinion dated Nov. 18, 2020.

U.S. Appl. No. 16/296,087, filed Mar. 7, 2019 Notice of Allowance dated Mar. 8, 2022.

U.S. Appl. No. 16/490,023, filed Aug. 29, 2019 Notice of Allowance dated Mar. 14, 2022.

U.S. Appl. No. 16/696,844, filed Nov. 26, 2019 Non-Final Office Action dated Aug. 1, 2022.

U.S. Appl. No. 16/867,349, filed May 5, 2020 Non-Final Office Action dated Jun. 16, 2022.

U.S. Appl. No. 16/868,461, filed May 6, 2020 Final Office Action dated May 25, 2022.

U.S. Appl. No. 16/996,769, filed Aug. 18, 2020 Non-Final Office Action dated Mar. 2, 2022.

U.S. Appl. No. 16/996,769, filed Aug. 18, 2020 Notice of Allowance dated Jun. 13, 2022.

U.S. Appl. No. 16/696,844, filed Nov. 26, 2019 Notice of Allowance dated Apr. 17, 2023.

U.S. Appl. No. 16/867,349, filed May 5, 2020 Advisory Action dated Mar. 13, 2023.

U.S. Appl. No. 17/353,602, filed Jun. 21, 2021 Non-Final Office Action dated Mar. 30, 2023.

U.S. Appl. No. 14/044,623, filed Oct. 2, 2013 Notice of Allowance dated Nov. 6, 2014.

U.S. Appl. No. 14/099,050, filed Dec. 6, 2013 Advisory Action dated Jun. 1, 2017.

U.S. Appl. No. 14/099,050, filed Dec. 6, 2013 Final Office Action dated Jan. 30, 2017.

U.S. Appl. No. 14/099,050, filed Dec. 6, 2013 Non-Final Office Action dated Dec. 22, 2015.

U.S. Appl. No. 14/099,050, filed Dec. 6, 2013 Non-Final Office Action dated Jul. 19, 2016.

U.S. Appl. No. 14/099,050, filed Dec. 6, 2013 Notice of Allowance dated Sep. 14, 2017.

U.S. Appl. No. 14/099,050, filed Dec. 6, 2013 Notice of Panel Decision dated Aug. 1, 2017.

U.S. Appl. No. 14/167,149, filed Jan. 29, 2014 Non-Final Office Action dated Oct. 21, 2015.

U.S. Appl. No. 14/167,149, filed Jan. 29, 2014 Notice of Allowance dated Jul. 6, 2016.

U.S. Appl. No. 14/174,071, filed Feb. 6, 2014 Final Office Action dated Dec. 2, 2016.

U.S. Appl. No. 14/174,071, filed Feb. 6, 2014 Non-Final Office Action dated Jul. 29, 2016.

U.S. Appl. No. 14/174,071, filed Feb. 6, 2014 Non-Final Office Action dated Mar. 31, 2016.

U.S. Appl. No. 14/192,541, filed Feb. 27, 2014 Non-Final Office Action dated Jul. 20, 2016.

U.S. Appl. No. 14/192,541, filed Feb. 27, 2014 Notice of Allowance dated Dec. 6, 2016.

U.S. Appl. No. 14/192,541, filed Feb. 27, 2014 Notice of Corrected Allowability dated Mar. 8, 2017.

U.S. Appl. No. 14/250,093, filed Apr. 10, 2014 Advisory Action dated May 19, 2017.

U.S. Appl. No. 14/250,093, filed Apr. 10, 2014 Examiner's Answer dated Jun. 20, 2018.

U.S. Appl. No. 14/250,093, filed Apr. 10, 2014 Final Office Action dated Mar. 9, 2017.

U.S. Appl. No. 14/250,093, filed Apr. 10, 2014 Final Office Action dated Nov. 6, 2017.

U.S. Appl. No. 14/250,093, filed Apr. 10, 2014 Non-Final Office Action dated Nov. 16, 2016.

U.S. Appl. No. 14/250,093, filed Apr. 10, 2014 Notice of Allowance dated Aug. 19, 2020.

U.S. Appl. No. 14/250,093, filed Apr. 10, 2014 Panel Decision dated Jul. 14, 2017.

U.S. Appl. No. 14/250,093, filed Apr. 10, 2014 Patent Board Decision dated Jun. 8, 2020.

U.S. Appl. No. 14/477,717, filed Sep. 4, 2014, Notice of allowance dated Feb. 17, 2015.

U.S. Appl. No. 14/477,717, filed Sep. 4, 2014, Office action dated Dec. 18, 2014.

U.S. Appl. No. 14/585,800, filed Dec. 30, 2014 Final Office Action dated May 11, 2018.

U.S. Appl. No. 14/585,800, filed Dec. 30, 2014 Non-Final Office Action dated May 16, 2016.

U.S. Appl. No. 14/585,800, filed Dec. 30, 2014 Non-Final Office Action dated Nov. 29, 2016.

U.S. Appl. No. 14/585,800, filed Dec. 30, 2014 Non-Final Office Action dated Nov. 3, 2017.

U.S. Appl. No. 14/585,800, filed Dec. 30, 2014 Non-Final Office Action dated Oct. 8, 2015.

U.S. Appl. No. 14/585,800, filed Dec. 30, 2014 Notice of Allowance dated Feb. 25, 2019.

U.S. Appl. No. 14/585,800, filed Dec. 30, 2014 Notice of Allowance dated Jul. 3, 2017.

U.S. Appl. No. 14/702,580, filed May 1, 2015 Advisory Action dated Nov. 13, 2017.

U.S. Appl. No. 14/702,580, filed May 1, 2015 Final Office Action dated Sep. 1, 2017.

U.S. Appl. No. 14/702,580, filed May 1, 2015 Non-Final Office Action dated May 3, 2017.

U.S. Appl. No. 14/702,580, filed May 1, 2015 Notice of Allowance dated Dec. 8, 2017.

U.S. Appl. No. 14/750,658, filed Jun. 25, 2016 Non-Final Office Action dated Mar. 9, 2017.

U.S. Appl. No. 14/750,658, filed Jun. 25, 2016 Notice of Allowance dated Jul. 20, 2017.

U.S. Appl. No. 14/846,387, filed Sep. 4, 2015 Advisory Action dated May 10, 2018.

U.S. Appl. No. 14/846,387, filed Sep. 4, 2015 Final Office Action dated Mar. 22, 2018.

U.S. Appl. No. 14/846,387, filed Sep. 4, 2015 Non-Final Office Action dated Sep. 22, 2017.

U.S. Appl. No. 14/846,387, filed Sep. 4, 2015 Notice of Allowance dated Oct. 29, 2018.

U.S. Appl. No. 14/866,441, filed Sep. 25, 2015 Advisory Action dated Dec. 22, 2016.

U.S. Appl. No. 14/866,441, filed Sep. 25, 2015 Final Office Action dated Jun. 5, 2018.

U.S. Appl. No. 14/866,441, filed Sep. 25, 2015 Final Office Action dated Sep. 23, 2016.

(56) References Cited

OTHER PUBLICATIONS

U.S. Appl. No. 14/866,441, filed Sep. 25, 2015 Non-Final Office Action dated Apr. 7, 2017.
U.S. Appl. No. 14/866,441, filed Sep. 25, 2015 Non-Final Office Action dated Mar. 14, 2016.
U.S. Appl. No. 14/866,441, filed Sep. 25, 2015 Notice of Allowance dated Oct. 17, 2018.
U.S. Appl. No. 14/866,738, filed Sep. 25, 2015 Final Office Action dated Feb. 24, 2017.
U.S. Appl. No. 14/866,738, filed Sep. 25, 2015 Non-Final Office Action dated Nov. 6, 2017.
EP 20855351.1 filed Mar. 7, 2022 Extended European Search Report dated Sep. 7, 2023.
U.S. Appl. No. 16/867,349, filed May 5, 2020 Non-Final Office Action dated Jul. 20, 2023.
U.S. Appl. No. 16/902,031, filed Jun. 15, 2020 Final Office Action dated Aug. 18, 2023.
U.S. Appl. No. 17/353,602, filed Jun. 21, 2021 Final Office Action dated Sep. 28, 2023.
U.S. Appl. No. 17/471,051, filed Sep. 9, 2021 Final Office Action dated Aug. 23, 2023.
U.S. Appl. No. 17/471,051, filed Sep. 9, 2021 Non-Final Office Action dated May 24, 2023.
U.S. Appl. No. 17/863,179, filed Jul. 12, 2022 Advisory Action dated Aug. 23, 2023.
U.S. Appl. No. 17/863,179, filed Jul. 12, 2022 Final Office Action dated Jun. 14, 2023.
U.S. Appl. No. 18/094,917, filed Jan. 9, 2023 Non-Final Office Action dated Jun. 8, 2023.
U.S. Appl. No. 18/094,917, filed Jan. 9, 2023 Notice of Allowance dated Sep. 13, 2023.

\* cited by examiner

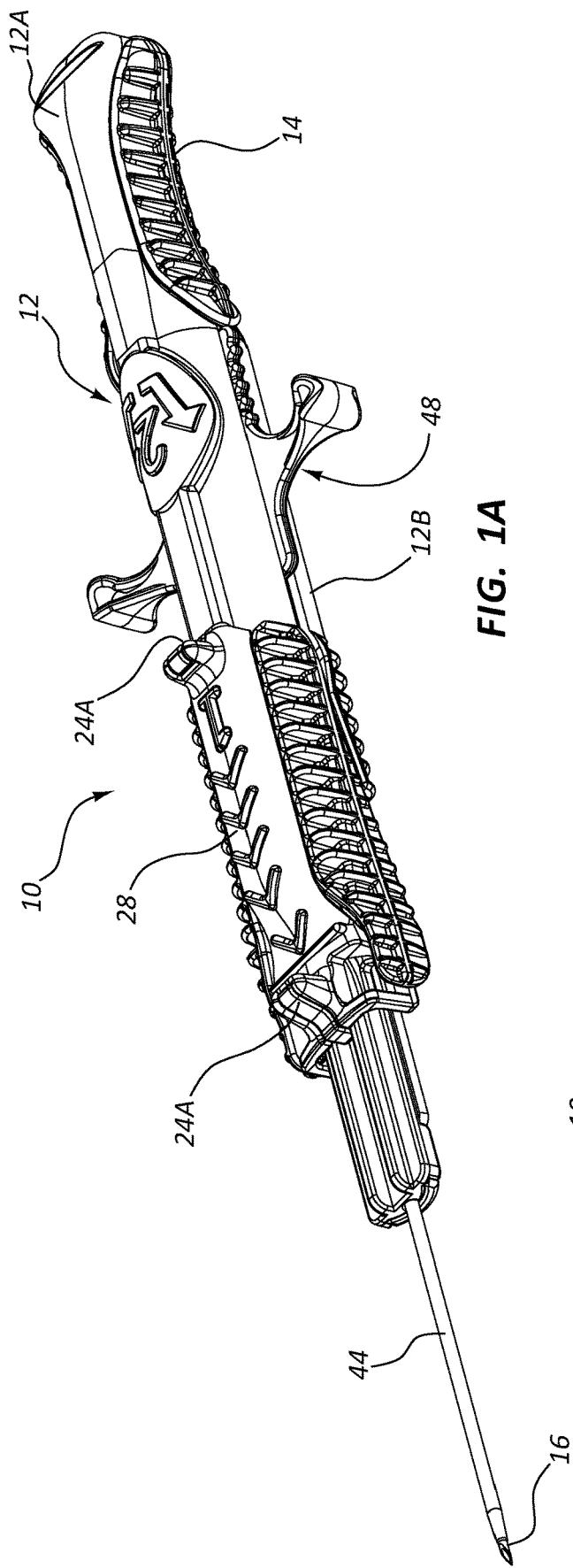
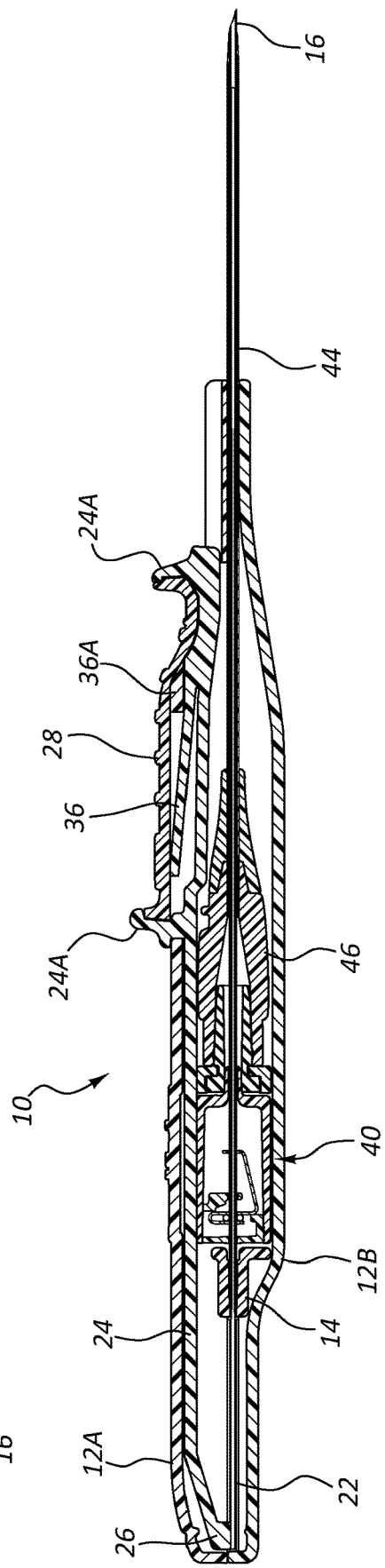
FIG. 1A
FIG. 1B

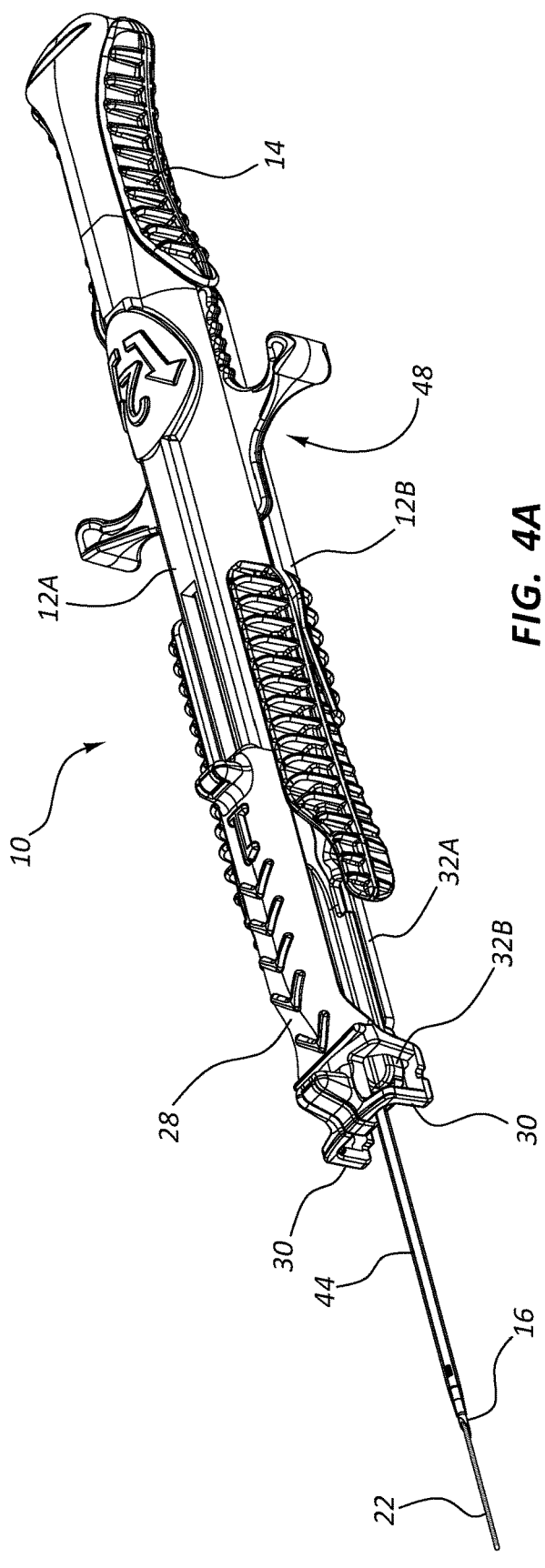
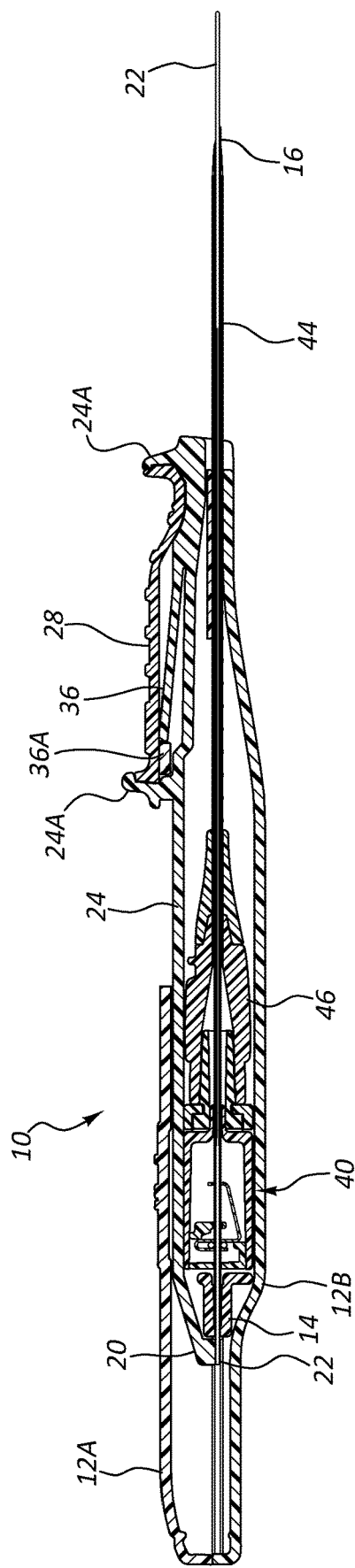
FIG. 4A
FIG. 4B

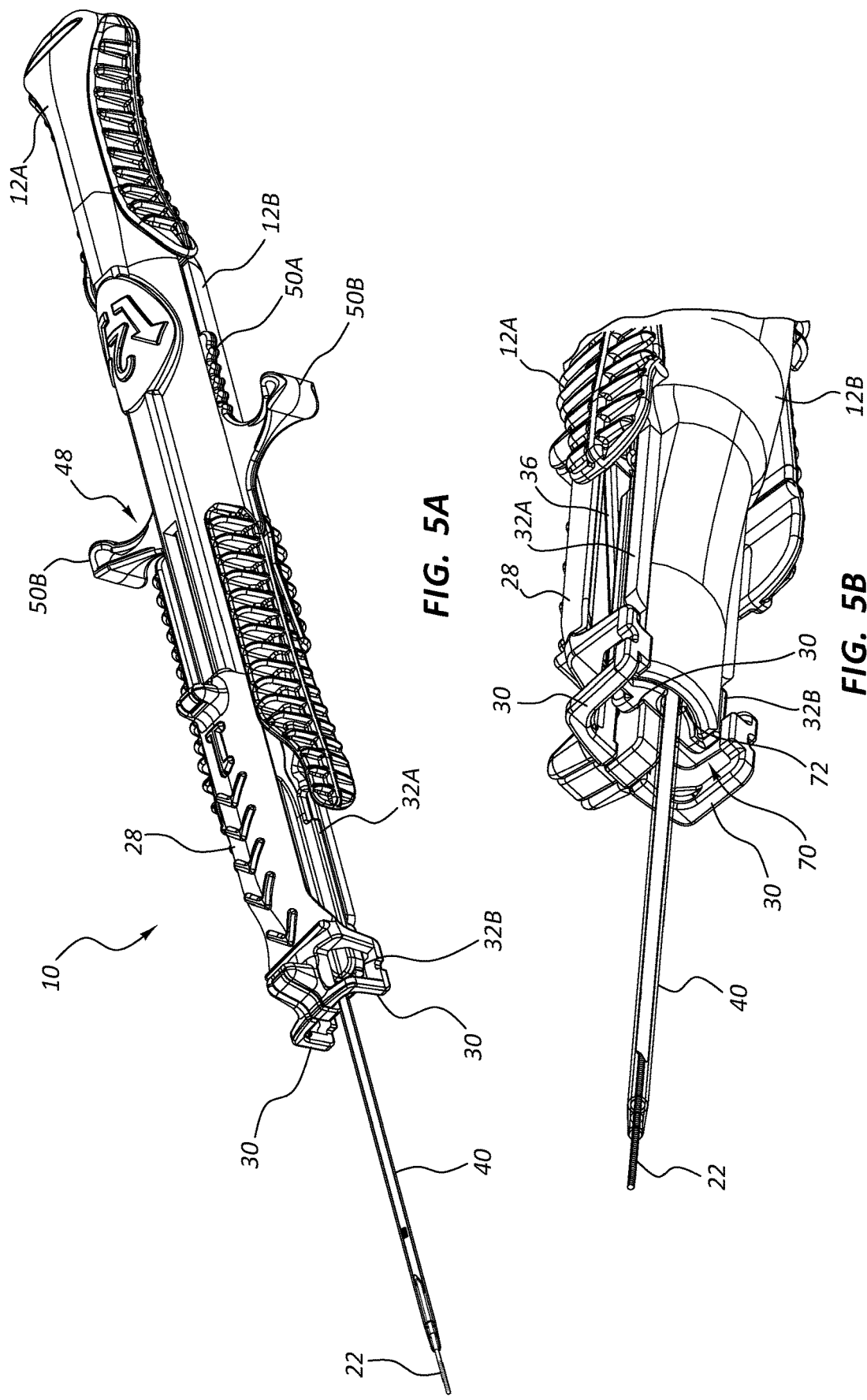

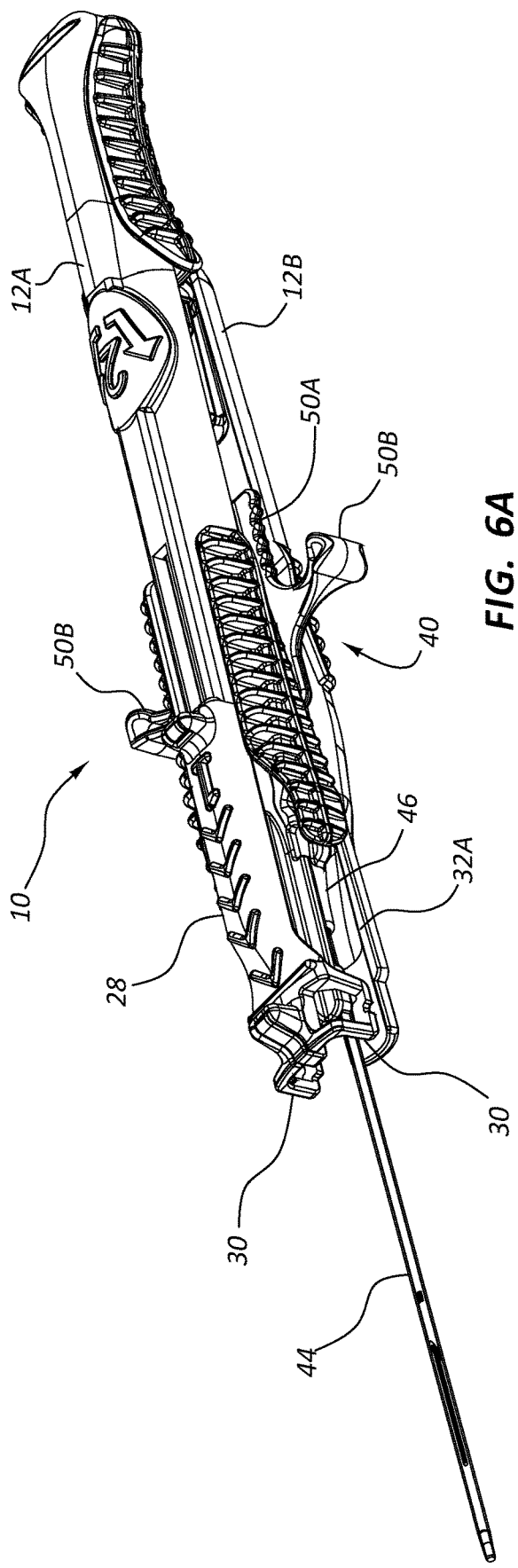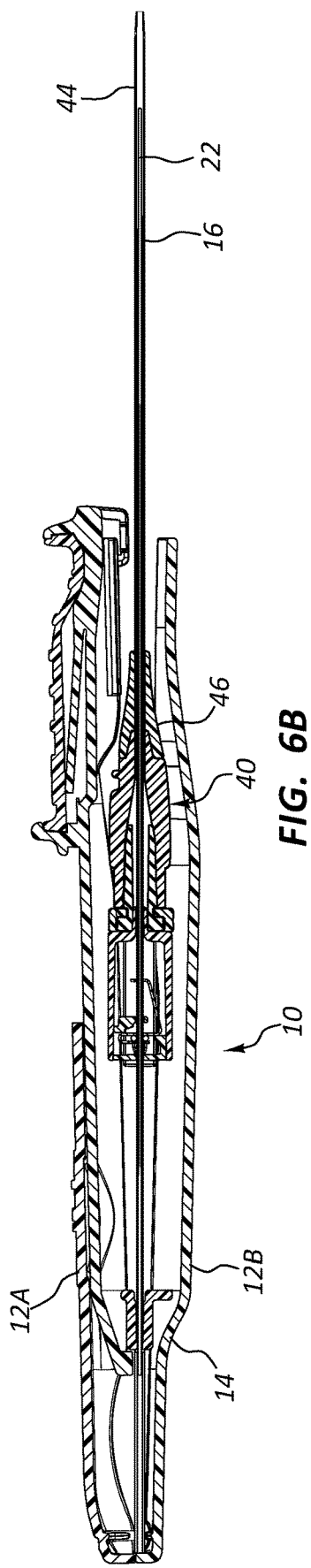
FIG. 6A
FIG. 6B

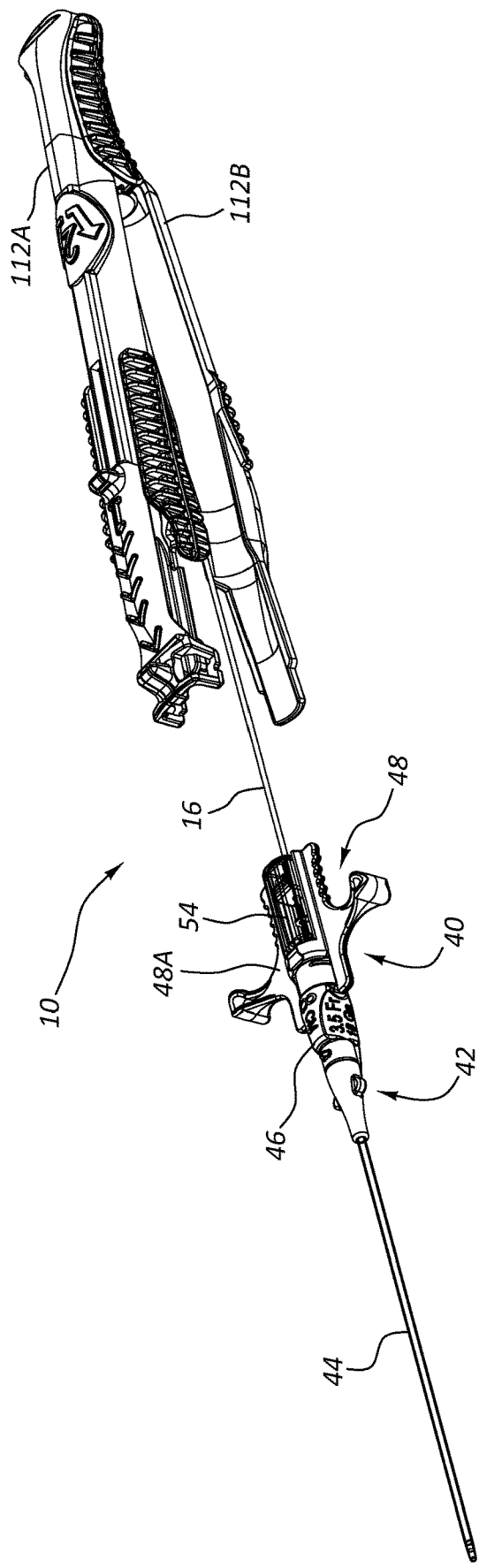
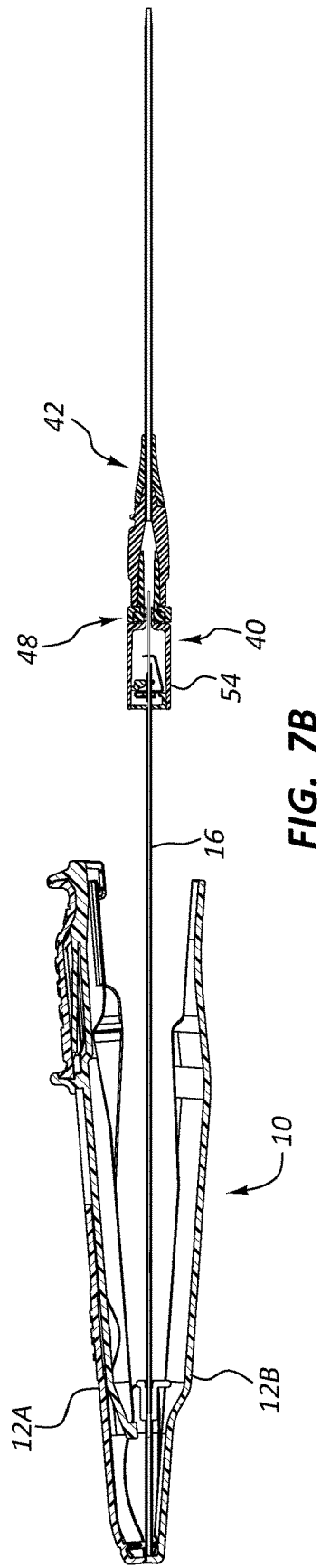
FIG. 7A
FIG. 7B

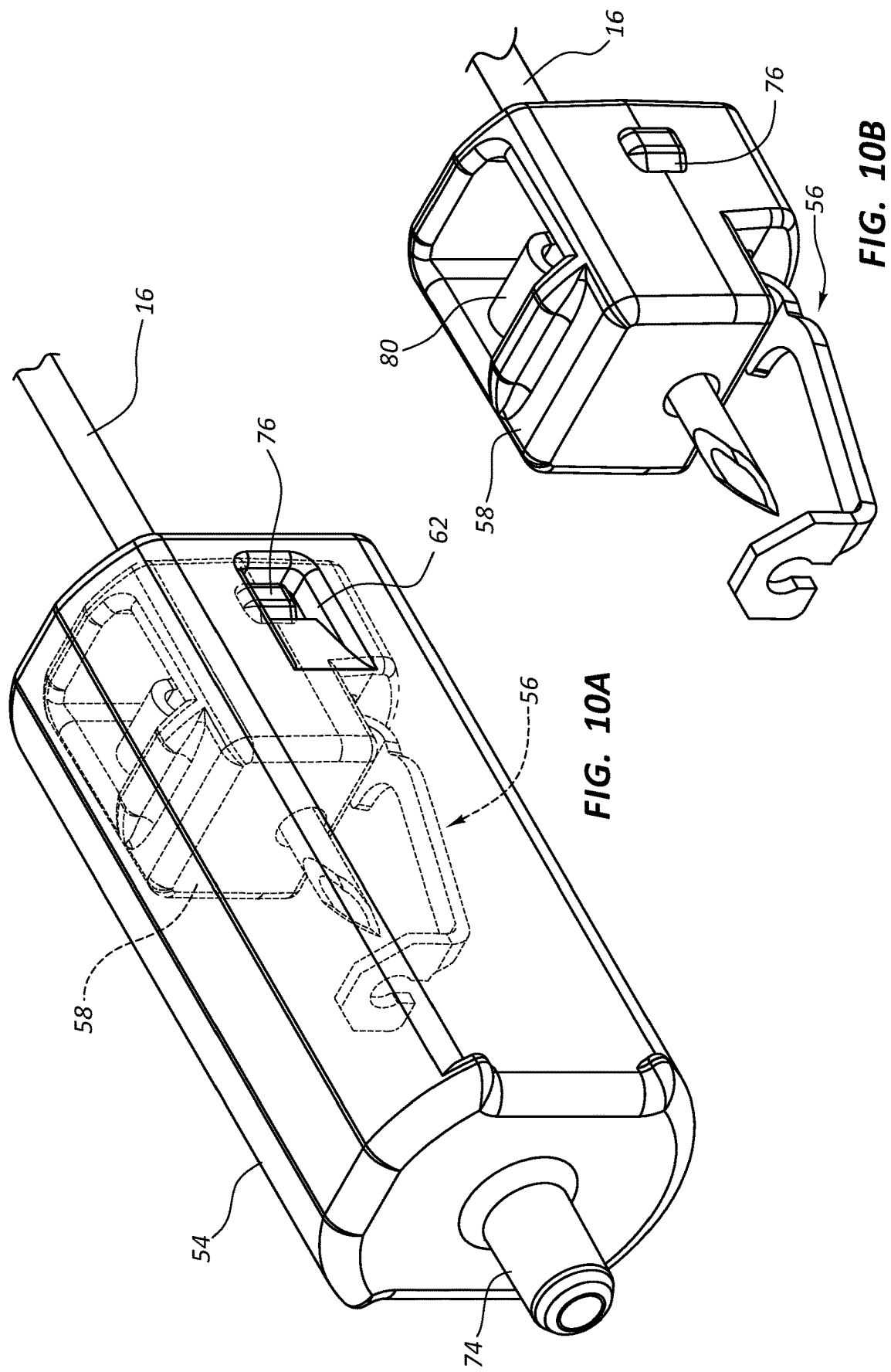

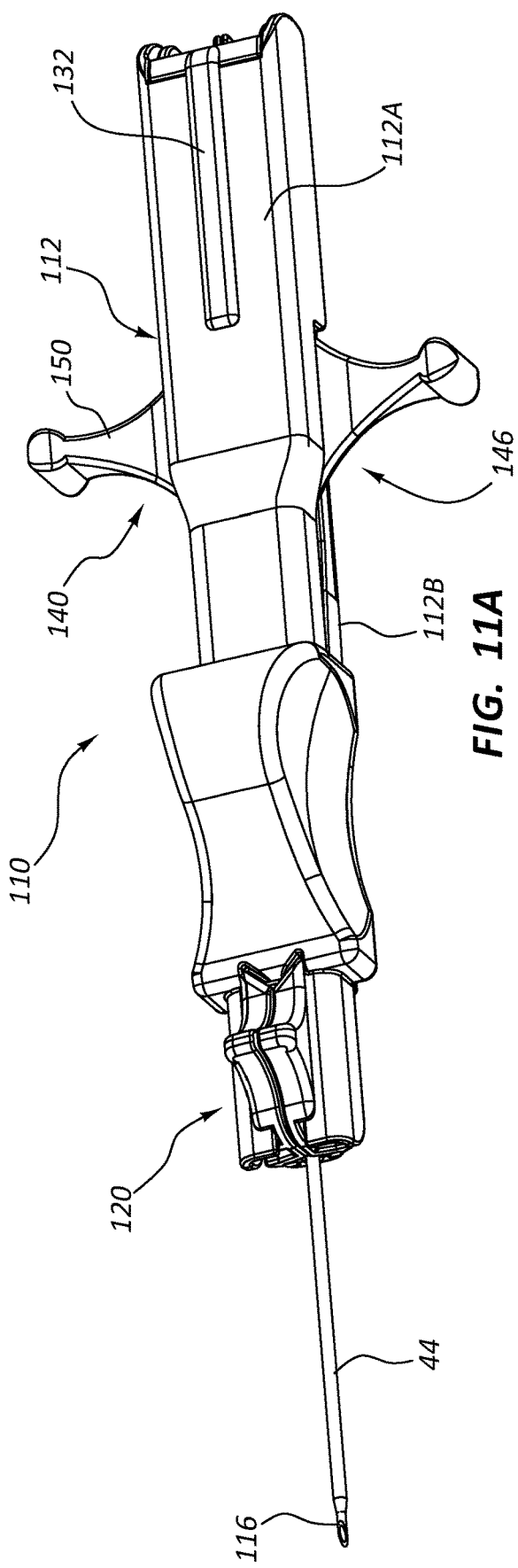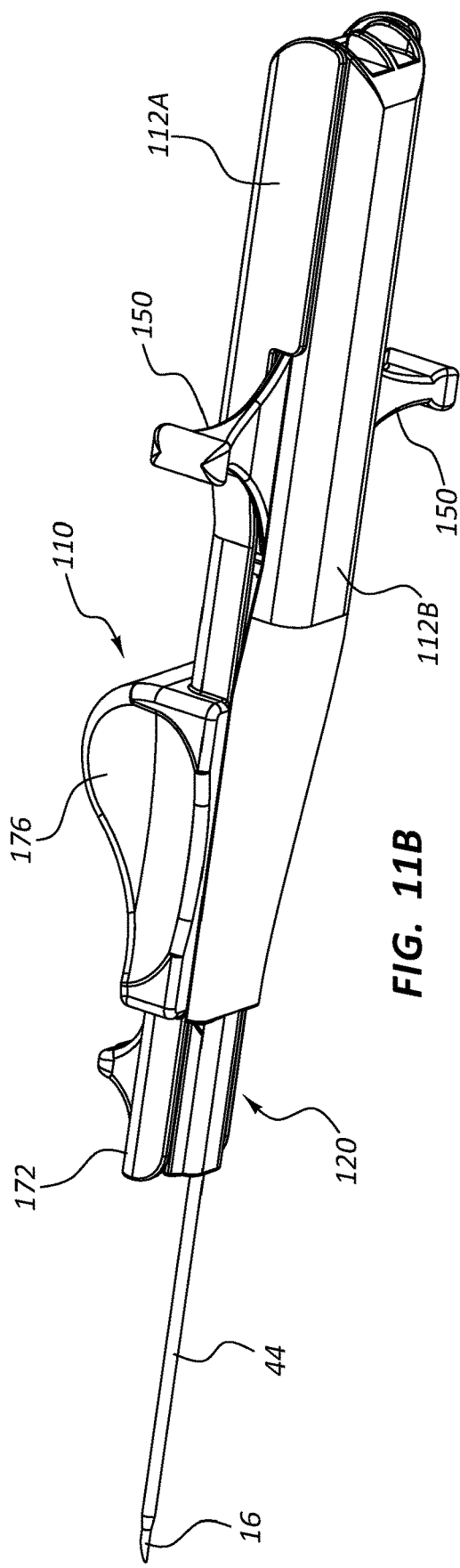
FIG. 11A
FIG. 11B

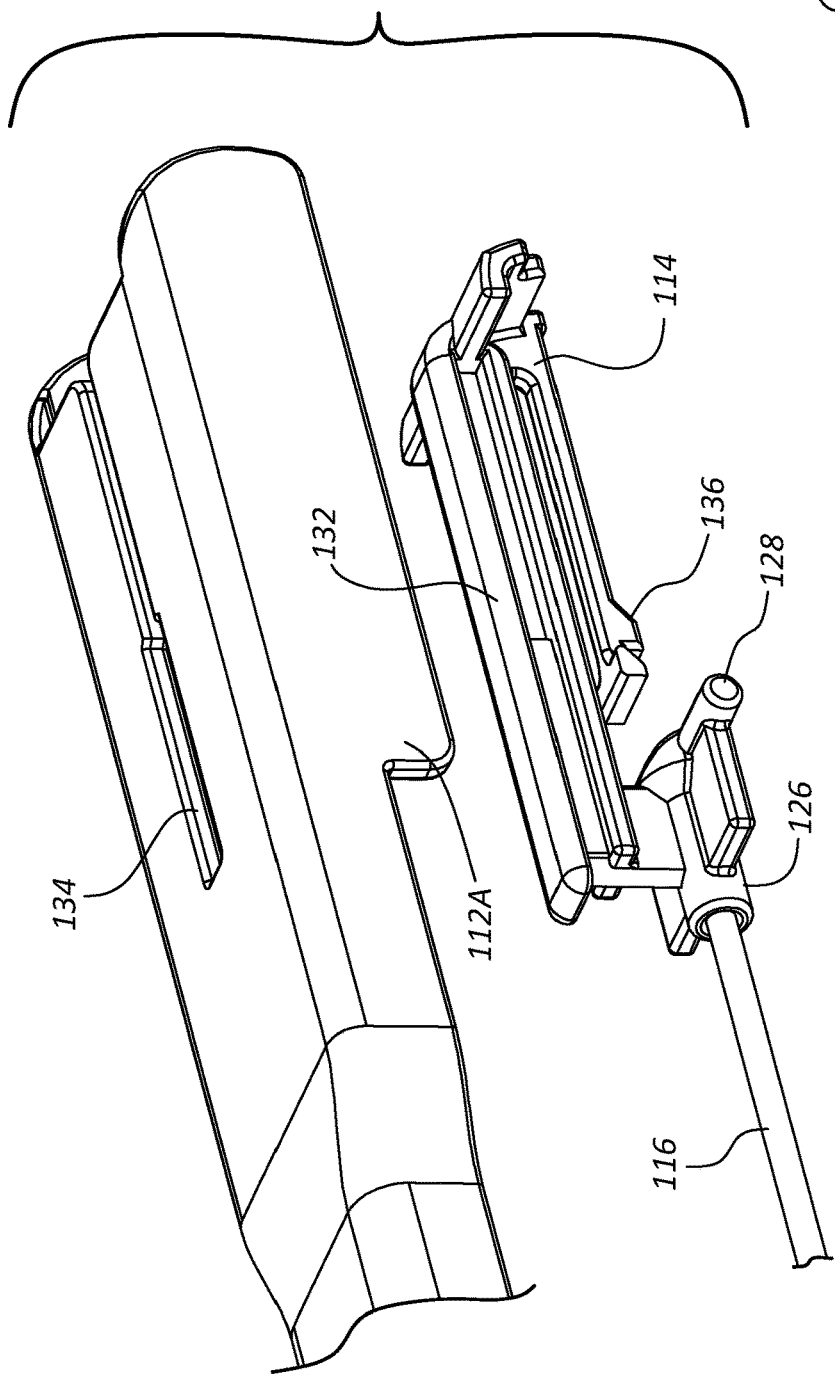
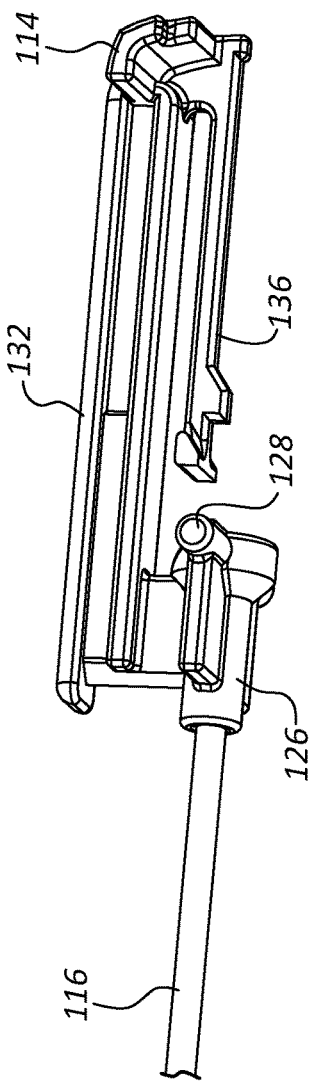
FIG. 13A
FIG. 13B

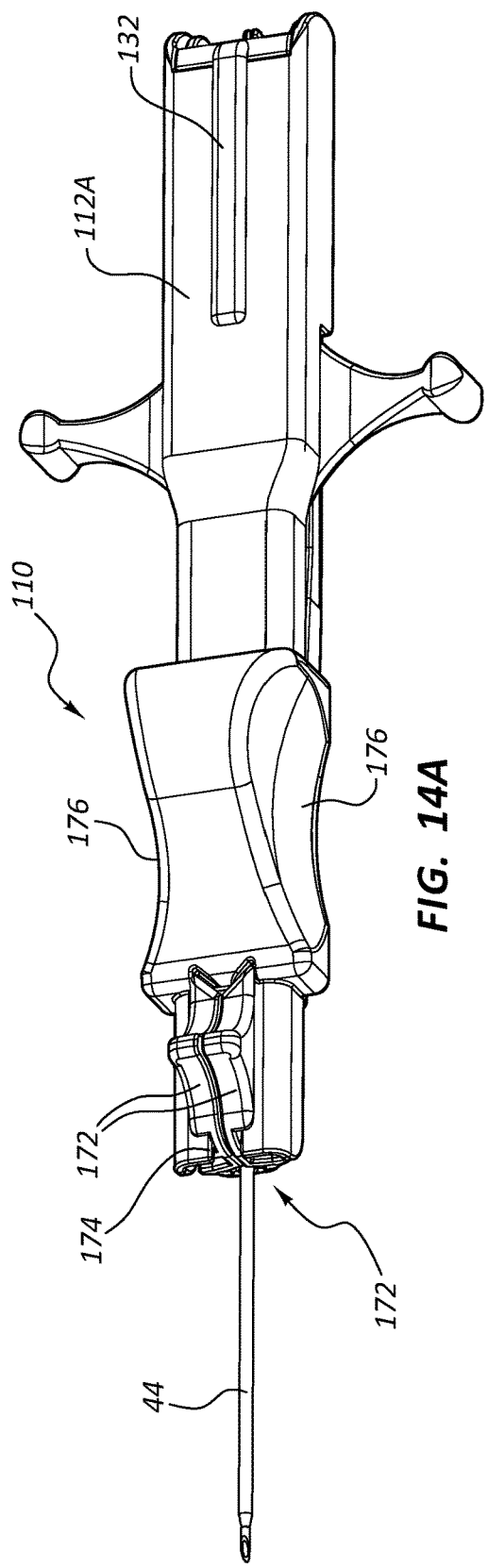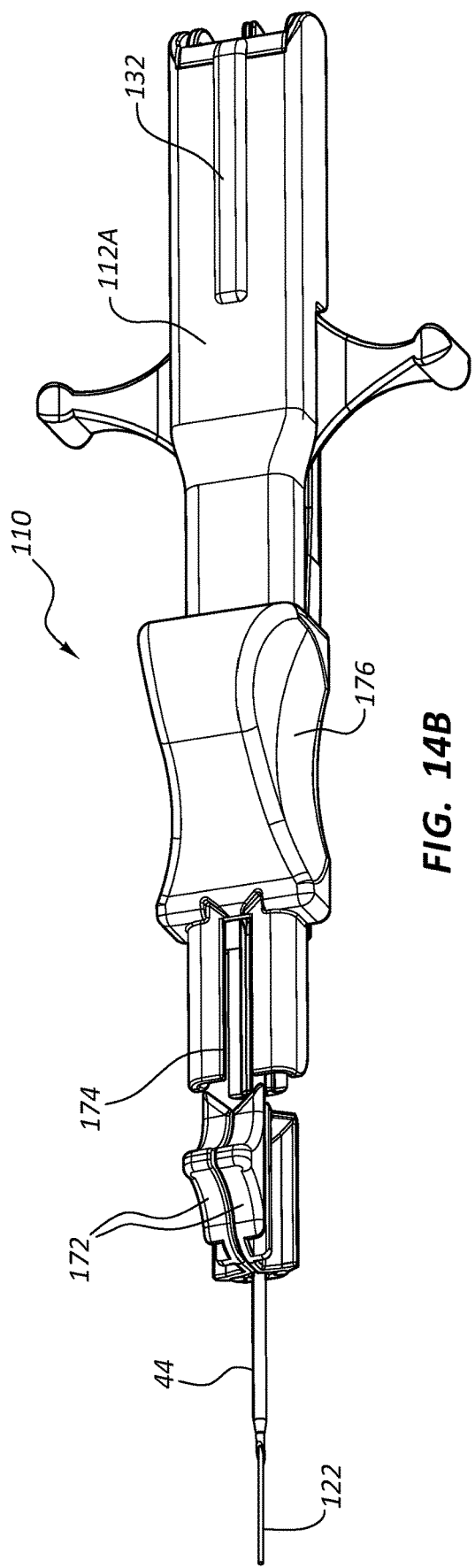
FIG. 14A
FIG. 14B

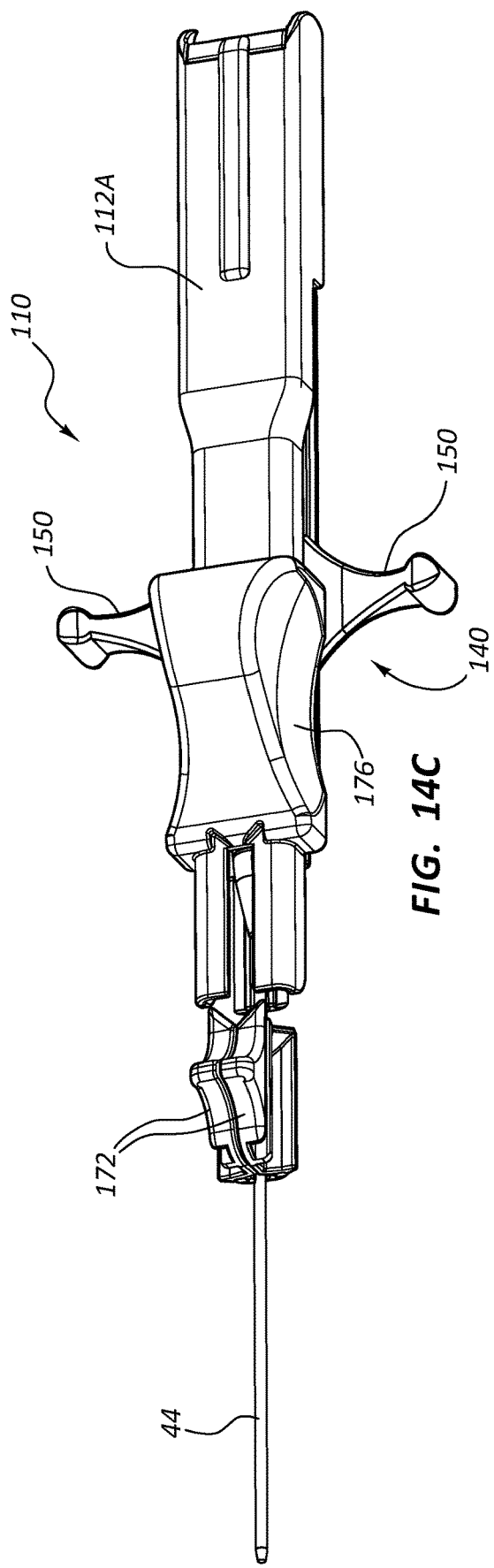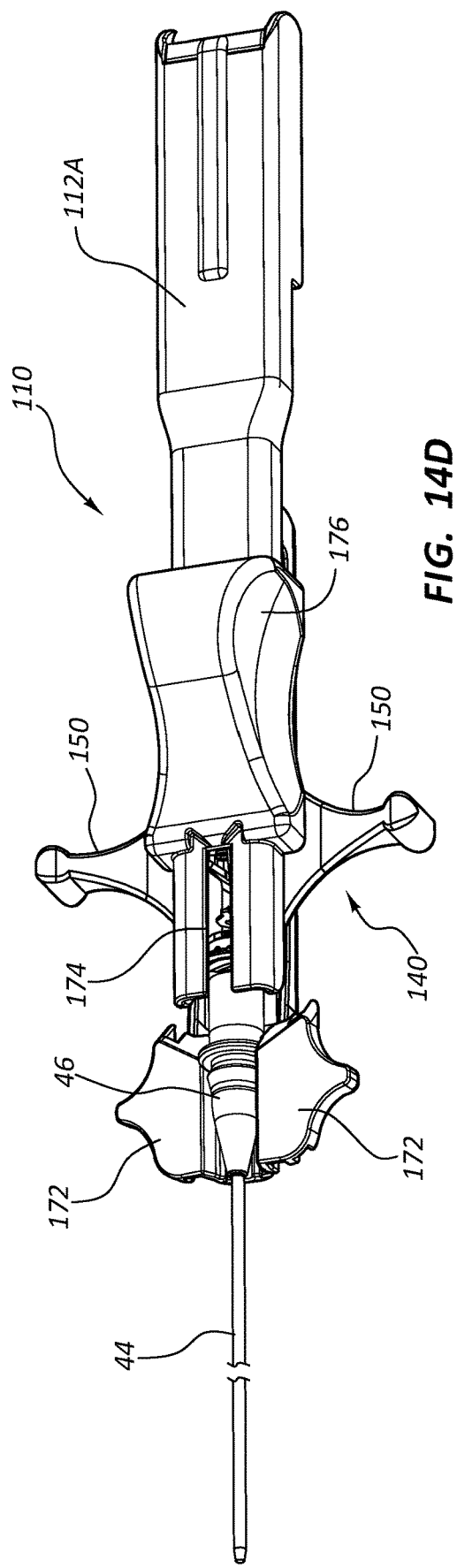

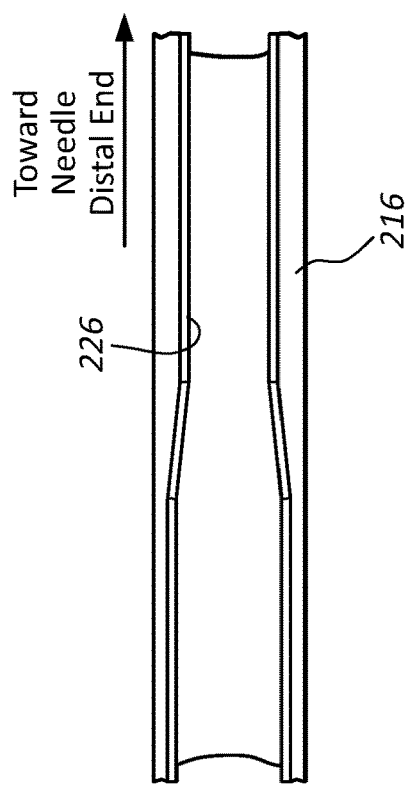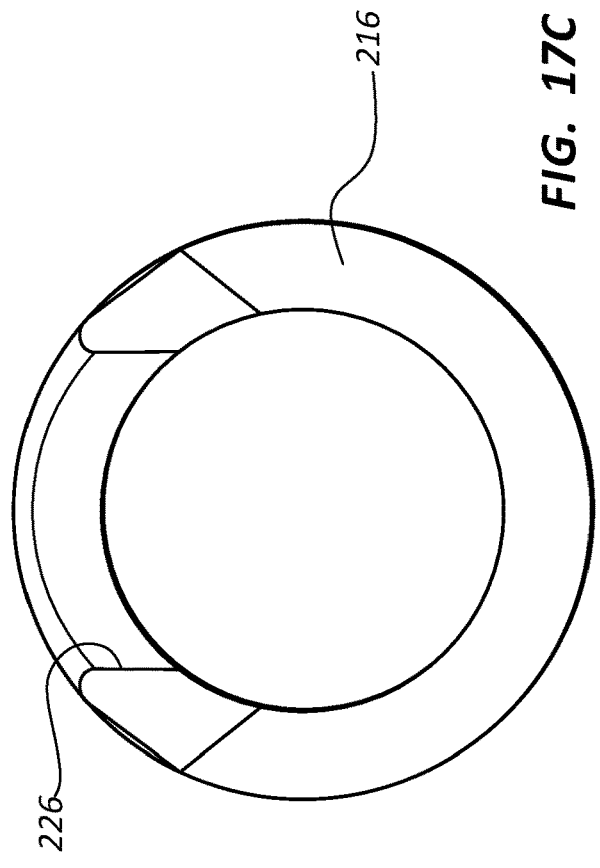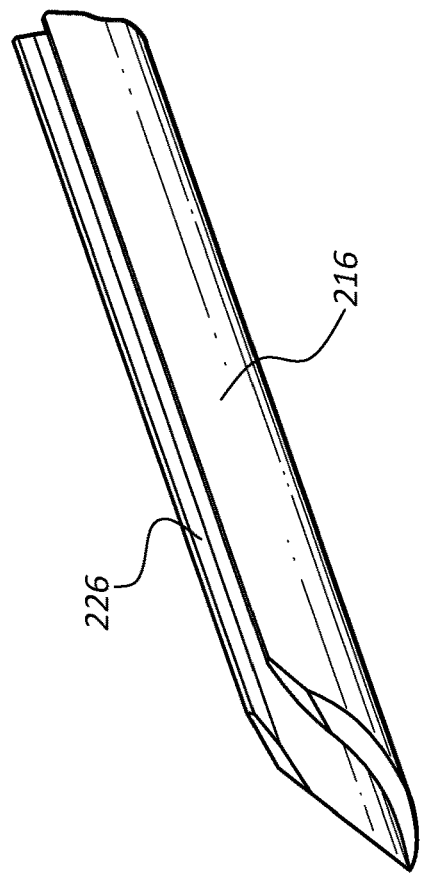
FIG. 17A
FIG. 17B
FIG. 17C

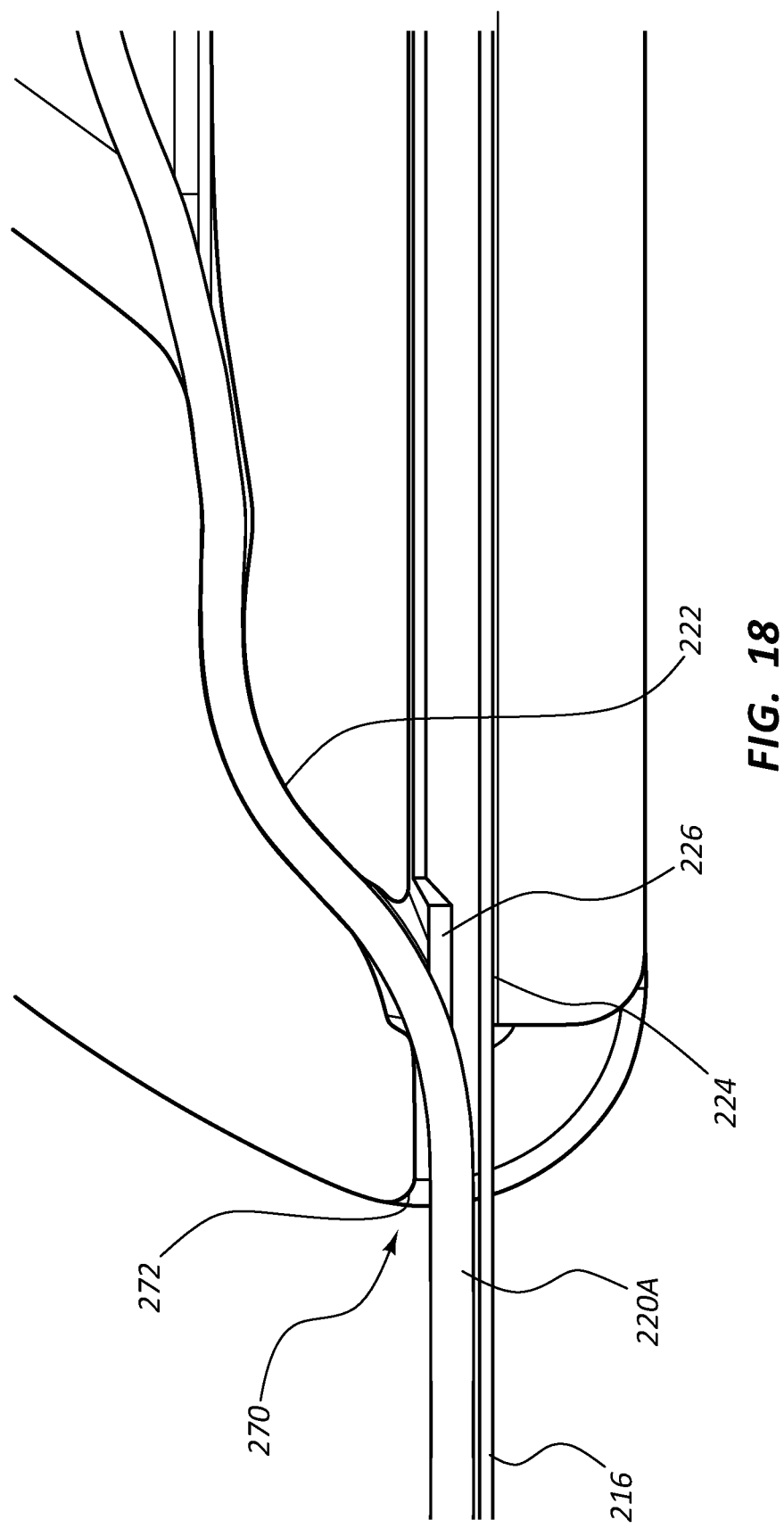

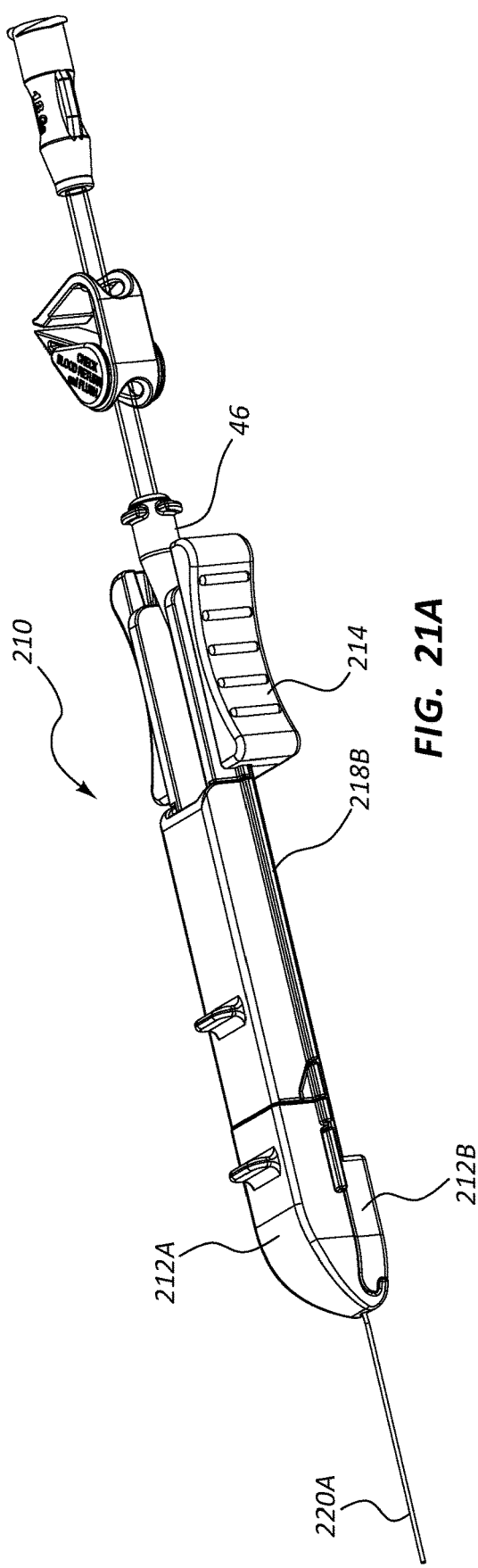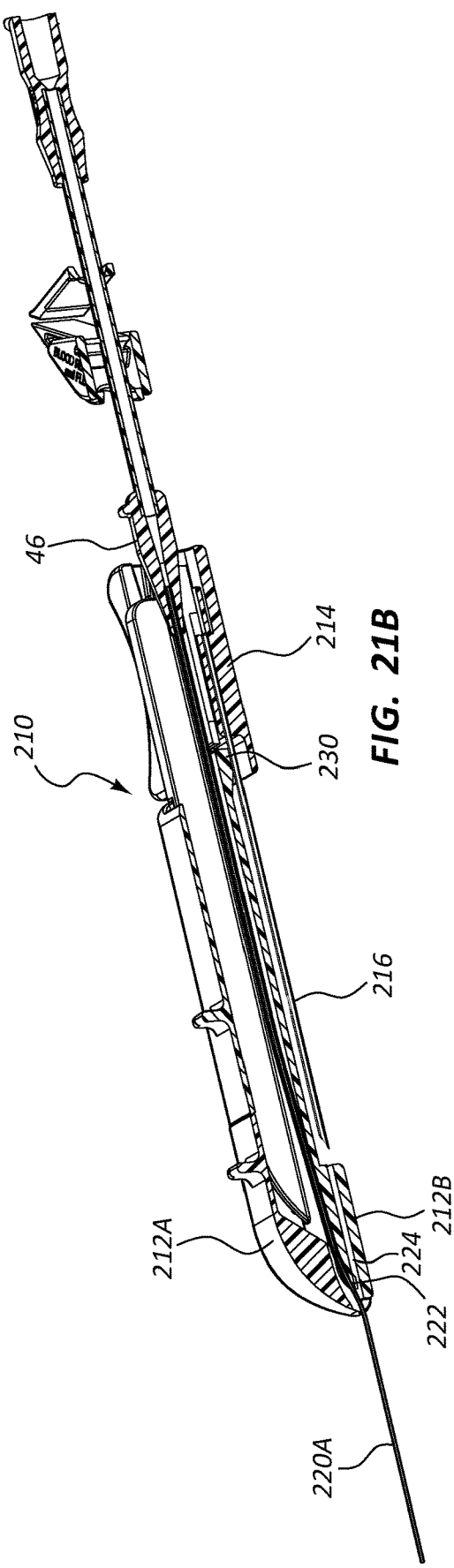

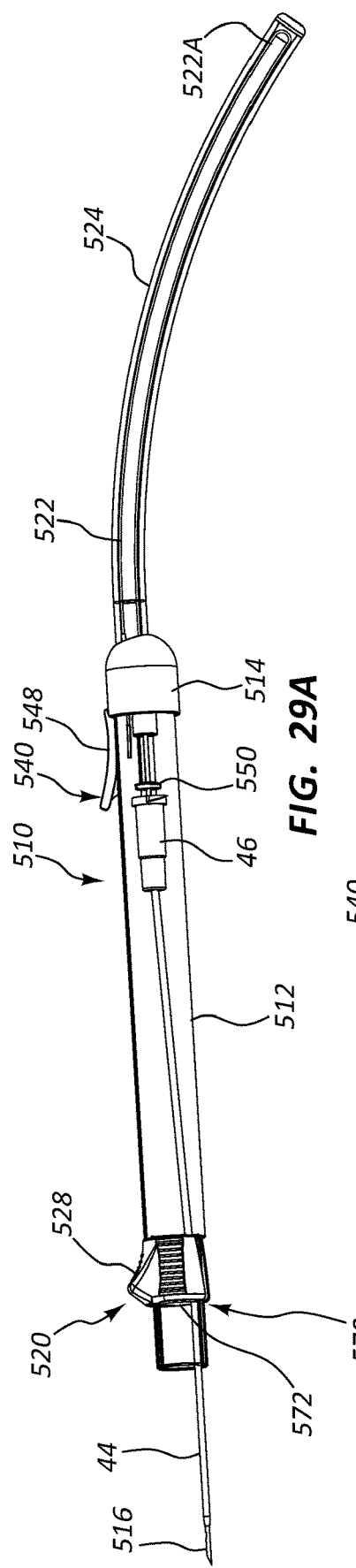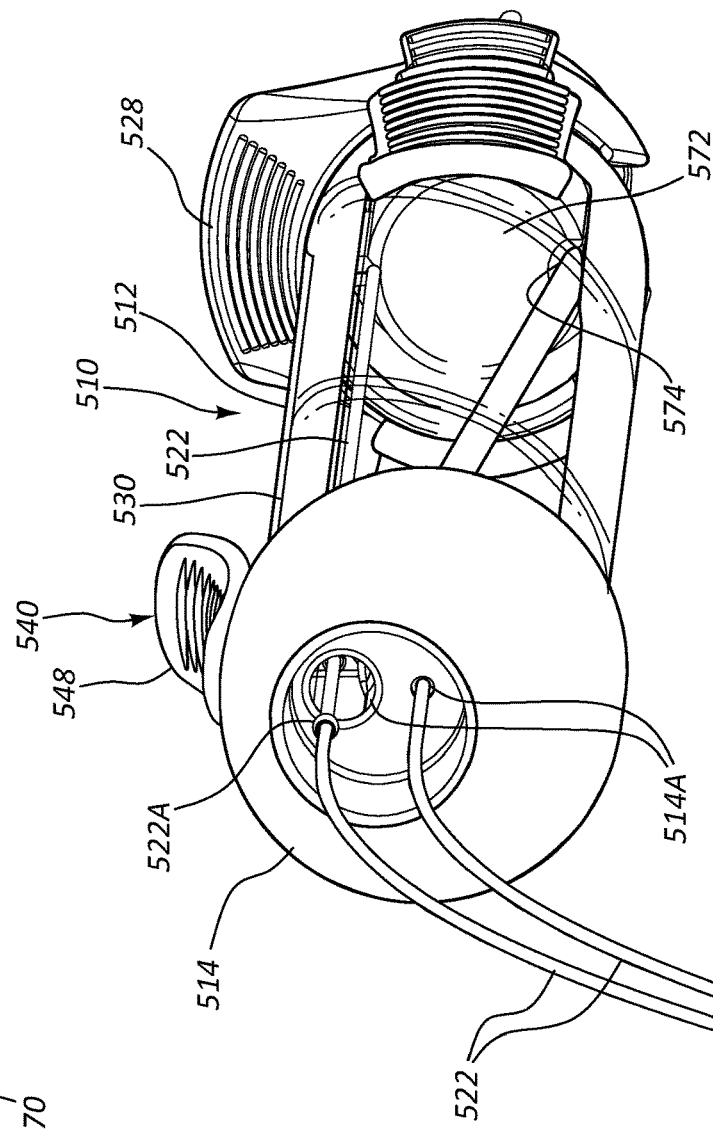

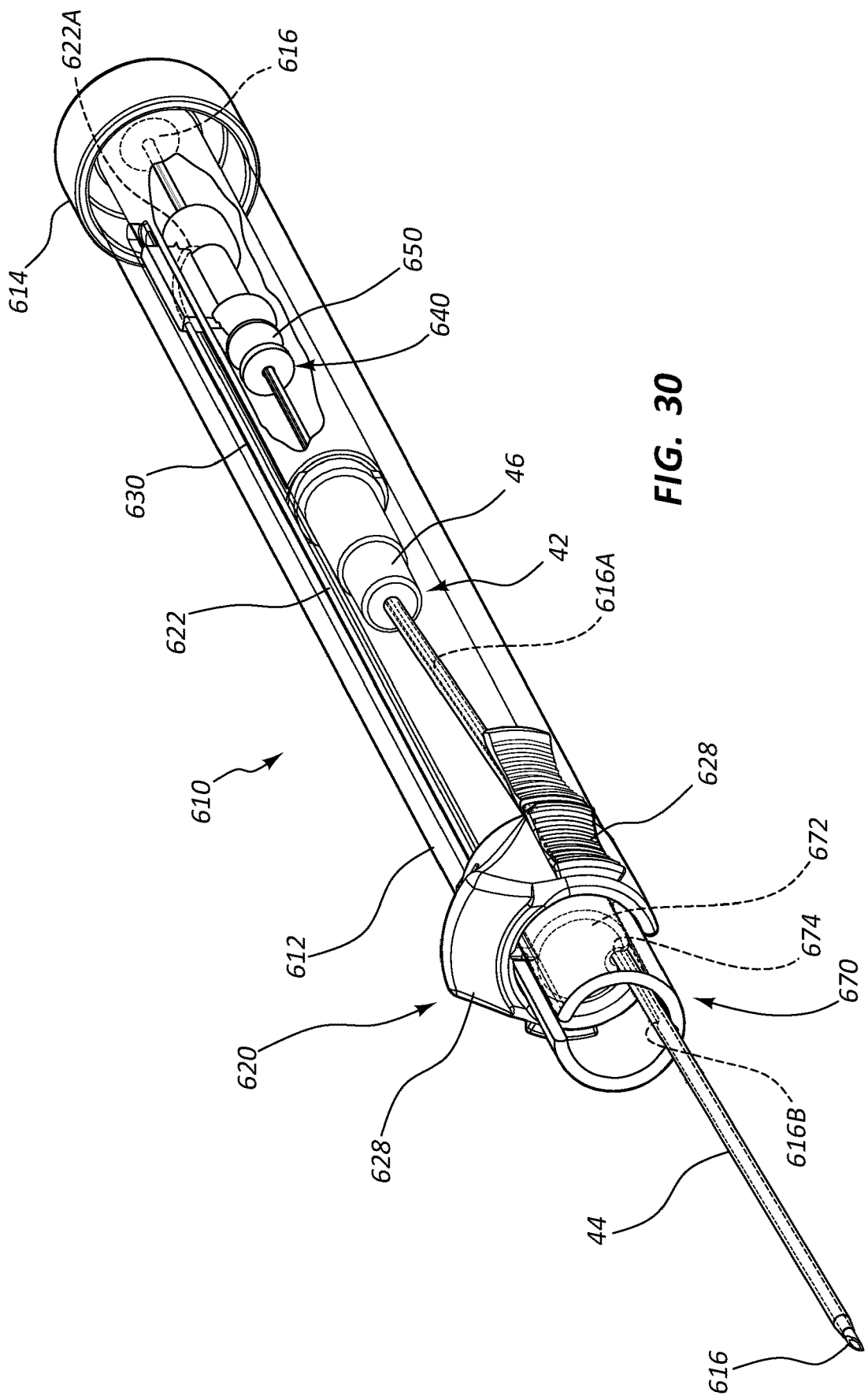

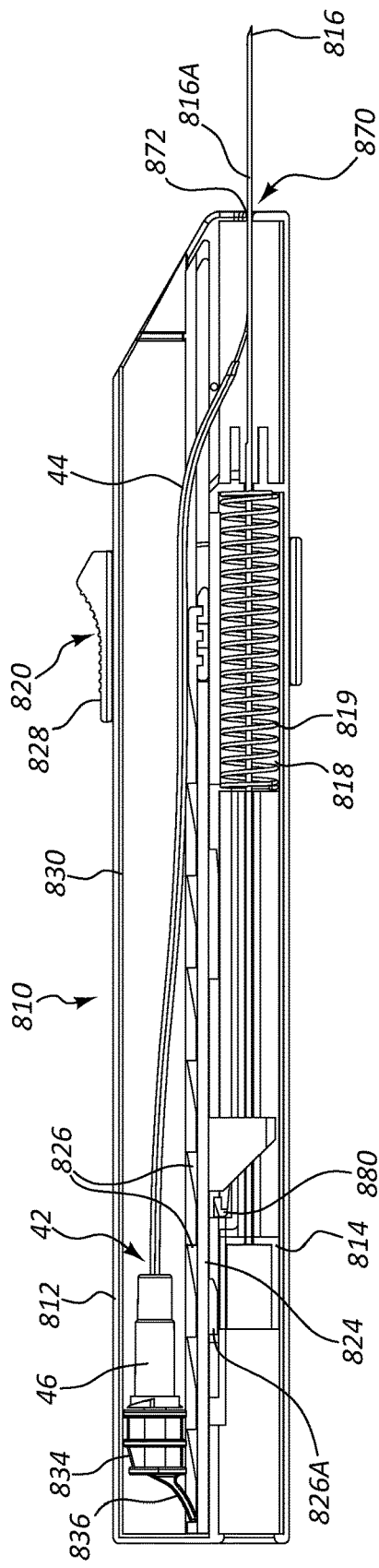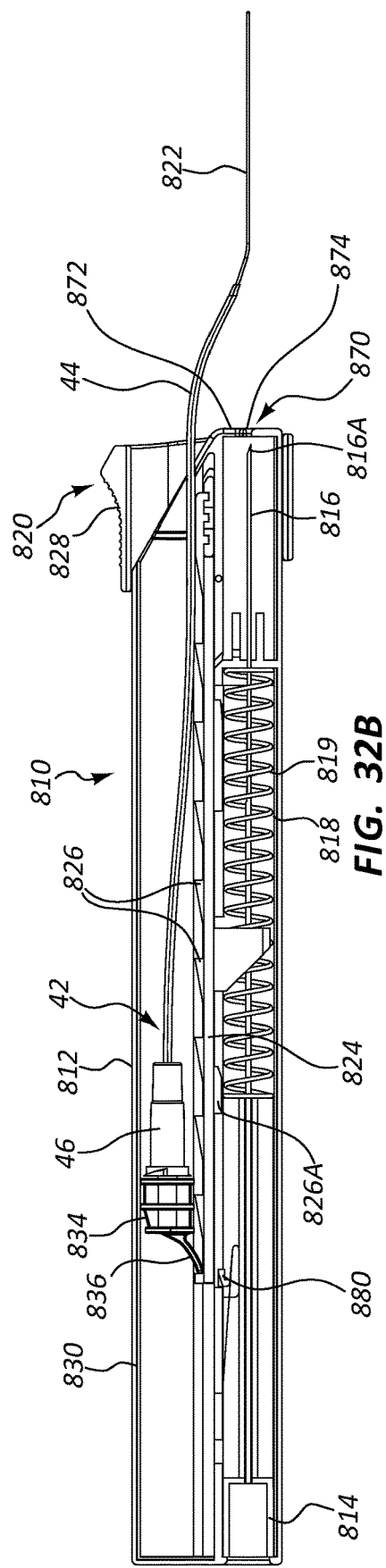
FIG. 32A
FIG. 32B

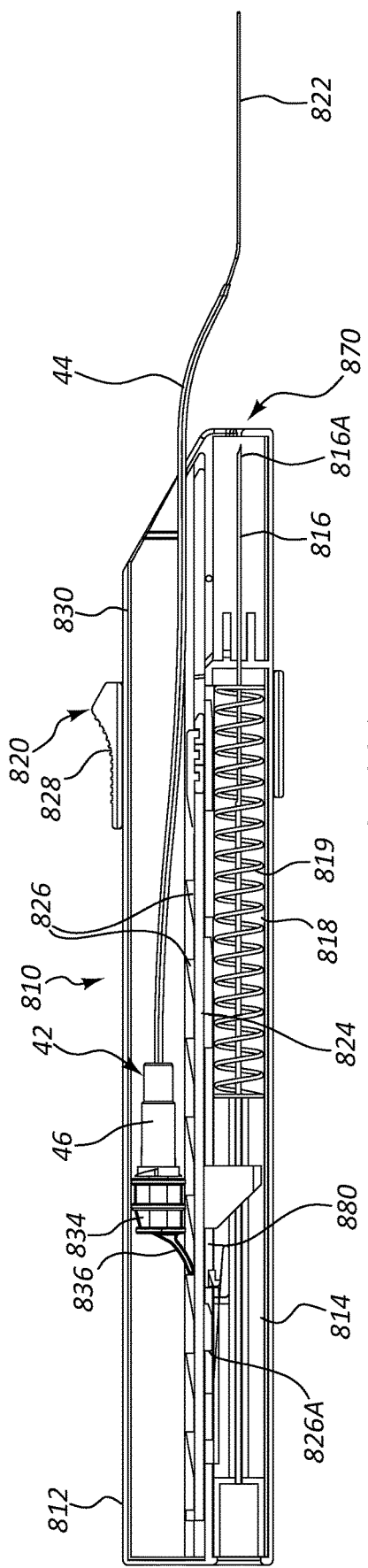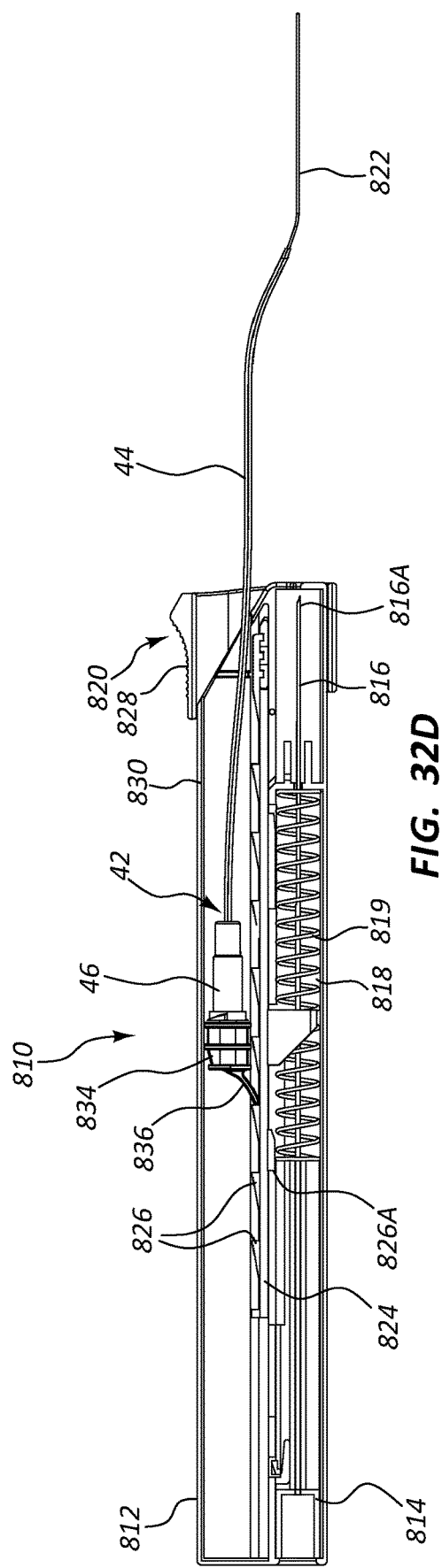

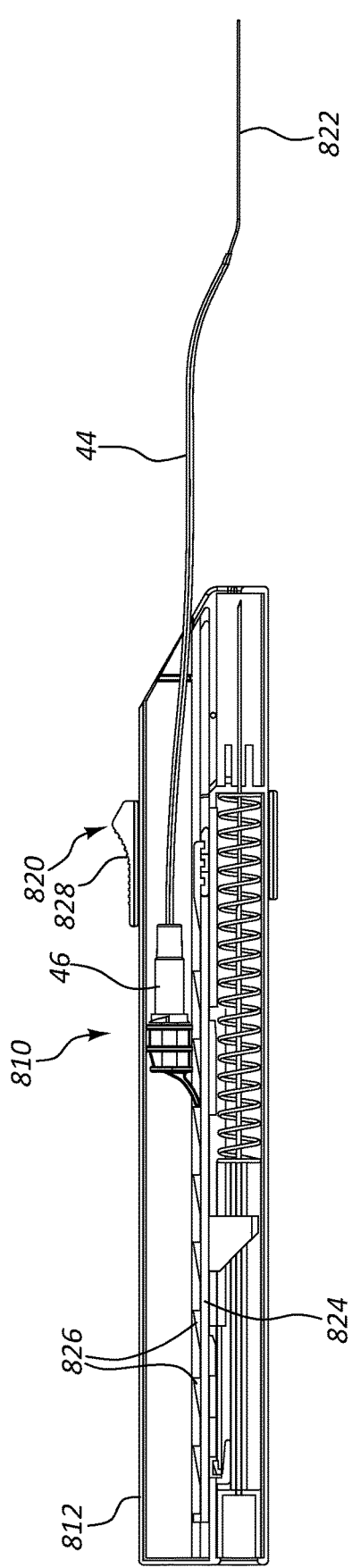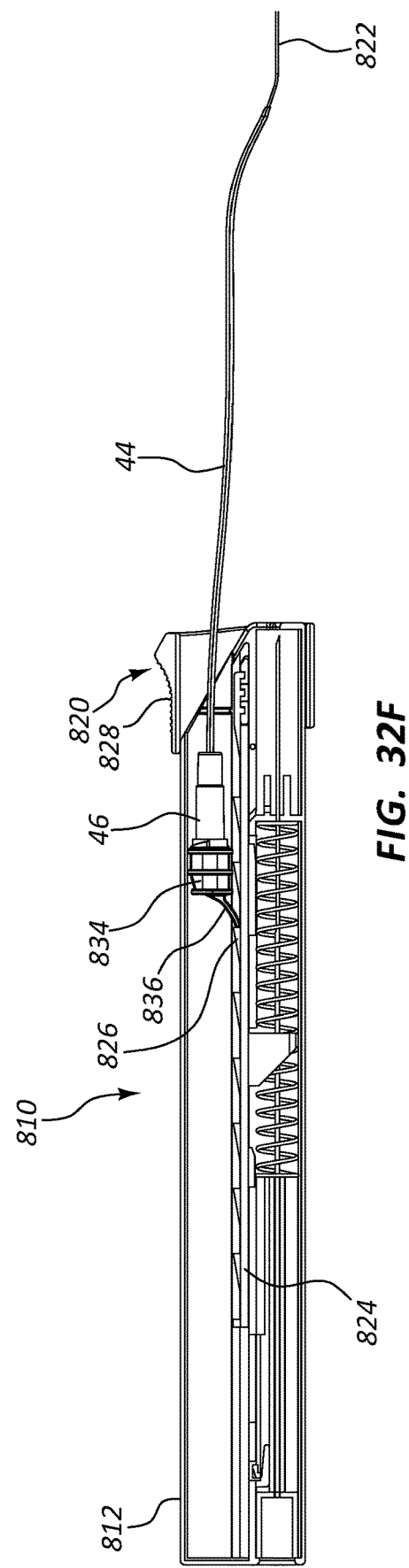

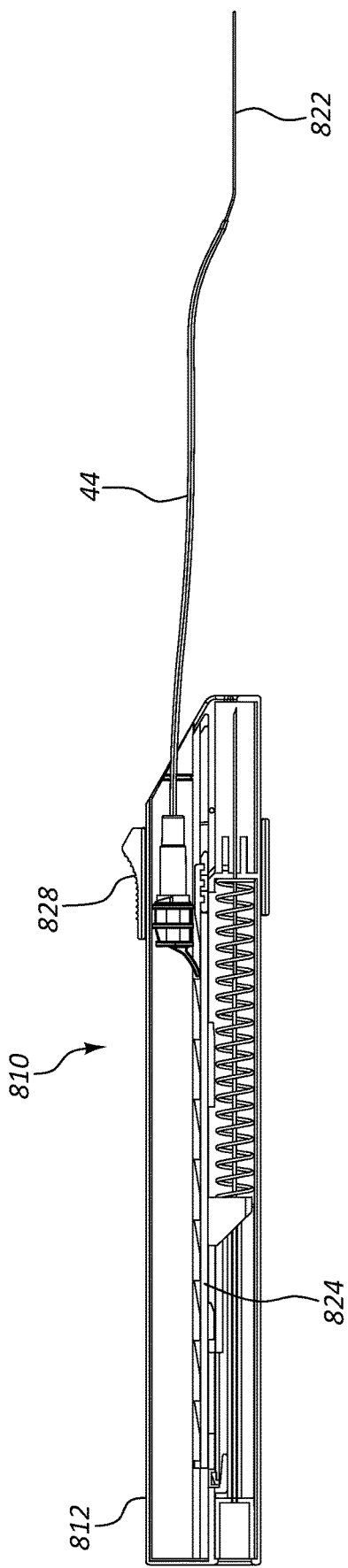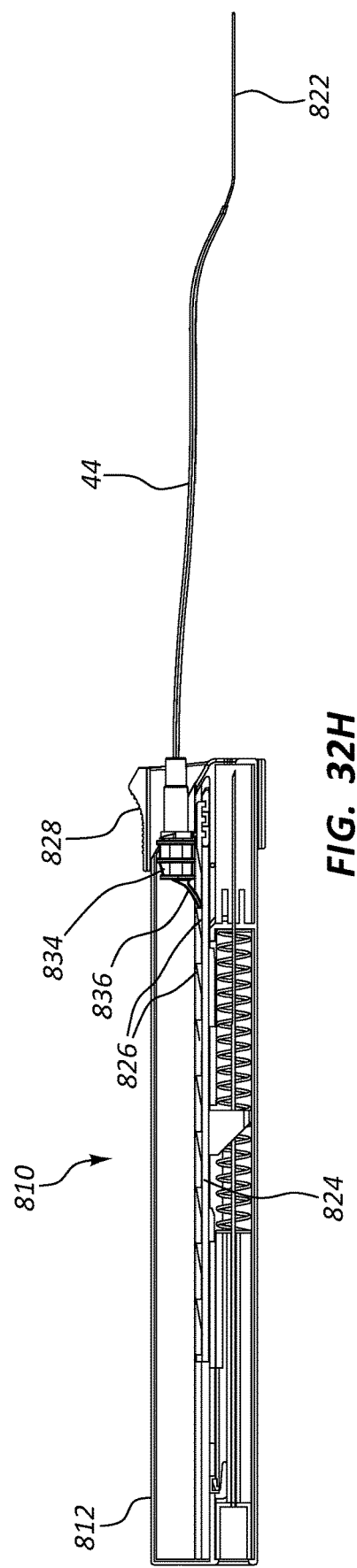
FIG. 32G
FIG. 32H

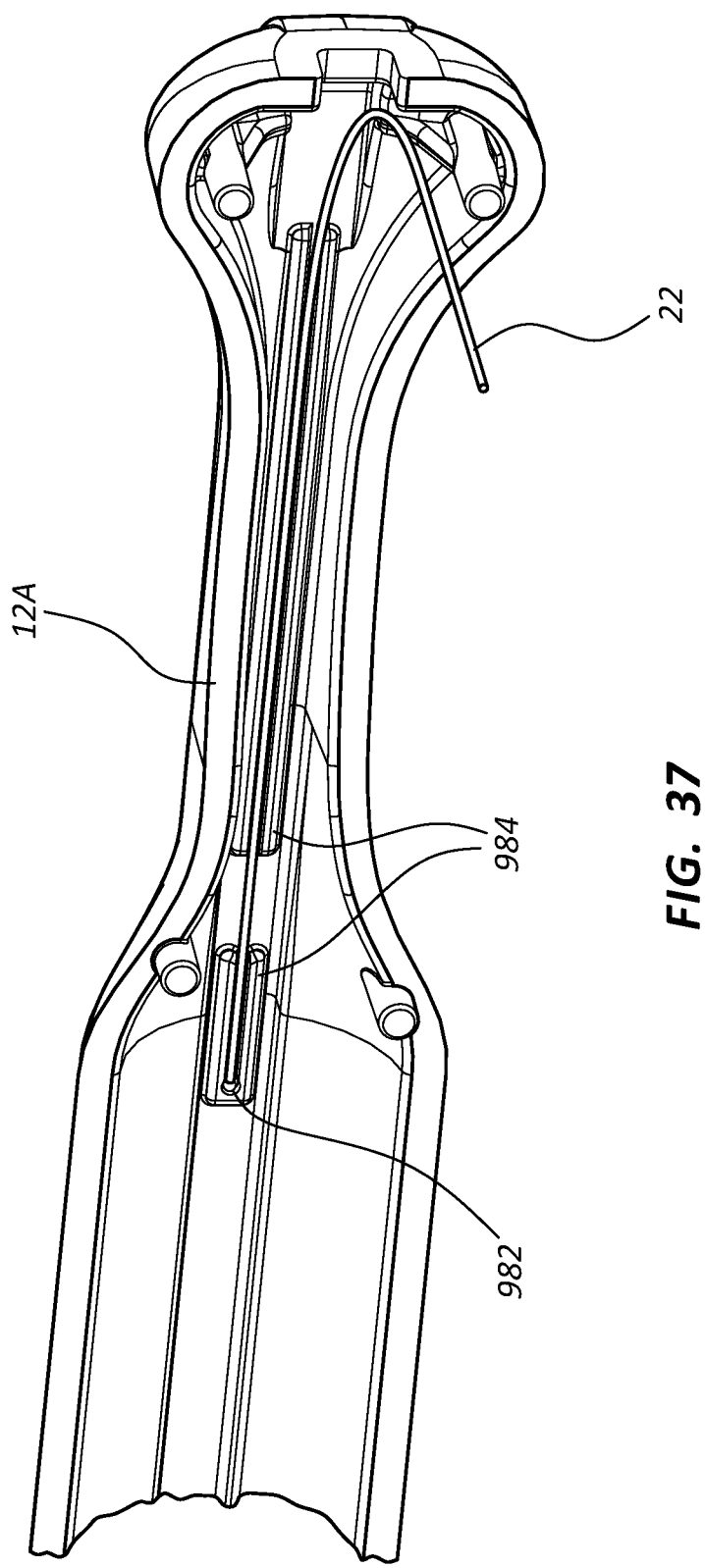

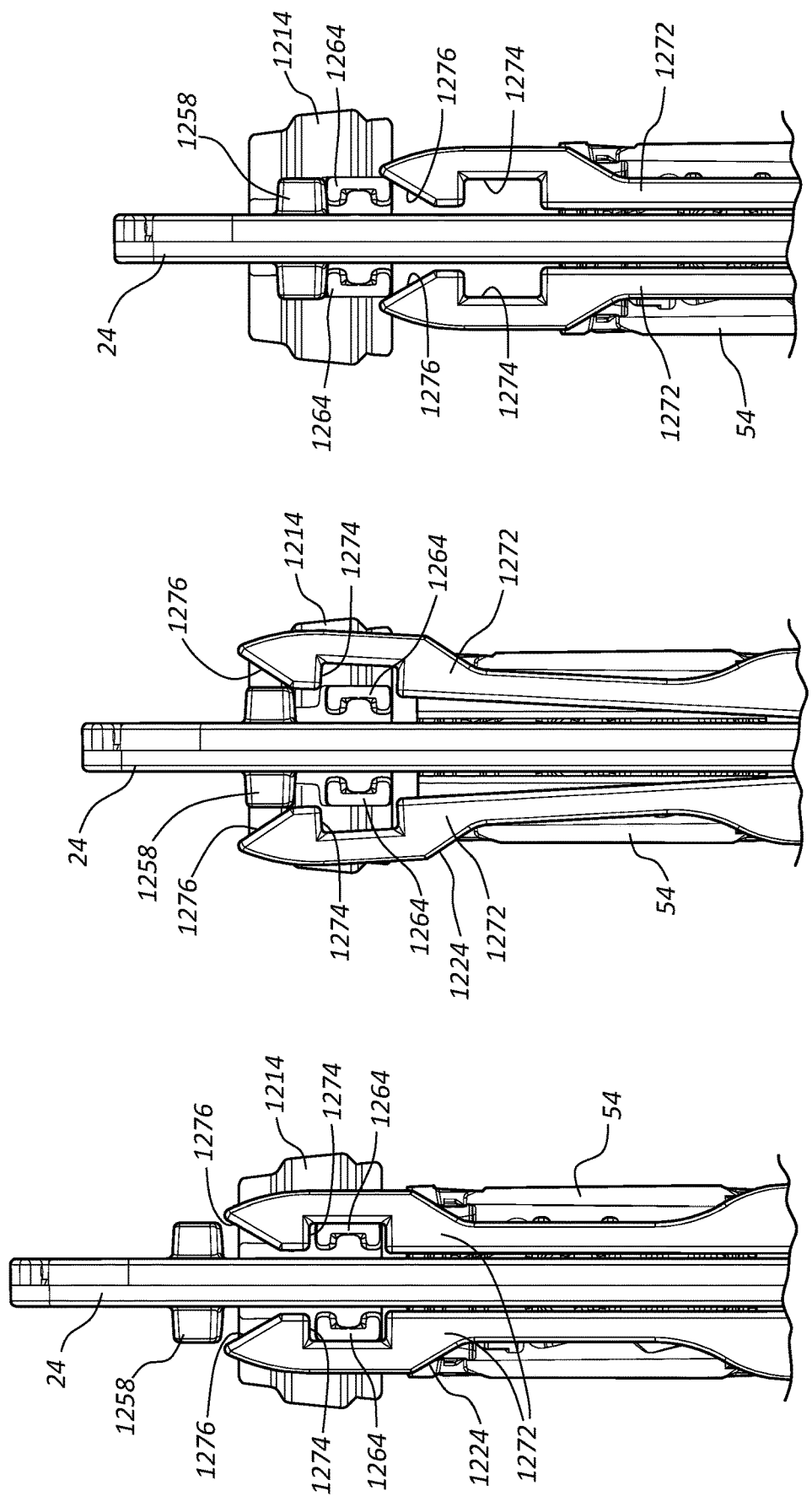

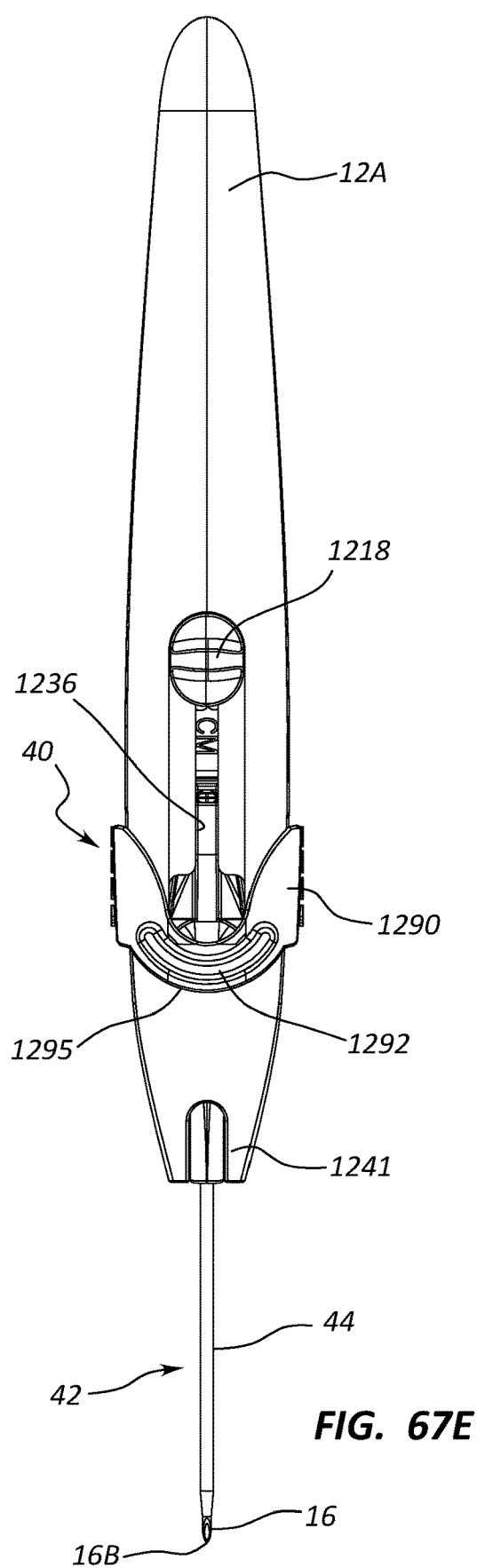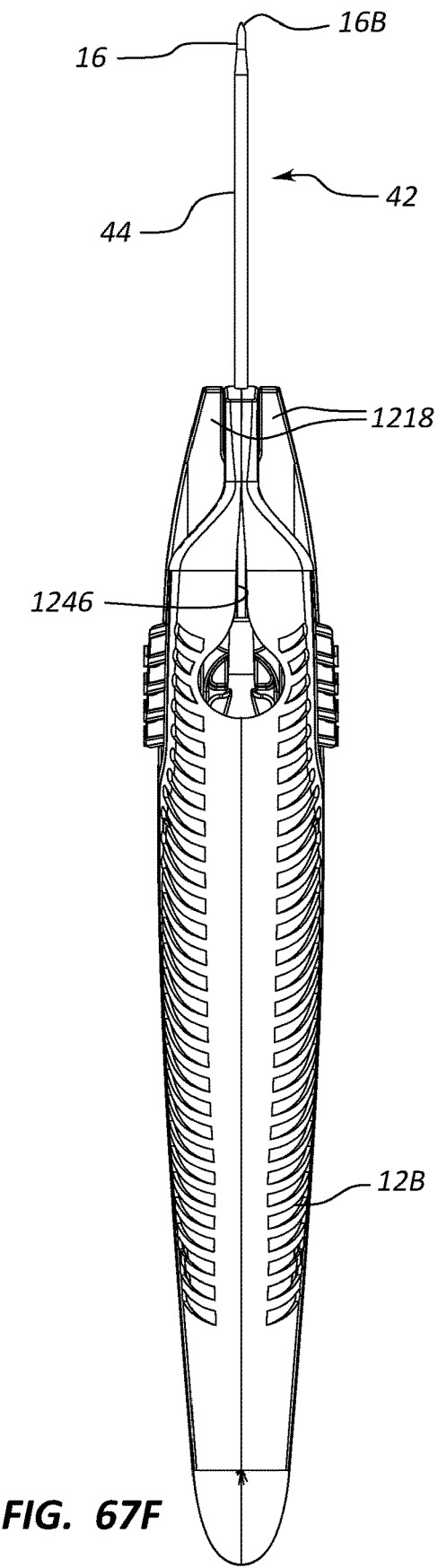
*FIG. 67E*
*FIG. 67F*

CATHETER INSERTION DEVICE INCLUDING TOP-MOUNTED ADVANCEMENT COMPONENTS

PRIORITY

This application is a division of U.S. patent application Ser. No. 16/529,622, filed Aug. 1, 2019, now U.S. Pat. No. 11,135,406, which is a division of U.S. patent application Ser. No. 15/154,808, filed May 13, 2016, now U.S. Pat. No. 10,384,039, which claims the benefit of U.S. Provisional Patent Application No. 62/162,580, filed May 15, 2015, and which is a continuation-in-part of U.S. patent application Ser. No. 14/702,580, filed May 1, 2015, now U.S. Pat. No. 9,950,139, which claims the benefit of U.S. Provisional Application No. 61/988,114, filed May 2, 2014, and which is a continuation-in-part of U.S. patent application Ser. No. 14/099,050, filed Dec. 6, 2013, now U.S. Pat. No. 9,872,971, which claims the benefit of U.S. Provisional Application No. 61/771,703, filed Mar. 1, 2013, and which is a continuation-in-part of U.S. patent application Ser. No. 13/107,781, filed May 13, 2011, now U.S. Pat. No. 8,932,258, which claims the benefit of U.S. Provisional Application Nos.: (1) 61/345,005, filed May 14, 2010; (2) 61/345,022, filed May 14, 2010; (3) 61/372,050, filed Aug. 9, 2010; (4) 61/385,844, filed Sep. 23, 2010; and (5) 61/415,248, filed Nov. 18, 2010. Each of the aforementioned applications is incorporated herein by reference in its entirety.

BRIEF SUMMARY

Briefly summarized, embodiments of the present invention are directed to an insertion tool for inserting a catheter or other tubular medical device into a body of a patient. The insertion tool in one embodiment unifies needle insertion, guidewire advancement, and catheter insertion in a single device to provide for a simple catheter placement procedure.

In one embodiment, the insertion tool comprises a housing in which at least a portion of the catheter is initially disposed, a hollow needle distally extending from the housing with at least a portion of the catheter pre-disposed over the needle, and a guidewire pre-disposed within the needle. An advancement assembly is also included for selectively advancing the guidewire distally past a distal end of the needle in preparation for distal advancement of the catheter. In one embodiment a catheter advancement assembly is also included for selectively advancing the catheter into the patient. Each advancement assembly can include a slide or other actuator that enables a user to selectively advance the desired component.

In one embodiment the catheter advancement assembly further includes a handle that is initially and removably attached to a hub of the catheter within the housing. Distal movement of handle by a user in turn distally moves the catheter distally from the housing. The handle can include a needle safety component for isolating a distal tip of the needle when the needle is removed from the catheter and the distal tip received into the handle. In addition, various guidewire and catheter advancement assemblies are disclosed herein.

In yet another embodiment, various features are included with the insertion tool, including: actuation of the guidewire and catheter advancement assemblies without moving the hand of the user that grasps the insertion tool during the catheter insertion procedure; selective advancement of one of the guidewire or catheter based upon previous advancement of the other; and guidewire blunting features.

In another embodiment the guidewire and catheter advancement assemblies each include user engagement components that are configured such that the user can begin to advance the second user component after advancing the first user engagement component without substantially repositioning the thumb or finger used by the user for advancement.

In yet another embodiment, the catheter advancement assembly includes a handle assembly with first and second wings. A cover portion extends between the first and second wings and is positioned such that advancement of the guidewire advancement assembly and the catheter advancement assembly can be accomplished by a single thumb or finger of the user.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 1A and 1B are various views of a catheter insertion device according to one embodiment;

FIGS. 4A and 4B show various views of one stage of use of the catheter insertion tool of FIGS. 1A and 1B according to one embodiment;

FIGS. 5A and 5B show various views of one stage of use of the catheter insertion tool of FIGS. 1A and 1B according to one embodiment;

FIGS. 6A and 6B show various views of one stage of use of the catheter insertion tool of FIGS. 1A and 1B according to one embodiment;

FIGS. 7A and 7B show various views of one stage of use of the catheter insertion tool of FIGS. 1A and 1B according to one embodiment;

FIGS. 10A-10C shows various views of a needle safety component and environment for a catheter insertion tool, according to one embodiment;

FIGS. 11A-11D are various views of a catheter insertion device according to one embodiment;

FIGS. 13A and 13B are various views of a portion of the catheter insertion device of FIGS. 11A-11D;

FIGS. 14A-14F show various stages of use of the catheter insertion tool of FIGS. 11A-11D according to one embodiment;

FIGS. 17A-17C are various views of a slotted needle for use with the catheter insertion device of FIGS. 15A and 15B according to one embodiment;

FIG. 18 is a cross sectional side view of a portion of the catheter insertion device of FIGS. 15A and 15B;

FIGS. 21A and 21B show one stage of use of the catheter insertion tool of FIGS. and 15B according to one embodiment;

FIGS. 29A and 29B are various views of a catheter insertion tool according to one embodiment;

FIG. 30 is a perspective view of a catheter insertion tool according to one embodiment;

FIGS. 32A-32I are various views of a configuration of a catheter insertion tool during use, according to one embodiment;

FIG. 37 is a perspective view of a proximal portion of the top housing portion of the catheter insertion device of FIG. 34;

FIGS. 56A-56C are various views of a portion of a catheter advancement assembly of the insertion tool of FIGS. 48A-48F;

FIGS. 67A-67F are various views of a catheter insertion tool according to one embodiment;

DETAILED DESCRIPTION

Figure 2A:
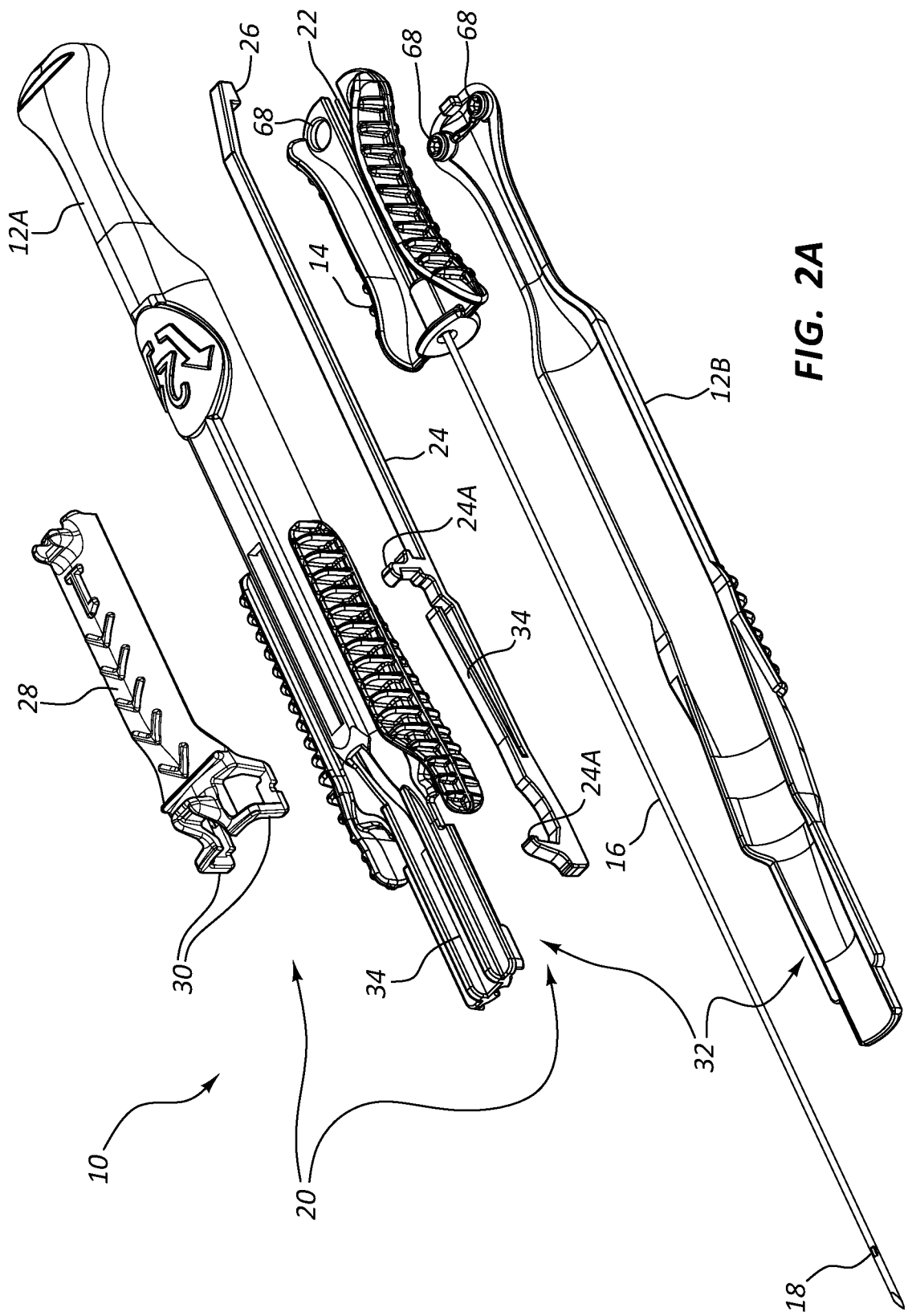
FIGS. 2A and 2B are various exploded views of the catheter insertion device of FIGS. 1A and 1B.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a tool for assisting with the placement into a patient of a catheter or other tubular medical device. For example, catheters of various lengths are typically placed into a body of a patient so as to establish access to the patient's vasculature and enable the infusion of medicaments or aspiration of body fluids. The catheter insertion tool to be described herein facilitates such catheter placement. Note that, while the discussion below focuses on the placement of catheters of a particular type and relatively short length, catheters of a variety of types, sizes, and lengths can be inserted via the present device, including peripheral IV's intermediate or extended-dwell catheters, PICC's, central venous catheters, etc. In one embodiment, catheters having a length between about 2.5 inches and about 4.5 inches can be placed, though many other lengths are also possible. In another embodiment a catheter having a length of about 3.25 inches can be placed.

Reference is first made to FIGS. 1A-1B and 2A-2B, which depict various details regarding a catheter insertion tool ("insertion tool"), generally depicted at 10, according to one embodiment. As shown, the insertion tool 10 includes a housing 12 that in turn includes a top housing portion 12A separably mated with a bottom housing portion 12B. A needle hub 14 supporting a hollow needle 16 is interposed between the housing portions 12A and 12B. The needle 16 extends distally from the needle hub 14 so as to extend through the body of the insertion tool 10 and out a distal end of the housing 12. In another embodiment, the needle is at least partially hollow while still enabling the functionality described herein.

A notch 18 is defined through the wall of the needle 16 proximate the distal end thereof. The notch 18 enables flashback of blood to exit the lumen defined by the hollow needle 16 once access to the patient's vasculature is achieved during catheter insertion procedures. Thus, blood exiting the notch 18 can be viewed by a clinician to confirm proper needle placement in the vasculature, as will be explained further below.

The insertion tool 10 further includes a guidewire advancement assembly 20 for advancing a guidewire 22 through the needle 16 and into the vasculature of the patient once access by the needle has been achieved. The guidewire 22 is pre-disposed within the lumen of the needle 16, with a proximal end of the guidewire positioned proximate the proximal end of the needle hub 14, as best seen in FIGS. 1B and 2A. The guidewire advancement assembly 20 includes a guidewire lever 24 that selectively advances the guidewire in a distal direction during use of the insertion tool 10 such that the distal portion of the guidewire extends beyond the distal end of the needle 16. The guidewire lever 24 includes a lever tab 26 that engages the proximal end of the guidewire 22 so to push the guidewire through the lumen of the needle 16.

The guidewire advancement assembly 20 further includes a slide 28 that is slidably attached to the top housing portion 12A. Two tabs 24A of the guidewire lever 24 operably attach to the slide 28 so that selective movement by a user of the slide results in corresponding movement of the lever 24, and by extension, the guidewire 22. Engagement of the lever tabs 24A to the slide 28 also maintains attachment of the slide to the housing 12. Of course, other engagement schemes to translate user input to guidewire movement could also be employed. Suitable tracks are included in the top housing portion 12A to enable sliding movement of the slide 28 and the lever 24, including a track 34 extending to the distal end of the housing 12.

Figure 3A:
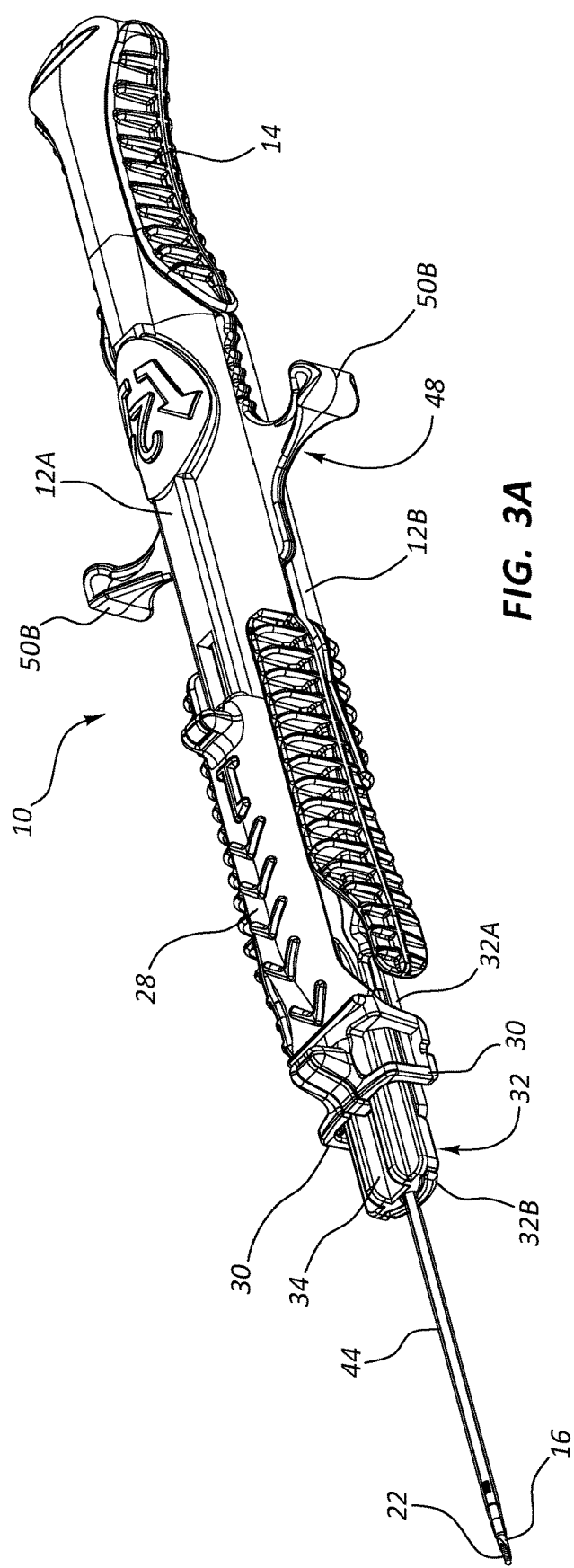
FIGS. 3A and 3B show various views of one stage of use of the catheter insertion tool of FIGS. 1A and 1B according to one embodiment.
Figure 3B:
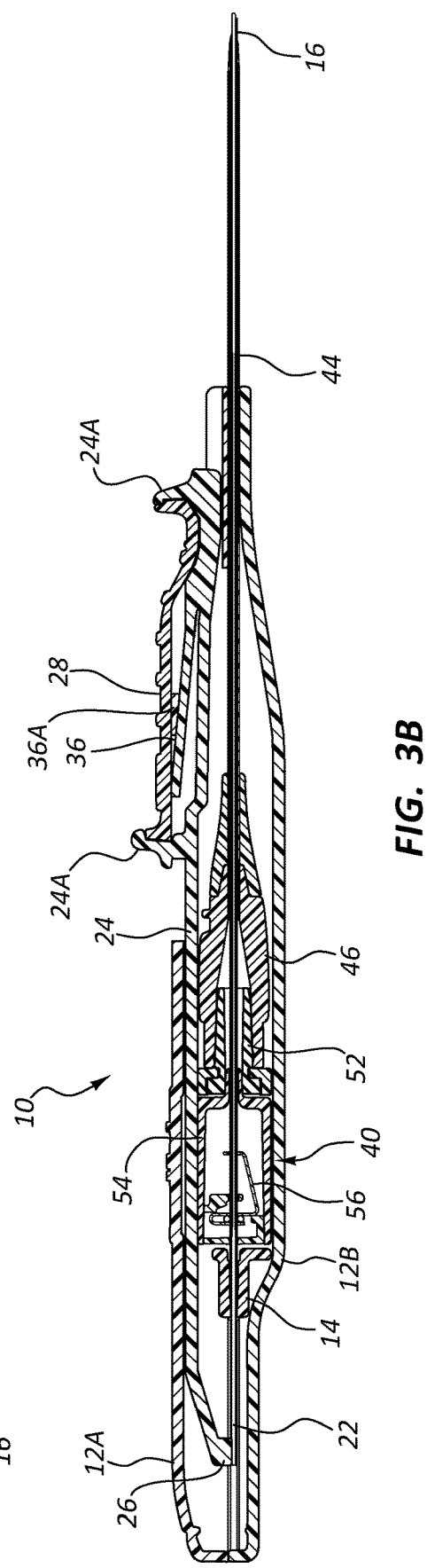

The slide 28 includes two arms 30 that wrap partially about rails 32 defined by the housing 12. In particular, during initial distal advancement of the slide 28, the arms 30 slide on a bottom housing rail 32A, best seen in FIG. 5B. During further distal advancement of the slide 28, the arms 30 slide past the bottom housing rail 32A and on to a top housing rail 32B, best seen in FIGS. 2A and 3A. With the arms 30 of the slide 28 no longer engaged with the bottom housing rail 32A, the two housing portions 12A and 12B are able to separate, as will be described further below.

The guidewire lever 24 includes a locking arm 36 resiliently disposed so as to spring up and engage an extension 36A defined in the interior of the top housing portion 12A when the slide 28 has been fully slid distally. This prevents inadvertent retraction of the guidewire 22 once distally extended, which could otherwise cause unintended severing of a distal portion of the guidewire by the distal tip of the needle 16 during insertion procedures. Note that engagement of the locking arm 36 with the extension 36A can provide tactile and/or audible feedback to the user in one embodiment so as to indicate full distal extension of the guidewire 22.

The insertion tool 10 further includes a catheter advancement assembly 40 for selectively advancing in a distal direction a catheter 42, pre-disposed in the housing 12, and including a catheter tube 44 and a hub 46 at a proximal end thereof. As seen in FIGS. 1A and 1B, the catheter 42 is partially and initially pre-disposed within a volume defined by the housing 12 such that the lumen of the catheter tube 44 is disposed over the needle 16, which in turn is disposed over the guidewire 22, as mentioned.

In particular, the catheter advancement assembly 40 includes a handle 48 that defines a base 48A and two arms 50 extending from the handle base. Each arm 50 defines a grip surface 50A, finger grabs 50B, and one of two teeth 50C. The grip surfaces 50A and finger grabs 50B enable the handle to be grasped or contacted by a user in order to selectively advance the catheter 42 in a distal direction during use of the insertion tool 10 to insert the catheter into the body of the patient. The teeth 50C engage corresponding raised surfaces on the hub 46 so as to removably connect the handle 48 to the catheter 42.

Figure 2B:
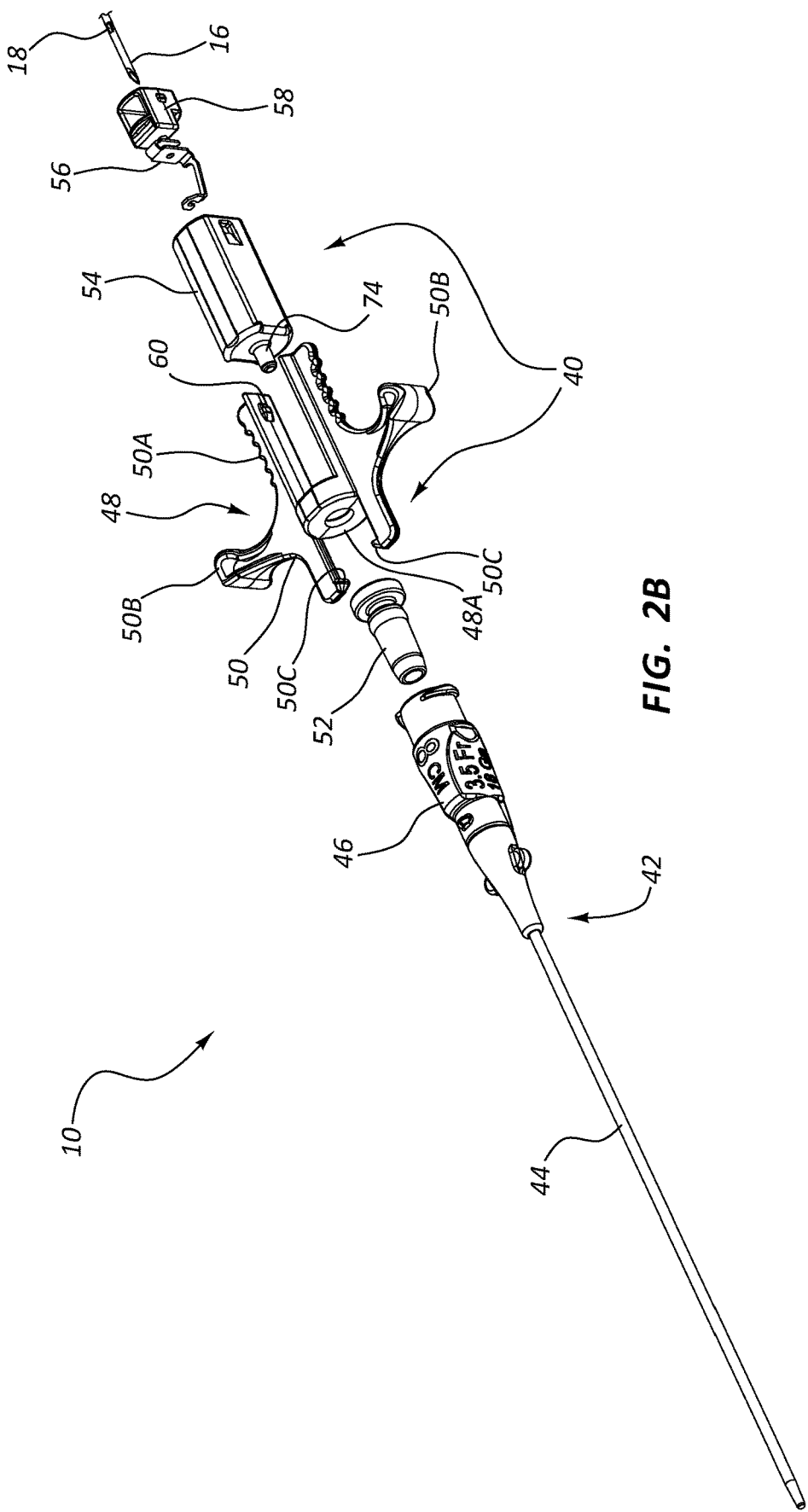

Additional components are included in relation to the handle 48 of the catheter advancement assembly 40. A plug, or valve 52, is interposed between the handle base 48A and the catheter hub 46 to prevent blood spillage when the catheter is first introduced into the patient vasculature. A safety housing 54, including a needle safety component 56 therein, is removably attached to the handle 48 between the arms 50. Specifically, protrusions 60 included on the inner surfaces of the handle arms 50 engage with corresponding recesses 62 (FIG. 10A) defined in the safety housing 54 to removably secure the safety housing to the handle 48. A cap 58 supports the needle safety component 56 and covers the end of the safety housing 54. As shown in FIG. 1B, the needle 16 initially extends through the aforementioned components in the order as shown in FIG. 2B. Further details regarding the operation of these components are given below.

Note that in one embodiment the outer diameters of the needle 16 and the catheter tube 44 are lubricated with silicone or other suitable lubricant to enhance sliding of the catheter tube with respect to the needle and for aiding in the insertion of the catheter into the body of the patient.

The insertion tool 10 further includes a support structure 70 for stabilizing the needle 16 proximate its point of exit from the housing 12. In the present embodiment, the support structure 70 includes an interface 72 of the top housing portion 12A and bottom housing 12B that is shaped to closely match the round shape of the needle 16 and catheter tube 44. The interface 72 stabilizes the needle 16 so as to prevent excessive "play" in the needle, thus improving user accuracy when initially accessing the vasculature of the patient.

As best seen in FIG. 2A, the top housing 12A, the needle hub 14, and the bottom housing 12B include engagement features 68 to maintain attachment of the proximal end of the housing 12 even when more distal portions of the housing are separated, discussed below. Note, however, that various types, sizes, and numbers of engagement features can be employed to achieve this desired functionality.

FIGS. 3A-9 depict various stages of use of the insertion tool 10 in placing the catheter 42 in the vasculature of a patient. For clarity, the various stages are depicted without actual insertion into a patient being shown. With the insertion tool 10 in the configuration shown in FIG. 1A, a user grasping the insertion tool 10 first guides the distal portion of the needle 16 through the skin at a suitable insertion site and accesses a subcutaneous vessel. Confirmation of proper vessel access having been achieved is evident via blood flash, i.e., the presence of blood between the outer diameter of the needle 16 and the inner diameter of the catheter tube 44 due to blood passing out the notch 18 from the hollow interior of the needle. Note that in one embodiment, the presence of blood in the safety housing 54, which in one embodiment is a translucent housing, can serve as a secondary blood flash indicator due to blood entering the housing from the needle 16 when the vessel is accessed.

After needle access to the vessel is confirmed, the guidewire advancement assembly 20 is actuated, wherein the slide 28 is advanced by the finger of the user to distally advance the guidewire 22 (FIGS. 3A and 3B), initially disposed within the hollow needle 16. Note that the guidewire is distally advanced by the lever 24, which is operably attached to the slide 28. Note also that during distal advancement of the slide 28, the slide arms 30 thereof travel along the rails 32 on either side of the housing 12: first the bottom housing rails 32A, then the top housing rails 32B.

Distal guidewire advancement continues until the slide 28 has been distally slid its full travel length, resulting in a predetermined length of the guidewire 22 extending past the distal end of the needle 16, as shown in FIGS. 4A and 4B. In one embodiment, further distal advancement of the slide 28 is prevented by contact of the lever tab 26 with a distal portion of the needle hub 14, as shown in FIG. 4B. FIGS. 5A and 5B show that, upon full distal advancement of the slide 28, the slide arms 30 thereof are no longer engaged with the bottom housing rails 32A, but rather with only the top housing rails 32B. This in turn enables the housing portions 12A and 12B to separate, as seen further below.

As seen in FIGS. 5A and 5B, once the guidewire 22 has been fully extended within the vessel of the patient (FIGS. 4A and 4B), the catheter advancement assembly 40 is actuated, wherein the handle 48 is distally advanced by the user to cause the catheter tube 44 to slide over distal portions of the needle 16 and guidewire 22 and into the patient's vasculature via the insertion site. FIGS. 6A and 6B show that, as the catheter is advanced via the handle 48, the housing portions 12A and 12B are easily separated so as to enable the catheter hub 46 to exit the distal end of the housing 12 and for the catheter to be inserted into the patient vasculature to a suitable degree.

Figure 8:
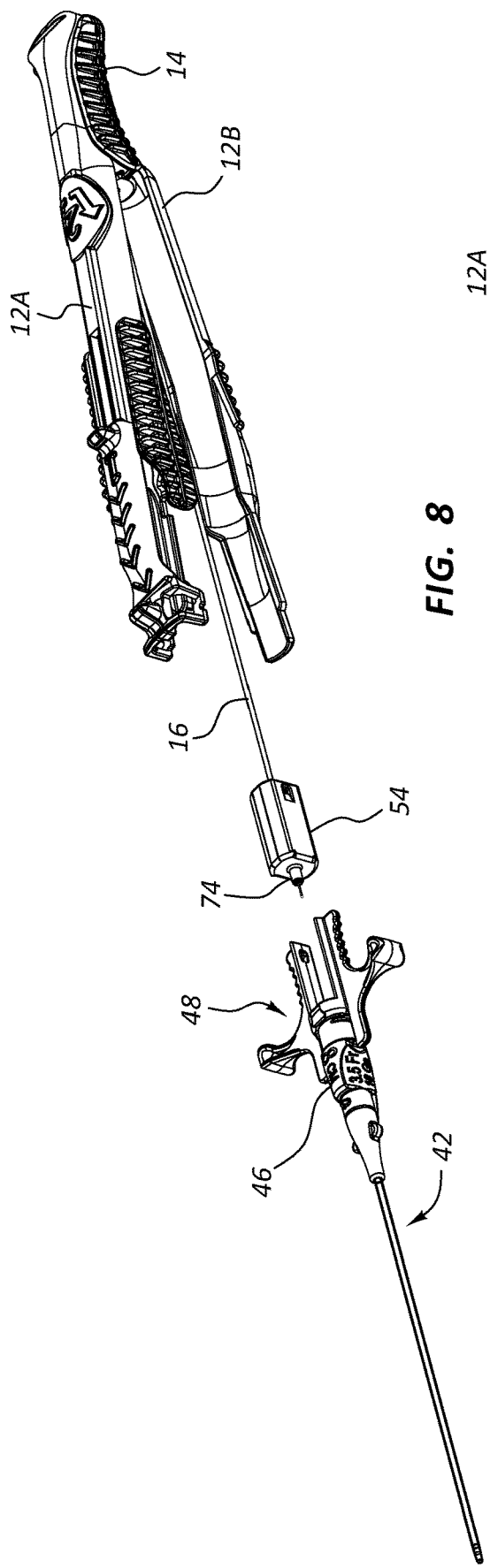
FIG. 8 shows one stage of use of the catheter insertion tool of FIGS. 1A and 1B according to one embodiment.
Figure 9:
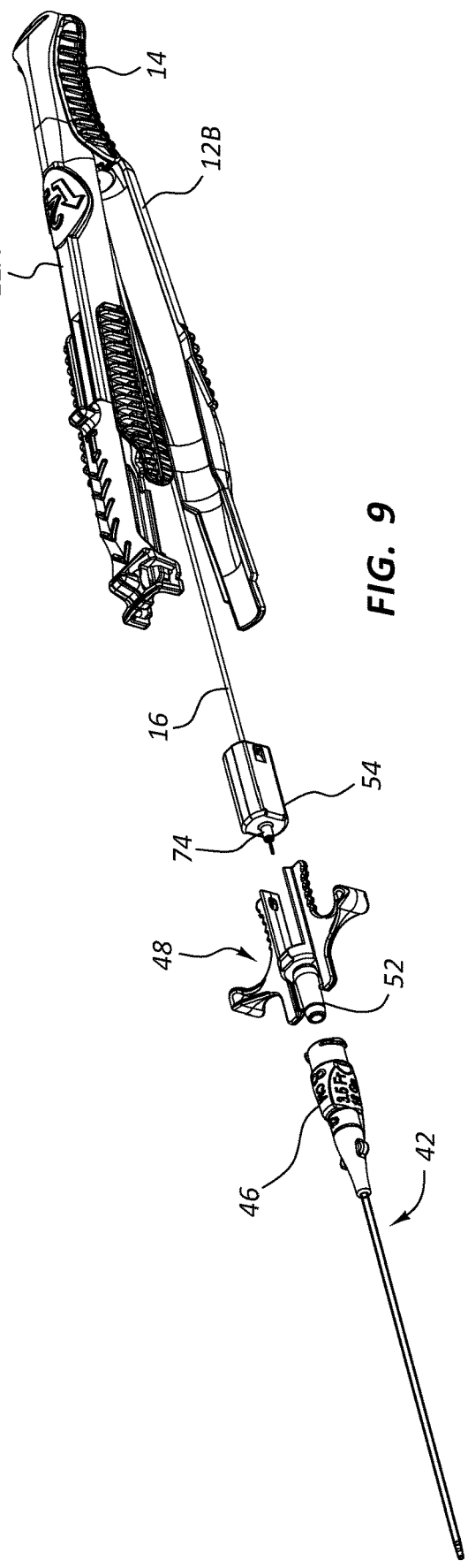
FIG. 9 shows one stage of use of the catheter insertion tool of FIGS. 1A and 1B according to one embodiment.

Note that, as shown in FIGS. 7A and 7B, during removal of the catheter from within the housing 12 of the insertion tool 10, the catheter slides distally along the needle 16 until the distal needle tip is received into the safety housing 54 and engaged with the needle safety component 56. FIG. 8 shows that the insertion tool 10 can then be separated from the catheter 42, leaving the handle 48 still attached to the catheter hub 46. As mentioned, the handle 48 includes the valve 52 interposed between the catheter hub 46 and the handle 48. Upon removal of the needle 16 and safety housing 54 from the catheter 42, the valve 52 occludes the catheter lumen so as to prevent inadvertent blood spillage from the catheter hub 46. As shown in FIG. 9, the handle 48 can be removed from engagement with the catheter hub 46 via pulling, twisting, etc., so as to disengage the teeth 50C of the handle from the hub. An extension leg can be attached to the catheter hub and the catheter 42 dressed down, per standard procedures. Then housing 12 and handle 48 of the insertion tool 10 can be discarded.

Figure 10C:
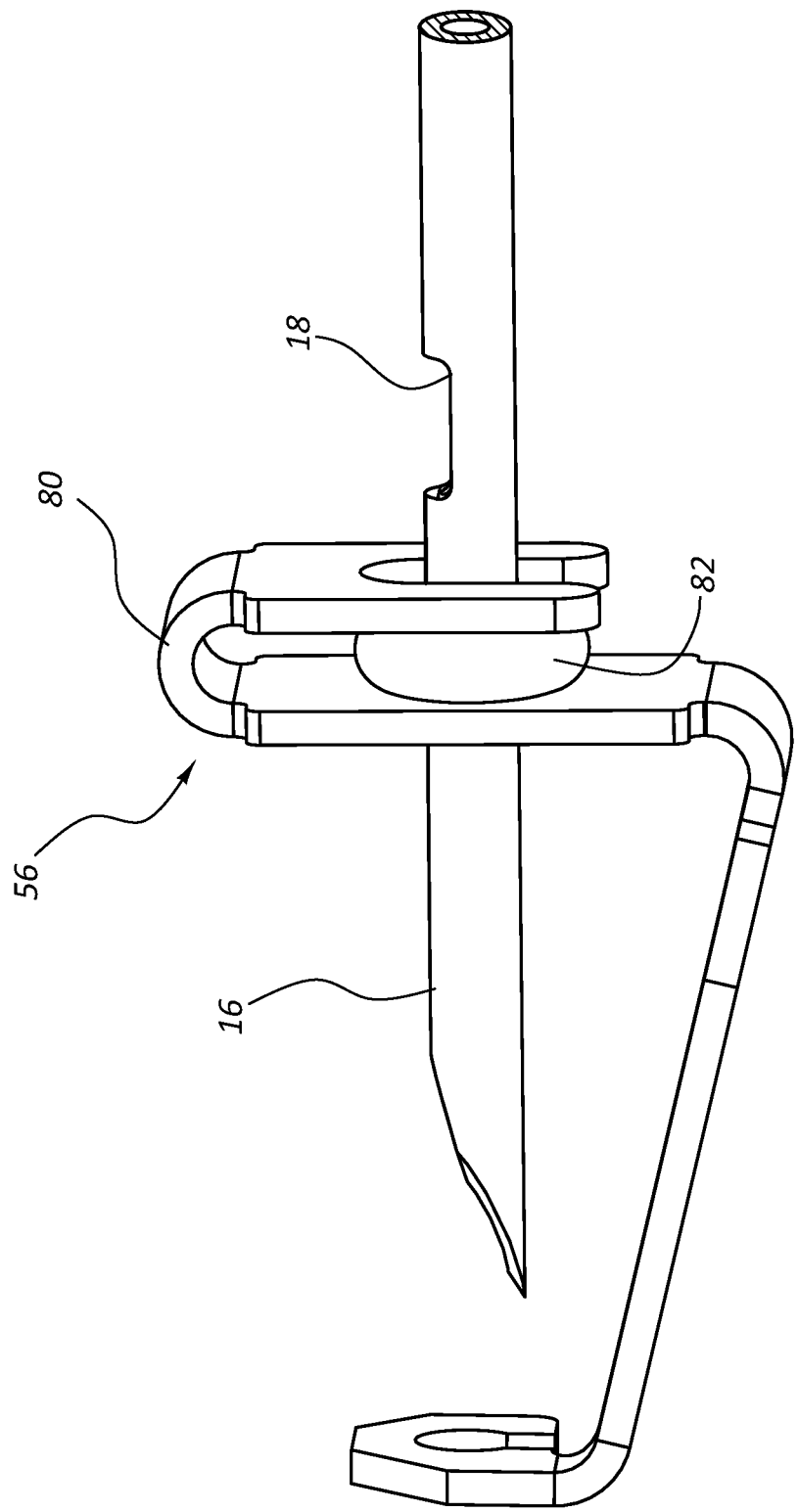

FIGS. 10A-10C give further details regarding the safety housing 54, as well as the needle safety component 56 and its interaction with the needle 16 in isolating the distal end thereof. As shown, the safety housing 54 is configured to enable the needle 16 to pass therethrough during use of the insertion tool 10, as has been described, exiting the housing via the extension 74 on the distal end of the housing. The cap 58 is placed into the proximal end of the safety housing 54 and is configured to support the needle safety component 56 such that he needle 16 initially passes through the safety housing, the cap, and the needle safety component. Note that the extension 74 of the safety housing 54 in the present embodiment extends into the valve 52 so as to open the valve during use of the insertion tool 10, which eliminates undesired friction between the valve and the needle.

FIG. 10C shows that the needle safety component 56 includes a bent body, or binding element 80 through which the needle initially extends, and a friction element 82. As seen in FIG. 10A, when the needle 16 is withdrawn from the catheter 42 (FIG. 8), the distal tip of the needle is withdrawn proximally through the extension 74 and past the distal portion of the needle safety component such that the needle is no longer in contact therewith. This enables the friction element 82 to cause the binding element 80 to cant slightly, thus binding the needle 16 in place and preventing its further travel with respect to the safety housing 54 and isolating the needle distal tip within the housing so as to prevent inadvertent needle sticks. In the present embodiment the friction element 82 includes a suitably sized O-ring. Suitable O-rings can be acquired from Apple Rubber Products, Lancaster, NY, for instance. Note that further details regarding the needle safety component, its operating principles, and similar devices are disclosed in U.S. Pat. Nos. 6,595, 955, 6,796,962, 6,902,546, 7,179,244, 7,611,485, and 7,618, 395, each of which is incorporated herein by reference in its entirety. Of course, other needle safety devices can be employed to isolate the distal end of the needle.

Reference is now made to FIGS. 11A-13B in describing a catheter insertion tool 110 according to one embodiment. Note that in this and succeeding embodiments, various features are similar to those already described in connection with the above embodiment. As such, only selected aspects of each embodiment to follow will be described.

The insertion tool 110 includes a housing 112 defined by a top housing portion 112A and a bottom housing portion 112B that together partially enclose the catheter 42. A needle hub 114 supporting a distally extending needle 116 is included for disposal within the housing 112 and positioned such that the catheter tube 44 of the catheter 42 is disposed over the needle. Note that partial enclosure of the catheter by the insertion tool in this and other embodiments enables a clinician to manipulate the insertion tool with hands that are closer to the distal end of the needle than what would otherwise be possible.

FIGS. 13A and 13B give further details regarding the needle hub 114, which is attached to the top housing portion 112A. A needle holder 126, included on a distal end of the needle hub 114, receives the proximal end of the needle 116 therein. The needle 116 is secured within the needle holder 126 via adhesive, welding, or other suitable manner. Extensions 128 are included on opposite sides of the needle holder 126 and are configured to be slidably received within corresponding slots 130 defined on the sides of the bottom housing portion 112B. Such engagement enables the bottom housing portion 112B to slide distally with respect to the top housing portion 112A.

Figure 11C:
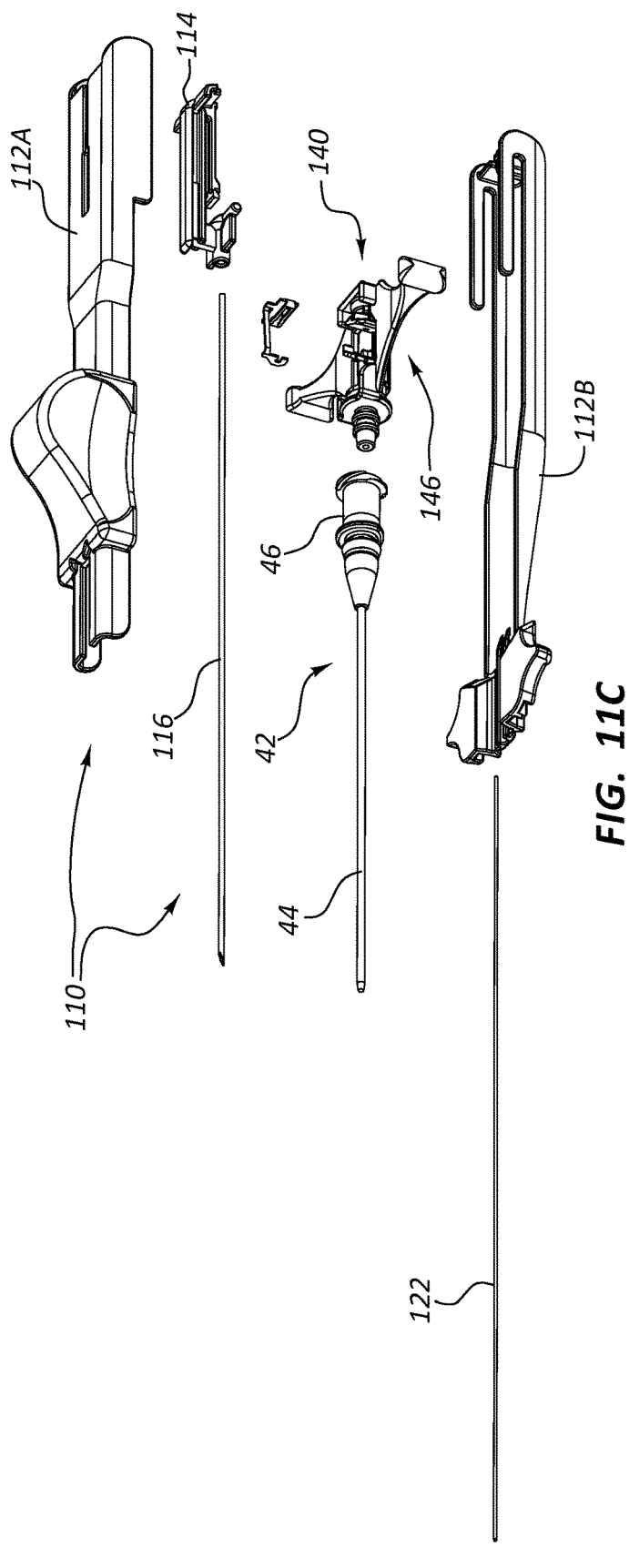
Figure 11D:
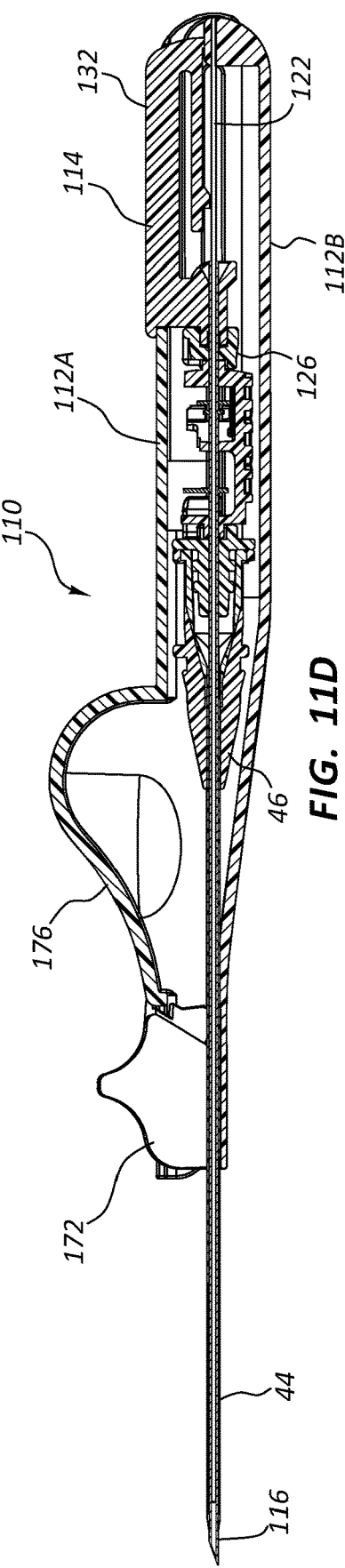

A top rail 132 is included on the needle hub 114 and is configured to engage a corresponding slot 134 defined in the proximal portion of the top housing portion 112A so as to secure the needle hub to the top housing portion. A lock out arm 136 is also included with the needle hub 114 and positioned to engage the back plate 124 when the bottom housing portion 112B is slid distally to extend the guidewire from the needle 116, thus preventing its retraction. Note that the guidewire 122 initially distally extends from the back plate 124 and through the needle holder 126 and needle 116, as best seen in FIG. 11D.

A guidewire advancement assembly 120 is included to selectively advance a guidewire 122, initially disposed within the lumen of the needle, distally past the distal end of the needle 116. The guidewire advancement assembly 120 includes the bottom housing portion 112B to which the guidewire 122 is attached at a proximal back plate 124 thereof. As will be seen, the bottom housing portion 112B is distally slidable with respect to the top housing portion 112A to enable selective distal advancement of the guidewire 122.

Figure 12A:
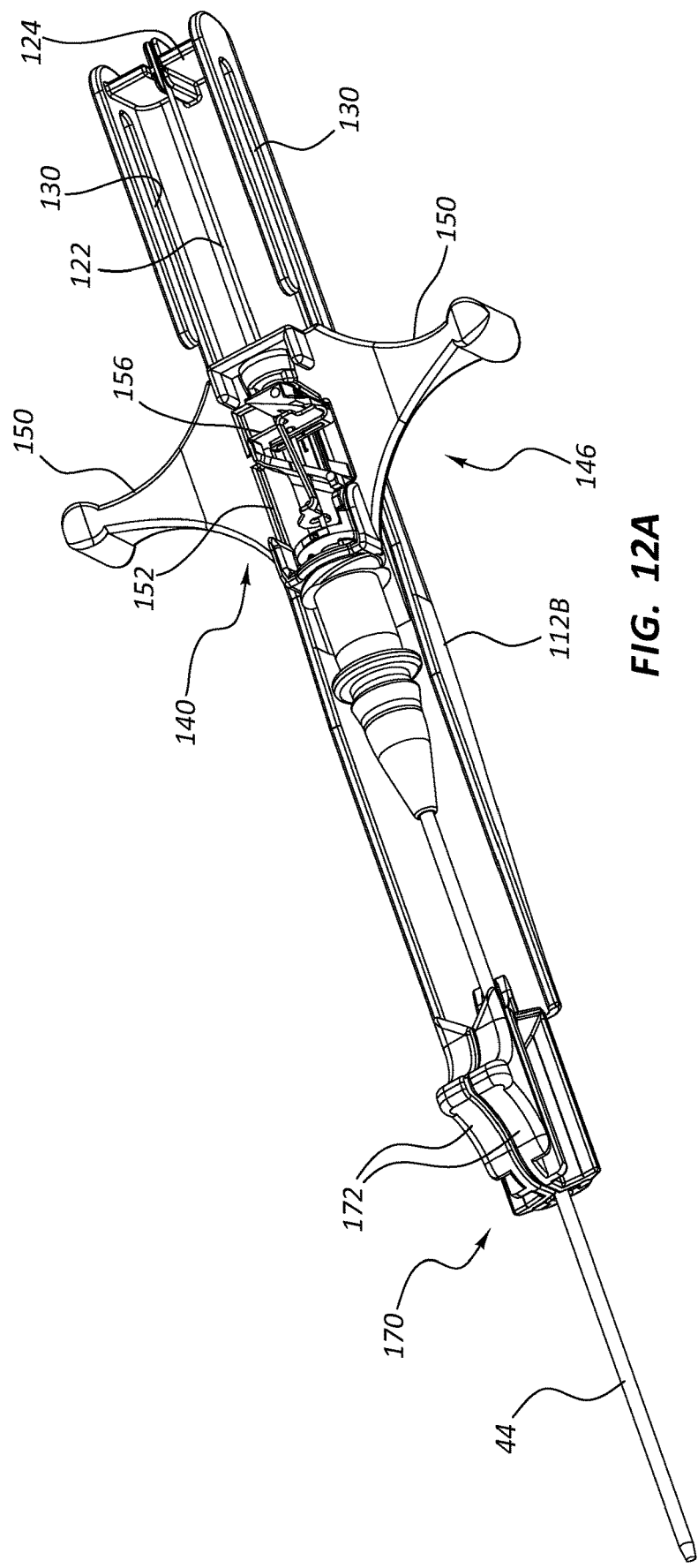
FIGS. 12A and 12B are various views of a portion of the catheter insertion device of FIGS. 11A-11D.
Figure 12B:
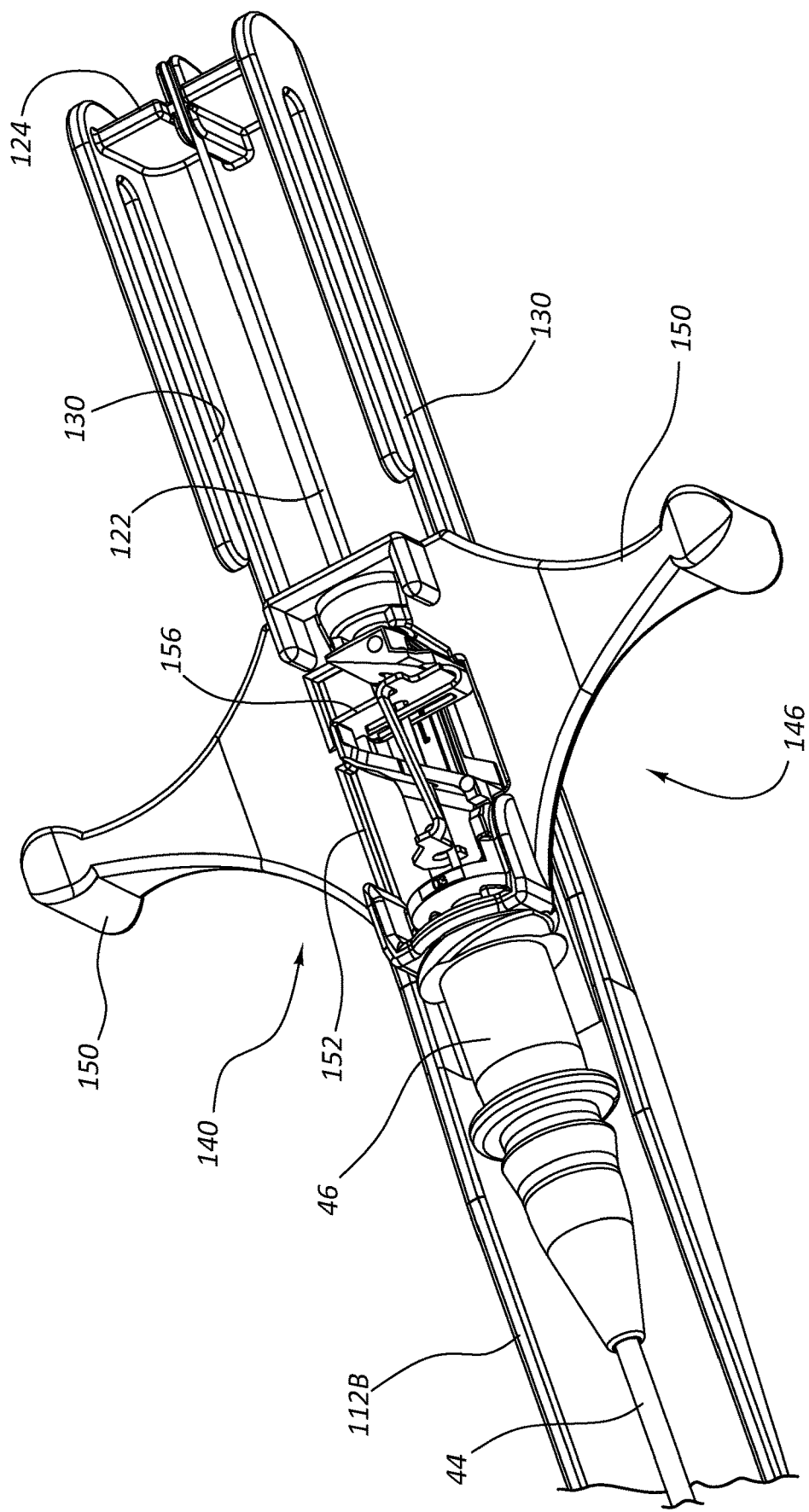

The insertion tool 110 further includes a catheter advancement assembly 140 for selectively advancing the catheter 42 over the needle 116. The advancement assembly 140 includes a handle 146 initially and slidably disposed between the top and bottom housings 112A and 112B and removably attached to the hub 46 of the catheter 42. As best seen in FIGS. 12A and 12B, the handle 146 includes two arms 150 for allowing a user to selectively slide the handle in order to advance the catheter 42. The handle 146 further includes a recess 152 in which is placed a needle safety component 156 for isolating the distal tip of the needle 116 when the needle is withdrawn from the catheter 42. Further details regarding the needle safety component are disclosed in U.S. Pat. Nos. 6,595,955, 6,796,962, 6,902,546, 7,179, 244, 7,611,485, and 7,618,395, each incorporated by reference above.

The insertion tool 110 further includes a support structure 170 for stabilizing the needle 116 proximate the distal end of the housing 112. The support structure 170 in the present embodiment includes two flaps 172 that are hingedly connected to the distal portion of the bottom housing portion 112B. When closed as seen in FIGS. 11D and 12A, the flaps 172 serve to stabilize the needle 116 to assist the user of the insertion tool 110 in inserting the needle into the patient. When open (FIG. 14D), the flaps 172 provide an opening to enable the catheter hub 46 to be removed from the distal end of the housing 112, as will be detailed further below. Before the bottom housing portion 112B is slid with respect to the top housing portion 112A, the flaps 172 are disposed in a track 174 defined by the top housing portion. Other types and configurations of support structures can also be employed. The insertion tool 110 further includes gripping surfaces 176 on either side of the housing 112 to aid in use of the tool during catheter insertion procedures, detailed below.

FIGS. 14A-14E depict various stages of use of the insertion tool 110 in inserting a catheter into a patient. With the insertion tool 110 in the configuration shown in FIG. 14A, vascular access is achieved with the needle 116 via user insertion of the needle into the patient at an insertion site. Confirmation of vessel access can be achieved via the observation of blood flashback via a distal notch in the needle 116, as described in the previous embodiment, or in other suitable ways.

Once the distal portion of the needle 116 is disposed within a vessel of the patient, the guidewire 122 is extended past the distal end of the needle and into the vessel by distally advancing the bottom housing portion 112B. Such advancement is achieved in the present embodiment by placing a user's fingers on the folded-up flaps 172 of the bottom housing portion 112B and pushing the flaps distally, thus extending the guidewire 122. The guidewire 122 is advanced until fully extended. The lock out arm 136 of the needle hub 114 then engages the back plate 124 of the bottom housing portion 112B and prevents retraction of the guidewire 122.

At this stage, the handle 146 of the catheter advancement assembly 140 is distally advanced, by a user grasping of one or both arms 150 thereof, so as to distally advance the catheter 42 through the insertion site and into the patient vasculature. This is shown in FIG. 14C, wherein the catheter tube 44 is shown distally advancing over the needle 116 and the guidewire 122.

As shown in FIG. 14D, continued distal advancement of the catheter 42 causes the catheter hub 146 to urge the flaps 172 to open, thus providing a suitable opening through which the hub may pass from the insertion tool housing 112. Note that the flaps 172 are shaped such that contact with the catheter hub 46 urges each flap to fold outward, as seen in FIG. 14D. Note also that the flaps 172 are no longer disposed within the track 174 due to full distal advancement of the guidewire 122 via finger pressure applied to the flaps 172 as described above.

Figure 14E:
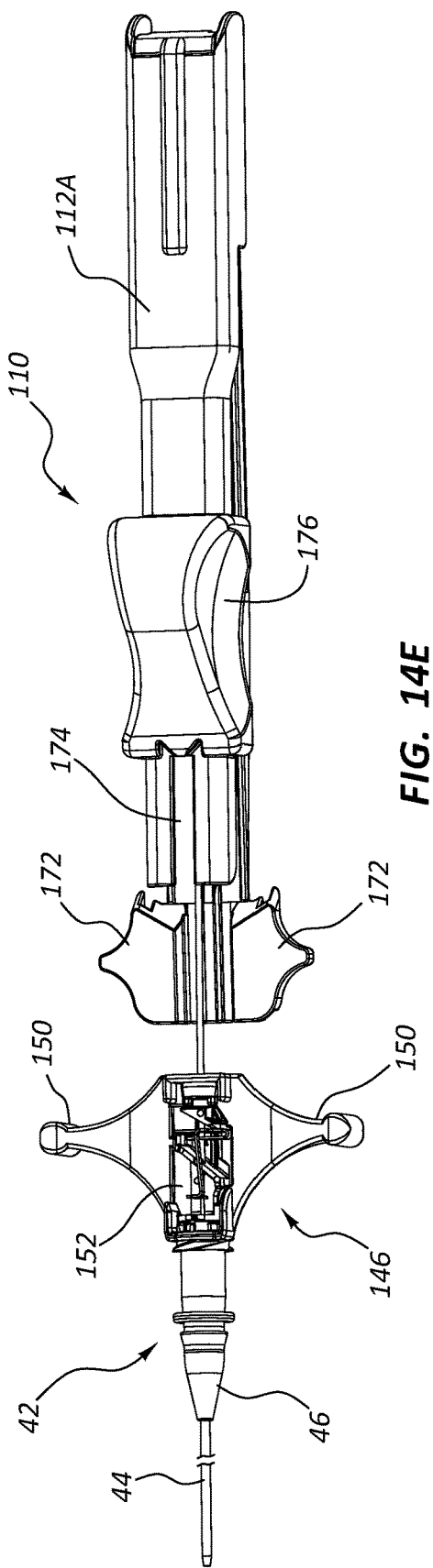
Figure 14F:
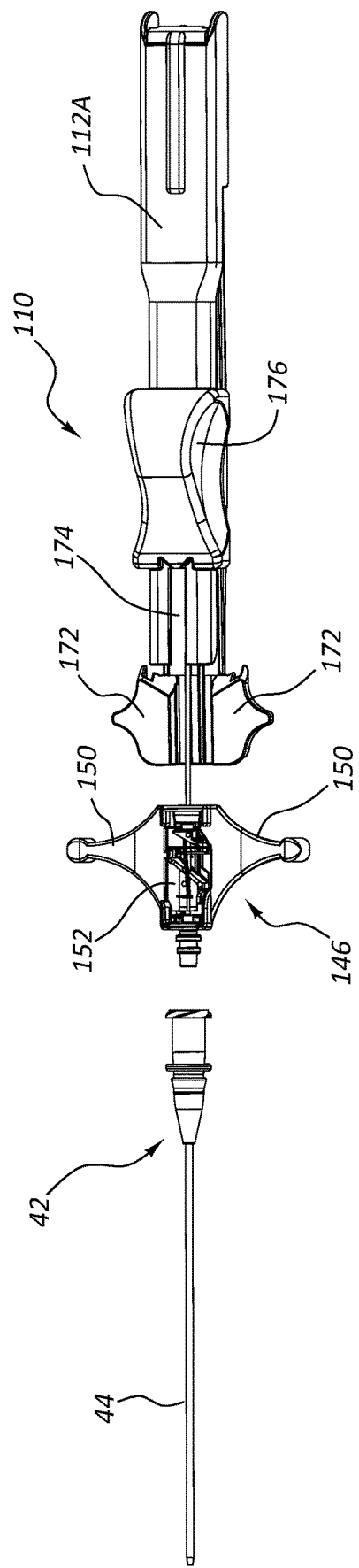

FIG. 14E shows that, with the flaps no longer engaged within the track 174, the top housing portion 112A and bottom housing portion 112B are able to separate at the distal ends thereof such that the handle 146, still attached to the catheter hub 46, can separate from the housing 112. Though not shown at this stage, the needle safety component 156 disposed in the recess 152 of the handle 146 isolates the distal end of the needle 116. The handle 146 can then be manually removed from the catheter hub 46 (FIG. 14F), and placement and dressing of the catheter 42 can be completed. The insertion tool 110, including the needle 116 isolated by the needle safety component 156 of the handle 146, can be safely discarded.

Figure 15A:
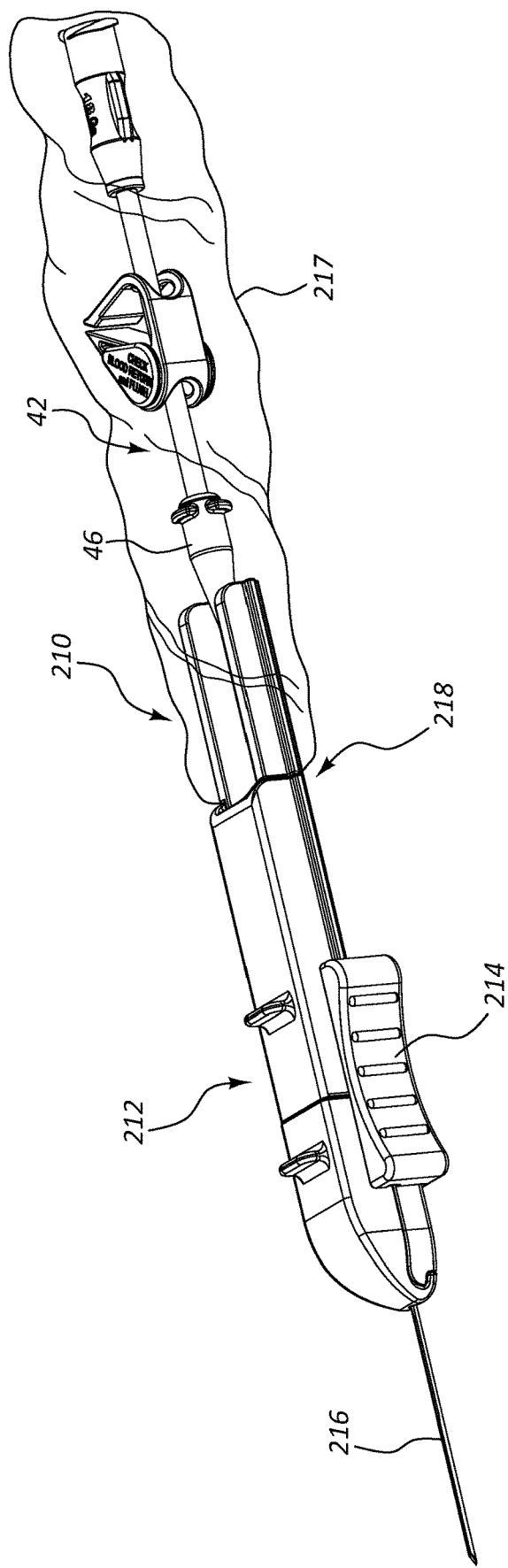
FIGS. 15A and 15B are various views of a catheter insertion device according to one embodiment.

Reference is now made to FIGS. 15A-18 in describing a catheter insertion tool 210 according to one embodiment. The insertion tool 210 includes a housing 212 defined by a top housing portion 212A and a bottom housing portion 212B that together partially enclose the catheter 42. A sliding needle hub 214 supporting a distally extending hollow needle 216 is slidably attached to the housing 212. In particular, the needle hub 214 includes tracks 214A that slidably engage corresponding rails 218 defined on the top and bottom housing portions 212A, 212B in a manner described further below. As shown in FIG. 15A, the needle hub 214 is positioned distally with respect to the housing 212 such that the needle 216 extends through a needle channel 224 (FIG. 18) and out a hole defined in a distal end of the top housing portion 212A so that the needle is positioned as shown in FIG. 15A.

Figure 15B:
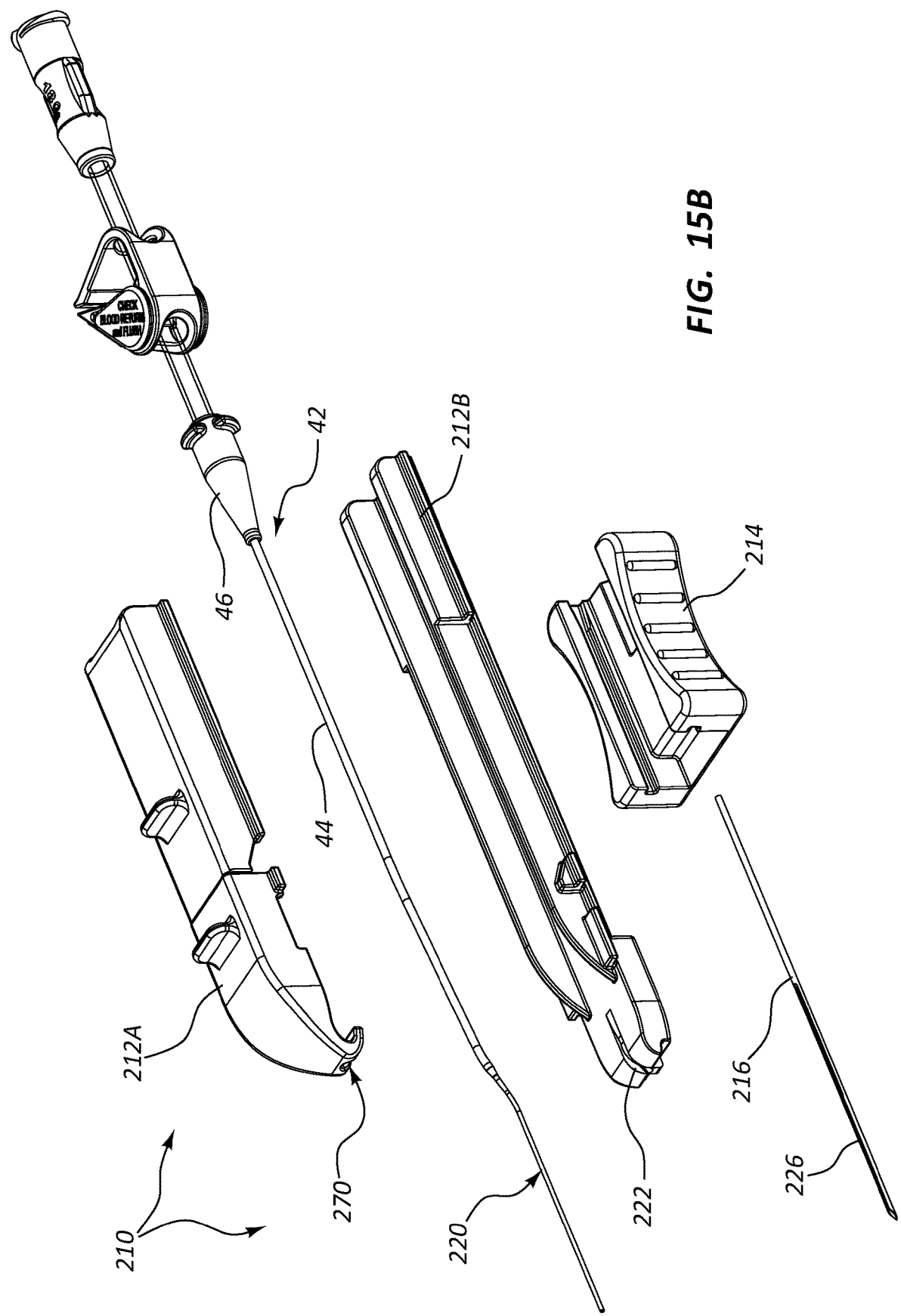
Figure 16:
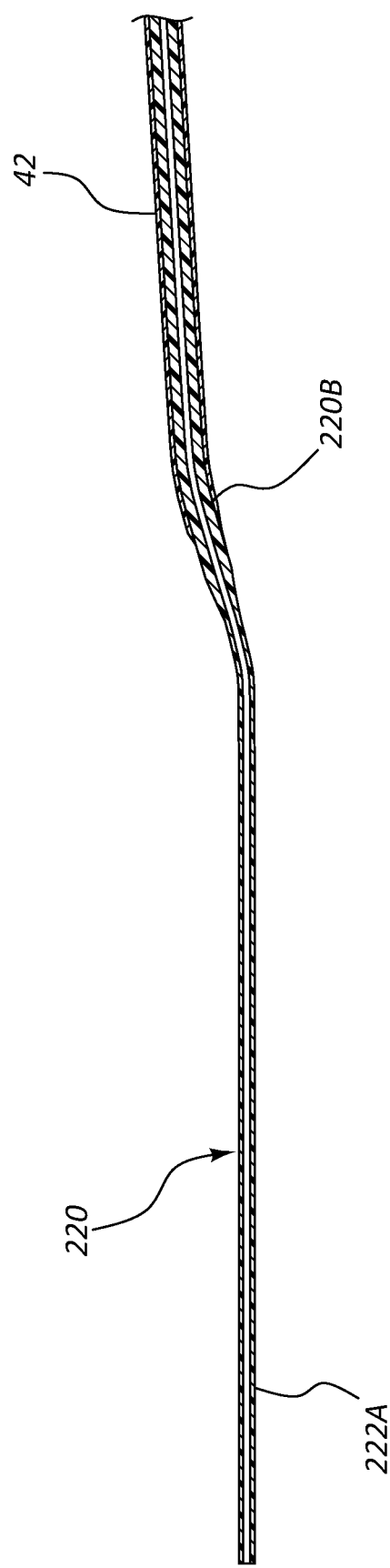
FIG. 16 is a cross sectional side view of an integrated guidewire/dilator for use with the catheter insertion device of FIGS. 15A and 15B.

As seen in FIG. 15A, the housing 212 of the insertion tool 210 encloses a portion of the catheter 42. An integrated guidewire/dilator 220 is included and disposed within the lumen of the catheter tube 44, as shown in FIGS. 15B and 16. The guidewire/dilator 220 includes a distal guidewire portion 220A and a proximal dilator portion 220B. So configured, the guidewire/dilator 220 can not only serve as a guidewire in directing the catheter tube 44 through the insertion site of the patient into the accessed vessel, but can dilate the insertion site in advance of catheter insertion therethrough. In other embodiment, no guidewire/dilator need be used. In one embodiment, it is appreciated that the guidewire/dilator 220 can proximally extend through the entire catheter 42 and include on a proximal end thereof a luer cap connectable to a proximal luer connector of the catheter. Note also that FIG. 15A shows a sterile bag 217 attached to the housing 212 so as to cover and isolate the proximal portion of the catheter 42. For clarity, the bag 217 is included only in FIG. 15A, but could be included with insertion tools of varying configurations so as to protect and isolate portions of the catheter.

As seen in FIGS. 17A-17C, the needle 216 includes a longitudinally extending needle slot 226 extending from a beginning point along the length of the needle to the distal end thereof. FIG. 17B shows that the slot 226 can be optionally wider in a proximal portion thereof relative to more distal slot portions. So configured, the needle slot 226 enables the guidewire/dilator 220 to be inserted into, slid relative to, and removed from the needle 216 during operation of the insertion tool 210, described below. Note that the needle slot can extend the entire length of the needle, in one embodiment.

FIG. 18 shows the manner of entry of the guidewire/dilator 220 into the slot 226 of the needle 216 according to one embodiment, wherein the guidewire/dilator extends distally along a guide channel 222 defined in the top housing portion 212A and into the hollow needle 216, which is disposed in the needle channel 224, via the needle slot. (The guide channel 222 is also seen in FIG. 15B.) In this way, the guidewire/dilator 220 can be distally slid through the hollow needle 216 so as to extend beyond the distal needle end while still being able to be removed from the needle via the slot 226 when the guidewire/dilator and needle are separated from one another, as will be seen.

Figure 19:
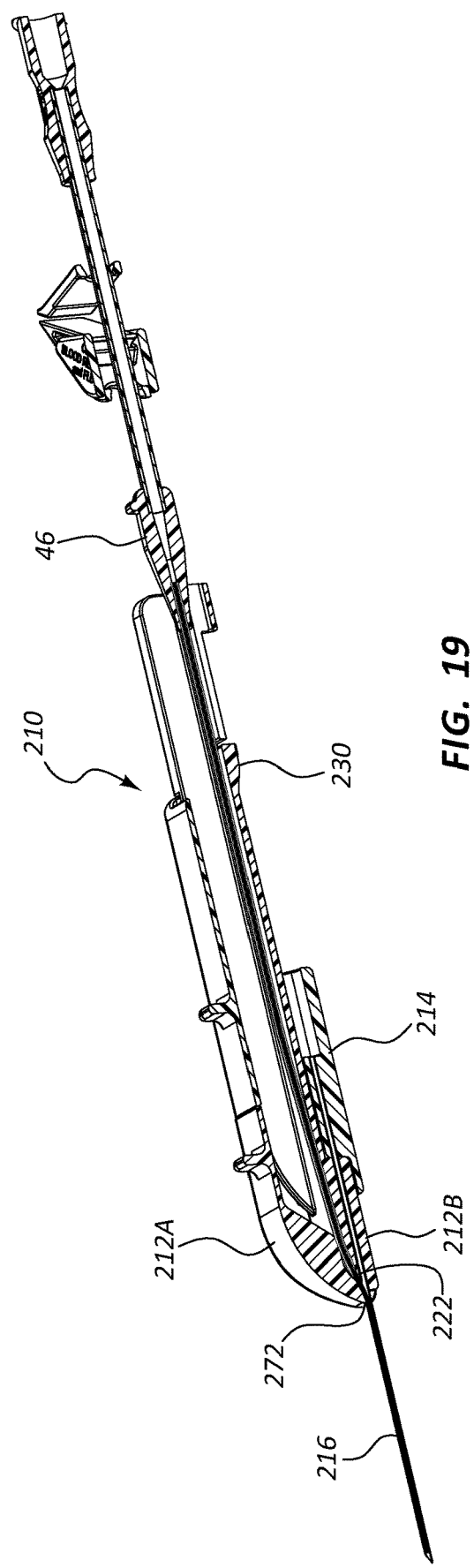
FIG. 19 shows one stage of use of the catheter insertion tool of FIGS. 15A and 15B according to one embodiment.

FIG. 18 also shows a support structure 270 for stabilizing the needle 216, including an interface 272 defined by portions of the top housing portion 212A and the bottom housing portion 212B about the hole through which the needle extends. Of course, other support structures can be employed to provide stability to the needle to assist in inserting the needle into the patient vasculature. FIG. 19 shows details of a lockout 230 for the needle hub 214, included on the bottom housing portion 212B, for preventing further movement of the needle hub after it has been retracted, as described below.

FIGS. 19-24 depict various stages of use of the insertion tool 210 in inserting a catheter into a patient. With the insertion tool 210 in the configuration shown in FIG. 19, vascular access is achieved with the needle 216 via user insertion of the needle into the patient at an insertion site.

Once the distal portion of the needle 116 is disposed within a vessel of the patient, the guidewire/dilator 220 is manually fed through the hollow needle 216 so as to extend past the distal end of the needle and into the vessel. Such advancement is achieved in the present embodiment by distally moving the housing 212 and catheter 42 together while keeping the needle hub 214 stationary. The guidewire 122 is advanced distally a suitable distance, which in the present embodiment, includes advancement until a distal end of the housing 212 arrives at the skin insertion site.

Figure 20A:
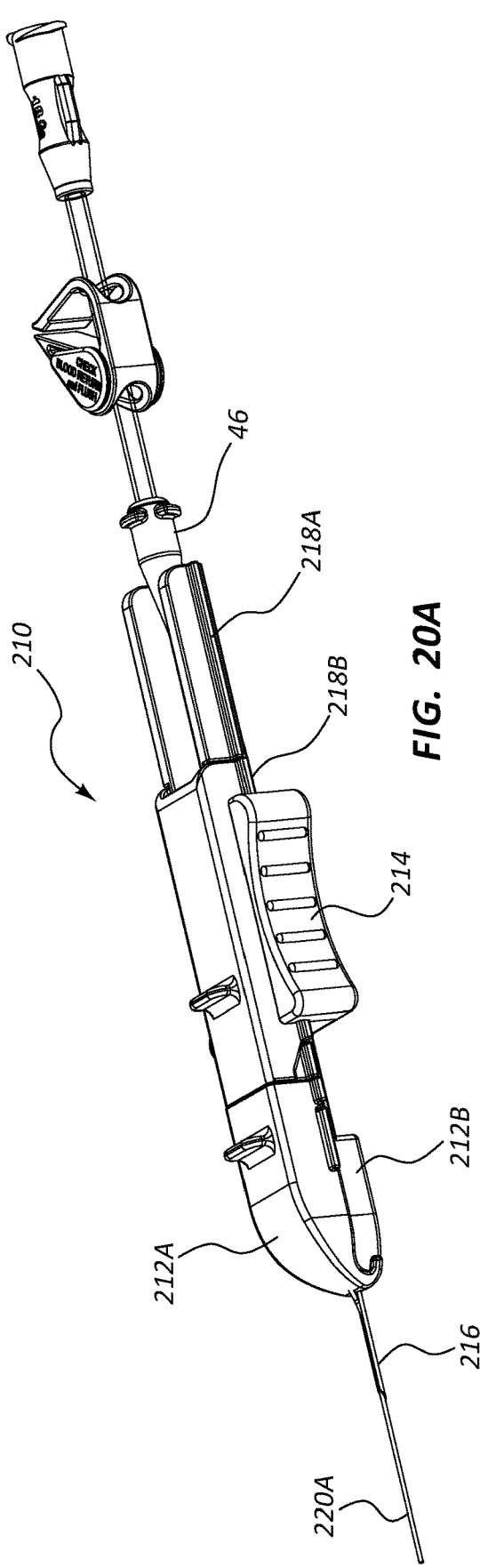
FIGS. 20A and 20B show one stage of use of the catheter insertion tool of FIGS. and 15B according to one embodiment.
Figure 20B:
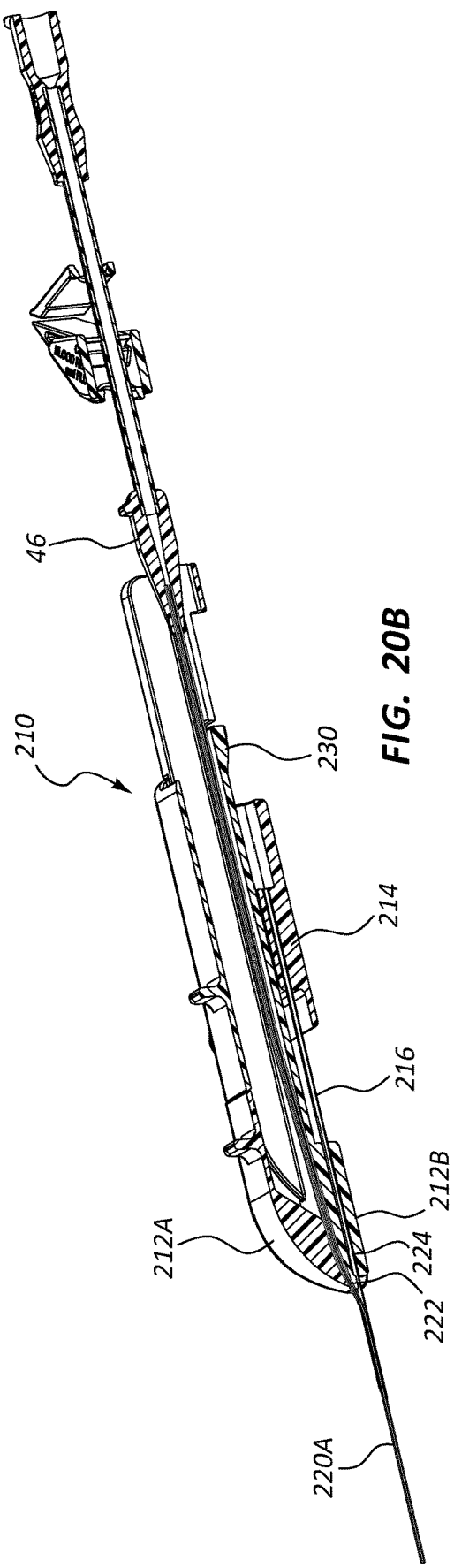
Figure 22:
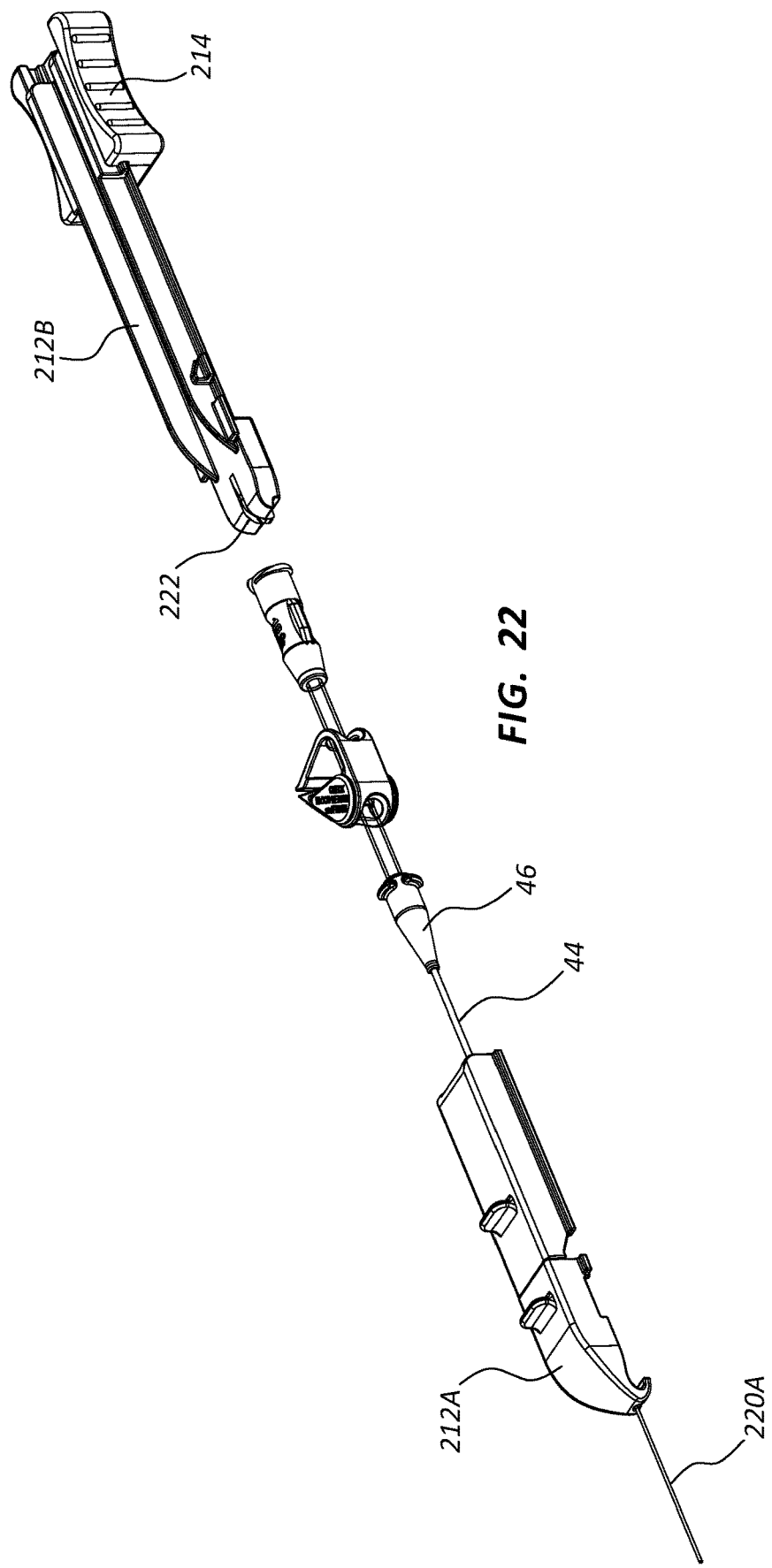
FIG. 22 shows one stage of use of the catheter insertion tool of FIGS. 15A and 15B according to one embodiment.
Figure 23:
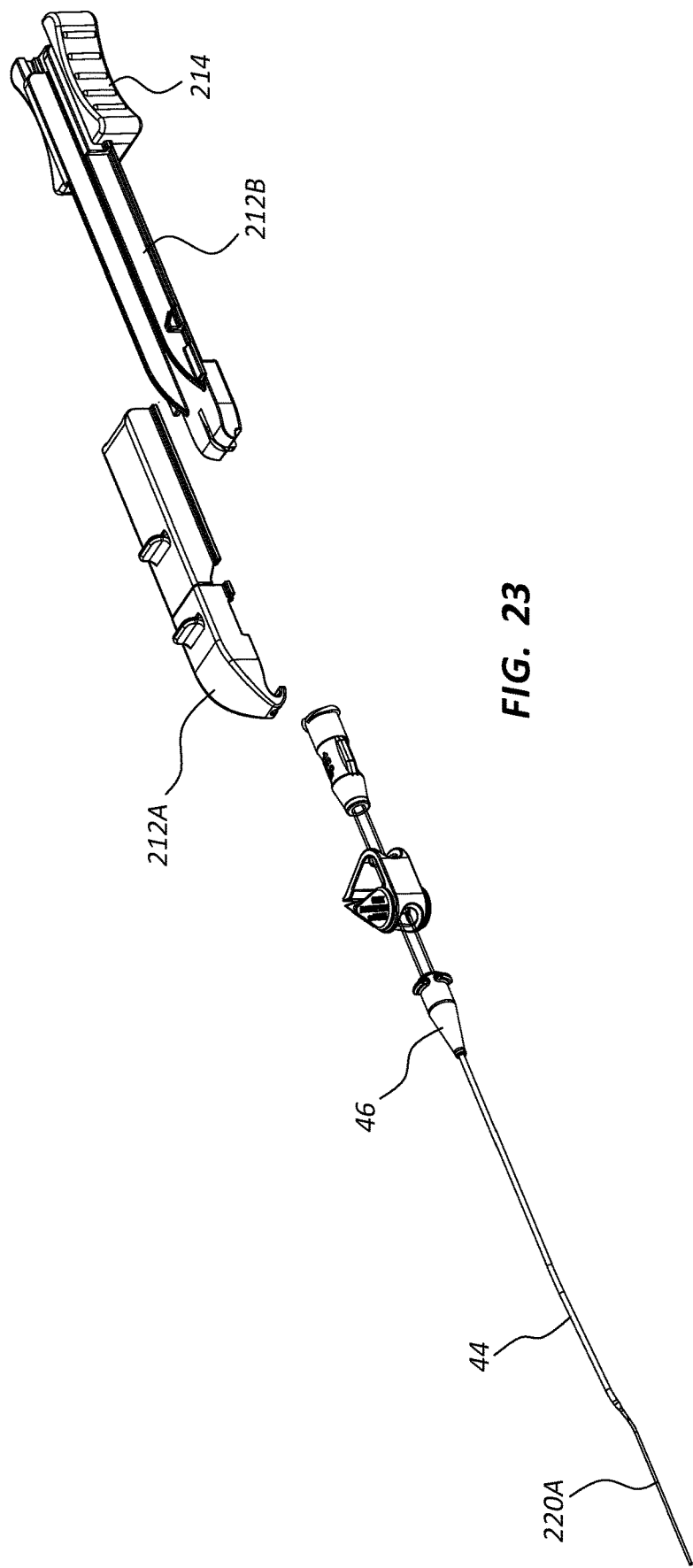
FIG. 23 shows one stage of use of the catheter insertion tool of FIGS. 15A and 15B according to one embodiment.

FIGS. 20A and 20B show that after the guidewire/dilator 220 has been distally extended into the vessel, the needle 216 is retracted from the vessel by proximally sliding the needle hub 214 along rail portions 218A disposed on the top housing portion 212A. Proximal sliding of the needle hub 214 continues until the hub engages the rail portions 218B of the bottom housing portion 212B and is fully slid to the proximal end of the housing 212, as shown in FIGS. 21A and 21B. The needle hub 214 engages the lock out 230 (FIG. 20B) so as to prevent future distal movement of the needle hub or needle 216. In this position, the needle 216 is fully retracted into the insertion tool housing 212 such that the distal end of the needle is safely isolated from the user (FIG. 21B). Note that in one embodiment a needle safety component can be added to the insertion tool to further isolate the tip of the needle. Note that the distal portion of the guidewire/dilator 220 remains in the vessel of the patient, having been able to separate from the needle 216 during retraction thereof via the needle slot 226.

At this stage, the bottom housing portion 212B (FIG. 22) and the top housing portion 212A (FIG. 23) are removed from the catheter 42. The catheter 42 can then be inserted through the insertion site and into the vessel of the patient. Note that the guidewire/dilator 220 is still disposed within the catheter tube 44 and that the dilator portion assists the distal end of the catheter tube to enter the vessel by gradually enlarging the insertion site and the vessel entry point.

Figure 24:
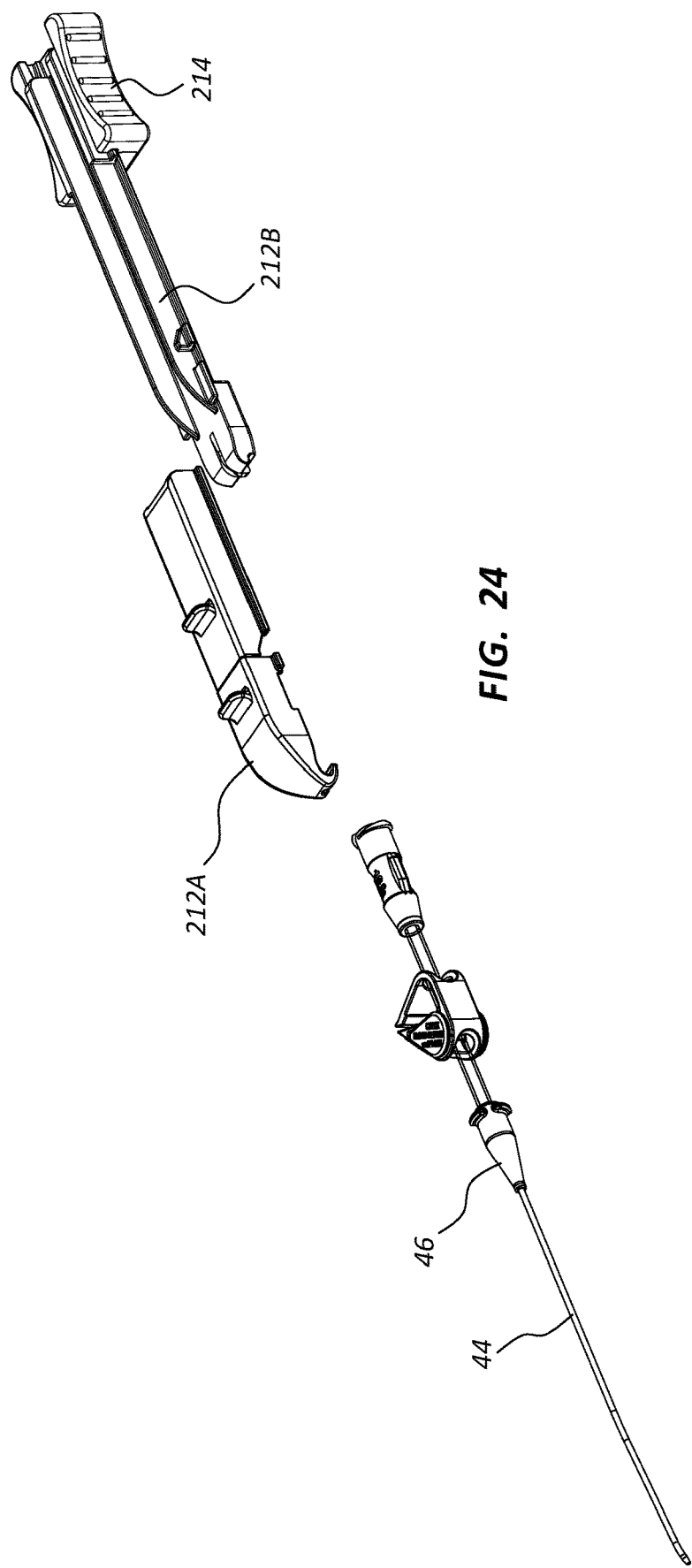
FIG. 24 shows one stage of use of the catheter insertion tool of FIGS. 15A and 15B according to one embodiment.

As mentioned, in one embodiment, the proximal portion of the catheter 42, including the hub 46 and connected extension leg, is covered by a sterile bag, which is attached to the housing 212. The sterile bag can be removed after the catheter is fully inserted into the patient vessel or can be removed when the housing portions 212A and 212B are removed. In FIG. 24, the guidewire/dilator 220 is then removed from the catheter 42 and the catheter dressed and finalized for use. The guidewire/dilator 220 and other portions of the insertion tool 210 are discarded.

Figure 25A:
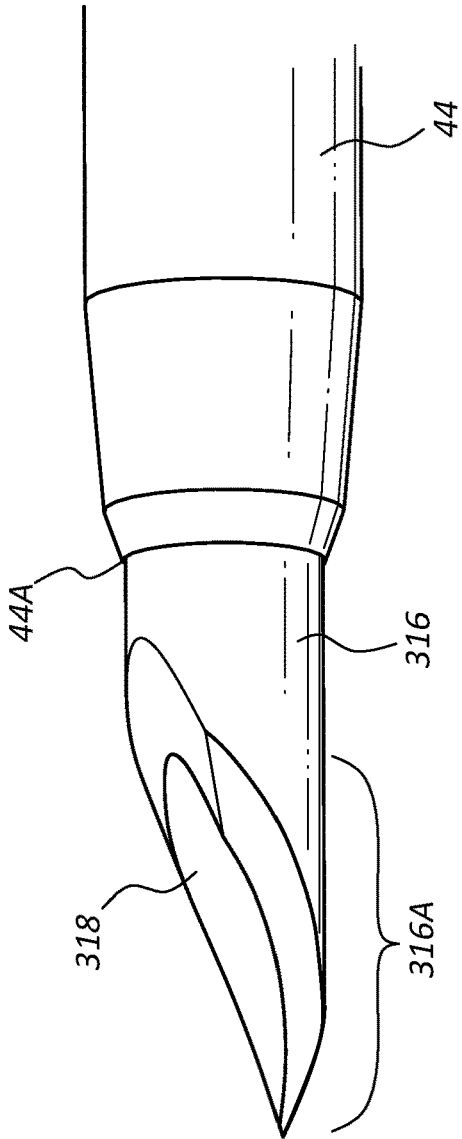
FIGS. 25A and 25B shows various views of a needle distal tip and guidewire blunting design according to one embodiment.
Figure 25B:
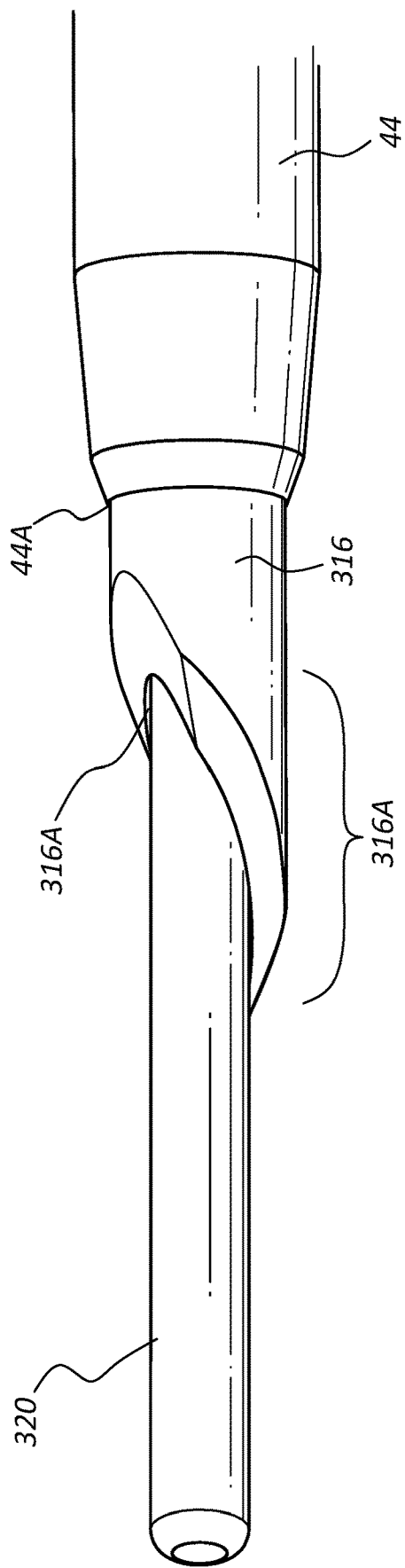
Figure 26:
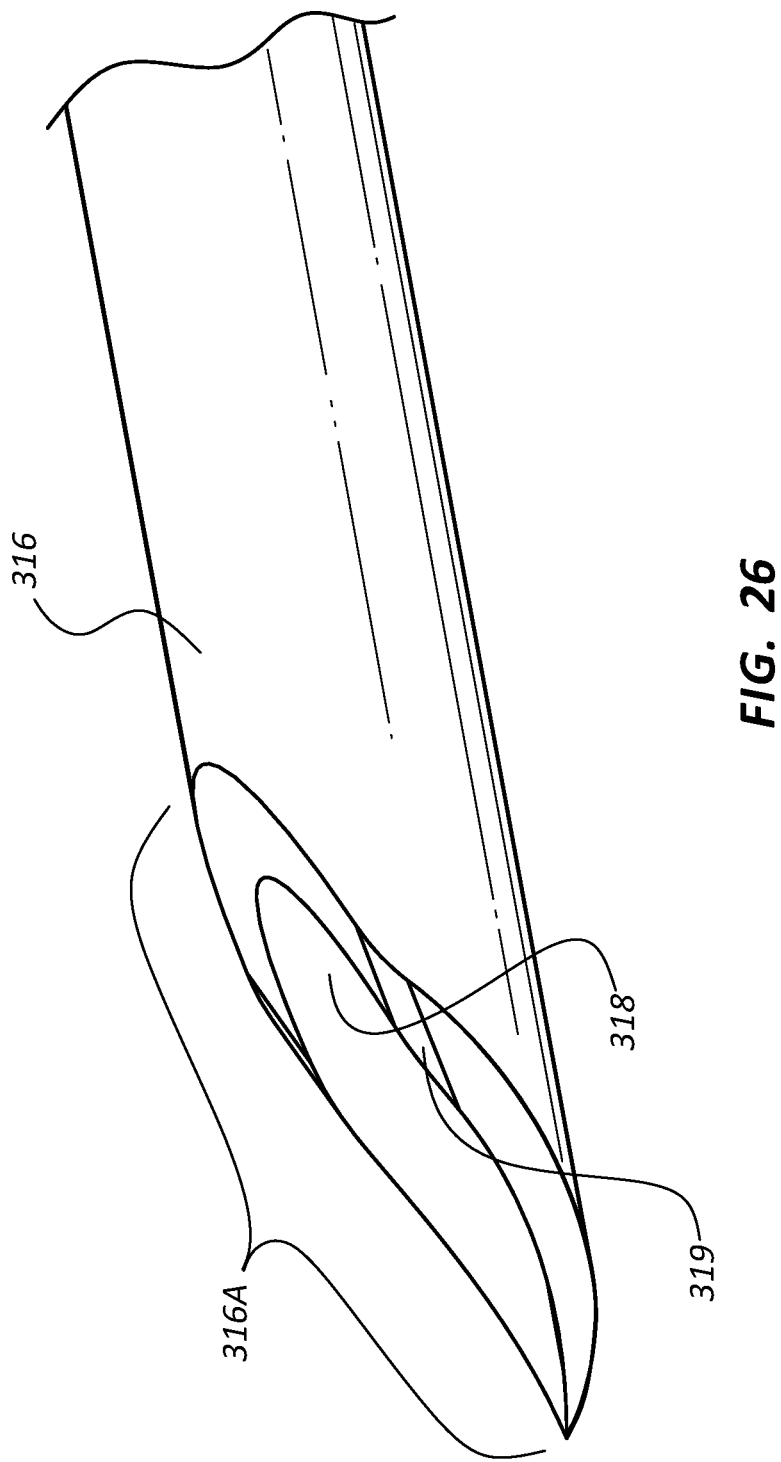
FIG. 26 is a perspective view of a needle distal tip design according to one embodiment.

FIGS. 25A and 25B depict details regarding a needle blunting system for isolating a distal end 316A of a hollow needle 316, according to one embodiment. As shown, the needle distal end 316A includes a bevel that is configured such that its cutting surfaces are disposed at an inner diameter 318 of the needle 316. Thus, when a suitably sized guidewire 320 is distally extended past the distal end 316A of the needle 316, the cutting surfaces of the needle are blocked by the proximity thereto of the guidewire, thus safely isolating the needle end from a user. In addition, blunting the distal end 316A of the needle 316 in this manner prevent the needle end from damaging sensitive inner walls of the vessel after the needle tip has been inserted herein. At this point, a distal end 44A of the catheter tube 44 can then be distally advanced over the needle 316 and guidewire 320. FIG. 26 depicts a needle end bevel 316A according to another embodiment, including an additional fillet component 319. Such a blunting system can be employed in one or more of the insertion tools described herein.

Figure 27:
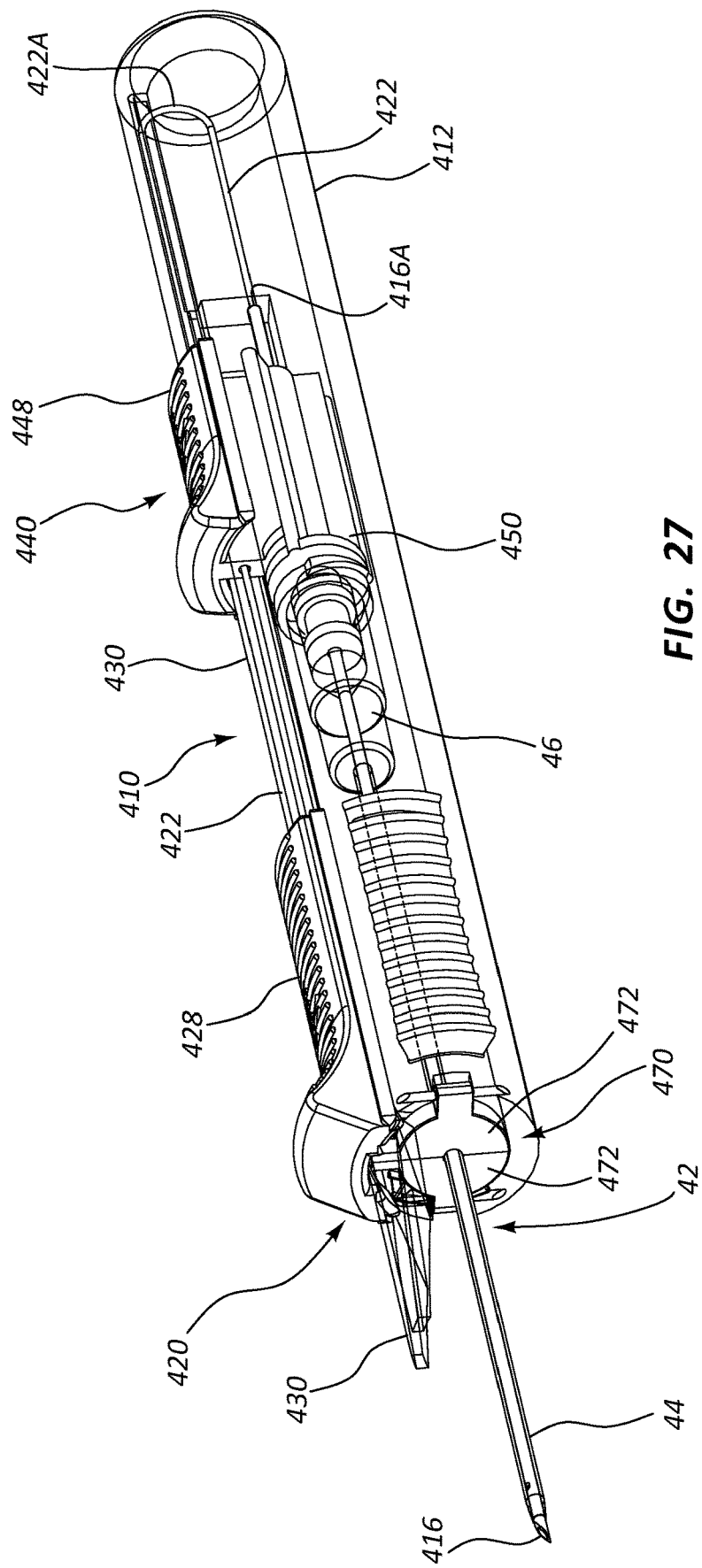
FIG. 27 is a perspective view of a catheter insertion tool according to one embodiment.

Reference is now made to FIG. 27 in describing a catheter insertion tool 410 according to one embodiment. The insertion tool 410 includes a housing 412 that partially encloses the catheter 42. A distally extending hollow needle 416 is disposed with the housing 412 such that the needle extends out the distal end of the housing 412

A guidewire advancement assembly 420 is shown for selectively advancing a guidewire 422, including a slide 428 that slides along a track 430 defined in the housing 412. The guidewire 422 is attached to the slide 428 and extends proximally within the housing 412 until it bends, forming a guidewire bend 422A, toward the distal end of the housing and passes into the hollow needle 416 via a proximal end 416A thereof for selective distal advancement past the distal end of the needle via user actuation of the slide. Distal advancement of the guidewire 422 out the distal end of the needle 416 is stopped when the guidewire bend 422A engages the needle proximal end 416A.

A catheter advancement assembly 440 is also shown for selectively advancing the catheter tube 44 over the needle 416, including a slide 448 that slides along the track 430, and a carriage 450 disposed within the housing 412 and operably connected to the slide 448. The carriage 450 is initially engaged with the catheter hub 46 such that distal sliding of the slide 448 causes the catheter to be distally advanced toward the distal housing end.

The insertion tool 410 further includes a support structure 470 for stabilizing the needle 416, including two doors 472 hingedly attached via pins to the distal end of the housing 412. The doors 472 serve to stabilize the needle 416 during insertion into the patient. Later, when the catheter tube 44 and catheter hub 46 are advanced distally by the slide 448, the doors 472 are opened, enabling the catheter 42 to pass through the doors and be separated by the user from the insertion tool 410. In the present embodiment, a wedge feature is included on the bottom surface of the slide 428, the wedge feature being configured to push the doors 472 open when the slide is slid distally, as described herein. Such a wedge or other suitable feature can be included in other embodiments described herein as well.

After separation from the insertion tool 410, the catheter 42 can then be advanced and placed as needed into the patient by the user. Note that, though none is shown, a needle safety component can be included for isolating the distal tip of the needle 416. In one embodiment, distal sliding of the guidewire slide 428 can partially open the doors 472 in preparation for catheter advancement.

Figure 28:
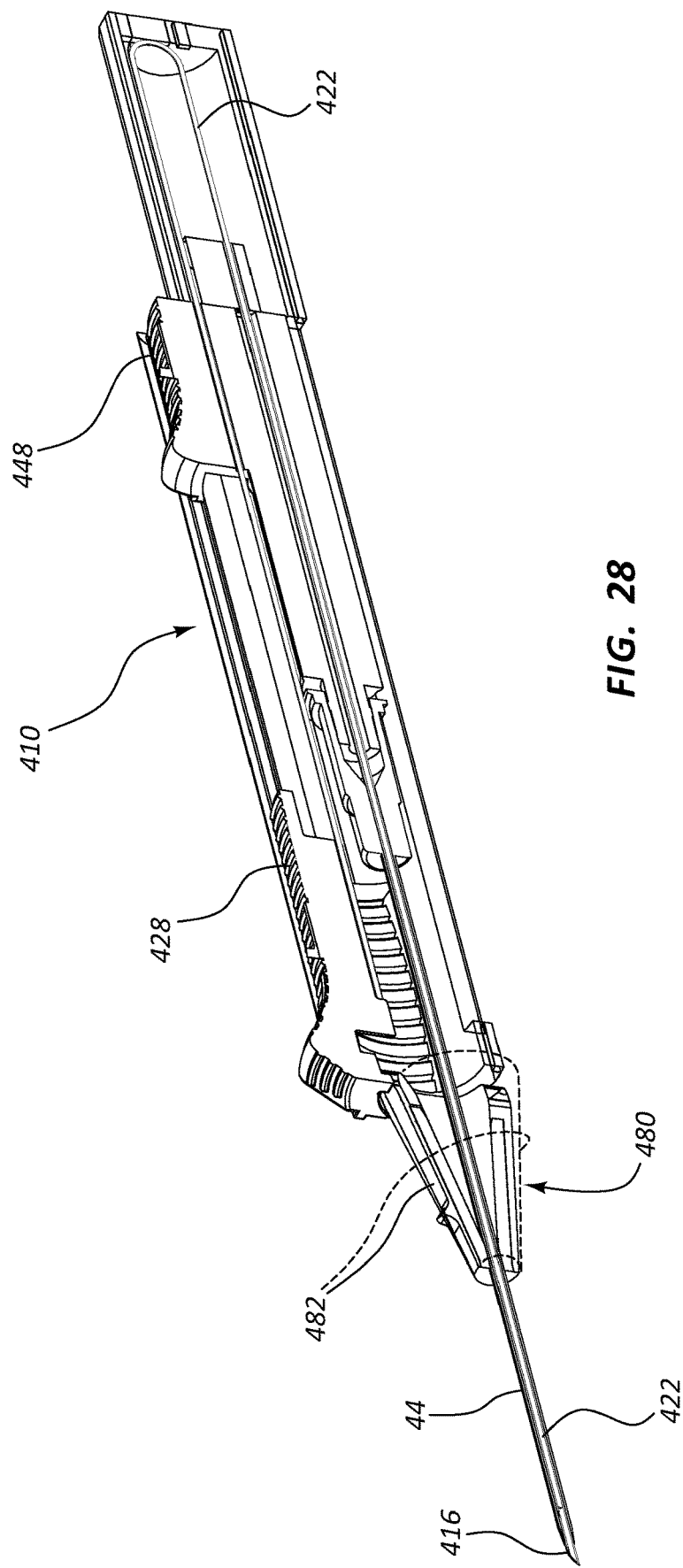
FIG. 28 is a cross sectional view of a catheter insertion tool according to one embodiment.

FIG. 28 shows the insertion tool 410 including a support structure 480 according to another embodiment, wherein two half-conically shaped doors 482 are hingedly connected to the housing 412 (via living hinges or other suitable connective scheme) and configured to stabilize the needle 416. The carriage of the insertion tool 410 in FIG. 28 is also longer relative to that of FIG. 27. Thus, it is appreciated that various different support structures and configurations can be employed for stabilizing the needle at or near its exit point from the insertion tool housing.

Reference is now made to FIGS. 29A and 29B in describing a catheter insertion tool 510 according to one embodiment. The insertion tool 510 includes a housing 512 that partially encloses the catheter 42. A hollow needle 516 distally extends from a needle hub 514 that caps a proximal end of the housing 512 such that the needle extends out the distal end of the housing 512.

A guidewire advancement assembly 520 is shown for selectively advancing a guidewire 522, including a slide 528 that slides along a track 530 defined in the housing 512. The guidewire 522 is attached to the slide 528 and extends proximally within the housing 512 and out through a pigtail 524, attached to the proximal end of the housing 512, via a top one of two holes 514A defined in the needle hub 514. Near the proximal end of the pigtail 524, the guidewire 522 bends to form a U-shaped guidewire bend 522A and distally extends back into the housing 512 to pass into the hollow needle 516 via a bottom one of the two needle hub holes 514A, for eventual distal advancement out the distal end of the needle when the slide 528 is selectively actuated by a user. Such distal advancement of the guidewire 522 out the distal end of the needle 416 is stopped when the guidewire bend 522A abuts the holes 514A defined in the needle hub 514.

A catheter advancement assembly 540 is also shown for selectively advancing the catheter tube 44 over the needle 516, including a slide 548 that slides along the track 530, and a carriage 550 disposed within the housing 512 and operably connected to the slide. The carriage 550 can be initially engaged with the catheter hub 46 such that distal sliding of the slide 548 causes the catheter to be distally advanced toward the distal housing end. In the present embodiment a bulge 522B is included on the guidewire 522 such that, when the guidewire is distally advanced by user actuation of the (guidewire advancement) slide 528, the bulge is advanced and engages an internal portion of the (catheter advancement) slide 548. This in turn causes the slide 548 to be advanced as well, resulting in distal advancement of the catheter 42. Thus, the catheter can be advanced directly via the slide 548, or indirectly via the slide 528, in one embodiment.

The insertion tool 510 further includes a support structure 570 for stabilizing the needle 516, including a plug 572 that includes a plug hole 574 defined therein through which the needle 516 extends. The plug 572 is attached via the track 530 to the slide 528 and occludes the distal end of the housing 512, thus serving to stabilize the needle 516 that passes therethrough during needle insertion into the patient. Later, when the guidewire 522 is advanced distally by the slide 528, the plug 572 also distally advances out the housing 512, thus opening the housing distal end and enabling the catheter 42 to pass therethrough. The catheter 42 can then be separated by the user from the insertion tool 510 and advanced into final position by the user. Note that, though none is shown, a needle safety component can be included for isolating the distal tip of the needle 516. Note also that after the plug 572 is removed from its initial position in the housing 512, the catheter tube 44 and needle 516, no longer being constrained by the support structure plug hole 574, can axially relocate toward the center of the housing, in one embodiment. This holds true for the embodiments of FIGS. 30 and 31 as well.

Reference is now made to FIG. 30 in describing a catheter insertion tool 610 according to one embodiment. The insertion tool 610 includes a housing 612 that partially encloses the catheter 42. A hollow needle 616 distally extends from a needle hub 614 that caps a proximal end of the housing 612 such that the needle extends out the distal end of the housing 612. The needle 616 includes a longitudinally extending proximal slot 616A that extends from the proximal end of the needle 616 to a distal end 616B of the slot.

A guidewire advancement assembly 620 is shown for selectively advancing a guidewire 622, including a slide 628 that slides along a track 630 defined in the housing 612. The guidewire 622 is attached to the slide 628 and extends proximally within the housing 612 until it bends, forming a U-shaped guidewire bend 622A, toward the distal end of the housing and passes into the hollow needle 616 via the proximal slot 616A thereof for selective distal advancement past the distal end of the needle via user actuation of the slide. Note that distal advancement of the slide 628 causes the slide to separate from the housing 612 while still being attached to the guidewire 622. Distal advancement of the guidewire 622 out the distal end of the needle 616 is stopped when the guidewire bend 622A engages the distal end 616B of the proximal slot 616A of the needle.

A catheter advancement assembly 640 is also shown for selectively advancing the catheter tube 44 over the needle 616, including a carriage 650 disposed within the housing 612 and operably connected to the slide 628 such that actuation of the slide distally advances both the guidewire 622 and the carriage 650. The carriage 650 is not initially engaged with the catheter hub 46, but engages the hub after an amount of distal advancement. This in turn causes the catheter 42 to be distally advanced toward the distal housing end.

The insertion tool 610 further includes a support structure 670 for stabilizing the needle 616, including a plug 672 that includes a plug hole 674 defined therein through which the needle 616 extends. The plug 672 is attached via the track 630 to the slide 628 and occludes the distal end of the housing 612, thus serving to stabilize the needle 616 that passes therethrough during needle insertion into the patient. Later, when the guidewire 622 is advanced distally by the slide 628, the plug 672 also distally advances out the housing 612, thus opening the housing distal end and enabling the catheter 42 to pass therethrough. The catheter 42 can then be separated by the user from the insertion tool 610 and advanced into final position by the user. Note that, in one embodiment, the carriage 650 can include a needle safety component for isolating the distal end of the needle 616.

Figure 31:
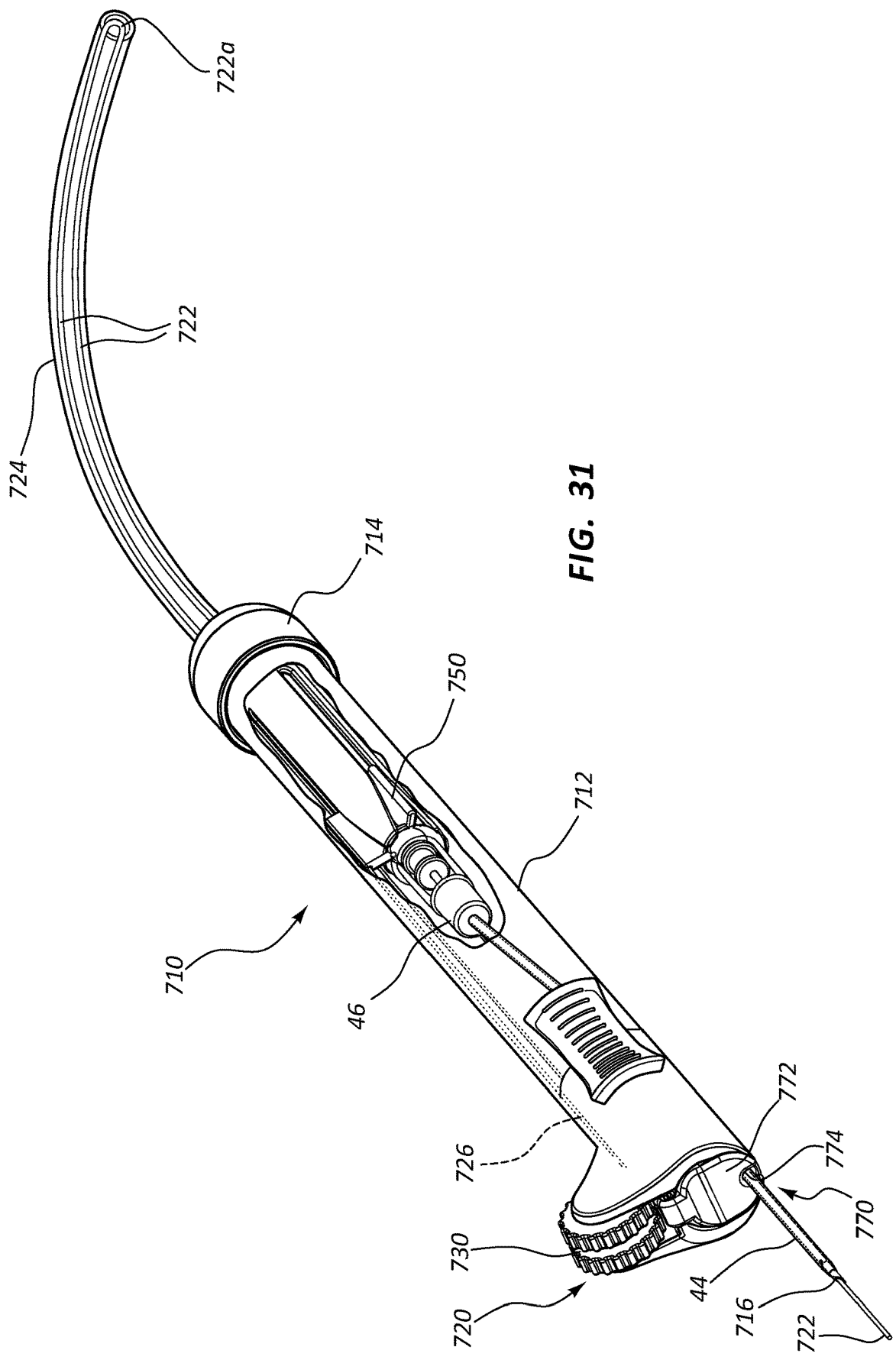
FIG. 31 is a perspective view of a catheter insertion tool according to one embodiment.

Reference is now made to FIG. 31 in describing a catheter insertion tool 710 according to one embodiment. The insertion tool 710 includes a housing 712 that partially encloses the catheter 42. A hollow needle 716 distally extends from a needle hub 714 that caps a proximal end of the housing 712 such that the needle extends out the distal end of the housing 712.

An advancement assembly 720 is shown for selectively advancing a guidewire 722 and catheter 42. The advancement assembly 720 includes a wheel 730, selectively rotatable by a user, that is attached via a filament 726 or other suitable component to a carriage 750. The guidewire 722 is attached to the carriage 750 and extends proximally within the housing 712 and out through a pigtail 724, attached to the proximal end of the housing 712, via a one of two holes defined in the needle hub 514 (similar to the holes 514A in the needle hub 514 of FIGS. 29A, 29B). Near the proximal end of the pigtail 724, the guidewire 722 bends to form a U-shaped guidewire bend 722A and distally extends back into the housing 712 to pass into the hollow needle 716 via the other of the two holes defined in the needle hub 714 for eventual distal advancement out the distal end of the needle when the wheel 730 is selectively actuated by a user. Such distal advancement of the guidewire 722 out the distal end of the needle 716 is stopped when the guidewire bend 722A abuts the above-mentioned holes defined in the needle hub 714.

The advancement assembly 720 selectively advances the catheter tube 44 over the needle 716 and includes the aforementioned carriage 750 disposed within the housing 712 and operably connected to the wheel 730 via the filament 726 such that rotation of the wheel distally advances the carriage 750. The guidewire 722, a proximal end of which being attached to the carriage 750, is also advanced distally through the needle, as described above. Note that in one embodiment the wheel 730, by virtue of the non-rigid filament 726 connecting the wheel to the carriage 750, ensures that the guidewire 722 is only distally advanced, and not proximally retractable.

Distal advancement of the carriage 750 causes the carriage—which is not initially engaged with the catheter hub 46—to engage the hub after an amount of distal advancement. This in turn causes the catheter 42 to be distally advanced toward the distal housing end.

The insertion tool 710 further includes a support structure 770 for stabilizing the needle 716, including a door 772 hingedly attached to the distal end of the housing 712 and including a hole 774 therein for enabling passage of the needle 716 therethrough. The door 772 serves to stabilize the needle 716 during insertion into the patient. Later, when the catheter tube 44 and catheter hub 46 are advanced distally by the wheel 730 and the carriage 750, the door 772 is pushed open by the hub, enabling the catheter 42 to be separated by the user from the insertion tool 710. The catheter 42 can then be advanced for final placement within the patient by the user. Note that, though none is shown, a needle safety component can be included for isolating the distal tip of the needle 716.

Reference is now made to FIGS. 32A-32I in describing a catheter insertion tool 810 according to one embodiment. The insertion tool 810 includes a housing 812 that at least partially encloses the catheter 42. A hollow needle 816 distally extends from a needle hub 814 included within the housing 812 such that the needle initially extends out the distal end of the housing 812. The needle 816 includes a distal slot 816A, similar to the previously described needle slot 226 (FIGS. 17A-17C), for enabling a guidewire/dilator 822, similar to the previously described guidewire/dilator 220 (FIG. 16) to be removably inserted therein. The catheter 42 is disposed over the guidewire/dilator 822.

The needle hub 814 further includes a needle retraction system 818 for selectively retracting the needle 816 into the housing 812 so as to isolate the distal tip of the needle from the user in a safe manner. The retraction system 818 includes a spring 819 or other suitable retraction device operably coupled to the needle 816 for effecting the needle retraction.

An advancement assembly 820 is shown for selectively advancing the guidewire/dilator 822 as well as the catheter 42. The advancement assembly 820 includes a slide 828 that travels in a track 830 defined in the housing 812. The slide 828 is operably attached to a ratchet bar 824 slidably disposed within the housing 812. The ratchet bar 824 includes a plurality of upper teeth 826 for selective catheter advancement, and at least one lower tooth 826A for actuating a retraction trigger 880 of the needle retraction system 818, as will be described. The hub 46 of the catheter 42 disposed within the housing 812 has removably attached thereto a cap 834 including a prong 836 for engaging the upper teeth 826 of the ratchet bar 824.

The insertion tool 810 further includes a support structure 870 for stabilizing the needle 816, including a housing hole 872 defined by the distal end of the housing 812. The housing hole 872 is sized to provide stability to the needle 816 at its point of exit from the housing.

Figure 32I:
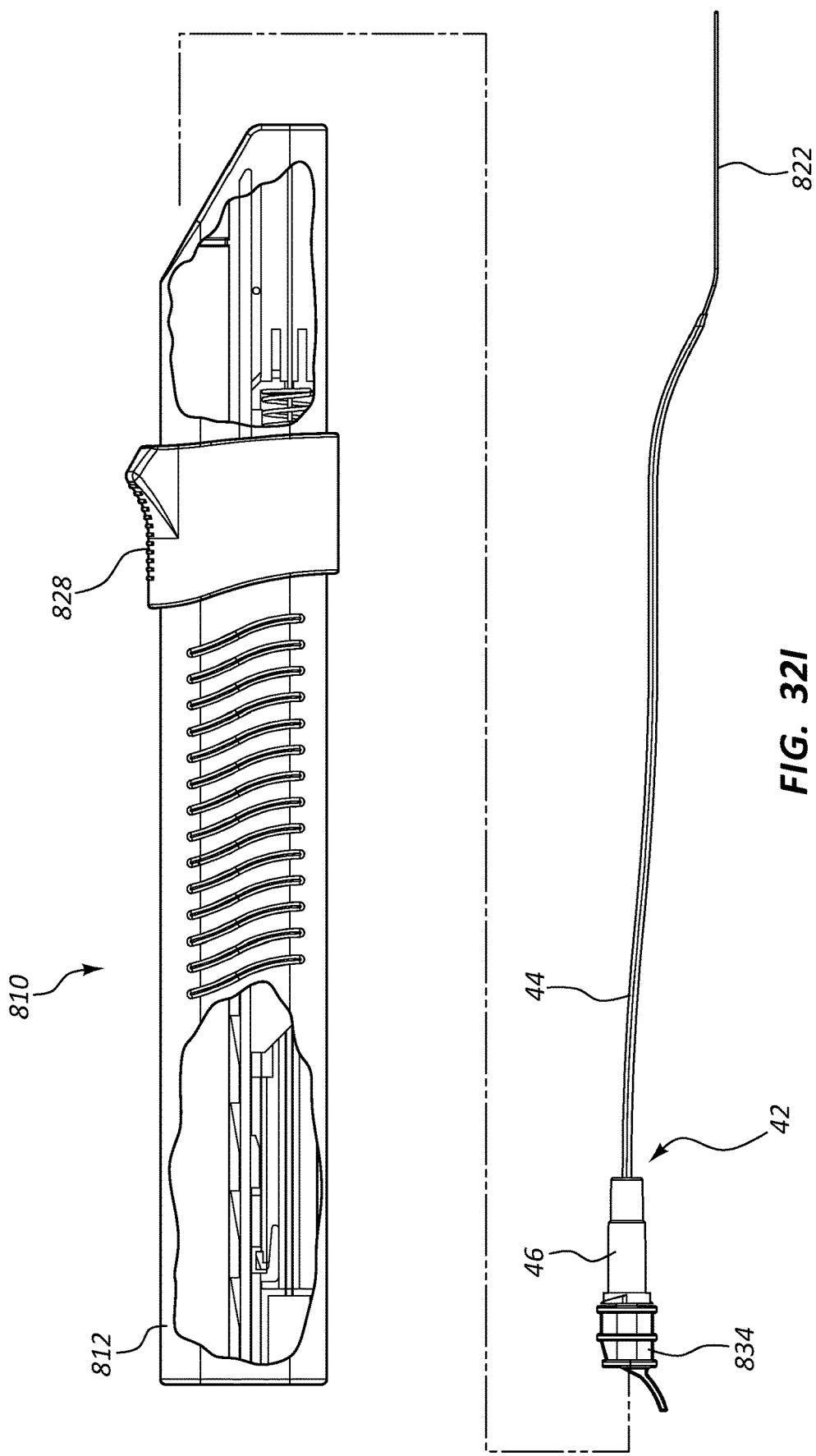

FIGS. 32A-32I depict various stages of use of the insertion tool 810 in inserting a catheter into a patient. With the insertion tool 810 in the configuration shown in FIG. 32A, vascular access is achieved with the needle 816 via user insertion of the needle into the patient at an insertion site. Blood flashback can be observed via the distal slot 816A of the needle 816 to confirm proper positioning of the distal end of the needle within the patient's vessel. As shown in FIG. 32B, the slide 828 is slid distally to advance the guidewire/dilator 822, a distal portion of which is pre-disposed within the needle 816 via the distal slot 816A, distally out the distal end of the needle and into the vessel of the patient. As shown, the guidewire/dilator 822 is advanced indirectly by the ratchet bar 824, which is moved by the slide 828. In particular, a proximate one of the upper teeth 826 of the ratchet bar 824 engages the prong 836 of the cap 834 fitted over the catheter hub 46. Thus, when the slide 828 and ratchet bar 824 are moved distally, the catheter 42 and guidewire/dilator 822 disposed therein are also moved distally, as shown in FIG. 32B. Similar ratcheting movement occurs in the successive steps as well.

Sliding of the slide 828 in the stage shown in FIG. 32B also causes the bottom tooth 826A of the ratchet bar 824 to engage the retraction trigger 880 of the needle retraction system 818. This in turn enables the spring 819 to expand and retract the needle 816 and retraction system 818 into the housing 812 such that the distal tip of the needle is isolated from the user within the housing.

FIG. 32C shows the return of the slide 828 to its initial position, which causes the ratchet bar 824 to also return to its initial position. Because the prong 836 of the cap 834 attached to the catheter hub 46 is distally angled, however, the teeth 826 of the ratchet bar slide past without retracting the catheter 42 such that the catheter remains in position.

In FIG. 32D, the slide 828 is again distally advanced, which causes a proximate upper tooth 826 of the ratchet bar 824 to engage the cap prong 836 and further advance the guidewire/dilator 822 distally into the vessel. As it is disposed over the guidewire/dilator 822, the catheter 42 at this or a successive stage is also advanced into the vessel, depending on catheter length, distance to insertion site, etc. The slide 828 is subsequently retracted to its initial position, as shown in FIG. 32E. Note that ratchet retraction can be user activated or automatically activated by a suitable system included in the insertion tool 810.

In FIG. 32F, the slide 828 and ratchet bar 824 are again distally advanced, resulting in further distal advancement out of the housing 812 of the guidewire/dilator 822 and catheter 42. The slide 828 is subsequently retracted to its initial position, as shown in FIG. 32G. In FIG. 32H, the slide 828 and ratchet bar 824 are distally advanced a final time, resulting in near-complete distal advancement of the guidewire/dilator 822 and attached catheter 42 from the housing 812 of the insertion tool 810. At this stage, the hub 46 of the catheter 42 can be grasped and the catheter removed from the insertion tool 810, which can then be discarded. Final positioning of the catheter 42 within the vessel can then be manually performed by the user. The cap 834 is also removed from the catheter hub 46.

Figure 33A:
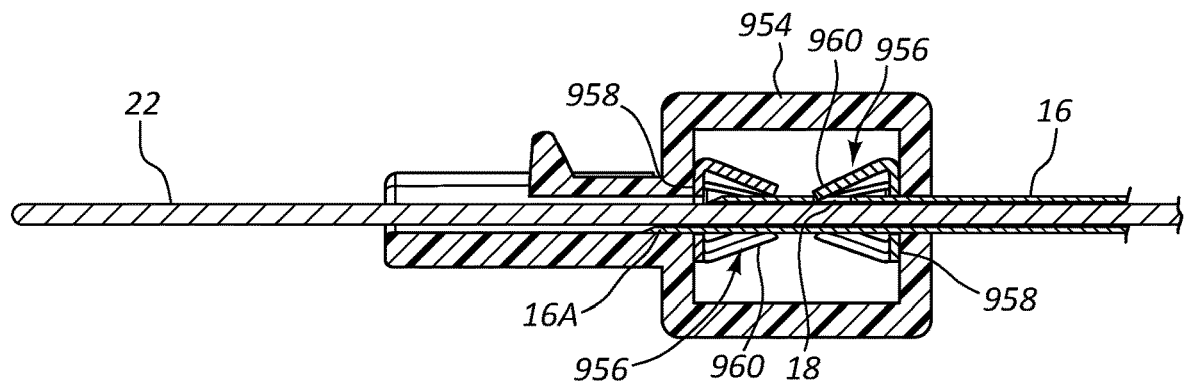
FIGS. 33A-33C are various views of a safety needle component according to one embodiment.
Figure 33B:
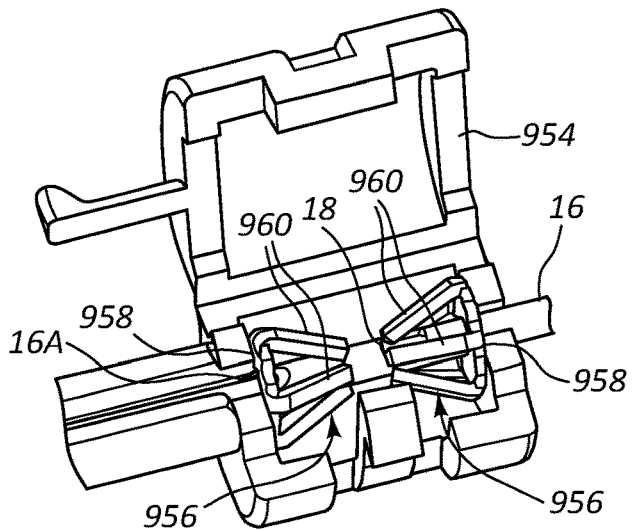
Figure 33C:
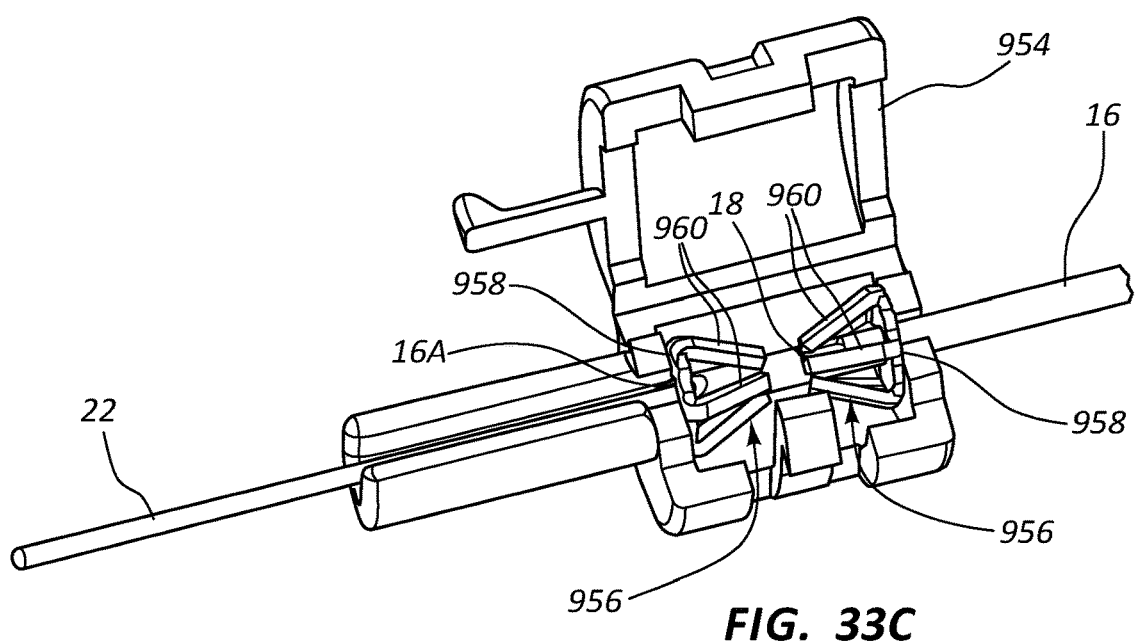

FIGS. 33A-33C depict details of a needle safety component for isolating the distal end 16A of the needle 16, the needle including the distal notch 18 as discussed above in connection with FIGS. 1A-10C, according to one embodiment. As shown, a safety housing 954 including a hinged door is included so as to ride over the needle 16. Two needle safety components 956 are oppositely disposed within the safety housing 954 and each also rides over the needle 16. Each needle safety component includes a base 958 defining a hole through which the needle 16 passes and a plurality of arms 960. The arms 960 extend from the base 958 and converge toward one another in conical fashion such that an end of each arm abuts the needle surface. The arms 960 are configured to engage the notch 18 defined in the distal portion of the needle 16 and prevent further movement of the needle 16 with respect to the needle safety component 956. In particular, each arm 960 compressively engages the outer surface of the needle 16 such that when one of the arms encounters the needle notch 18, the arm will descend into the notch slightly so as to lock the needle 16 in place with respect to the needle safety component 956. Two needle safety components 956 are disposed in the safety housing 954 so as to prevent further needle movement in either direction, distally or proximally. Thus, the distal end 16A of the needle 16 is safely isolated within the safety housing 954, as seen in FIGS. 33A-33C. Note that the needle safety component described here is useful for isolating a needle even when the guidewire 22 still extends therethrough, as seen in FIG. 33C, for example.

In other embodiments, only one needle safety component as described above may be used. Thus, the needle safety component described here serves as one example of a variety of needle safety components that may be employed in connection with the present disclosure.

It is appreciated that in one embodiment the insertion tool can include a sterile sheath or bag that is disposed over a distal portion of the catheter that distally extends from the insertion tool housing so as to isolate the catheter. The needle, pre-disposed within the catheter and retractable into the insertion tool housing, can extend from the bag to gain vascular access. Thereafter, the bag can be compressed toward the housing as the catheter is advanced into the vasculature, then disposed of once the catheter is fully inserted. In one embodiment, the bag can include a grip wing or other device that helps to grasp the catheter or needle through the bag during insertion. Further note that the insertion tools described herein can include a cap or other protective device that is removably attached to the insertion tool before use so as to preserve the sterility of the needle and catheter.

Figure 34:
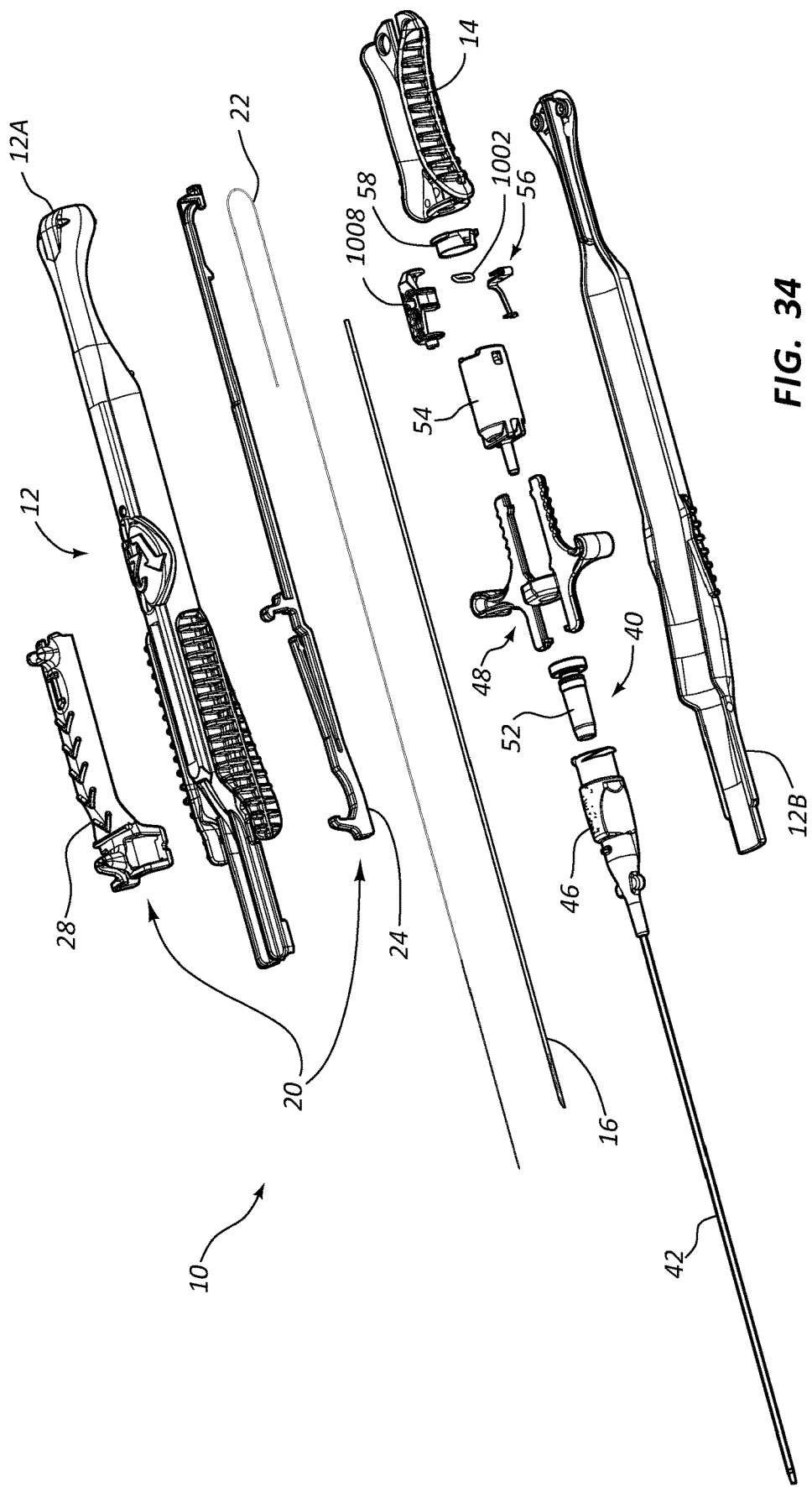
FIG. 34 is an exploded view of a catheter insertion device according to one embodiment.

Reference is now made to FIG. 34, which depicts an exploded view of the catheter insertion device 10 according to one embodiment, including components similar to those that have already been described above. As such, only selected differences are discussed below.

Figure 35:
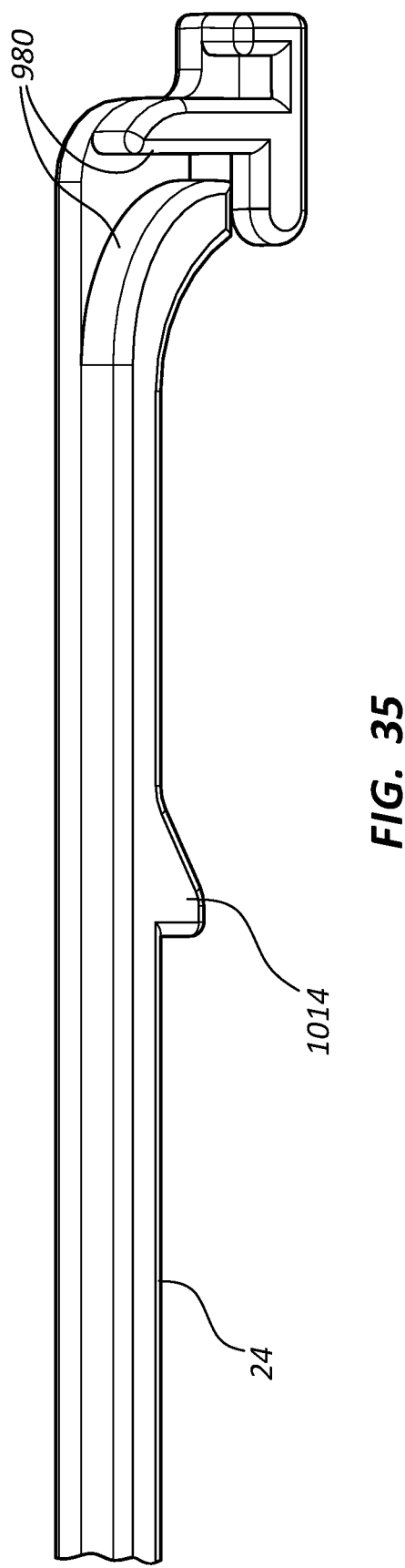
FIG. 35 is a perspective view of a portion of a guidewire lever according to one embodiment.
Figure 36A:
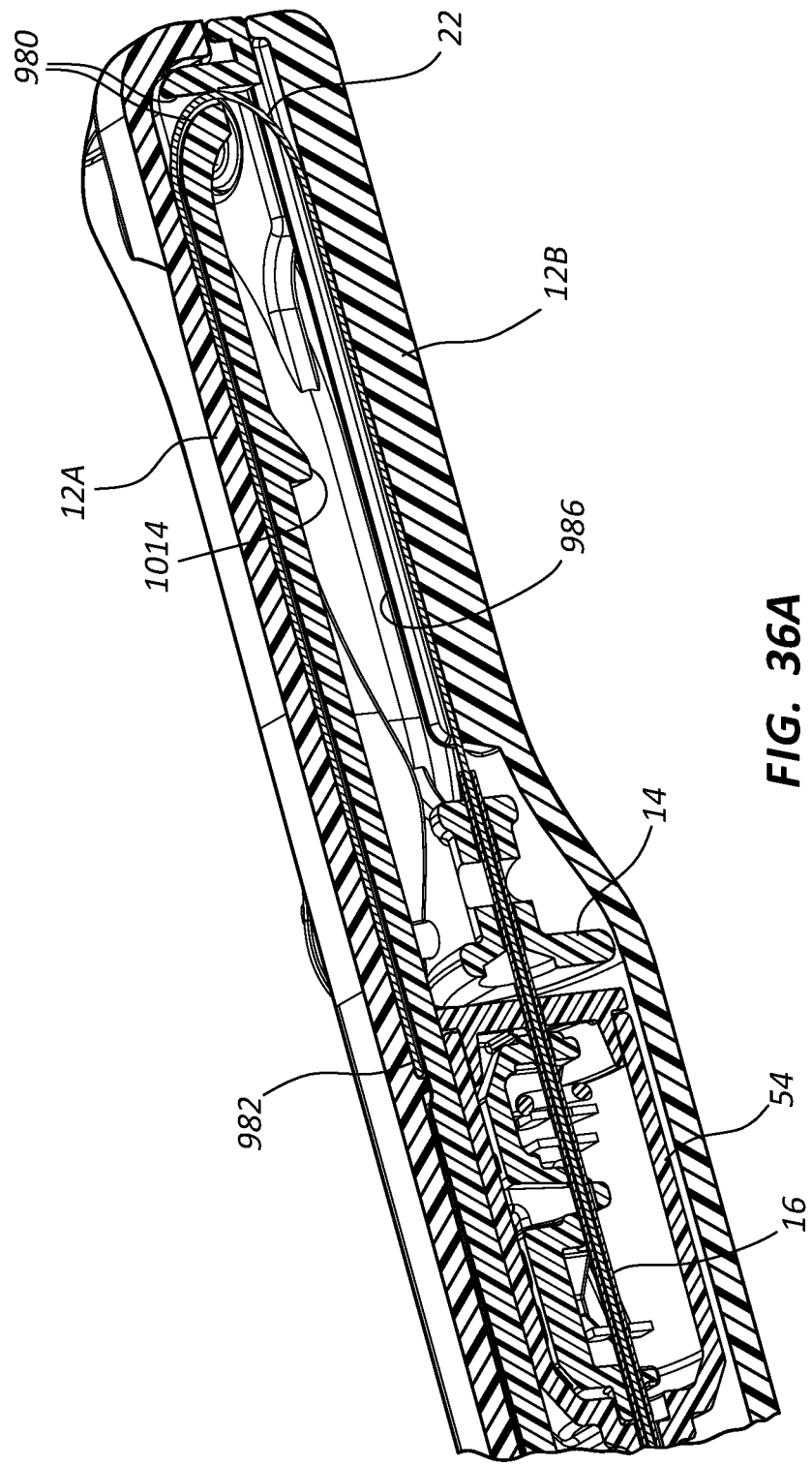
FIGS. 36A and 36B are cutaway views of a proximal portion of the catheter insertion device of FIG. 34.
Figure 36B:
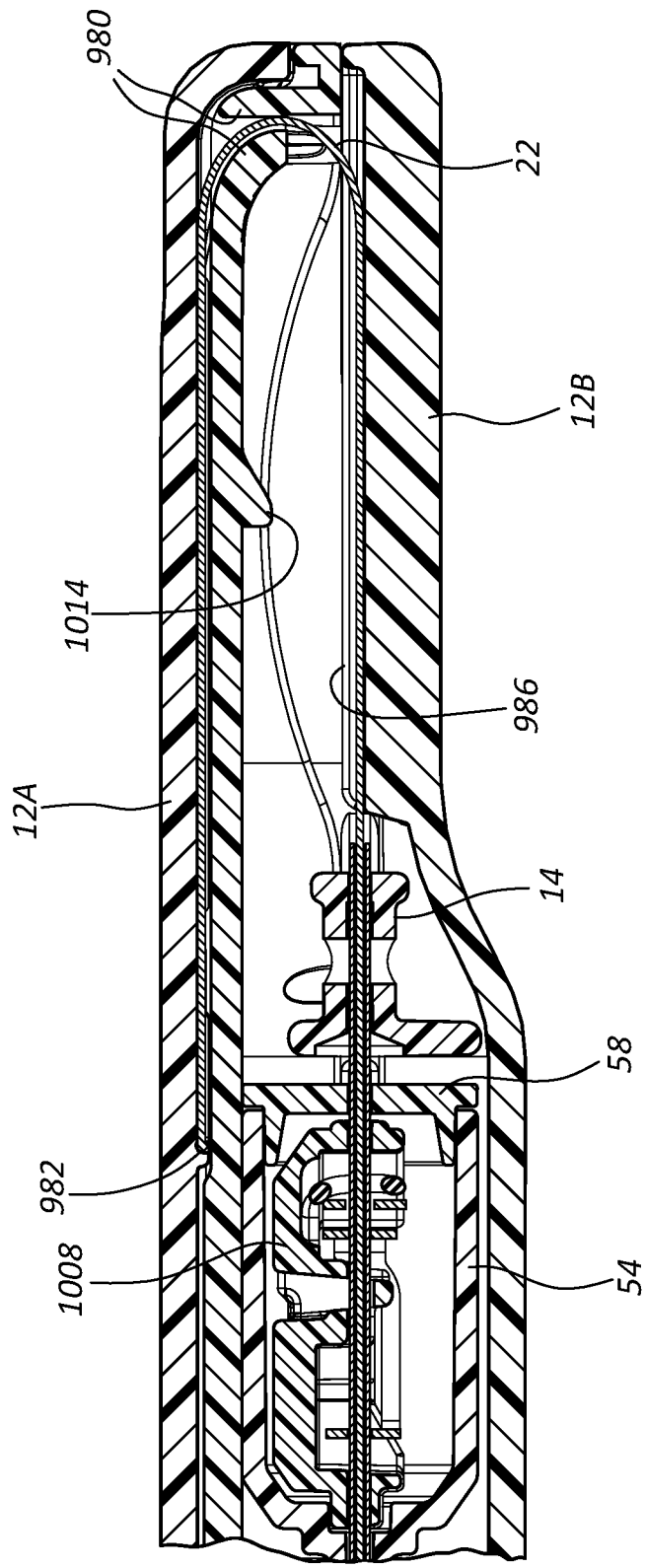
Figure 38:
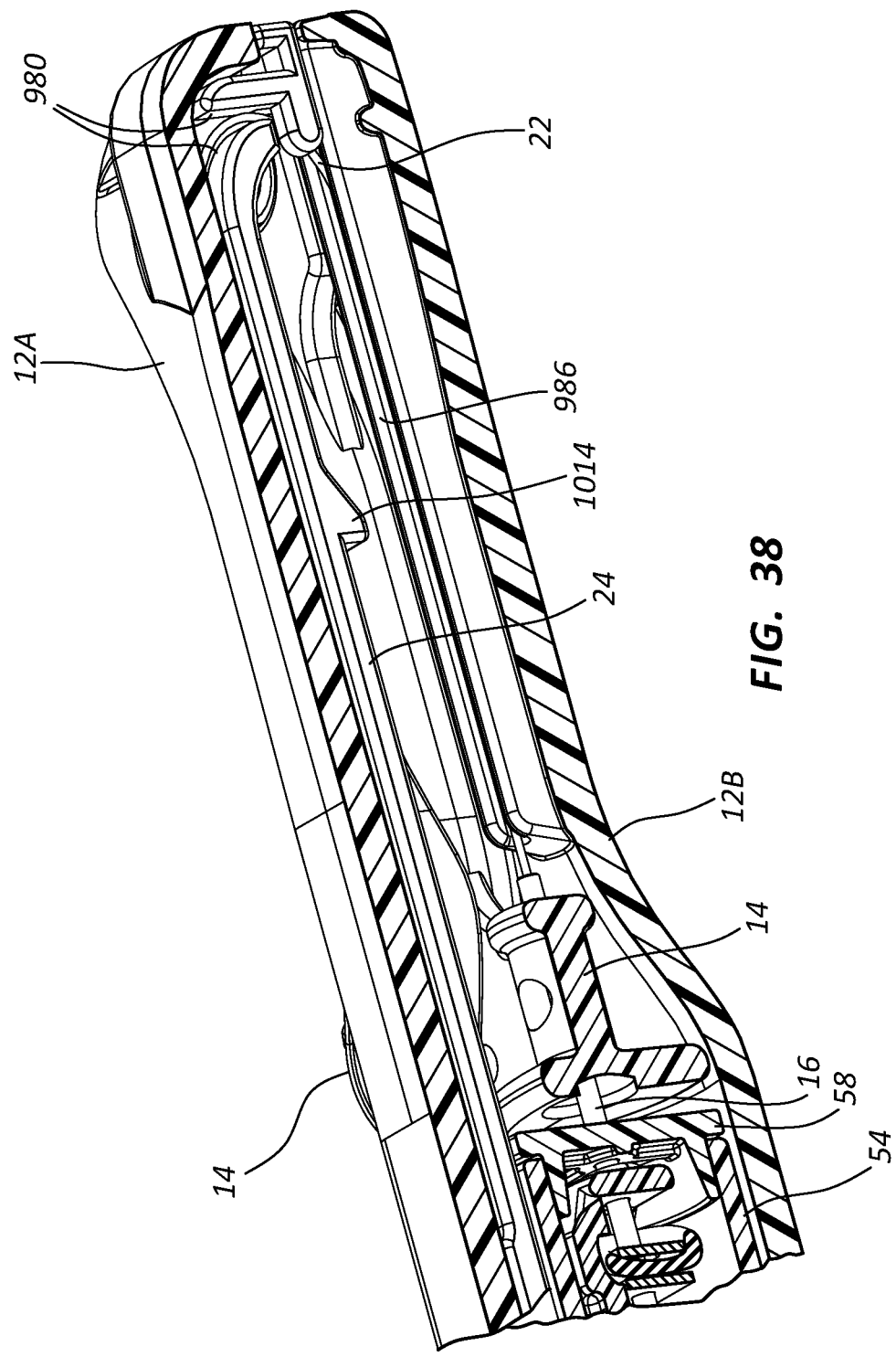
FIG. 38 is a cutaway view of a proximal portion of the catheter insertion device of FIG. 34.

FIG. 34 shows that in the present embodiment the guidewire 22 is looped back on itself to substantially define a U-shaped configuration. FIGS. 36A and 36B shows the manner in which the guidewire 22 is disposed within the housing 12 of the catheter insertion device 10. In particular, these figures show that a proximal end of the guidewire 22 is anchored to a portion of the device 10, namely, at an anchor point 982 on the top portion 12A of the housing 12. FIG. 37 shows that the guidewire 22 extends proximally and removably within a guide channel 984 defined on an interior surface of the top housing portion 12A. FIGS. 36A and 36B show that an intermediate portion of the guidewire 22 loops back on itself proximate the proximal end of the device 10. Guide surfaces 980 (FIG. 35) disposed near the proximal end of the guidewire lever 24 constrain the flexible guidewire 22 into the looped, substantially U-shaped configuration. The looped-back intermediate portion of the guidewire 22 then extends toward the distal end of the device 10 along a channel 986, best seen in FIG. 38, defined on an interior surface of the bottom housing portion 12B of the housing 12 before it passes into the hollow needle 16. The free distal end of the guidewire 22 initially resides within the needle 16.

So disposed as described immediately above, the guidewire 22 is positioned for selective advancement by the guidewire advancement assembly 20 such that the free distal end thereof can distally extend from the open distal tip of the needle 16. This selective advancement of the guidewire 22 is achieved in the present embodiment via distal movement of the guidewire advancement slide 28 included on the device housing 12. Distal movement of the guidewire advancement slide 28 causes corresponding distal sliding movement of the guidewire lever 24. The guide surfaces 980 of the guidewire lever 24 push the bend of the guidewire 22 distally as the lever advances. Note that the guidewire 22 is sufficiently rigid so as to be advanced by the guidewire lever 24 without buckling. Also, the guide surfaces 980 and guidewire 22 are configured to enable retraction of the guidewire 22 back into the insertion tool housing 12 when the guidewire advancement slide 28 or other suitable mechanism is slid proximally.

This pushing movement of the slidable guidewire lever 24 causes the distal end of the guidewire 22 to extend distally from the open distal tip of the needle 16. Because of its anchored proximal end at anchor point 982 and its bent or looped U-shape configuration, the guidewire 22 is distally advanced at a rate of about twice the rate of sliding of the guidewire advancement slide 28 and about twice the rate of guidewire advancement in the device configuration of FIGS. 1A-9, which results in about twice the length of guidewire extension when compared with the length of movement of the guidewire advancement slide 28. This further desirably results in a relatively longer length of guidewire extension into the vein or other patient vessel so as to more suitably guide the catheter 42 into the patient's body. As such, the guidewire and advancement assembly described here operates as a type of "reverse pulley" system for distal guidewire advancement. Note that other looping configurations of the guidewire can be included with the device 10 in addition to those shown and described herein. Also, differing ratios of guidewire extension vs. advancement assembly movement are also possible in other embodiments.

Note that the looping conduit and guidewire advancement handle are only examples of structures that can suitably perform the desired functionality described herein. Indeed, other structures can be employed to accomplish the principles described in connection with the present embodiment. Also, though shown and described above to be attached to the catheter insertion device housing, the proximal end of the guidewire can be attached to other structures within/on the device, such as the needle hub 14, for instance. The majority length of the guidewire in one embodiment includes a metal alloy of nickel and titanium commonly referred to as nitinol, which is sufficiently rigid and can be disposed in the U-shaped configuration without retaining a memory of that position when the guidewire is advanced. Note that other suitable guidewire materials can also be employed.

Figure 39B:
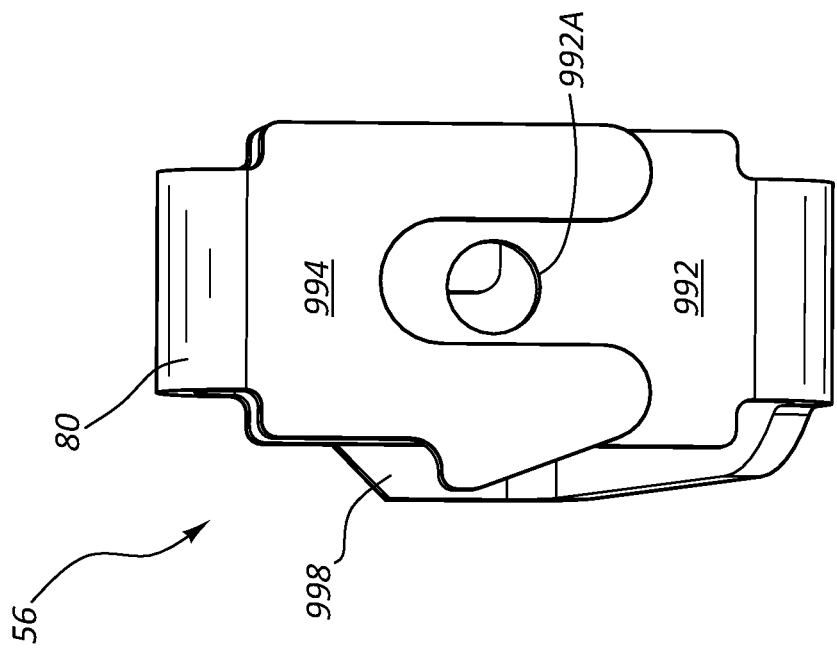
FIGS. 39A and 39B are various views of a needle safety component according to one embodiment.
Figure 39A:
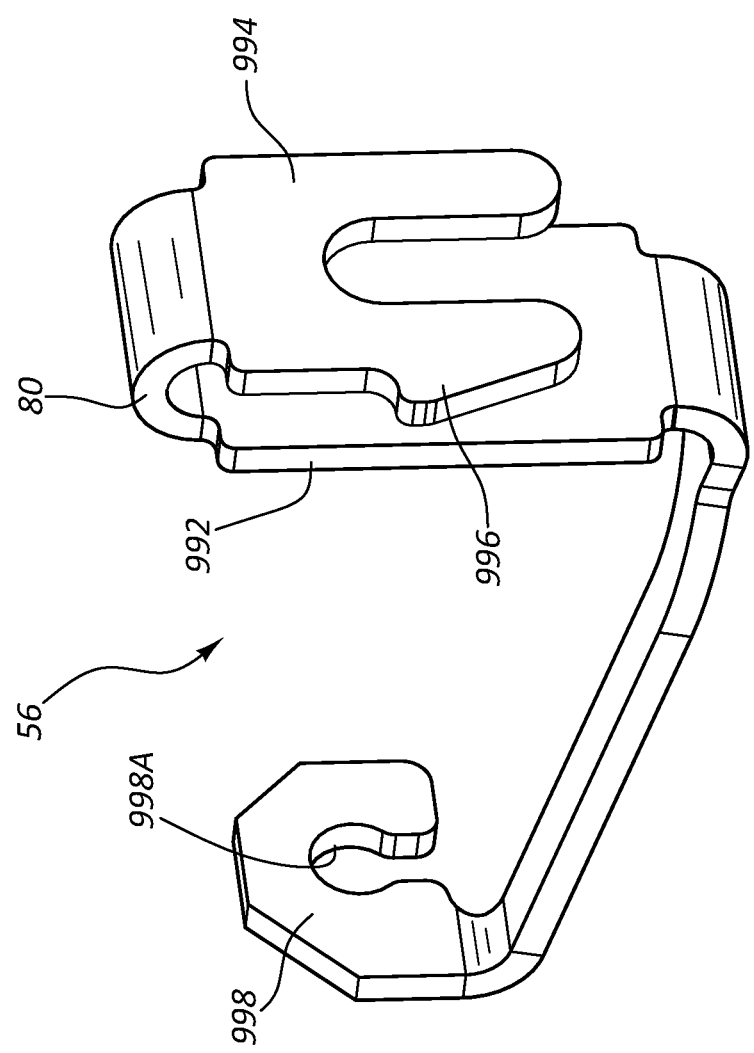

FIGS. 39A and 39B depict various details regarding the binding element 80, described further above, of the needle safety component 56 for shielding the distal tip of the needle 16 once catheter insertion is complete. As shown, the binding element 80 (which is also referred to herein as a binding member) includes a front plate 992 defining a hole 992A, and a forked back plate 994. A protuberance 996 extends from one of the forks of the back plate 994. A horseshoe-shaped needle pass-through element 998 is also included in a spaced-apart arrangement from the front plate 992 and defines a hole 998A in coaxial alignment with the hole 992A of the front plate.

Figure 40B:
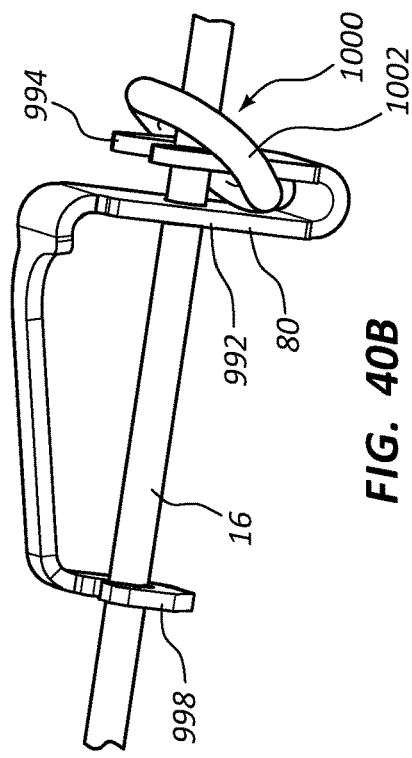
FIGS. 40A-40D are various views of the needle safety component of FIGS. 39A and 39B and an accompanying carriage.
Figure 40D:
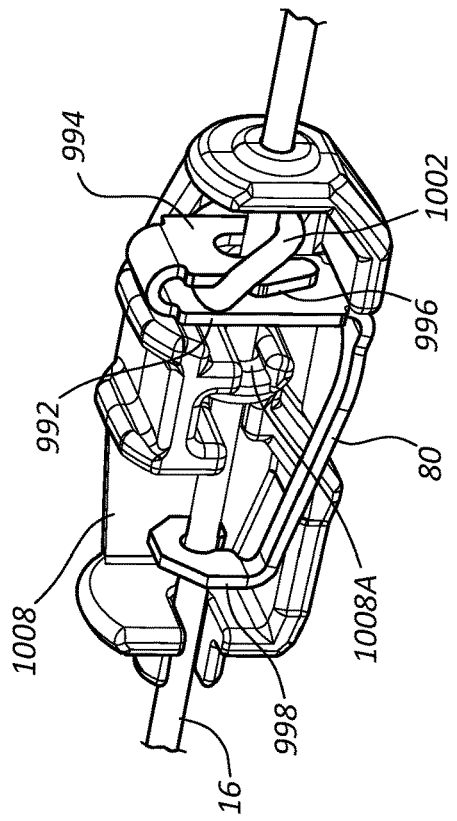
Figure 40A:
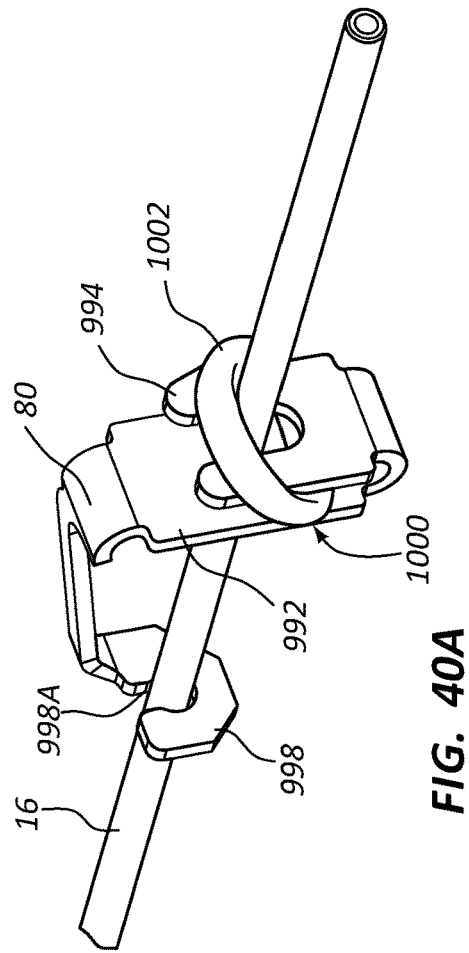

A friction element 1000, also referred to herein as a friction member, is also included with the binding element 80 in the present embodiment, namely, an annular elastomeric element, or O-ring 1002, as seen in FIGS. 40A and 40B. As shown, the O-ring 1002 is configured to wrap around both a portion of the needle 16 and the forked back plate 994. The protuberance 996 is employed to aid in maintaining the O-ring 1002 in place as shown in FIGS. 40A and 40B. With the O-ring 1002 so positioned, a relatively constant urging force is imparted by the O-ring to the binding element 80, for use in shielding the distal tip of the needle 16, as will be described further below. Note that the elastomeric element can take forms other than an O-ring while performing the same functionality. For instance, a rod or length of elastomeric material that is wrapped about a portion of the binding element and the needle could also be employed.

Figure 40C:
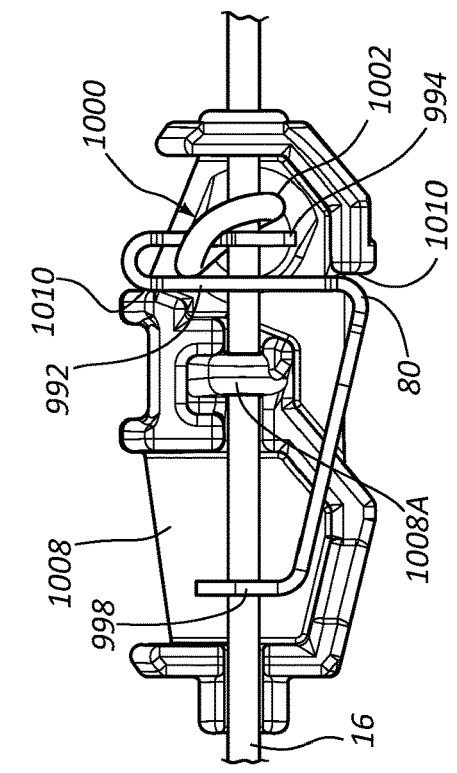

FIGS. 40C and 40D show the binding element 80 disposed in the carriage 1008, which is in turn disposed within the safety housing 54. As shown, the carriage 1008 defines two constraining surfaces 1010 against which corresponding portions of the front plate 992 of the binding element initially rest when the needle 16 initially extends through the carriage and the binding element. A retaining ring 1008A through which the needle 16 slidably passes enables engagement of the needle with the carriage 1008.

The binding element 80 is initially slidably disposed with the needle 16 in the state shown in 40A-40D (showing the binding element before it has shielded the distal tip of the needle) such that relative sliding movement between the needle and the binding element is permitted. Passage of the needle 16 through the hole 998A of the needle pass-through element 998 initially limits canting movement of the binding element 80.

The needle 16 also passes through the hole 992A of the front plate 992 such that the needle is straddled by the forks of the forked back plate 994. As mentioned, the O-ring 1002 is disposed about the needle 16 and the back plate 994 so as to provide a drag force when the carriage 1008 and binding element 80 (both housed within the safety housing 54 (FIG. 34) are slid distally along the length of the needle 16 during use of the device 10. The drag force provided by the O-ring 1002 during such distal sliding in turn imparts a rotational moment on the binding element 80 (by virtue of forces provided via the contact of the binding element with the O-ring) to urge the binding element to rotate in a clockwise motion, from the perspective of the drawing shown in FIG. 40C.

Such clockwise rotation of the binding element 80 is prevented by the needle pass-through feature 998 while the needle 16 extends through the binding element. Once the safety housing 54 containing the carriage 1008 and binding element 80 has been slid distally a sufficient distance such that the needle pass-through element 998 slides past and off the distal end of the needle 16, however, the binding element is no longer constrained and the drag force imparted by the O-ring 1002 causes the binding element to cant clockwise with respect to the needle, from the perspective of the drawing shown in FIG. 40C. This canting locks movement of the binding element 80 and, by extension, the carriage 1008, with respect to the needle 16, by virtue of physical binding between the outer surface of the needle 16 with the perimeter of the front plate hole 992A, which thus acts as a binding surface. With the distal tip of the needle 16 safely disposed within the locked carriage 1008, the user is thus protected from an accidental needle stick.

As mentioned above, the O-ring 1002 imparts a relatively constant urging force for canting the binding element 80, which keeps the binding element canted (after withdrawal of the needle distal tip into the carriage as described above) so as to more securely lock the carriage 1008 over the distal tip of the needle 16. This constant urging force is beneficial, for example, in instances when the needle 16 is pushed back and forth with respect to safety housing 54/carriage 1008 after it has been locked over the needle distal tip to ensure that the binding element does not return to an orientation in which the needle pass-through feature 998 can re-engage the needle 16 and unlock the needle safety component 56. Note that the O-ring 1002 can be employed with needles and binding elements larger or smaller than those shown and described herein.

The O-ring 1002 in the above embodiments is sufficiently compliant so as to stretch over the aforementioned structures while imparting the desired force, as explained above. In one embodiment, the O-ring 1002 material includes any one or more of natural or synthetic rubber, elastomers, polymers, thermoplastics, silicones, etc. In one embodiment, the O-ring material is selected so as to provide sufficient tear resistance, ability to impart the desired friction, and chemical compatibility. The size of the O-ring can vary according to the size and configuration of the binding element and needle. In other embodiments, the O-ring can include other shapes, materials, and positional placements while still providing the intended functionality.

Figure 41A:
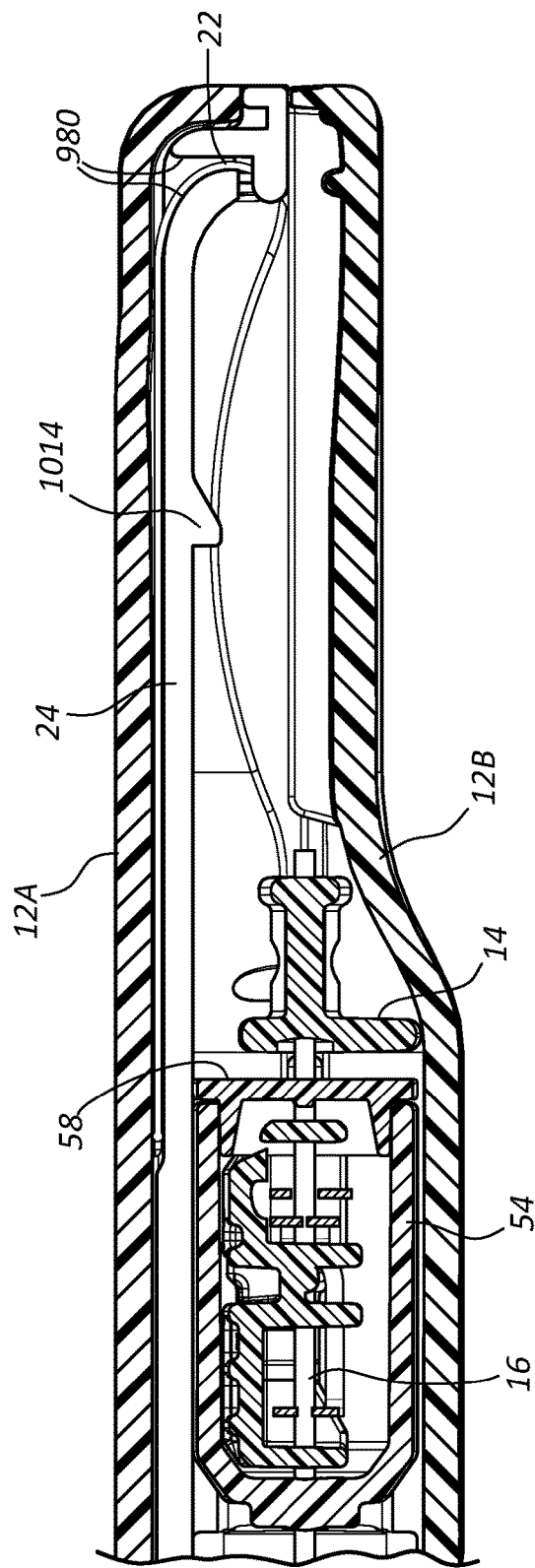
FIGS. 41A and 41B are cutaway views of a proximal portion of the catheter insertion device of FIG. 34.
Figure 41B:
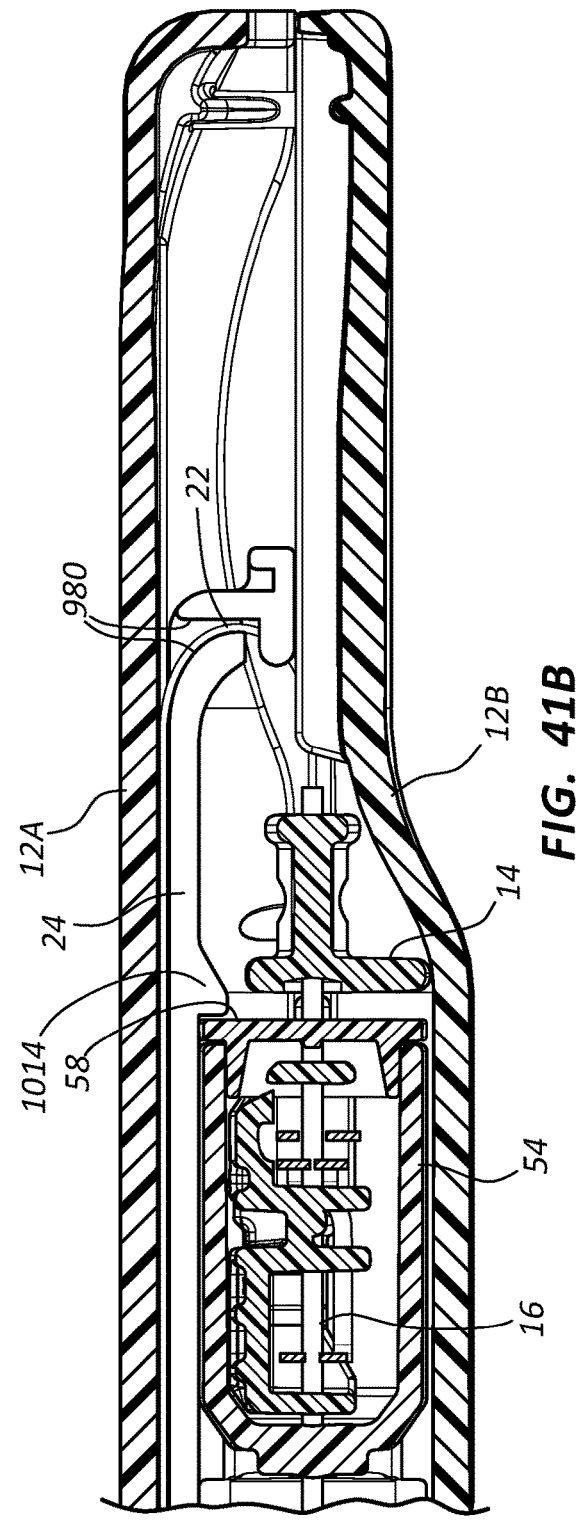

FIG. 41A shows that the guidewire lever 24 can include a catheter advancement feature that enables the guidewire lever to distally advance the catheter 42 in addition to advancing the guidewire 22 as described above. In the present embodiment, the catheter advancement feature includes an advancement tab 1014 disposed on the proximal portion 24A of the guidewire lever 24 and disposed so as to physically engage the cap 58 of the safety housing 54 when the guidewire lever 24 is moved distally via distal sliding by the user of the slide 28 (FIG. 34). Such engagement is shown in FIG. 41B. Further distal movement of the guidewire lever 24 results in distal advancement of the safety can 54 and the catheter 42 indirectly but operably attached thereto (FIG. 34). The slide 28 in the present embodiment can be slid to distally advance the catheter 42 a predetermined distance via the advancement tab 1014 of the guidewire lever 24. In one embodiment, the predetermined distance advances the catheter 42 until its distal end distally advances over the distal tip of the needle 16. Further distal advancement of the catheter 42 can be achieved via distal sliding of the handle 48 as needed (FIG. 34). In another embodiment, the slide 28 is configured to distally advance the catheter the full distal distance needed, via the advancement tab 1014.

The position of the advancement tab 1014 of FIG. 41A is such so as to provide staged advancement of the guidewire 22 and catheter 42. In particular, distal advancement of the guidewire lever 24 from the position shown in FIG. 41A produces immediate advancement of the guidewire 22 while the safety housing 54 and catheter 42 remain in place. Further distal advancement of the guidewire lever 24 to the position shown in FIG. 41B causes the advancement tab 1014 to engage and distally advance the safety can 54 and catheter 42, as described above, while continuing to distally advance the guidewire 22.

Thus, in addition to distally advancing the guidewire 22 out through the needle 16, the guidewire lever 24 can also advance the catheter 42 distally along the needle 16 and into a vessel of the patient, as described further above. Note that the particular shape and configuration of the advancement tab 1014, together with its manner of engagement with, and magnitude of travel imparted to, the safety housing and/or catheter can vary from what is shown and described herein.

Figure 42:
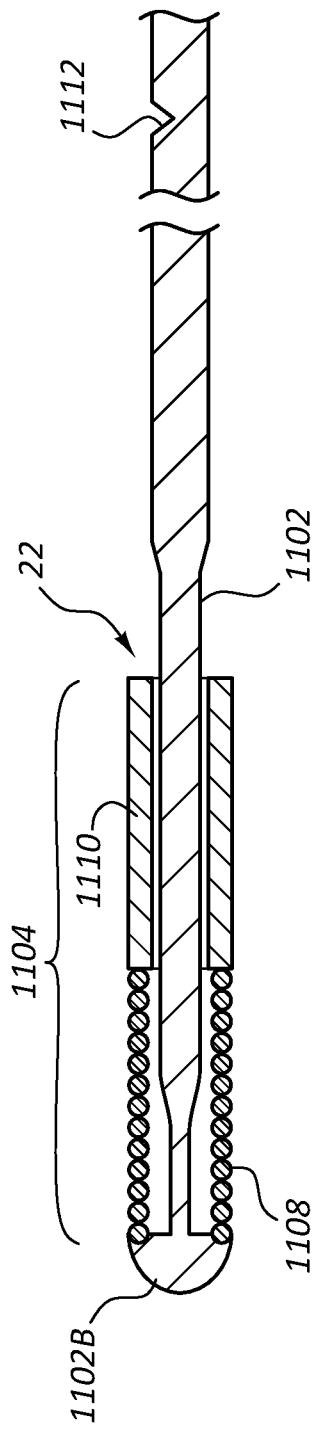
FIG. 42 is a cross-sectional view of a guidewire for use with a catheter insertion tool according to one embodiment.
Figure 43:
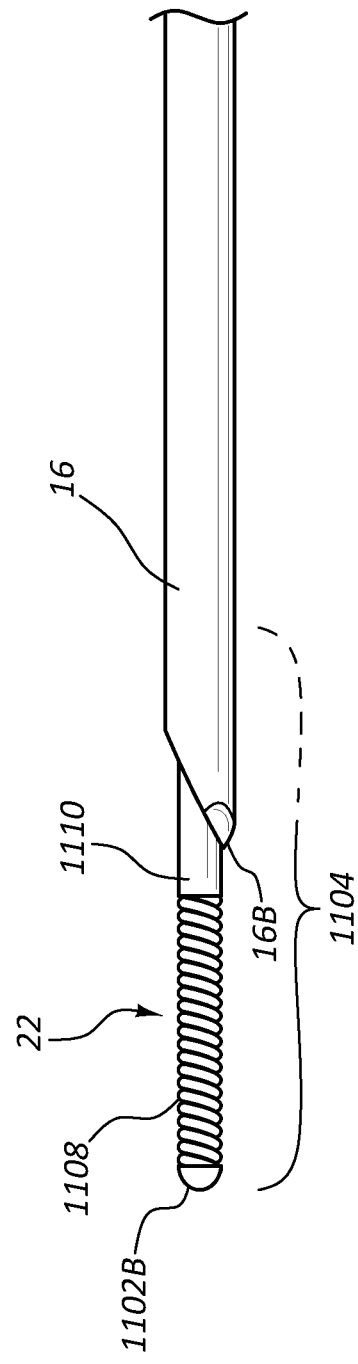
FIG. 43 is a side view of the guidewire of FIG. 42 partially disposed within a needle.

FIGS. 42 and 43 depict details of the guidewire 22 configured in accordance with one embodiment. As shown in FIG. 42, the guidewire 22 includes an elongate core wire 1102 that includes a reduced-diameter distal portion 1104. An outer coil 1108 extends about the core wire 1102 proximally from the distal end 1102B thereof. A stiffening sleeve 1110 is disposed about the core wire 1102 proximal and adjacent to the coil 1108 within the reduced-diameter distal portion 1104. The stiffening sleeve 1110 can be glued, welded, press-fit, or otherwise secured to the core wire 1102.

The portion of the guidewire 22 on which the coil 1108 is included is designed so as to be relatively flexible so as to non-traumatically enter a vein or other vessel of a patient and to guide the catheter 42 into the vein during catheter insertion using the insert tool described herein. In contrast, the portion of the guidewire 22 on which the stiffening sleeve 1110 is included is relatively rigid. As seen in FIG. 43, the stiffening sleeve 1110 is positioned so that it is disposed adjacent the distal tip 16B of the needle 16 of the insertion tool upon full extension of the guidewire 22 during insertion tool use. Together with the back-cut bevel of the needle distal tip 16B, the stiffening sleeve 1110 effectively blunts the needle distal tip, thus preventing inadvertent piercing or shearing of the catheter tube 44 by the needle distal tip during catheter insertion into the vein. The stiffening sleeve 1110 can be sized so as to substantially occupy the whole of the diameter of the needle lumen at the distal tip 16B so that it effectively prevents the needle distal tip from being able to pierce the catheter tube 44, even if the catheter tube is retracted while disposed over the needle, or if the needle is re-inserted into the catheter tube. Note that, in another embodiment, the core wire itself can be used to blunt the needle distal tip. In one embodiment, the coil 1108 can include platinum, stainless steel, titanium, nitinol, or other material having suitable tensile strength and formability. In one embodiment, the stiffening sleeve 1110 includes stainless steel, titanium, high-rigidity thermoplastic, or other suitable material, and the core wire 1102 includes nitinol, though other suitable materials may be used for these and other related components.

FIG. 42 further shows that the core wire 1102 of the guidewire 22 can include a notch 1112 disposed proximal to the distal portion 1104 of the core wire. The notch 1112 serves as a relative weak point for preferential breaking of the guidewire 22 at the notch should the guidewire be subjected to excessive physical forces. By breaking at the notch 1112, the broken-off distal segment of the guidewire is large enough as to not be embolized into the vessel of the patient and can be readily removed manually from the body. The particular location of the notch on the guidewire can vary.

Figure 44:
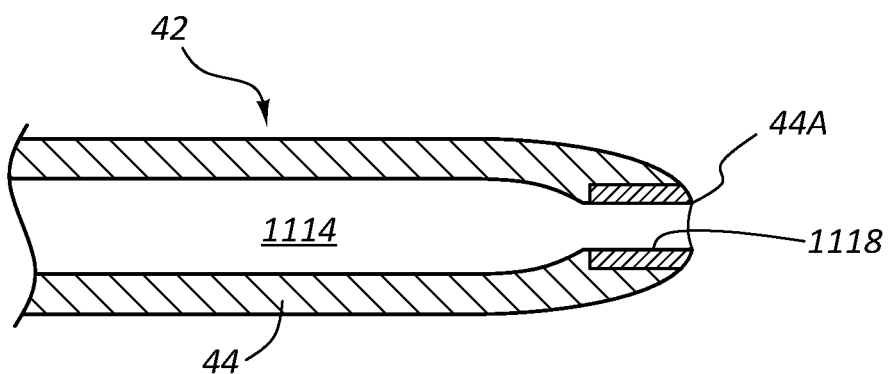
FIG. 44 is a cross-sectional view of a distal portion of a catheter tube including a reinforcement component according to one embodiment.

FIG. 44 shows that, in one embodiment, the distal end of the catheter tube 44 of the catheter 42 of the insertion tool can include a reinforcement component 1118 disposed substantially at the distal end 44A of the catheter tube. As shown in FIG. 44, the reinforcement component 1118 here includes an annular sleeve that defines the distal end 44A of the catheter tube 44. Including a sufficiently rigid material, such as aromatic polyurethane, carbothane, isoplast, pebax, nylon, or other suitable medical grade thermoplastic, metals including stainless steel, titanium, nitinol, etc., the reinforcement component 1118 is positioned and designed to prevent collapse of the distal end 44A of the catheter tube 44 during fluid aspiration through a lumen 1114 of the catheter tube after the catheter 42 has been placed within the patient vasculature. In one embodiment, the reinforcement component 1118 includes a material that is non-softening at internal body temperature, includes a similar melt temperature to that of the material of the catheter tube 44, and is biocompatible. In one embodiment, the reinforcement component 1118 includes a material having a hardness between about 60D and about 75D Shore hardness, though other hardness ratings are possible. In another embodiment, the reinforcement component 1118 can include a radiopacifier, such as bismuth trioxide, barium sulfate, etc., to enhance radiopacity of the distal end 44A of the catheter tube 44.

Figure 45A:
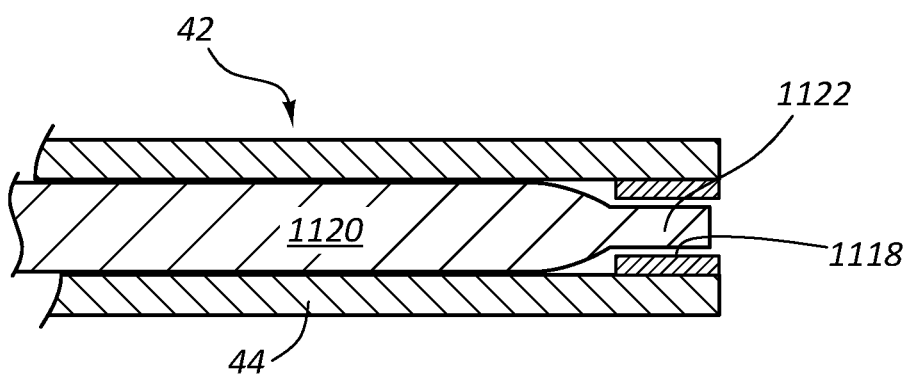
FIGS. 45A and 45B show various stages of manufacture of the catheter tube of FIG. 44.
Figure 45B:
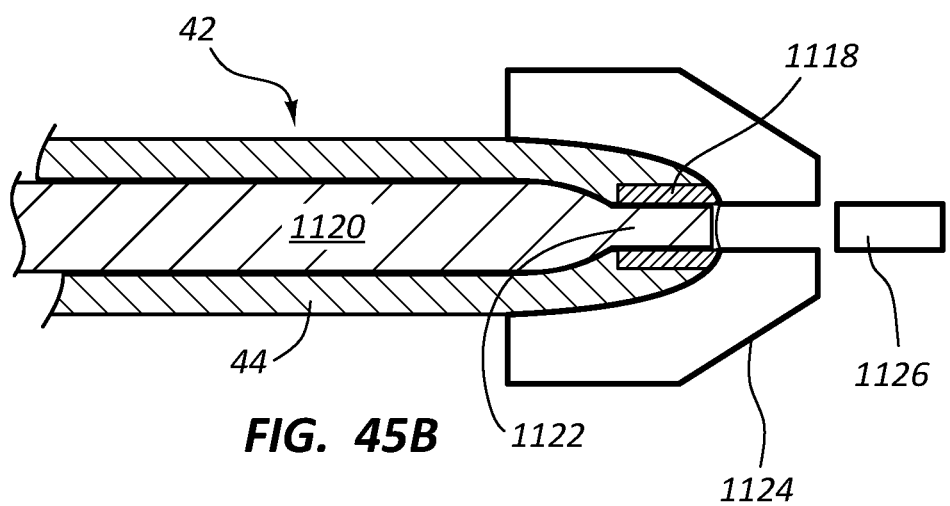

FIGS. 45A and 45B depict details regarding the manufacture of the catheter tube 44 of FIG. 44, according to one embodiment, though other techniques can be employed. As shown, during manufacture a shaped mandrel 1120 is disposed within the lumen 1114 of the catheter tube 44. The pre-formed, annular reinforcement component 1118 is disposed about a tip portion 1122 of the mandrel 1120 as to be interposed between the mandrel and the catheter tube 44 and substantially co-terminal with the distal end 44A thereof, in the present embodiment. In other embodiments, the reinforcement component 1118 can also positioned so as to produce a finished reinforcement component position that terminates proximal to the distal end 44A of the catheter tube 44, co-terminal therewith, or distal thereto, so as to customize a desired reinforcement profile, or to accommodate processing parameters, etc.

A tipping die 1124 is then paced over the distal end of the catheter tube 44, and a radio frequency ("RF") tipping process is carried out so as to form the distal end of the catheter tube with the reinforcement component 1118 included therein, as shown in FIG. 44. A plug 1126 of excess material is often created as a result of the tipping process, and can be discarded. In addition to this, other processes can be employed to form the reinforcement structure with the distal end of the catheter tube.

Figure 46:
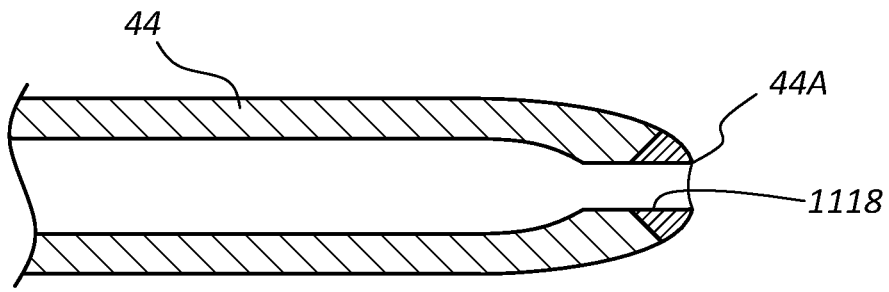
FIG. 46 is a cross-sectional view of a distal portion of a catheter tube including a reinforcement component according to one embodiment.
Figure 47A:
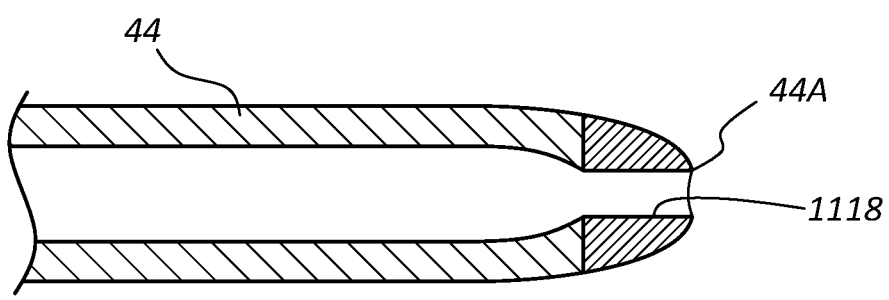
FIGS. 47A and 47B show cross-sectional views of distal portions of catheter tubes including a reinforcement component according to additional embodiments.
Figure 47B:
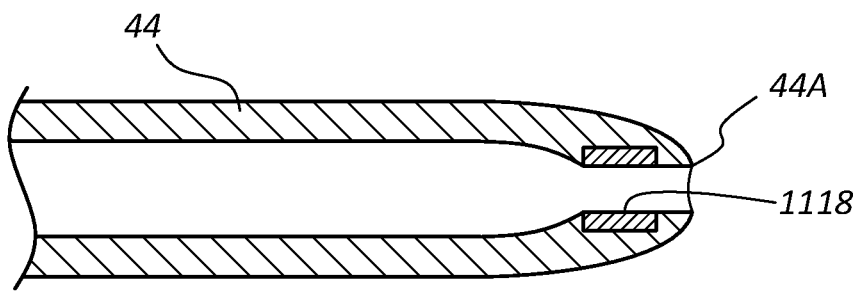

Other embodiments of reinforcement structures for the distal end 44A of the catheter tube 44 are possible, such as the reinforcement components 1118 shown in FIGS. 46 and 47A, for example. FIG. 47B shows another embodiment, wherein the reinforcement component 1118 is set back proximal to the distal end of the catheter tube 44, thus illustrating that the reinforcement component need not be disposed at the distal end of the catheter tube in one embodiment. As such, these and other reinforcement designs are therefore contemplated.

Figure 48A:
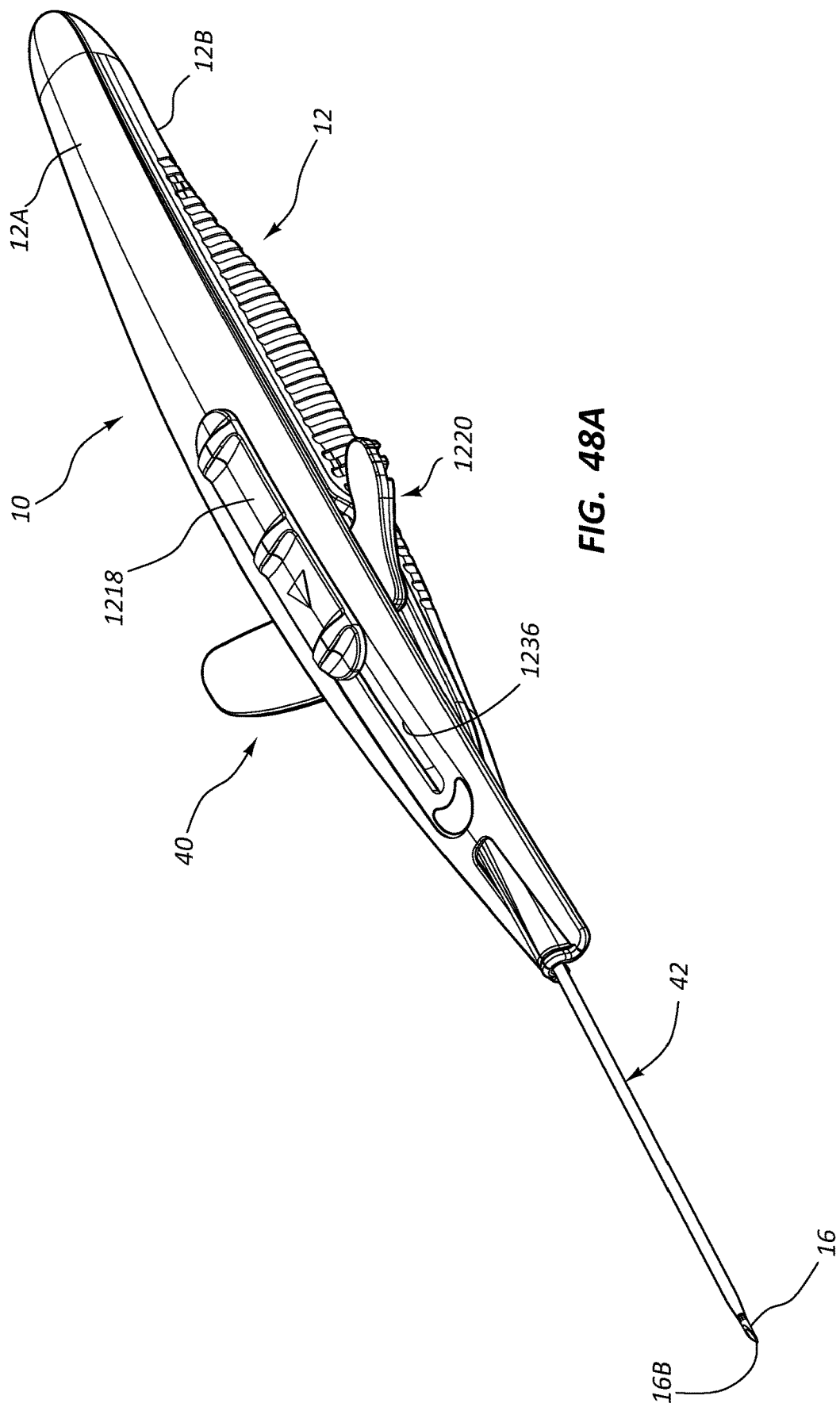
FIGS. 48A-48F are various views of a catheter insertion tool according to one embodiment.
Figure 48B:
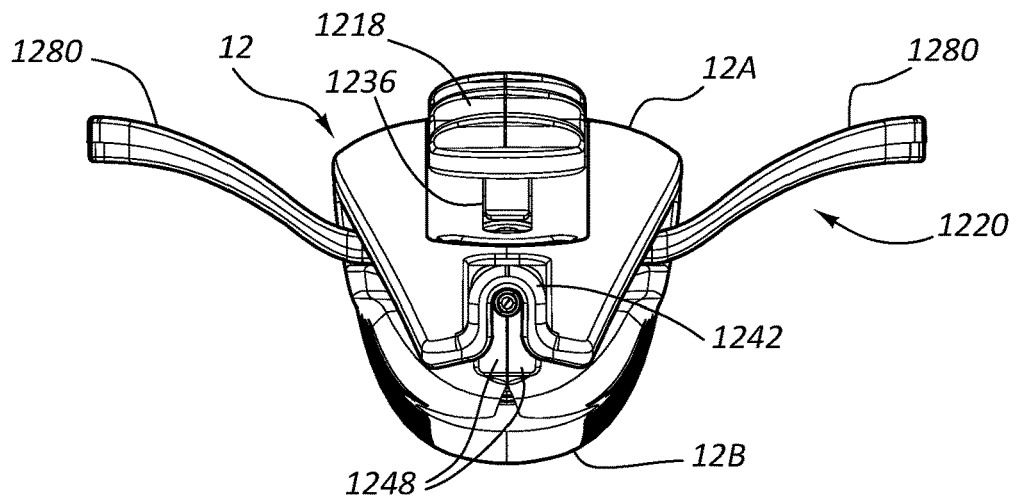
Figure 48C:
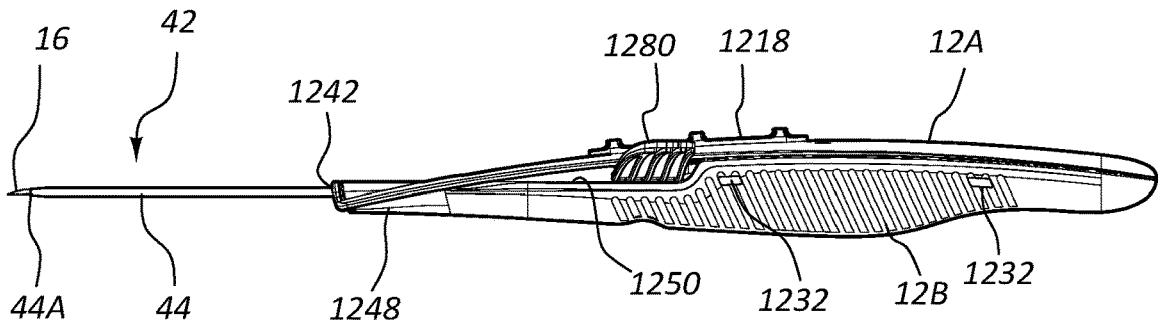
Figure 48D:
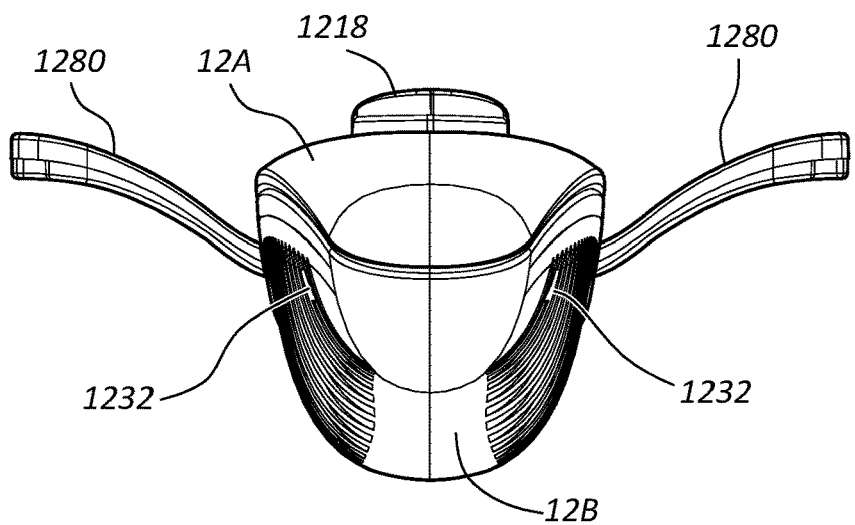
Figure 48E:
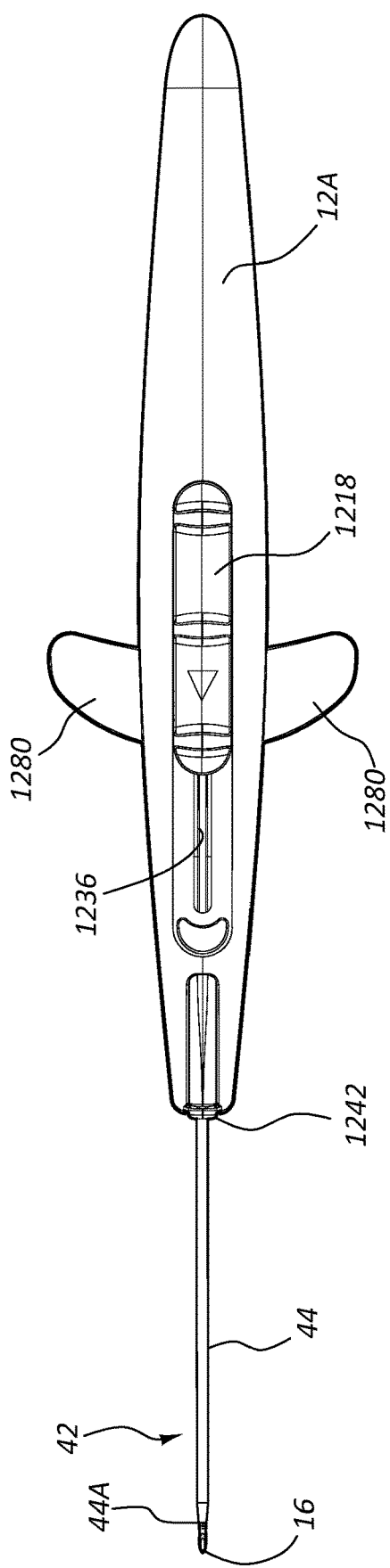
Figure 48F:
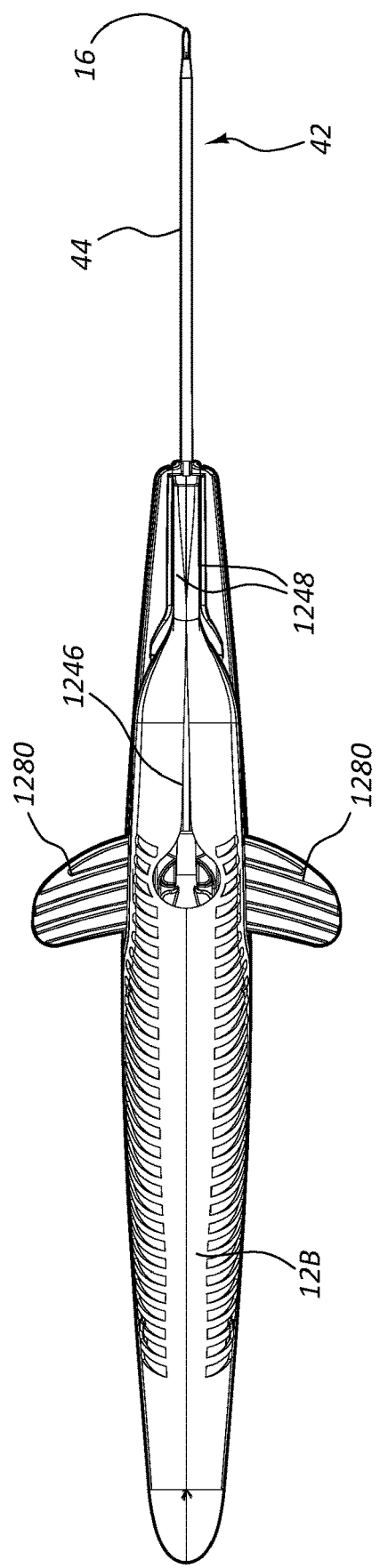

FIGS. 48A-48F depict various details of the insertion tool 10 according to another embodiment. As shown in FIG. 48A, the insertion tool 10 includes the top and bottom housing portions 12A, 12B of the housing 12, from which extends the catheter 42 disposed over the needle 16. Also shown is a finger pad 1218 of the guidewire advancement assembly 20 slidably disposed in a slot 1236 defined in the top housing portion 12A, and a portion of a handle assembly 1220 of the catheter advancement assembly 40. Further details are given below of the present insertion tool 10 and its various details in accordance with the present embodiment.

FIGS. 48A-48F show that the finger pad 1218 as part of the guidewire advancement assembly 20 can be slid by a finger(s) of the user distally along the slot 1236 in order to enable selective advancement of the guidewire 22 (initially disposed within the lumen of the needle 16) out past the distal end 16B of the needle 16. As before, a proximal end of the guidewire 22 is attached to an interior portion of the top housing portion 12A such that a single unit of distal sliding advancement of the finger pad 1218 results in two units of distal guidewire advancement. This, as before, is made possible by looping the guidewire 22 from its attachment point on the top housing portion 12A and through the guide surfaces 980 included on the guidewire lever 24 (FIGS. 53A and 53B) before extending into the lumen of the needle 16. Note that in the present embodiment the guidewire lever 24 and finger pad 1218 of the guidewire advancement assembly 20 are integrally formed with one another, though they may be separately formed in other embodiments. Note also that the guidewire 22 can be attached to other external or internal portions of the insertion tool 10, including the bottom housing portion 12B, the needle hub 1214, etc.

FIGS. 48A-48F further show that the catheter advancement assembly 40 for selectively advancing the catheter 42 in a distal direction out from the housing 12 of the insertion tool 10 includes a handle assembly 1220, which in turn includes among other components two wings 1280 that are grasped by the fingers of the user when the catheter is to be advanced. As will discussed in further detail below, the wings 1280 distally advanced via the gap 1250 defined between the top and bottom housing portions 12A, 12B.

The top and bottom housing portions 12A, 12B are mated together via the engagement of four tabs 1230 (FIGS. 48D, 49) of the top housing portion with four corresponding recesses 1232 located on the bottom housing portion. Of course, other mating mechanisms and schemes can be employed for joining the top and bottom housing portions together.

Figure 49:
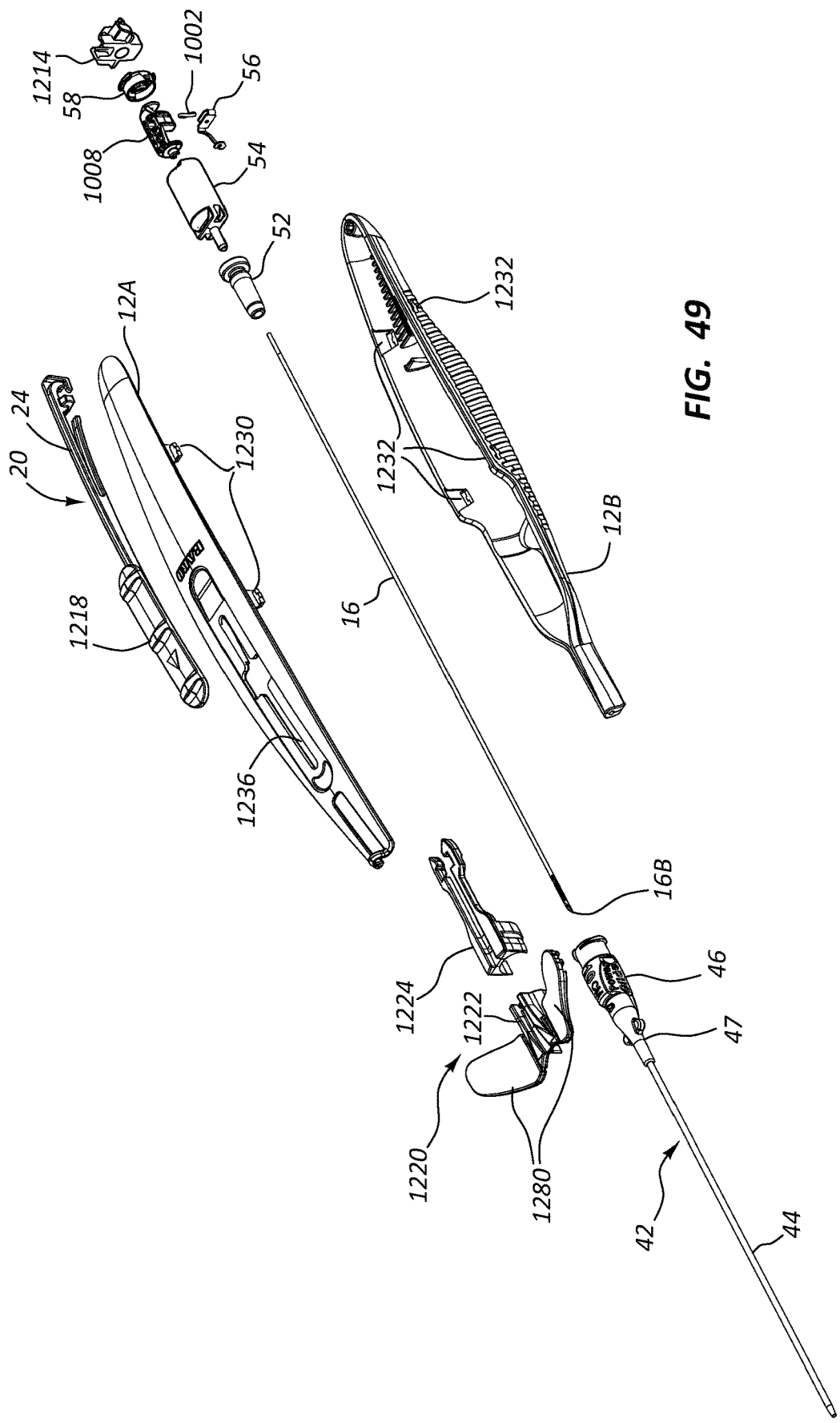
FIG. 49 is an exploded view of the insertion tool of FIGS. 48A-48F.

The exploded view of the insertion tool 10 in FIG. 49 shows that the handle assembly 1220 includes a head portion 1222 from which extend the wings 1280, and a tail portion 1224. Both the head portion 1222 and the tail portion 1224 are removably attached to the catheter hub 46, as will be discussed further below. Internal components of the insertion tool 10 that are disposed within the housing 12, each of which is passed through by the needle 16 include valve 52, the safety housing 54 in which the carriage 1008 and the needle safety component 56 is disposed, and the cap 58 of the safety housing. The O-ring 1002 that is included with the needle safety component 56 is also shown, as is a needle hub 1214, which is secured to a proximal end of the needle 16 and is mounted to the housing 12 to secure the needle 16 in place within the insertion tool 10. Note in FIG. 49 that, in one embodiment, the slot 1236 in which the finger pad of the guidewire advancement assembly 20 is disposed includes a relatively wide portion to enable the guidewire lever 24 to be inserted therethrough in order to couple the guidewire advancement assembly to the housing 12.

Figure 50:
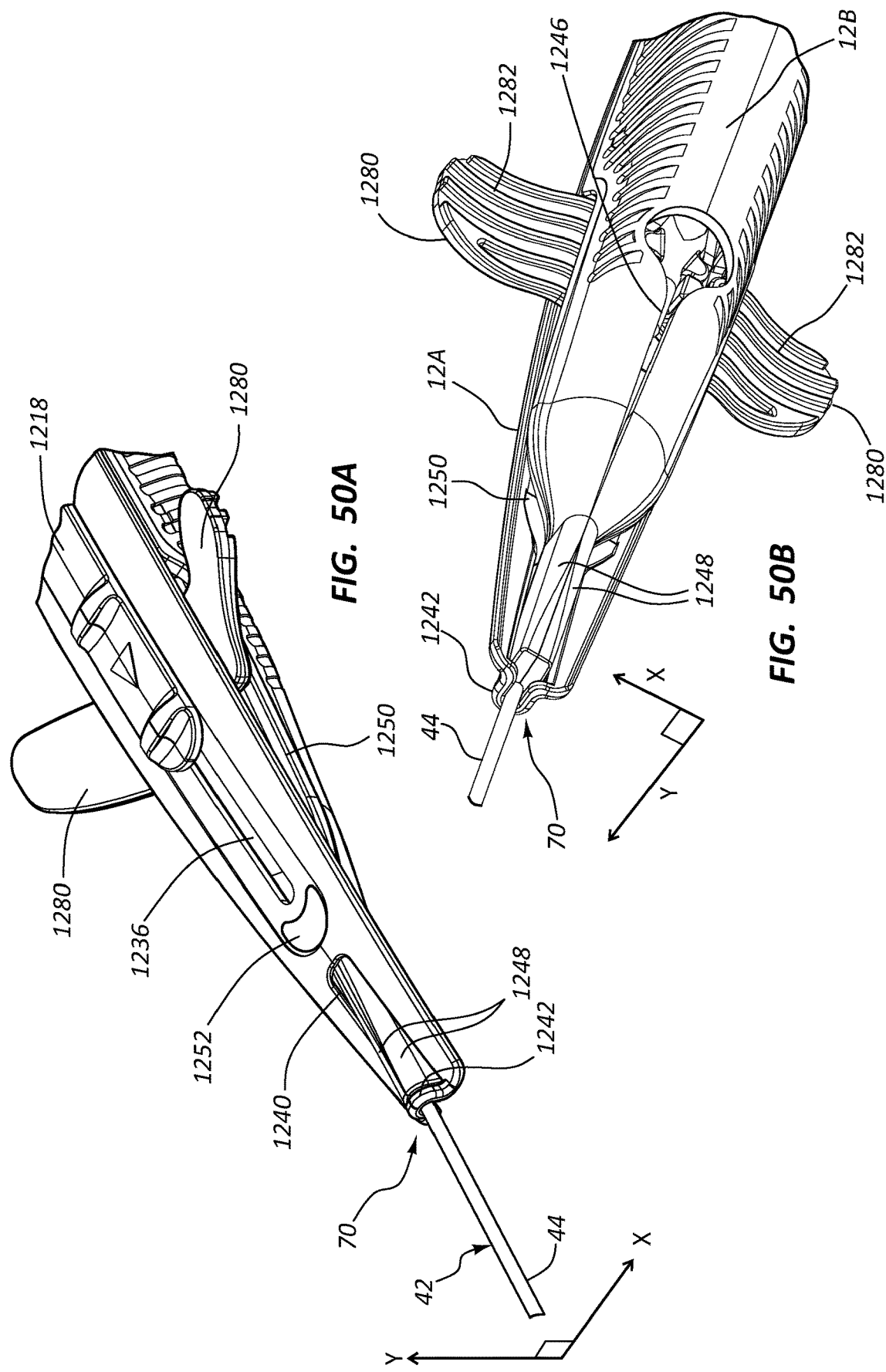
FIGS. 50A and 50B show various views of the insertion tool of FIGS. 48A-48F.
Figure 51:
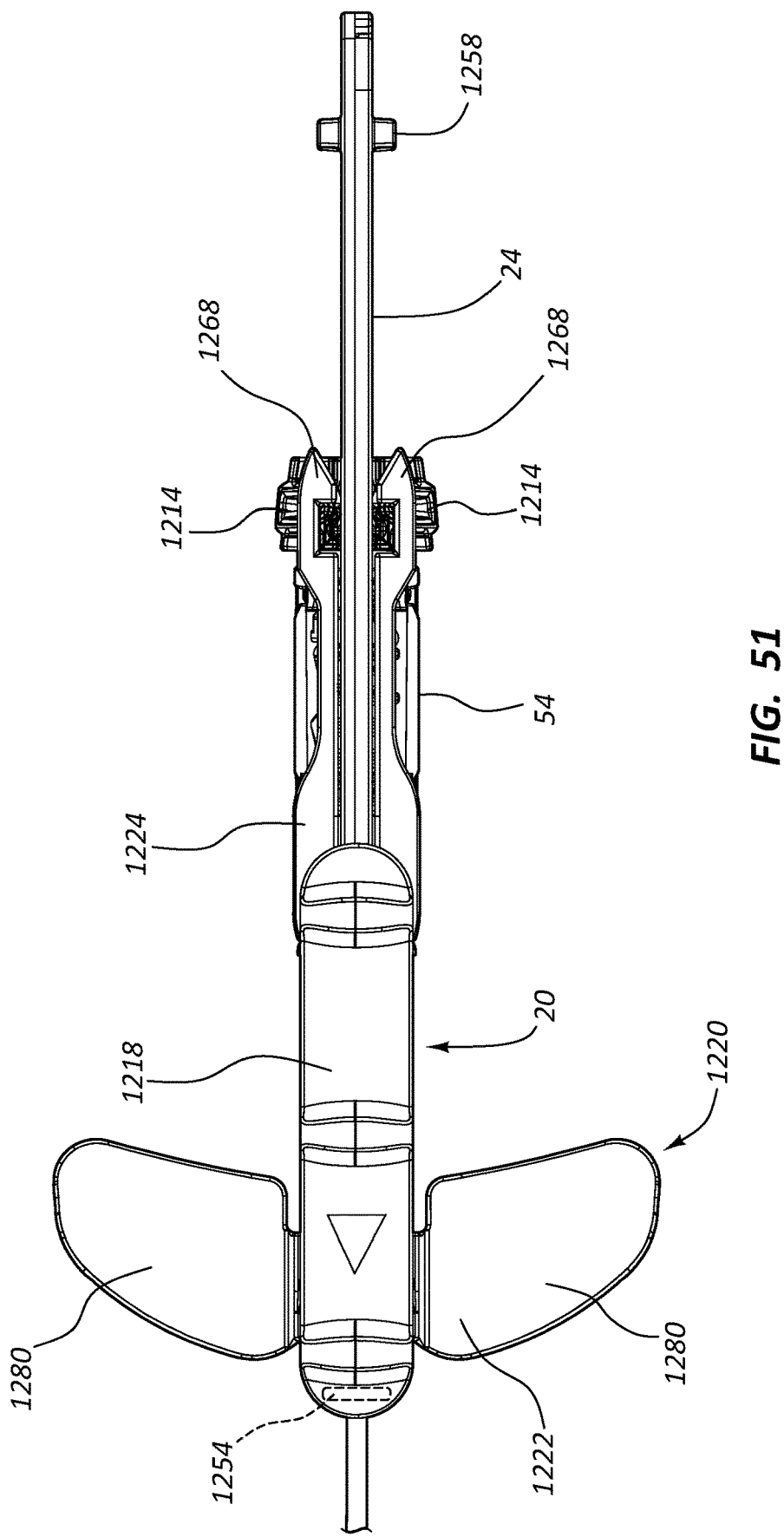
FIG. 51 is a top view of a guidewire advancement assembly and a catheter advancement assembly of FIGS. 48A-48F.

FIGS. 50A and 50B depict various details regarding the stability structure 70 for supporting and stabilizing the needle 16 at its exit point from the housing 12, according to the present embodiment. As shown, proximal portions of the top and bottom housing 12A, 12B inter-engage to provide the stability structure 70 for the needle 16. The bottom housing portion 12B includes two distally-disposed arms 1248 separated by a slot 1246 that enables the arms, when unconstrained, to separate from one another. The top housing portion 12A defines a distal slot 1240 and a horseshoe feature 1242 distal to the slot. Given the downward curvature of the top housing portion 12A (see FIG. 48C), the slot 1240 enables the arms 1248 of the bottom housing portion 12B to protrude upward through the slot to surround and support the needle 16 in order to stabilize it. The horseshoe feature 1242 is disposed about the needle 16 at the distal end of the bottom housing arms 1248 and acts as a collar to stabilize the needle.

The arms 1248 of the bottom housing portion 12B are configured to be able to move back and forth in the x-direction, according to the x-y axis shown in FIGS. 50A and 50B, while remaining substantially rigid in the y-direction. Conversely, the distal portion of the top housing portion 12A that includes the slot 1240 and the horseshoe feature 1242 is configured so as to flex in the y-direction according to the x-y axis shown in FIGS. 50A and 50B, while remaining substantially rigid in the x-direction. Thus, when overlapped or inter-engaged as shown in FIGS. 50A and 50B, the above-referenced components of the stability structure 70 cooperate to support the needle 16 and prevent its substantial movement when the housing 12 is in the configuration shown in FIGS. 50A, 50B, that is, before removal of the catheter 42 from the housing 12. This in turn assists the user in accurately piercing the skin and accessing a vessel of the patient. It is appreciated that the stability structure can include other components to stabilize the needle in addition to those explicitly described herein.

FIGS. 51-54 depict various details regarding the catheter advancement assembly 40 and the guidewire advancement assembly 20, according to the present embodiment. As discussed, the catheter advancement assembly 40 includes the handle assembly 1220, which in turn includes the head portion 1222 with the corresponding wings 1280, and the tail portion 1224 disposed about a portion of the catheter hub 46 and the safety housing 54. As will be discussed further below, the handle assembly 1220 is employed in distally advancing and removing the catheter 42 from the insertion tool 10.

FIGS. 51-54 further show the finger pad 1218 and the guidewire lever 24 of the guidewire advancement assembly 20 for the present embodiment. As shown, the guidewire lever 24 extends proximally from the finger pad 1218 and includes on its proximal end the previously discussed guide surfaces 980 for guiding the looping of the guidewire 22. An actuation block 1258 is also included near the proximal end of the guidewire lever 24 for use in enabling catheter advancement, as will be described further below. Note that the particular size, shape, and other configuration of the actuation block can vary from what is shown and described herein while retaining the desired functionality.

Figure 53A:
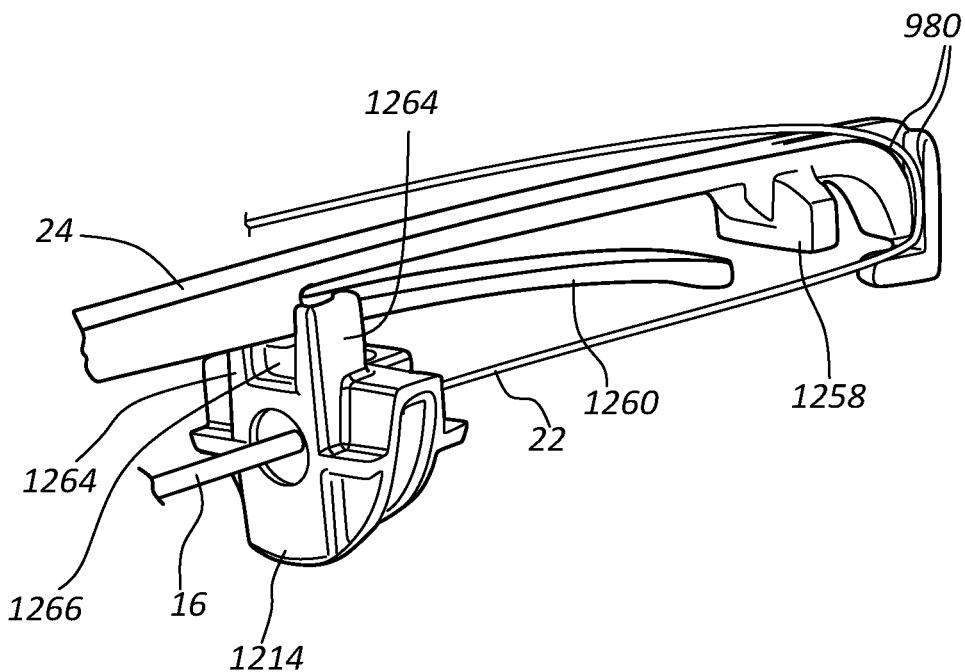
FIGS. 53A-53B show details of the operation of the guidewire advancement assembly of FIG. 52.
Figure 53B:
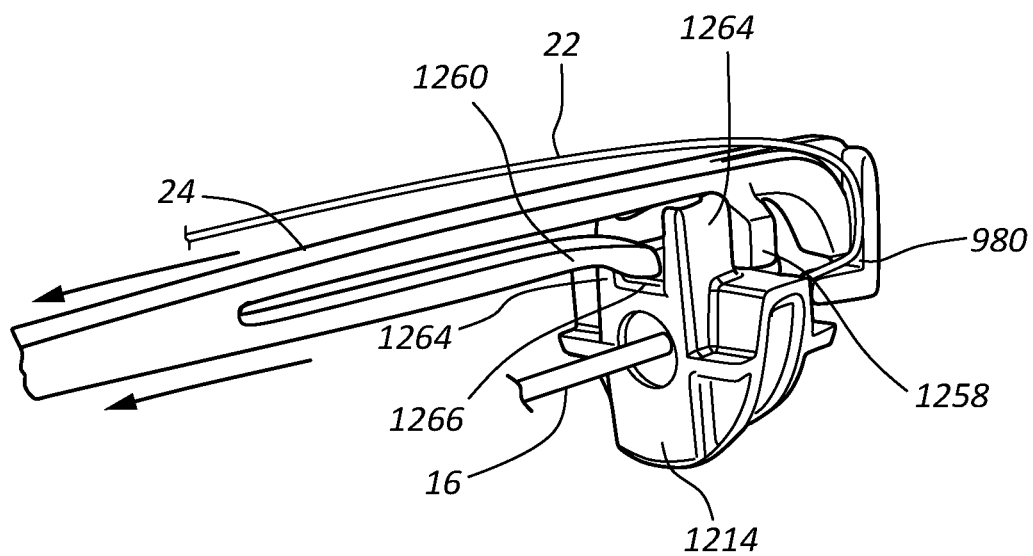

A spring arm 1260 extends downward from the guidewire lever 24 and is configured to be slidably retained between two guide posts 1264 of the needle hub 1214, as best seen in FIGS. 53A and 53B. The spring arm 1260 is employed for locking further movement of the guidewire advancement assembly 20 once the guidewire 22 has been fully distally extended from the insertion tool 10 and the catheter 42 advanced an incremental amount. In particular, distal sliding by the user of the finger pad 1218 causes the guidewire lever 24 to also distally move, which in turn distally advances the guidewire 22 (which internally loops past the guide surfaces 980 of the guidewire lever 24 and into the needle lumen) through the lumen of the needle 16 and past the needle distal end 16B, as seen in FIG. 54.

Figure 54:
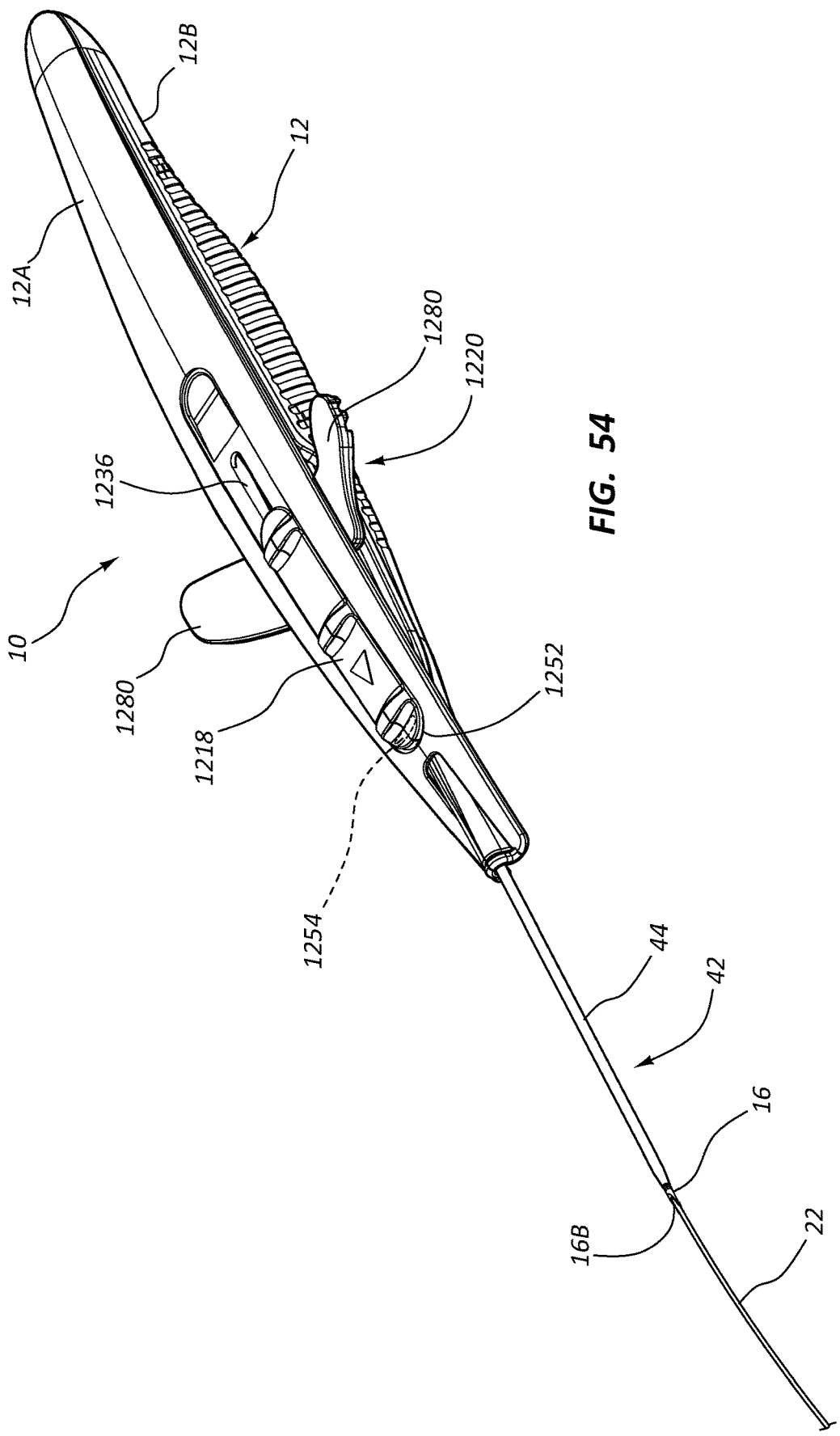
FIG. 54 is a perspective view of the insertion tool of FIGS. 48A-48F in one state.

Upon full distal advancement of the finger pad 1218 and guidewire lever 24 as seen in FIG. 54, the free end of the spring arm 1260 is disposed just above a pocket 1266 defined between the guide posts 1264 of the needle hub 1214, as seen in FIG. 53B. Because of the location of the safety housing 54 proximal and adjacent to the needle hub 1214 at this stage (the catheter 42—and also the attached safety housing—in its initial seated position due to it having not yet been distally advanced via distal advancement of the catheter advancement assembly 40 as described further below), the free end of the spring arm 1260 cannot yet seat in the pocket 1266. Once the catheter 42 is advanced an incremental distance distally, however, the attached safety housing 54 no longer impedes downward movement of the spring arm 1260 and the free end thereof seats into the pocket 1266 of the needle hub 1214. Further distal movement of the guidewire advancement assembly 20 is prevented by impingement of the finger pad 1218 on the distal end of the slot 1236, while proximal movement is prevented by the seating of the spring arm in the pocket 1266 of the needle hub.

Note that the finger pad 1218 includes on its underside proximate its distal end a protrusion 1254 that engages with a depression 1252 defined on the top housing portion 12A when the finger pad is completely distally advanced. This assists in keeping the finger pad 1218 seated in its distal position and provides a tactile cue that the finger pad has been fully distally advanced.

Figure 52:
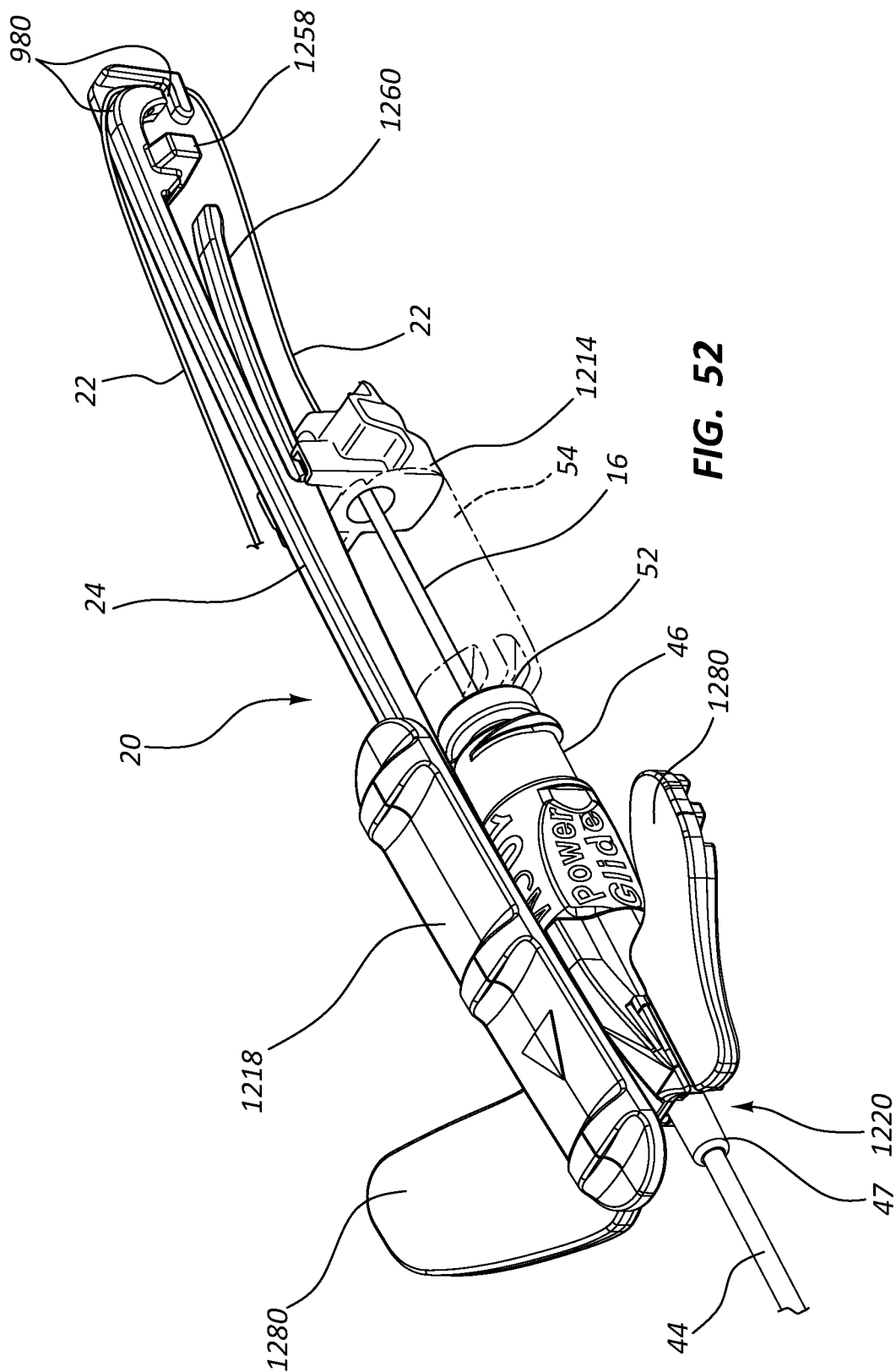
FIG. 52 is a perspective view of the guidewire advancement assembly of the insertion tool of FIGS. 48A-48F.

Note also that, should the catheter advancement assembly 40 be moved proximally back to its initial position (as seen in FIG. 52), the safety housing 54 will once again abut against the needle hub 1214 and push the free end of the spring arm 1260 up and out of the pocket 1266. This in turn enables the guidewire advancement assembly 20 to again move proximally and distally, causing corresponding proximal and distal advancement of the guidewire 22 itself. Thus, locking of the guidewire advancement is reversible, in the present embodiment.

In another embodiment it is appreciated that a push button can be included with the guidewire advancement assembly 20 to enable the guidewire to be extended or retracted anew after locking of the guidewire has initially occurred, such as via depressing of the button to disengage the spring arm 1260 from the pocket 1266 of the needle hub, for instance. These and other variations are therefore contemplated.

Figure 55:
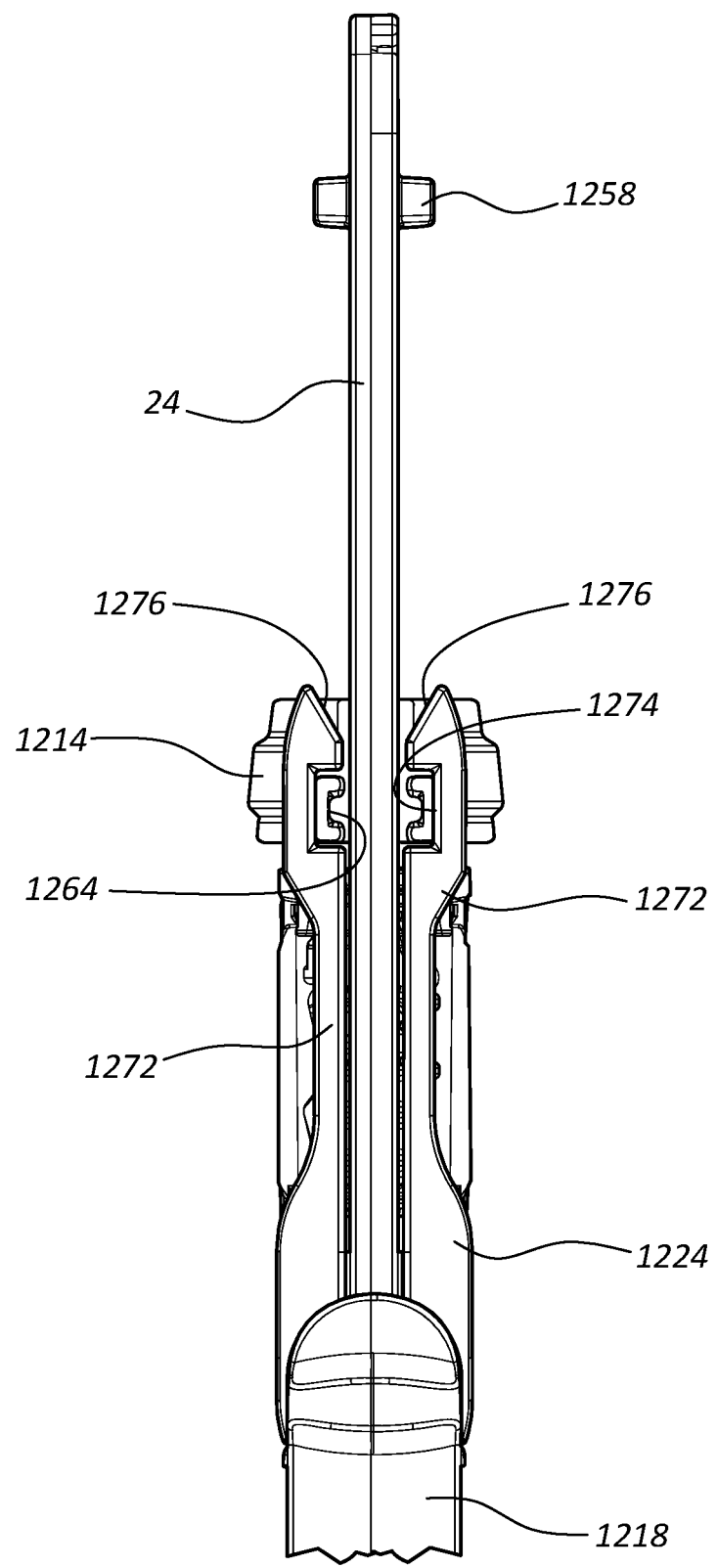
FIG. 55 is a top view of the guidewire advancement assembly of FIG. 52.

FIGS. 55-56C show that, in accordance with the present embodiment, the insertion tool 10 as presently described further includes locking of catheter movement prior to the distal advancement of the guidewire 22 as described above. In detail, FIGS. 55 and 56A shows the guidewire advancement assembly 20 and the tail portion 1224 of the handle assembly 1220 of the catheter advancement assembly 40 in their initial positions within the insertion tool housing 12, that is, prior to distal guidewire advancement and catheter distal advancement. In this position, two spring arms 1272 of the tail portion 1224 are positioned such that both guide posts 1264 of the needle hub 1214 are seated within respective notches 1274 of the spring arms, best seen in FIG. 56A. In this position, the tail portion 1224 is prevented from movement. Given the attachment of the tail portion 1224 to the hub 46 of the catheter 42, this also prevents distal advancement of the catheter or any other portion of the catheter advancement assembly 40.

As seen in FIGS. 56A and 56B, distal advancement of the guidewire lever 24 causes its actuation block 1258 to engage slanted surfaces 1276 of each spring arm 1272. As best seen in FIG. 56B, continued distal movement of the guidewire lever 24 causes the actuation block 1258 to spread open the spring arms 1272, which disengages the guide posts 1264 from spring arm notches 1274. The actuation block 1258 impacts the guide posts 1264, as seen in FIG. 56B, at the point of full distal advancement of the guidewire 22 and the positioning of the free end of the spring arm 1260 of the guidewire lever 24 just above the pocket 1266 of the needle hub 1214, as was described above in connection with FIGS. 52-54. At this point, the spring arms 1272 of the tail portion 1224 are disengaged from the guide posts 1264 of the needle hub 1214, and distal catheter advancement is thus enabled, as shown by the distal movement of the spring arms in FIG. 56C. Also, and as was described above in connection with FIGS. 52-54, this distal catheter advancement correspondingly distally moves the safety housing 54, which is attached to the catheter 42. Movement of the safety housing causes the free end of the spring arm 1260 of the distally advanced guidewire lever 24 fall into the pocket 1266 of the needle hub 1214, locking further movement of the guidewire 22 barring return of the safety housing to its initial position adjacent the needle hub.

Thus, it is seen that the configuration of the insertion tool 10 of the present embodiment prevents distal movement of the catheter 42 until full distal extension of the guidewire 22 has occurred. Also, further movement of the guidewire 22 is prevented while the catheter 42 has been distally advanced at least incrementally from its original proximal position. In another embodiment, an incremental amount of guidewire distal advancement could enable catheter advancement.

In yet another embodiment, locking of guidewire movement is made permanent after full distal advancement. This could be achieved, in one embodiment, by configuring the spring arm 1260 of the guidewire lever 24 and the pocket 1266 of the needle hub 1214 to not interact with the safety housing 54; as such, once the free end of the spring arm 1260 seats within the needle hub pocket 1266, it remains seated permanently. In another embodiment, locking of catheter movement is made after full distal catheter advancement. In still another embodiment, guidewire and/or catheter advancement can be achieved via a ratcheting mechanism.

In another embodiment, the ability to advance the catheter is unrelated to guidewire advancement. In yet another embodiment, the spring arm 1260 of the guidewire lever 24 can be removed such that no locking of the guidewire advancement assembly 20 occurs. In turn, this enables locking of catheter advancement until full distal guidewire advancement has occurred. These and other variations are therefore contemplated.

Figure 57A:
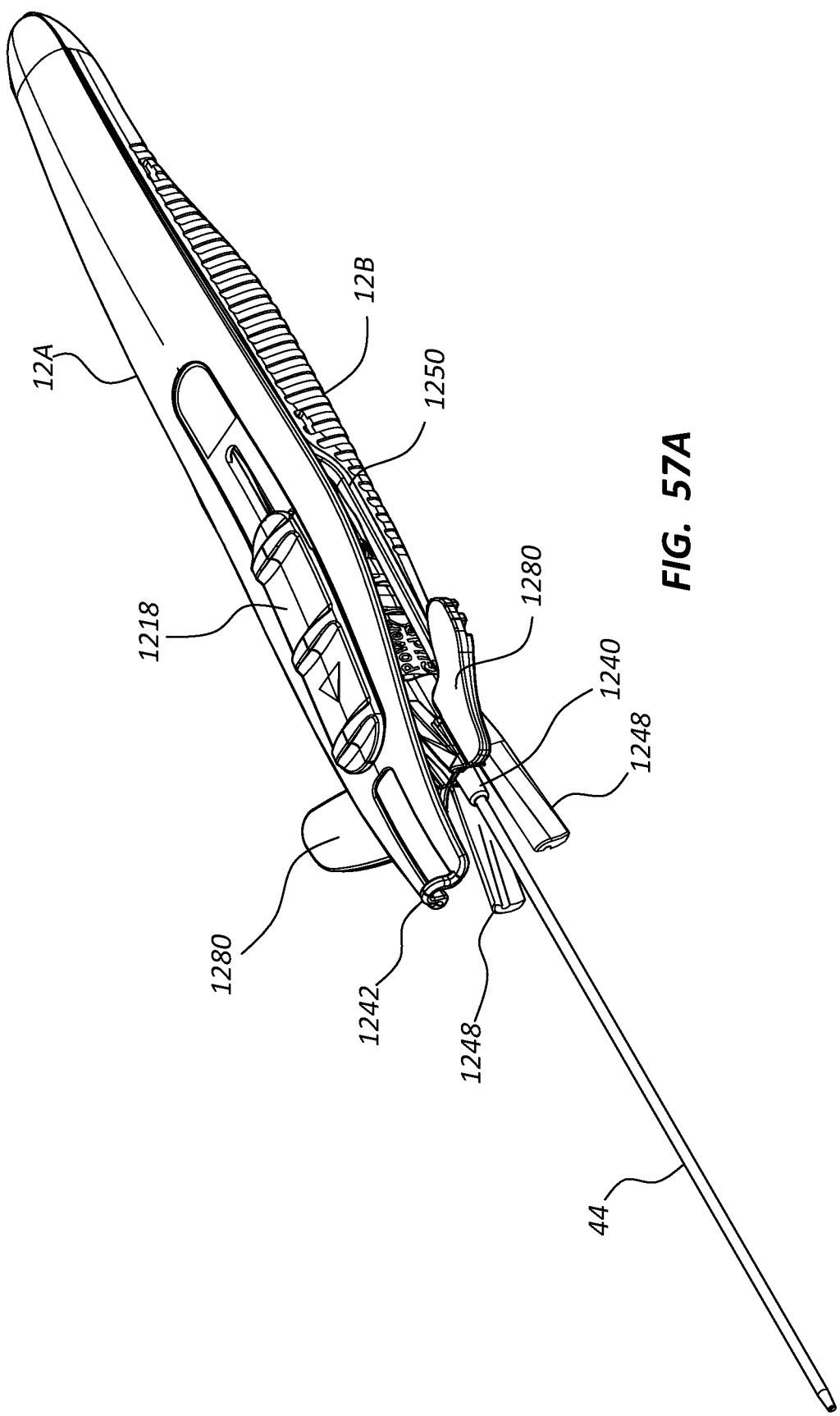
FIGS. 57A and 57B are various views of the distal portion of the insertion tool of FIGS. 48A-48F.
Figure 57B:
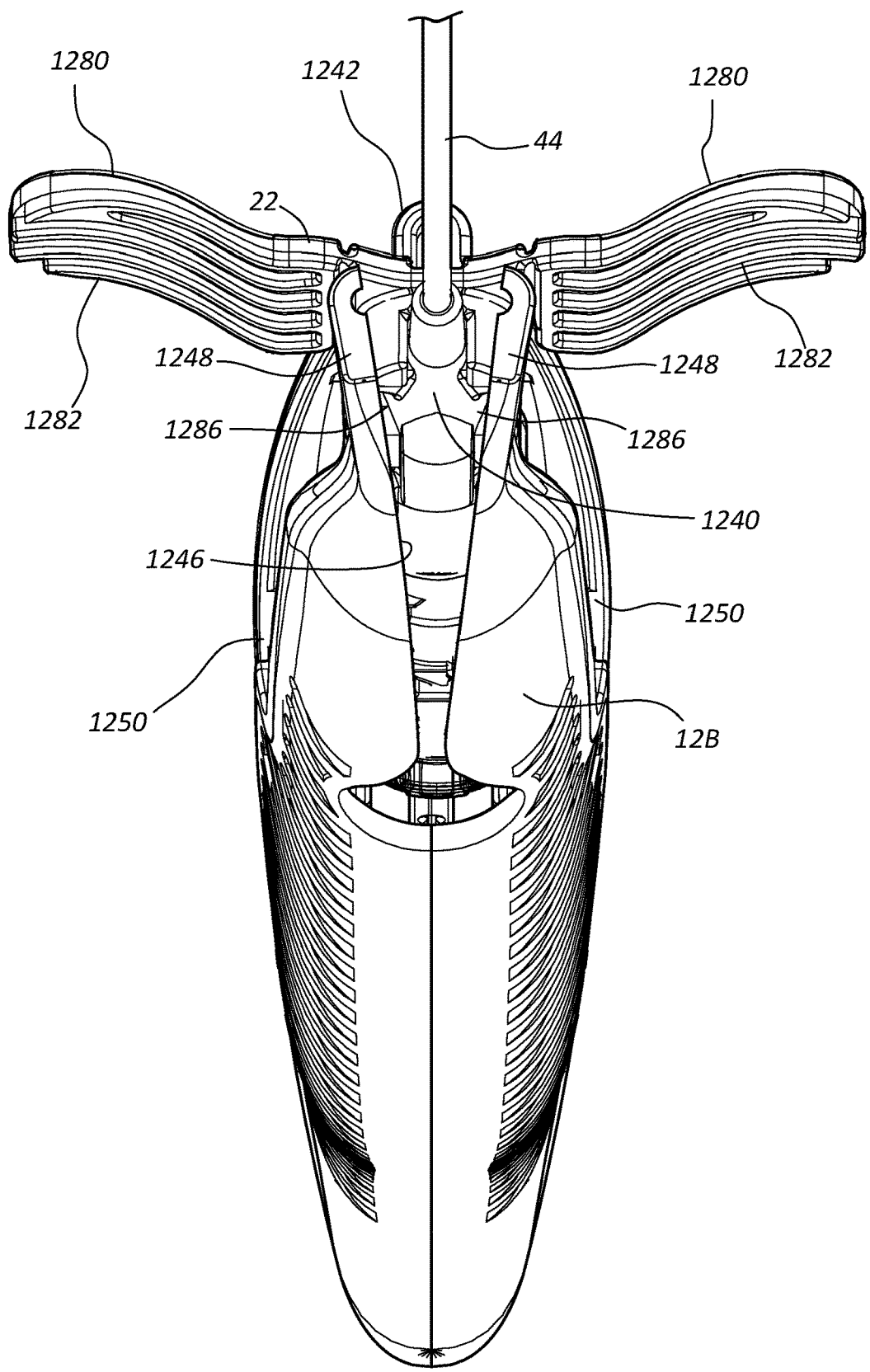

FIGS. 57A and 57B depict various details regarding the distal advancement of the catheter 42 from the insertion tool 10. As shown, once the guidewire advancement assembly 20 has distally advanced the guidewire 22 such that it extends past the distal end 16B of the needle 16, the catheter advancement assembly 40 is free (as described above in connection with FIGS. 55-56C) to be employed in distally advancing the catheter 42 out the distal end of the insertion tool housing 12. The catheter 42 is advanced by a user grasping one or both of the wings 1280 of the head portion 1222 of the handle assembly 1220 and moving the wings distally. Note that ridges 1282 (FIG. 50B) are included to assist the user in gripping the wings 1280. The wings 1280 slide distally in the gap 1250 defined between the top and bottom housing portions. Given the attachment of the wings 1280 to the head portion 1222, which in turn is attached to the hub 46 of the catheter 42, distal sliding of the wings distally advances the catheter.

FIGS. 57A and 57B show that, as the catheter 42 is distally advanced, the distal movement of the wings 1280 causes the wings to impinge on and push upwards the top housing portion 12A, which in turn lifts the distal portion of the top housing portion, including the slot 1240 and the horseshoe feature 1242 of the stability structure 70. Lifting of the slot 1240 causes the arms 1248 of the bottom housing portion 12B to disengage from the slot, thus enabling them to spread apart. FIGS. 57A and 57B show that two posts 1286 disposed on the head portion 1222 of the handle assembly 1220 (see also FIG. 60) push against each of the arms 1248 as the catheter distally advances, which causes the arms to separate. This separation of the arms 1248, together with the lifting by the wings 1280 of the top housing portion, enables the catheter 42 to pass through the distal end of the housing 12.

Figure 58:
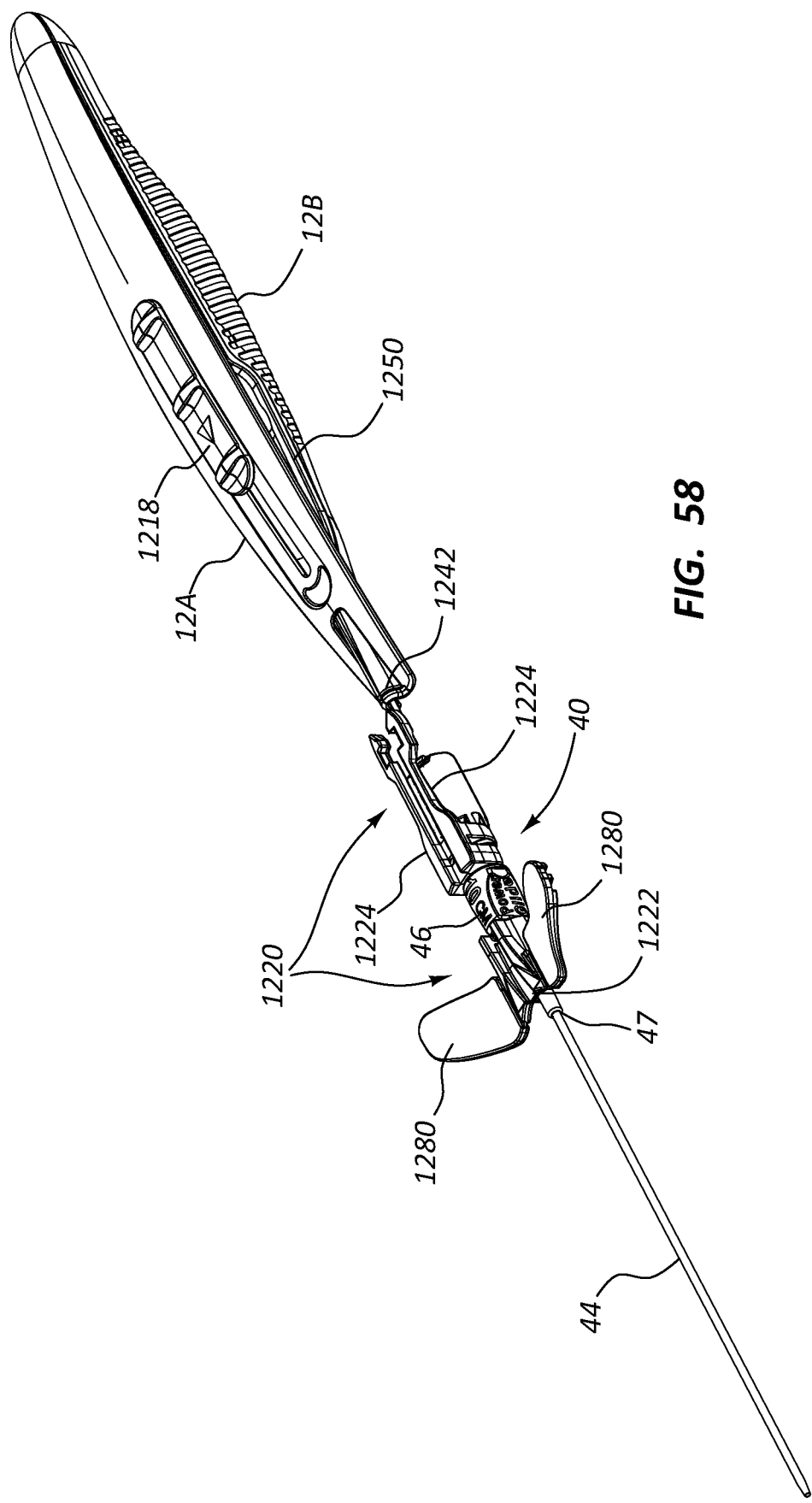
FIGS. 58 and 59 shows various views of the catheter advancement assembly of the insertion tool of FIGS. 48A-48F.
Figure 59:
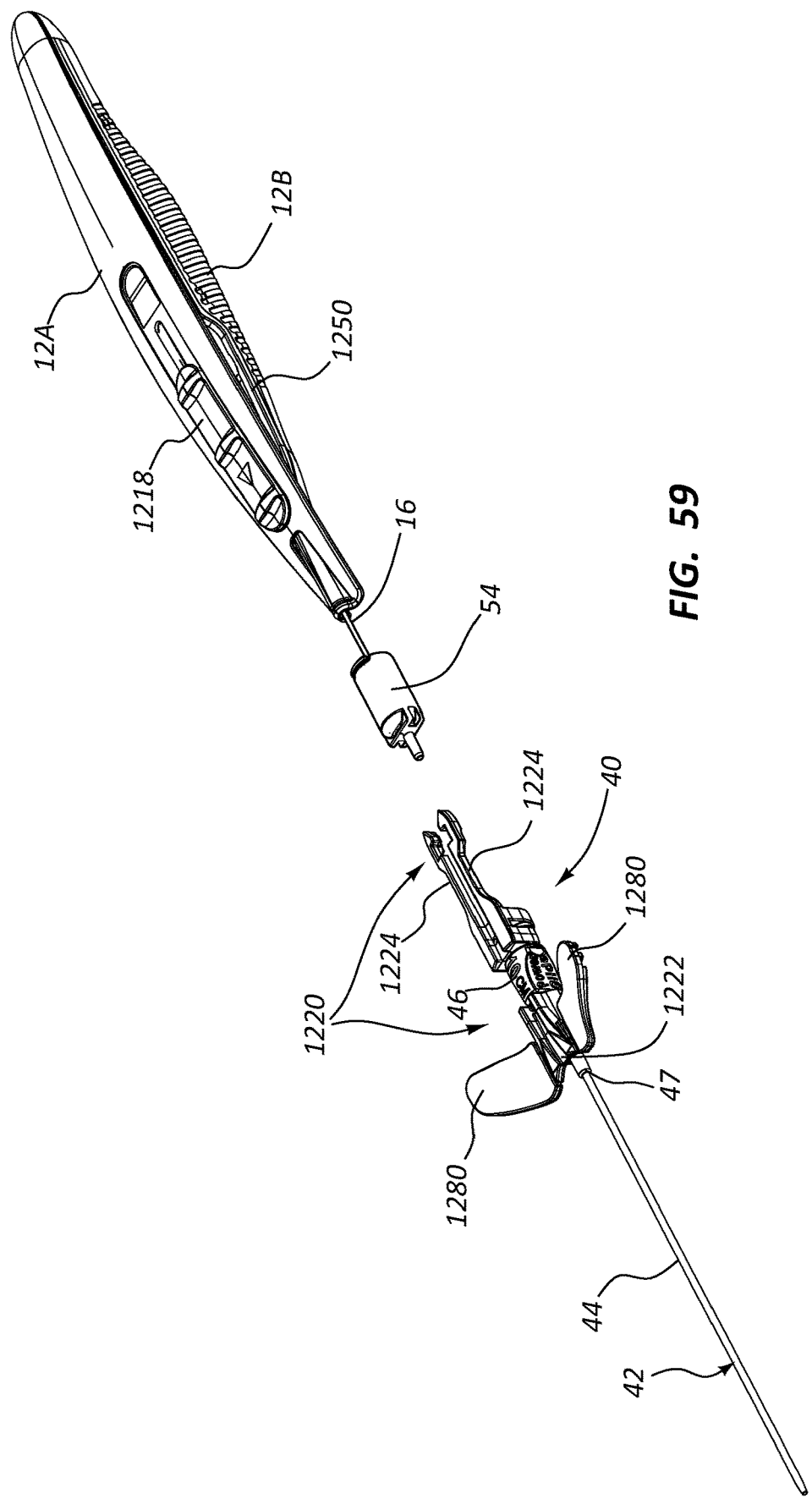

FIGS. 58 and 59 show removal of the catheter 42 and catheter advancement assembly 40 from the insertion tool housing 12, wherein continued distal advancement of the head portion 1222 via the user grasping and advancing the wings 1280 causes the catheter 42, the handle assembly 1220 (including the head portion 1222 and the tail portion 1224), and the safety housing 54 removably attached to the catheter hub 46 to slide distally along the needle 16 and out of the housing 12. This action is performed, for instance, to advance the catheter tube 44 into the vessel of the patient after the needle 16 and the guidewire 22 have cooperated to provide a pathway into the vessel.

FIG. 59 shows that further separation of the catheter 42 and handle assembly 1220 from the housing 12 causes the safety housing 54 to arrive at the distal end 16B of the needle 16, at which point the needle safety component 56 disposed in the safety housing (FIG. 49) engages the needle distal tip to prevent accidental needle sticks for the user, and the safety housing laterally detaches from the catheter hub 46 and remains with the needle.

Figure 60:
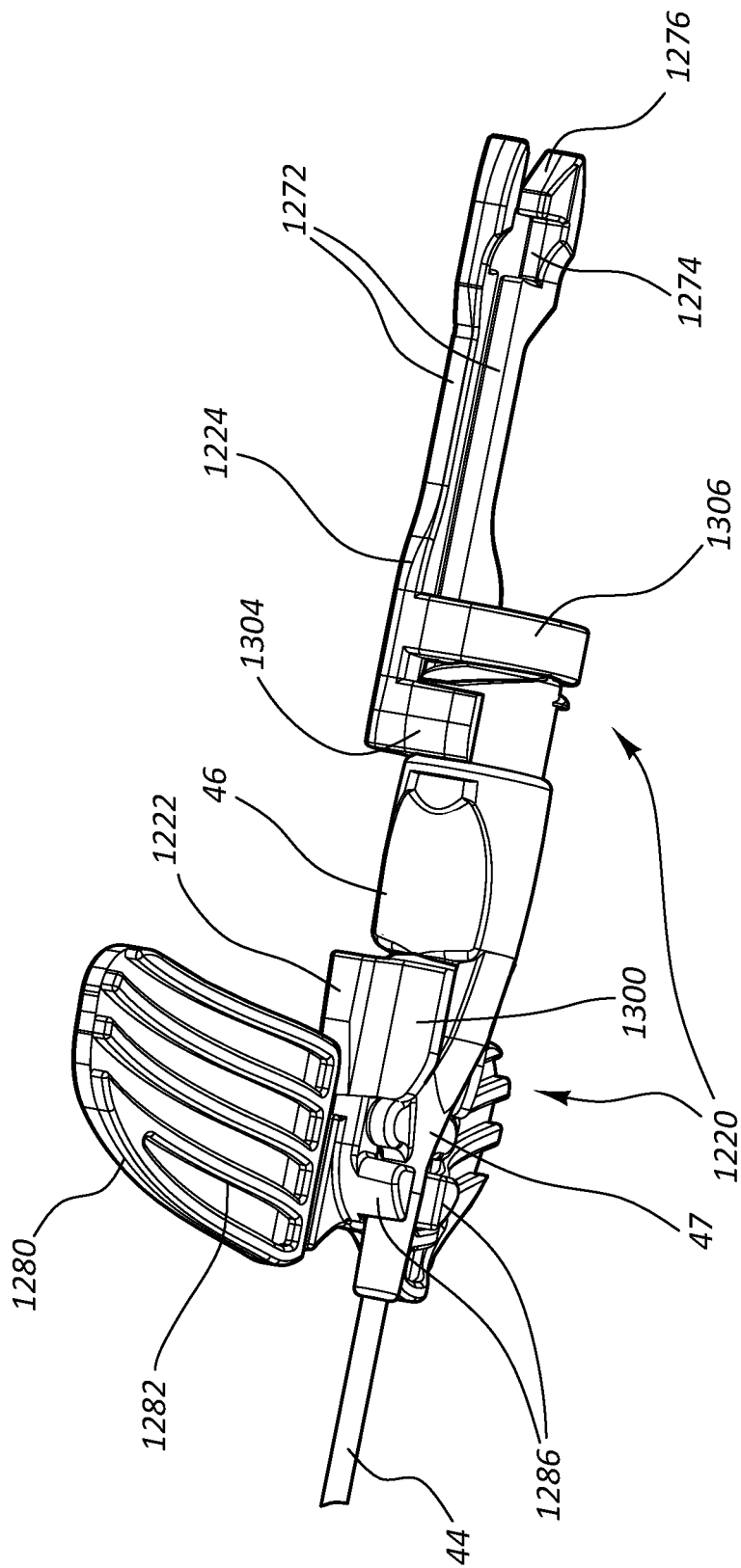
FIG. 60 is a perspective view of the catheter advancement assembly of the insertion tool of FIGS. 48A-48F.

FIG. 60 shows various features of the handle assembly 1220, which includes the head portion 1222 and the tail portion 1224. After the above separation of the safety housing 54 and needle 16 from the catheter 42 and handle assembly 1220, the head portion 1222 and the tail portion 1224 remain attached to the needle hub 46 and its corresponding strain relief 47 via clip arms 1300 and 1304, respectively. At this point, the head portion 1222 can be removed from the catheter hub 46/strain relief 47 by the hand of the user to overcome the friction fit of the clip arms 1300. The tail portion 1224, which includes a loop 1306 disposed about the valve 52, can also be removed via pulling and twisting by the user to overcome the friction fit of the clip arms 1304 and avoid the threads of the catheter hub 46. This action will remove the valve 52 (see FIG. 49), which is attached to the tail portion 1224. In another embodiment, the tail portion loop 1306 is configured so that the valve 52 is exposed after removal of the tail portion 1224 so as to enable removal of the valve by the user when desired. Once the head portion 1222 and the tail portion 1224 of the handle assembly 1220 have been removed from the catheter 42, the catheter can be dressed and used as desired.

Figure 61:
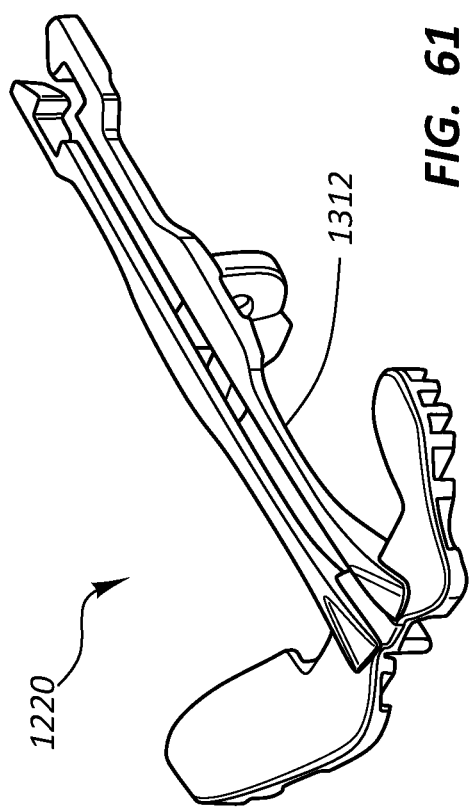
FIG. 61 is a perspective view of a handle of a catheter advancement assembly according to one embodiment.
Figure 62:
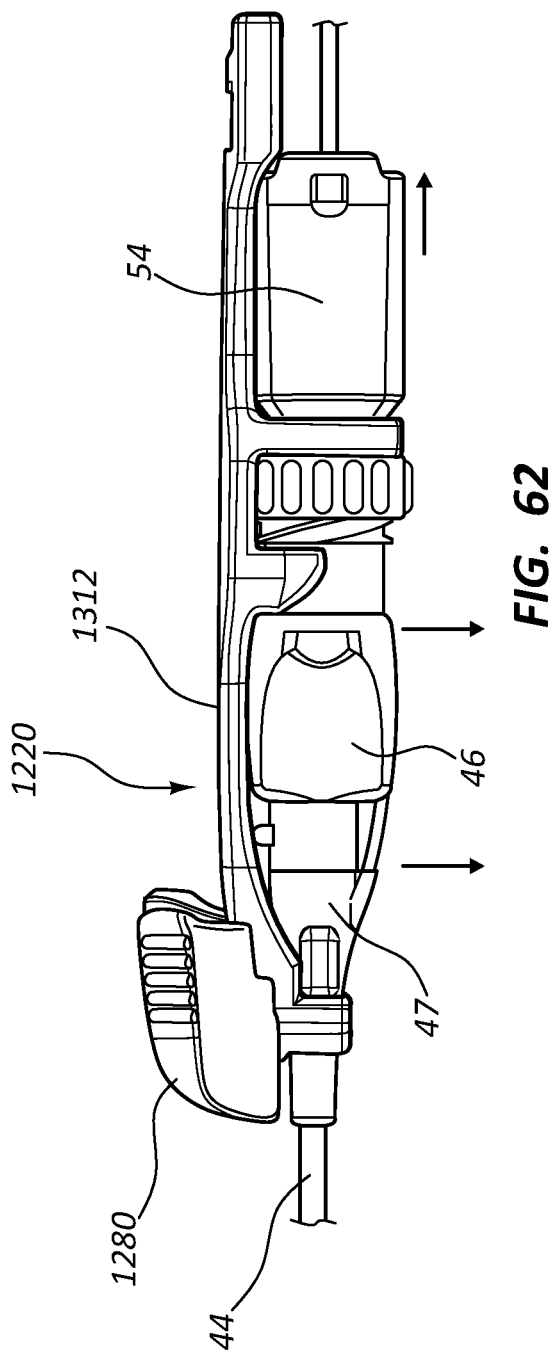
FIG. 62 is a side view of the handle of FIG. 61.
Figure 63:
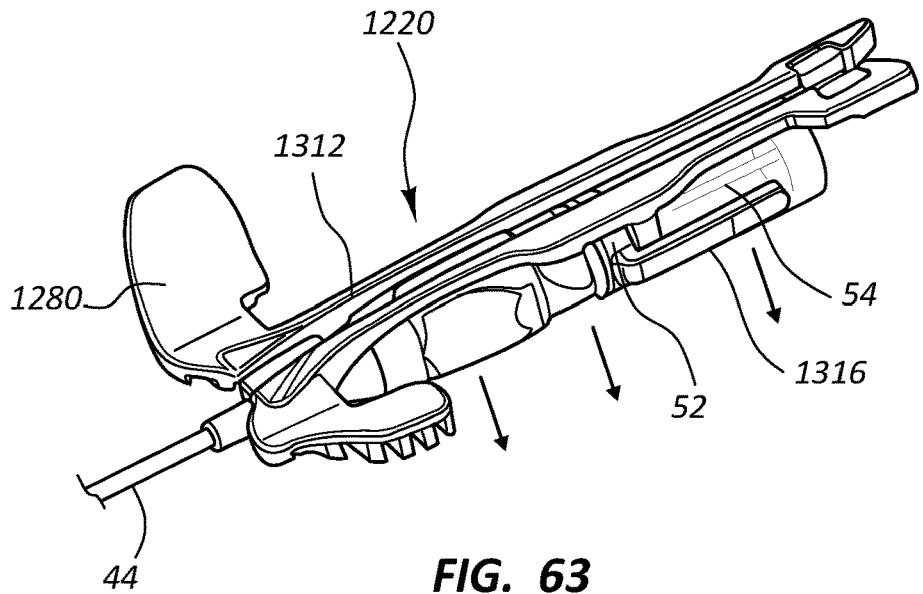
FIG. 63 is a perspective view of a handle of a catheter advancement assembly according to one embodiment.

The handle assembly 1220 can be configured in other ways, in addition to what has been described above. FIGS. 61 and 62 give one example of the handle assembly 1220, wherein the head portion and the tail portion are unified in a singular body 1312. As shown in FIG. 62, this enables the safety housing 54 to be removed laterally from the handle assembly 1220, after which the catheter hub 46 can be removed vertically therefrom. FIG. 63 includes a similar configuration for the handle assembly 1220, wherein the valve 52 includes oppositely-disposed extensions 1316, which enables the extensions to be gripped (after lateral removal of the safety housing 54) and the handle assembly 1220 is removed vertically. These actions leave the valve 52 and its extensions 1316 attached to the hub 46 of the catheter 42, at which point the valve can be removed from the hub laterally, using the extensions if desired.

Figure 64:
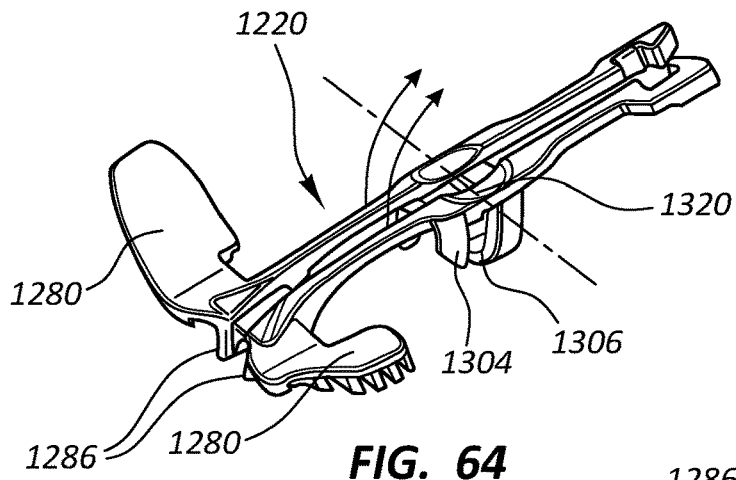
FIG. 64 is a perspective view of a handle of a catheter advancement assembly according to one embodiment.

In FIG. 64, the handle assembly 1220 includes a singular body that defines a living hinge 1320 disposed just distal to the loop 1306, though other locations for the living hinge are possible. Note that the loop 1306 captures the valve 52. In one embodiment, the valve 52 is integrally formed with or attached to the handle assembly body. In another embodiment, the valve 52 is separate from the handle assembly 1220 and is not affected by removal of the handle assembly 1220. The handle assembly 1220 further includes the clip arms 1304 that removably attach to the catheter hub 46 to secure the catheter 42 in place. Posts 1286 are also included on the handle assembly 1220, as in previous embodiments.

Figure 65:
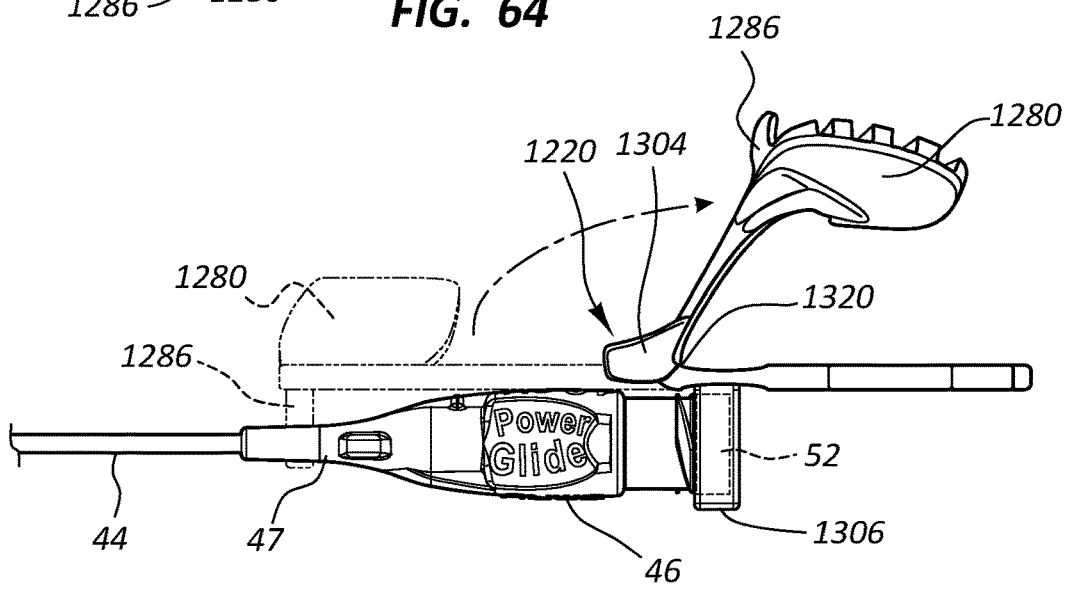
FIG. 65 is a side view of the handle of FIG. 64.

As FIG. 65 shows, the wings 1280 can be grasped to arcuately pull the distal portion of the handle assembly 1220 proximally, which then disengages the clip arms 1304 and posts 1286 from the catheter hub 46 and enables the handle assembly and valve 52 to be pulled from the catheter hub laterally. These and other handle assembly configurations are therefore contemplated.

Figure 66A:
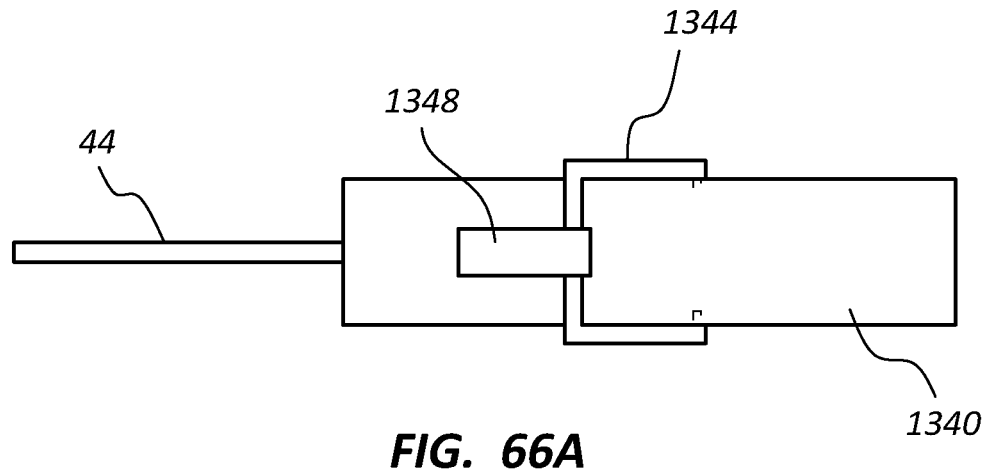
FIGS. 66A-66C are various views of an insertion tool according to one embodiment.
Figure 66B:
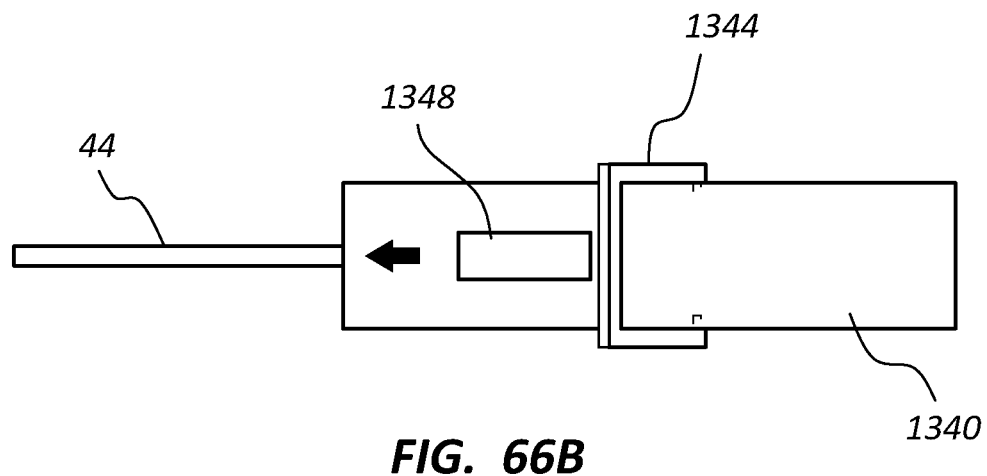
Figure 66C:
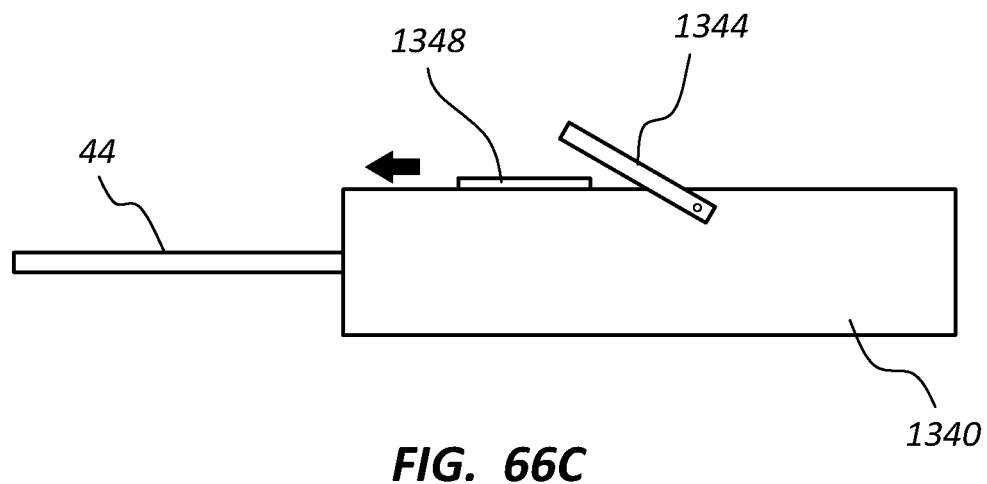
Figure 67A:
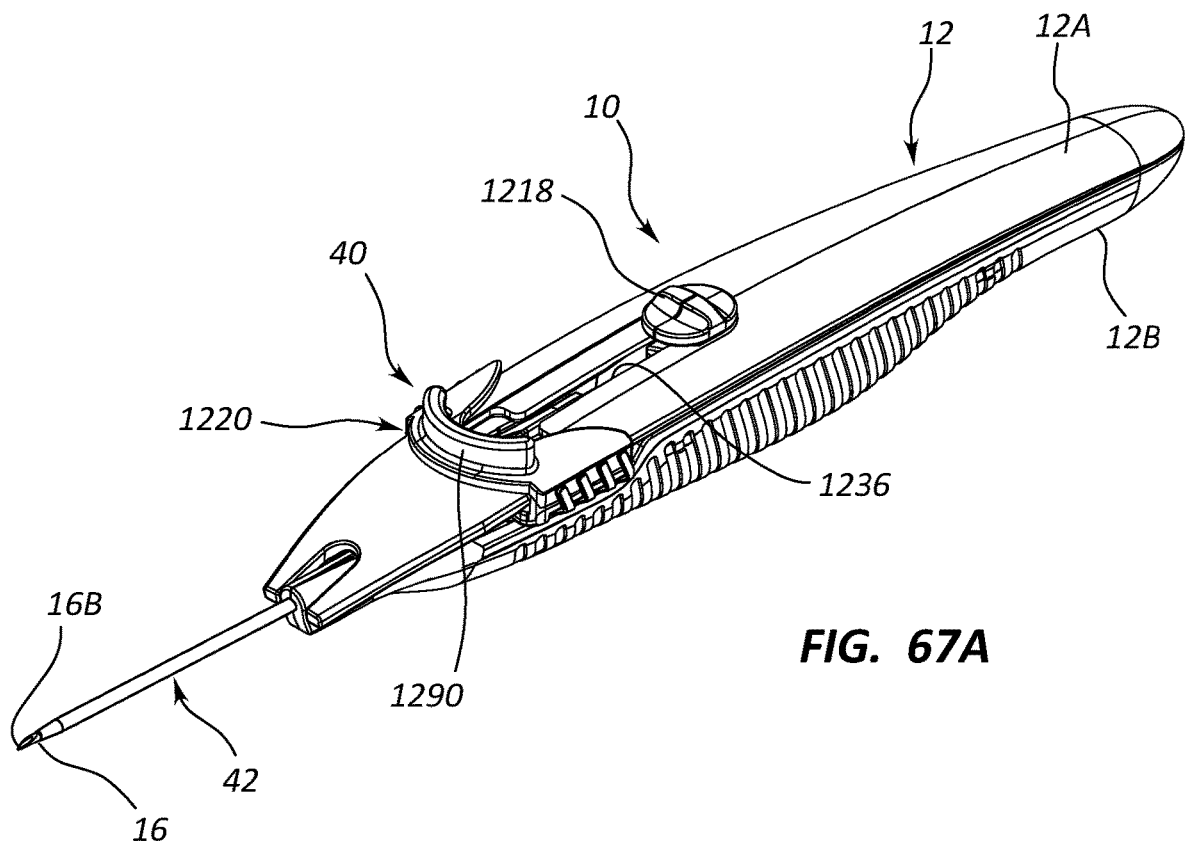
Figure 67B:
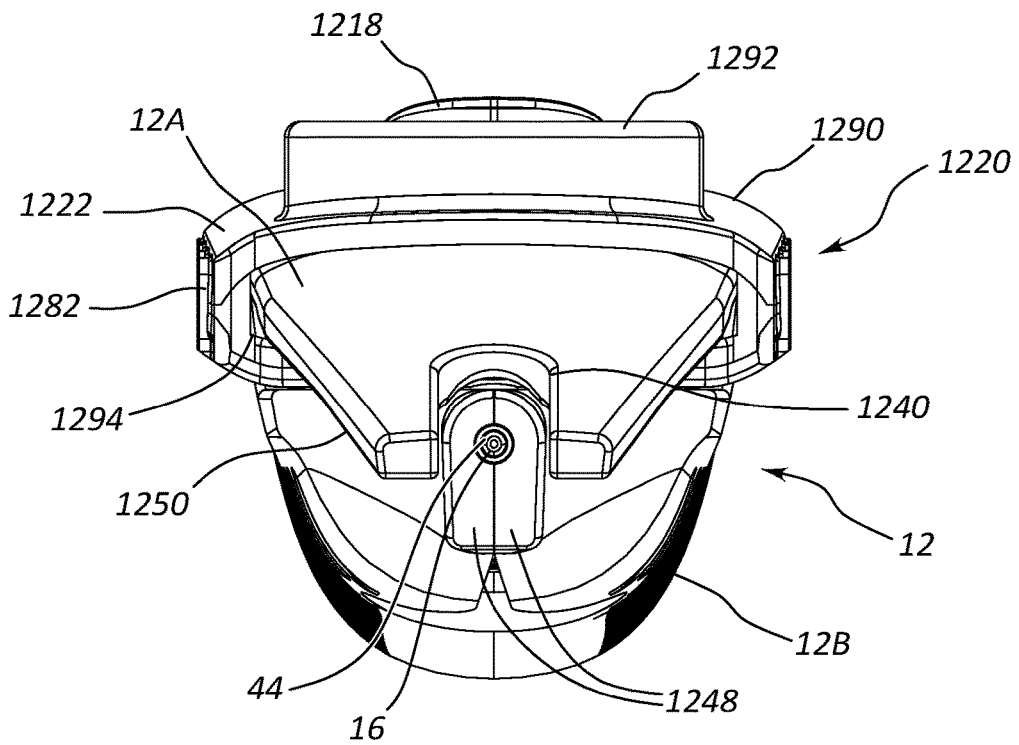
Figure 67C:
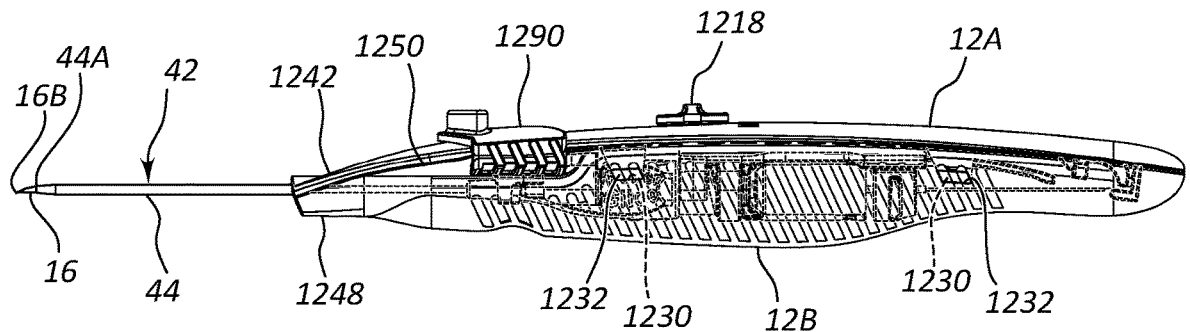
Figure 67D:
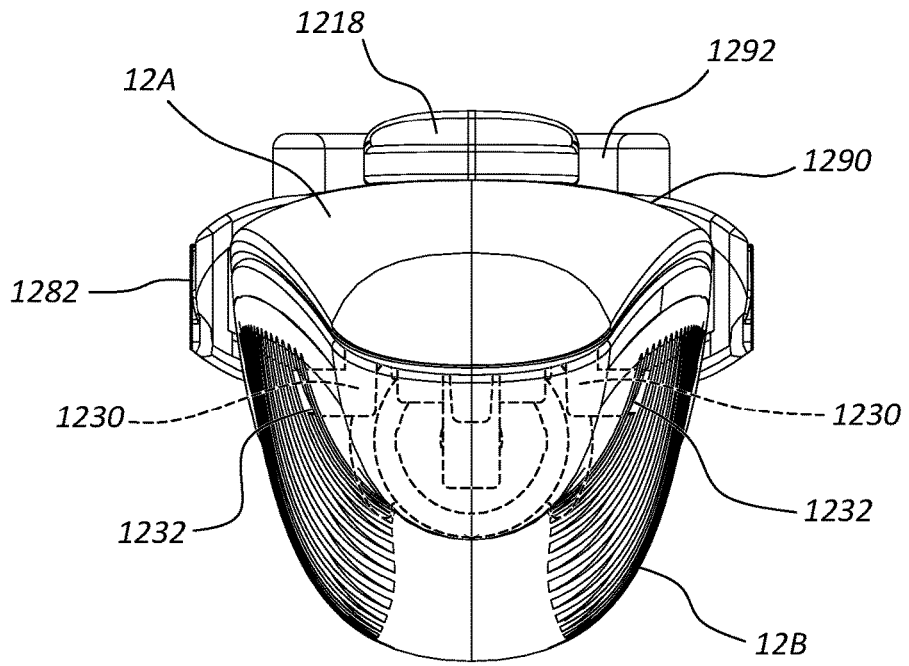

FIGS. 66A-66C depict details of an insertion tool including a catheter advancement configuration according to one embodiment, wherein an insertion tool housing 1340 includes a catheter advancement lever 1344 that engages with a guidewire advance button such that the catheter advancement lever is initially maintained in a depressed position underneath the guidewire advance button, preventing catheter advancement. Once the guidewire advance button 1348 is moved distally, the catheter advancement lever 1344 pops upward, which unlocks catheter advancement and enables the catheter tube 44 to be distally advanced, such as by distal movement of the catheter advancement lever. It is appreciated that one or more of a variety of internal mechanisms can be included in the housing 1340 to facilitate the functionality described here.

Note that the insertion tool 10 as described immediately above is configured so that it can be grasped by a hand of the user and employed in deploying the catheter into the patient without the need for the user to move the hand grasping the device. In particular, the finger pad 1218 of the guidewire advancement assembly 20 and the wings 1280 of the catheter advancement assembly 40 are positioned distal relative to the location where the user grasps the housing 12 in order to use the insertion tool 10, thus eliminating the need for the user to move the grasping hand during advancement of the finger pad or wings.

In one embodiment, the user grasps the insertion tool housing 12 with one hand and uses the other hand to advance at least one of the finger pad 1218 and the wings 1280, again without moving the hand grasping the insertion tool housing. In another embodiment, the user can use the fingers of the hand grasping the insertion tool housing to advance one or both of the finger pad 1218 and the wings 1280.

Reference is now made to FIGS. 67A-67F, which depict various details regarding a catheter insertion tool ("insertion tool" or "insertion device"), generally depicted at 10, according to one embodiment. Note that, while the discussion below focuses on the placement of catheters of a particular type and relatively short length, catheters of a variety of types, sizes, and lengths can be inserted via the present device, including peripheral IVs, intermediate or extended-dwell catheters, PICCs, central venous catheters, etc. In one embodiment, catheters having a length between about 2.0 inches and about 2.9 inches can be placed, though many other lengths are also possible. In another embodiment a catheter having a length between about 2.25 inches and about 2.75 inches can be placed.

As shown, the insertion tool 10 includes a housing 12 that in turn includes a top housing portion 12A separably mated with a bottom housing portion 12B. A needle 16 extends from the housing, over which is disposed a catheter 42. Also shown is a finger pad 1218 of the guidewire advancement assembly 20 slidably disposed in a slot 1236 defined in the top housing portion 12A, and a portion of a handle assembly 1220 of the catheter advancement assembly 40. The finger pad 1218 is also referred to herein as a first user engagement component. Further details are given below of the present insertion tool 10 and its various details in accordance with the present embodiment.

FIGS. 67A-67F show that the finger pad 1218 as part of the guidewire advancement assembly 20 can be slid by a thumb and/or finger(s) of the user distally along the slot 1236 in order to enable selective advancement of the guidewire 22 (initially disposed within the lumen of the hollow needle 16) out past the distal end 16B of the needle 16. As before, a proximal end of the guidewire 22 is attached to an interior portion of the top housing portion 12A such that a single distance unit of distal sliding advancement of the finger pad 1218 results in two distance units of distal guidewire advancement. This, as before, is made possible by looping the guidewire 22 from its attachment point on the top housing portion 12A and through the guide surfaces 980 included on the proximal portion of the guidewire lever 24 (FIGS. 72A and 72B) before extending into the lumen of the needle 16. Note that in the present embodiment the guidewire lever 24 and finger pad 1218 of the guidewire advancement assembly 20 are integrally formed with one another, though they may be separately formed in other embodiments. Note also that the guidewire 22 can be attached to other external or internal portions of the insertion tool 10, including the bottom housing portion 12B, the needle hub 1214, etc.

FIGS. 67A-67F further show that the catheter advancement assembly 40 for selectively advancing the catheter 42 in a distal direction out from the housing 12 of the insertion tool 10 includes a handle assembly 1220, which in turn includes among other components a finger pad portion 1290 that is moved by a thumb and/or finger(s) of the user when the catheter is to be advanced. As will be discussed in further detail below, the finger pad portion 1290 is distally advanced via the gap 1250 defined between the top and bottom housing portions 12A, 12B. The finger pad portion 1290 is also referred to herein as a second user engagement component, while the afore-mentioned finger pad 1218 of the guidewire advancement assembly 20 is also referred to herein as the second user engagement component.

The top and bottom housing portions 12A, 12B are mated together via the engagement of four tabs 1230 (FIGS. 67D, 68) of the top housing portion with four corresponding recesses 1232 located on the bottom housing portion. Of course, other mating mechanisms and schemes can be employed for joining the top and bottom housing portions together.

Figure 68:
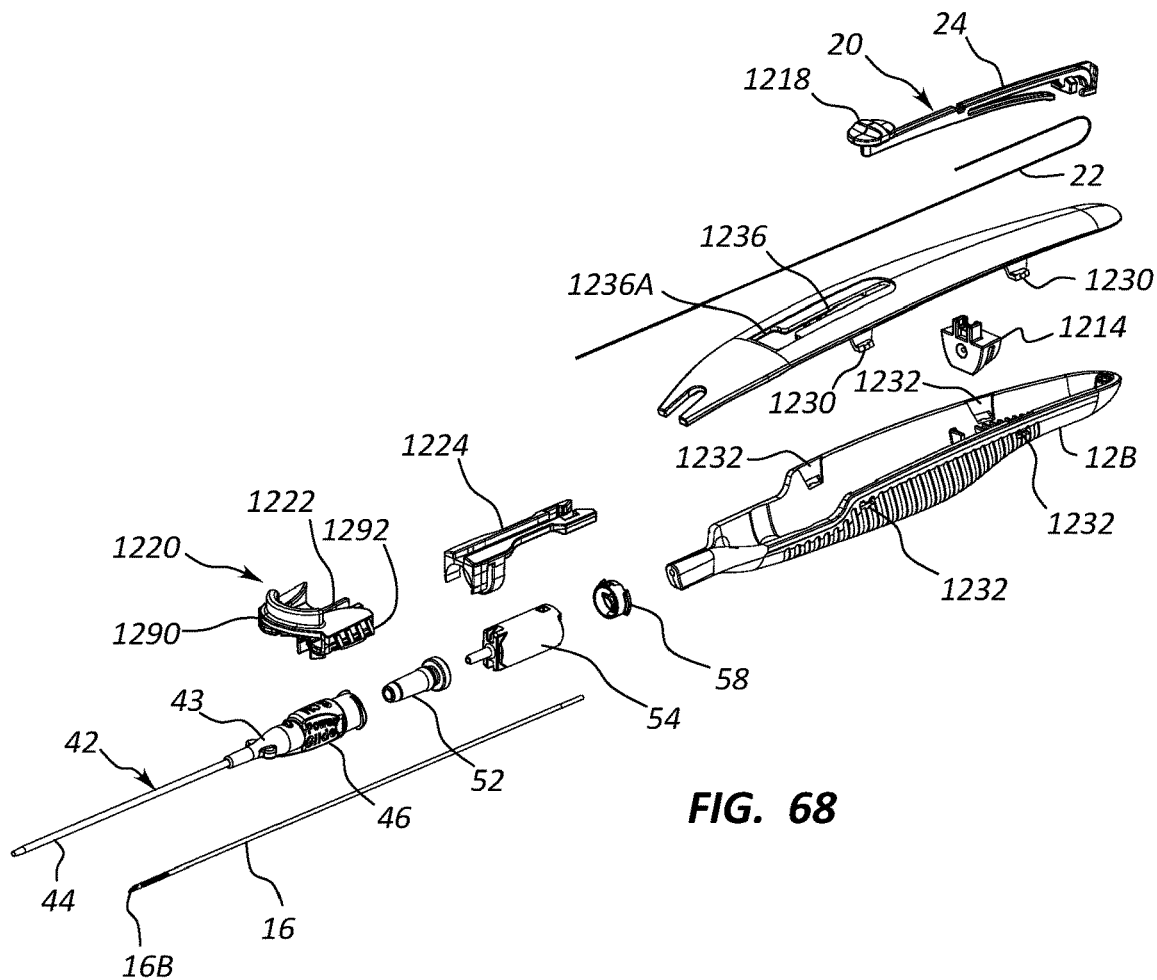
FIG. 68 is an exploded view of the insertion tool of FIGS. 67A-67F.

The exploded view of the insertion tool 10 in FIG. 68 shows that the handle assembly 1220 includes a head portion 1222 of which the finger pad portion 1290 is a part, and a tail portion 1224. Both the head portion 1222 and the tail portion 1224 are removably attached to the catheter hub 46, as will be discussed further below. Internal components of the insertion tool 10 that are disposed within the housing 12, each of which is passed through by the needle 16 include the valve 52, the safety housing 54 in which a carriage and a needle safety component is disposed, and the cap 58 of the safety housing. An O-ring may be included with the needle safety component. A needle hub 1214, which is secured to a proximal end of the needle 16, is mounted to the housing 12 to secure the needle 16 in place within the insertion tool 10. Note in FIG. 68 that, in one embodiment, the slot 1236 in which the finger pad of the guidewire advancement assembly 20 is disposed includes a relatively wide portion, or slot cavity 1236A, to enable the guidewire lever 24 to be inserted therethrough in order to couple the guidewire advancement assembly to the housing 12, as well as to lock guidewire movement, as will be seen.

Figure 69A:
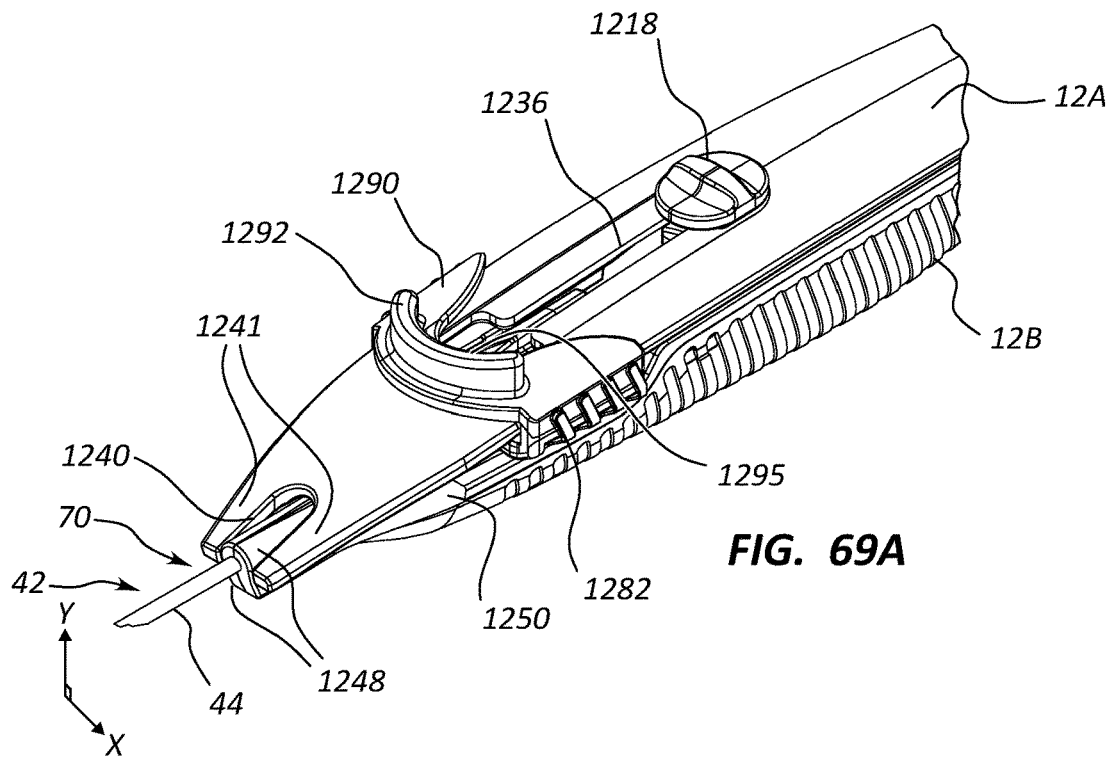
FIGS. 69A and 69B show various views of the insertion tool of FIGS. 67A-67F.
Figure 69B:
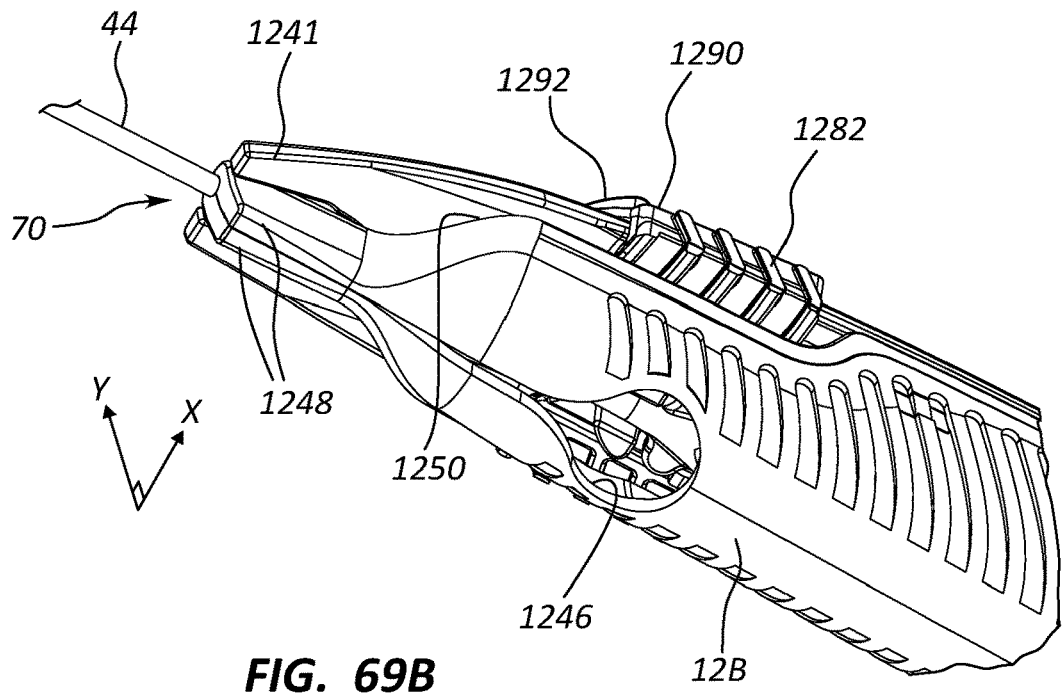

FIGS. 69A and 69B depict various details regarding the stability structure 70 for supporting and stabilizing the needle 16 at its exit point from the housing 12, according to the present embodiment. As shown, proximal portions of the top and bottom housing 12A, 12B inter-engage to provide the stability structure 70 for the needle 16. The bottom housing portion 12B includes two distally-disposed arms 1248 separated by a slot 1246 that enables the arms, when unconstrained, to separate from one another. The top housing portion 12A defines a distal slot 1240 and a fork 1241 adjacent the slot. Given the downward curvature of the distal portion of the top housing portion 12A (see FIG. 67C), the slot 1240 enables the arms 1248 of the bottom housing portion 12B to protrude upward through the slot to surround and support the needle 16 in order to stabilize it. Additionally, the fork 1241 of the top housing portion 12A abuts the arms 1248 of the bottom housing portion 12B so as to prevent spreading of the arms while stability structure is mated and has not been spread open, as described below. This provides stability and support for the needle 16, as is desired.

The arms 1248 of the bottom housing portion 12B are configured to be able to move back and forth in the x-direction, according to the x-y axis shown in FIGS. 69A and 69B, while remaining substantially rigid in the y-direction. Conversely, the distal portion of the top housing portion 12A that includes the slot 1240 and the fork 1241 is configured so as to flex in the y-direction according to the x-y axis shown in FIGS. 69A and 69B, while remaining substantially rigid in the x-direction. Thus, when overlapped or inter-engaged as shown in FIGS. 69A and 69B, the above-referenced components of the stability structure 70 cooperate to support the needle 16 and prevent its substantial movement when the housing 12 is in the configuration shown in FIGS. 69A, 69B, that is, before removal of the catheter 42 from the housing 12. This in turn assists the user in accurately piercing the skin and accessing a vessel of the patient. It is appreciated that the stability structure can include other components to stabilize the needle in addition to those explicitly described herein.

FIGS. 70-73 depict various details regarding the catheter advancement assembly 40 and the advancement assembly 20, according to the present embodiment. As discussed, the catheter advancement assembly 40 includes the handle assembly 1220, which in turn includes the head portion 1222 with the corresponding finger pad portion 1290, and the tail portion 1224 disposed about a portion of the catheter hub 46 and the safety housing 54. As will be discussed further below, the handle assembly 1220 is employed in distally advancing and removing the catheter 42 from the insertion tool 10.

FIGS. 70-73 further show the finger pad 1218 and the guidewire lever 24 of the guidewire advancement assembly 20 for the present embodiment. As shown, the guidewire lever 24 extends proximally from the finger pad 1218 and includes on its proximal end the previously discussed guide surfaces 980 for guiding the looping of the guidewire 22. An actuation block 1258 is also included near the proximal end of the guidewire lever 24 for use in enabling catheter advancement, as will be described further below. Note that the particular size, shape, and other configuration of the actuation block can vary from what is shown and described herein while retaining the desired functionality.

Figure 71:
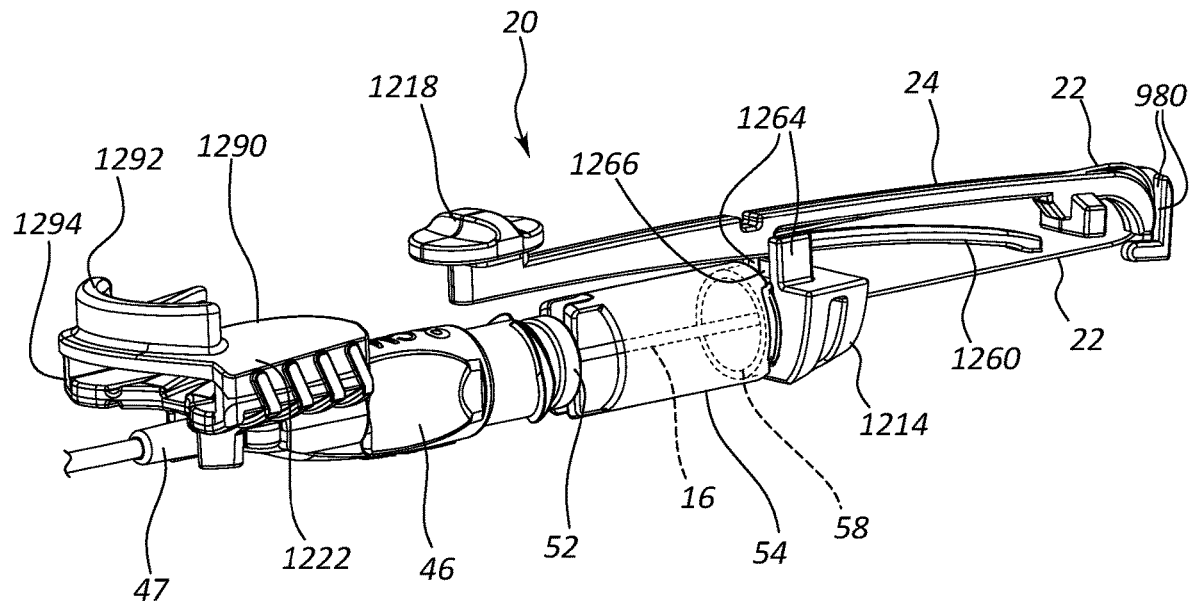
FIG. 71 is a perspective view of the guidewire advancement assembly of the insertion tool of FIGS. 67A-67F.
Figure 72A:
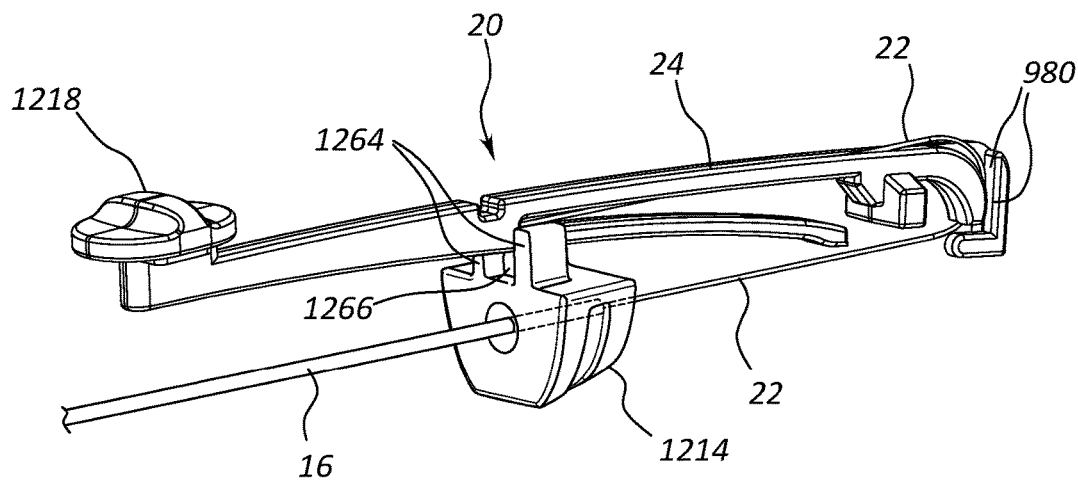
FIGS. 72A-72B show details of the operation of the guidewire advancement assembly of FIG. 71.
Figure 72B:
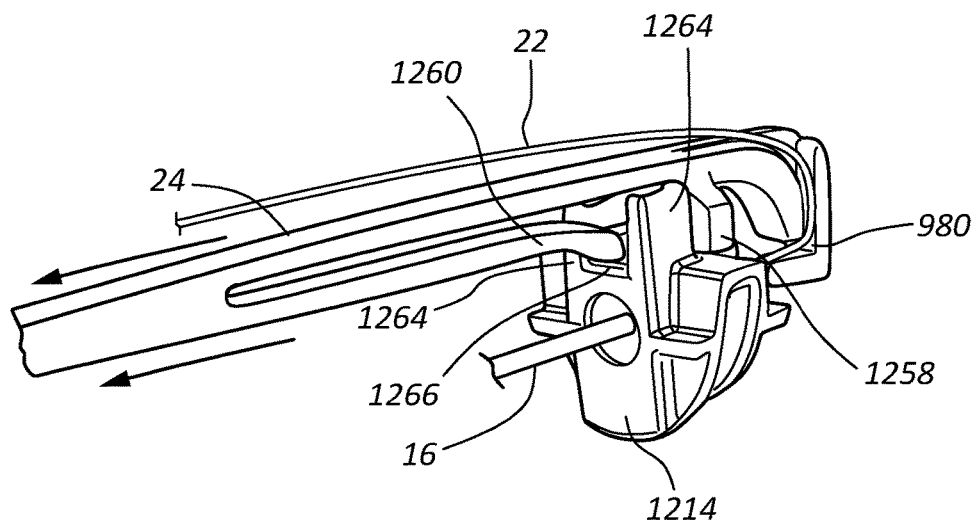

A spring arm 1260 extends downward (from the perspective shown in FIGS. 70-73) from the guidewire lever 24 and is configured to be slidably retained between two guide posts 1264 of the needle hub 1214, as best seen in FIGS. 72A and 72B. The spring arm 1260 is employed for locking further movement of the guidewire advancement assembly 20 once the guidewire 22 has been fully distally extended from the insertion tool 10 and the catheter 42 advanced an incremental amount. In particular, distal sliding by the user of the finger pad 1218 causes the guidewire lever 24 to also distally move, which in turn distally advances the guidewire 22 (which internally loops past the guide surfaces 980 of the guidewire lever 24 and into the needle lumen) through the lumen of the needle 16 and past the needle distal end 16B, as seen in FIG. 73.

Figure 73:
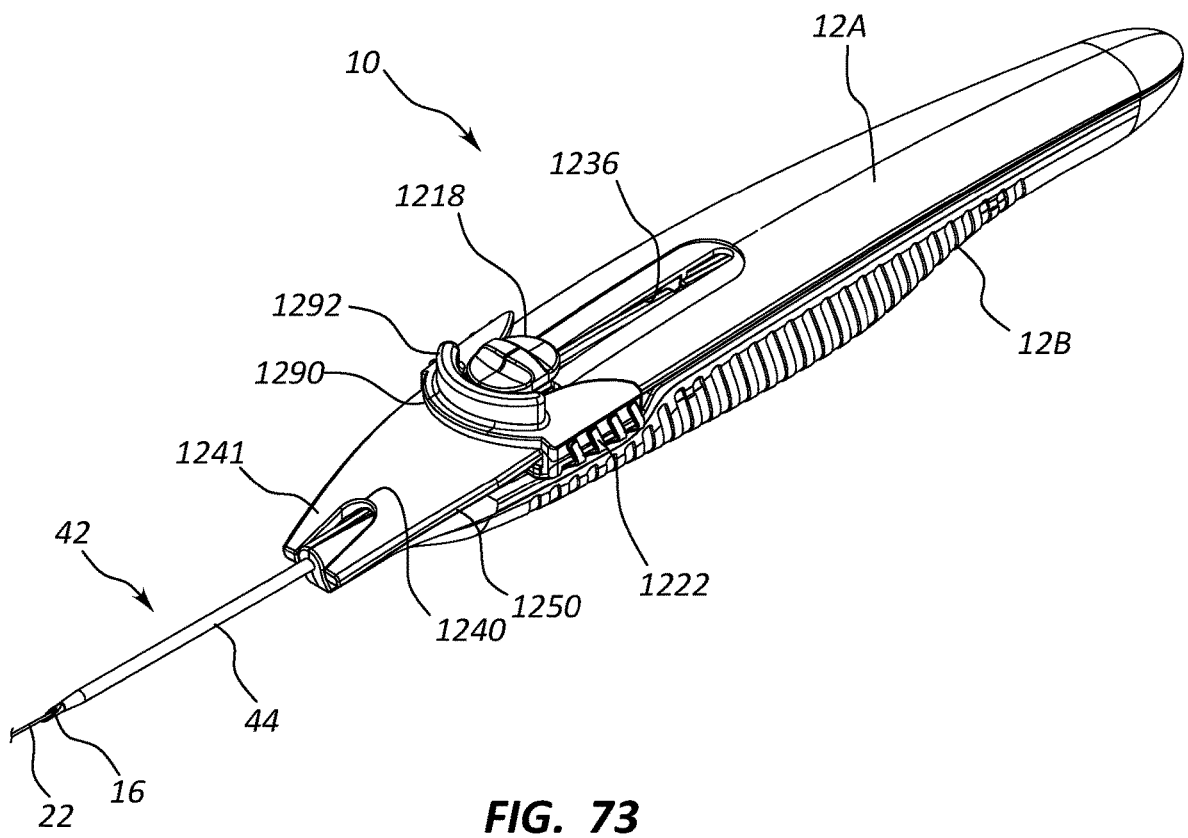
FIG. 73 is a perspective view of the insertion tool of FIGS. 67A-67F in one state.

Upon full distal advancement of the finger pad 1218 and guidewire lever 24 as seen in FIG. 73, wherein the finger pad advances to a distal termination point, the free end of the spring arm 1260 is disposed just above a pocket 1266 defined between the guide posts 1264 of the needle hub 1214, as seen in FIG. 72B. Because of the location of the safety housing 54 proximal and adjacent to the needle hub 1214 at this stage (the catheter 42—and also the attached safety housing—in its initial seated position due to it having not yet been distally advanced via distal advancement of the catheter advancement assembly 40 as described further below), the free end of the spring arm 1260 cannot yet seat in the pocket 1266. Once the catheter 42 is advanced an incremental distance distally from a point referred to herein as a proximal commencement point, however, the attached safety housing 54 no longer impedes downward movement of the spring arm 1260 and the free end thereof seats into the pocket 1266 of the needle hub 1214. Further distal movement of the guidewire advancement assembly 20 is prevented by impingement of the finger pad 1218 on the distal end of the slot 1236, while proximal movement thereof is prevented by the seating of the spring arm in the pocket 1266 of the needle hub.

Figure 79:
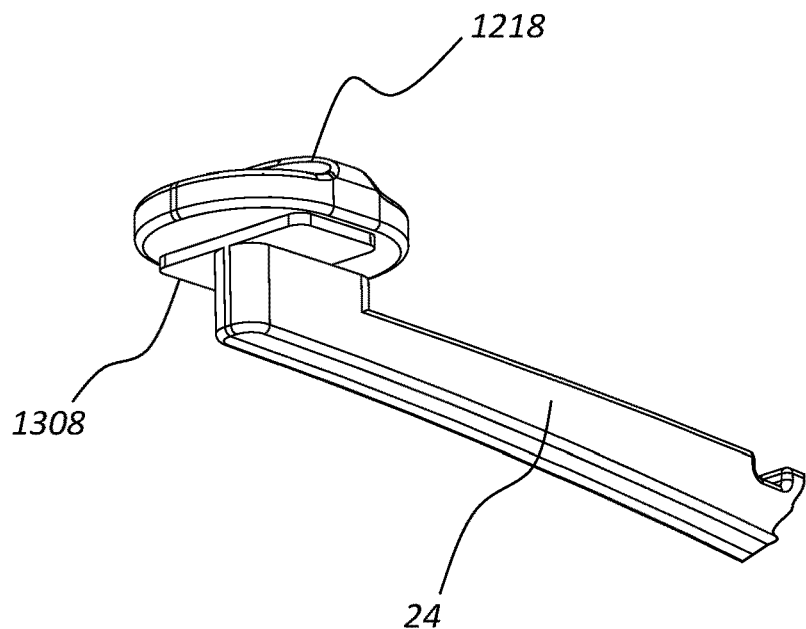
FIG. 79 is a perspective view of the finger pad of the insertion tool of FIGS. 67A-67F.

Note that, in one embodiment, the finger pad 1218 can include on its underside proximate its distal end a protrusion, or extended surface 1308 (FIG. 79) that engages with the slot cavity 1236A (FIG. 68) defined as part of the slot 1236 on the top housing portion 12A when the finger pad is completely distally advanced. This can assist in keeping the finger pad 1218 seated in its distal position and provide a tactile cue that the finger pad has been fully distally advanced. In another embodiment, the engagement of the finger pad extended surface 1308 with the slot cavity 1236A can be employed to prevent further distal and/or proximal movement of the guidewire 22 by preventing movement of the guidewire lever 24.

Note that, should the catheter advancement assembly 40 be moved proximally back to its initial position (as seen in FIG. 71), the safety housing 54 will once again abut against the needle hub 1214 and push the free end of the spring arm 1260 up and out of the pocket 1266. This in turn enables the guidewire advancement assembly 20 to unlock and again be able to move proximally and distally, causing corresponding proximal and distal advancement of the guidewire 22 itself. Thus, locking of guidewire advancement is reversible, in the present embodiment.

In another embodiment it is appreciated that a push button can be included with the guidewire advancement assembly 20 to enable the guidewire to be extended or retracted anew after locking of the guidewire has initially occurred, such as via depressing of the button to disengage the spring arm 1260 from the pocket 1266 of the needle hub, for instance. These and other variations are therefore contemplated.

Figure 74:
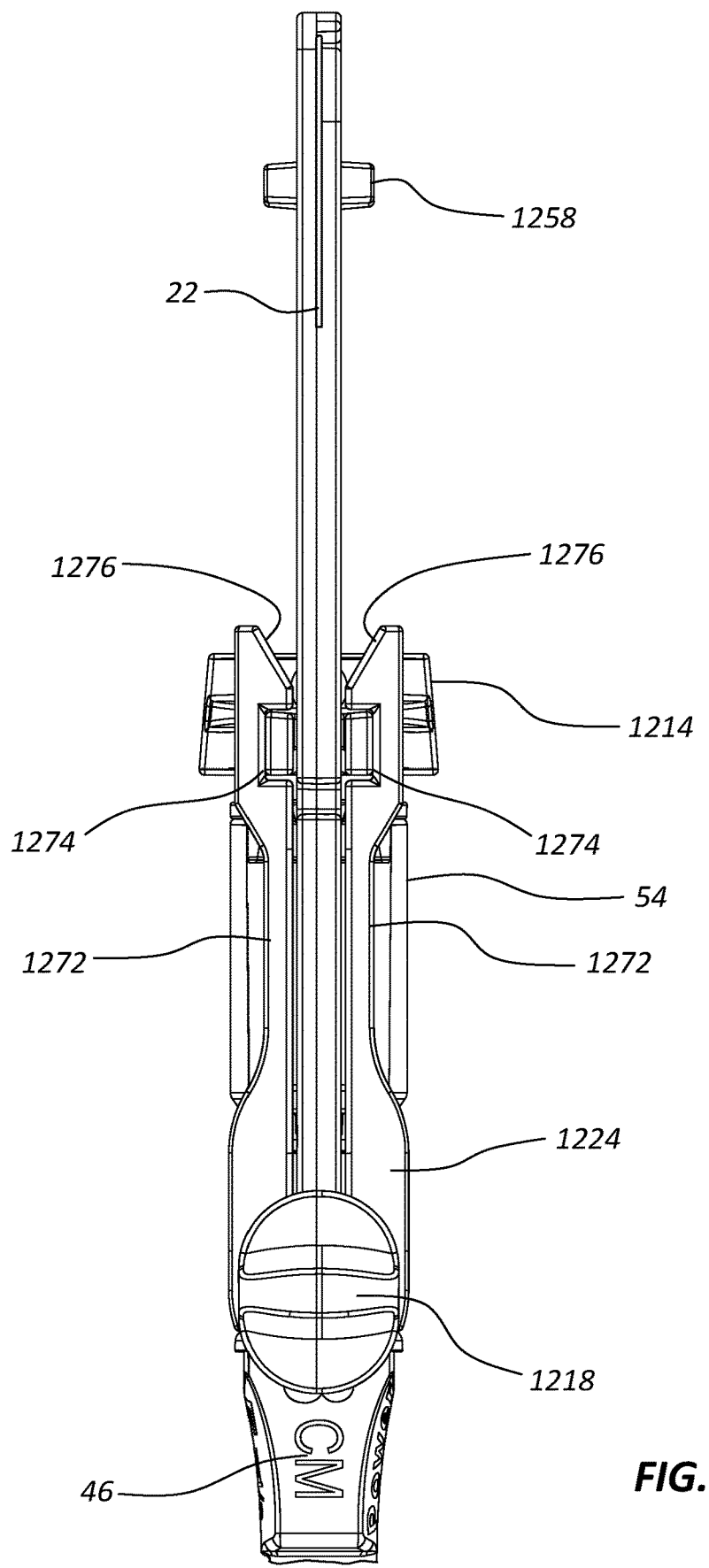
FIG. 74 is a top view of the guidewire advancement assembly of FIG. 71.
Figure 75A:
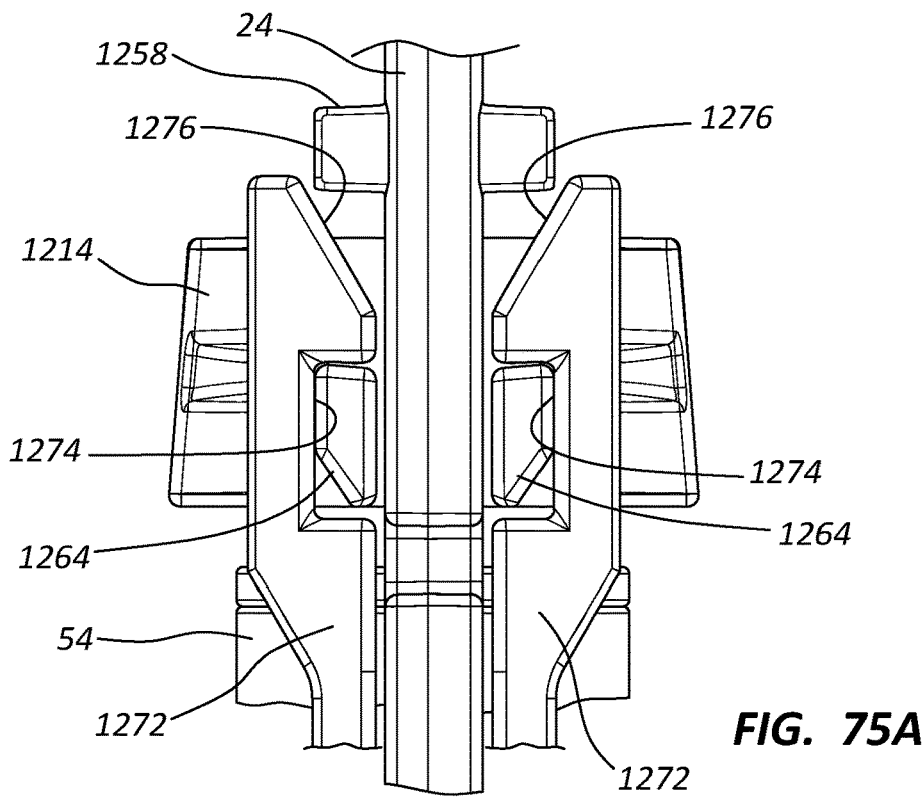
FIG. 75A-75C are various views of a portion of a catheter advancement assembly of the insertion tool of FIGS. 67A-67F.
Figure 75B:
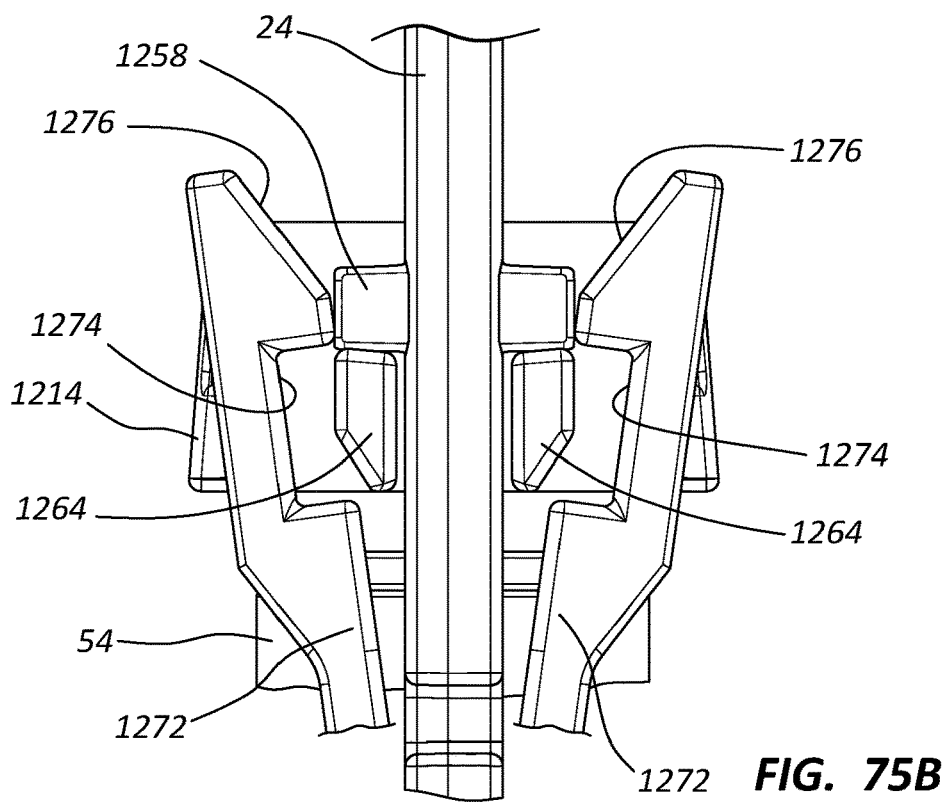
Figure 75C:
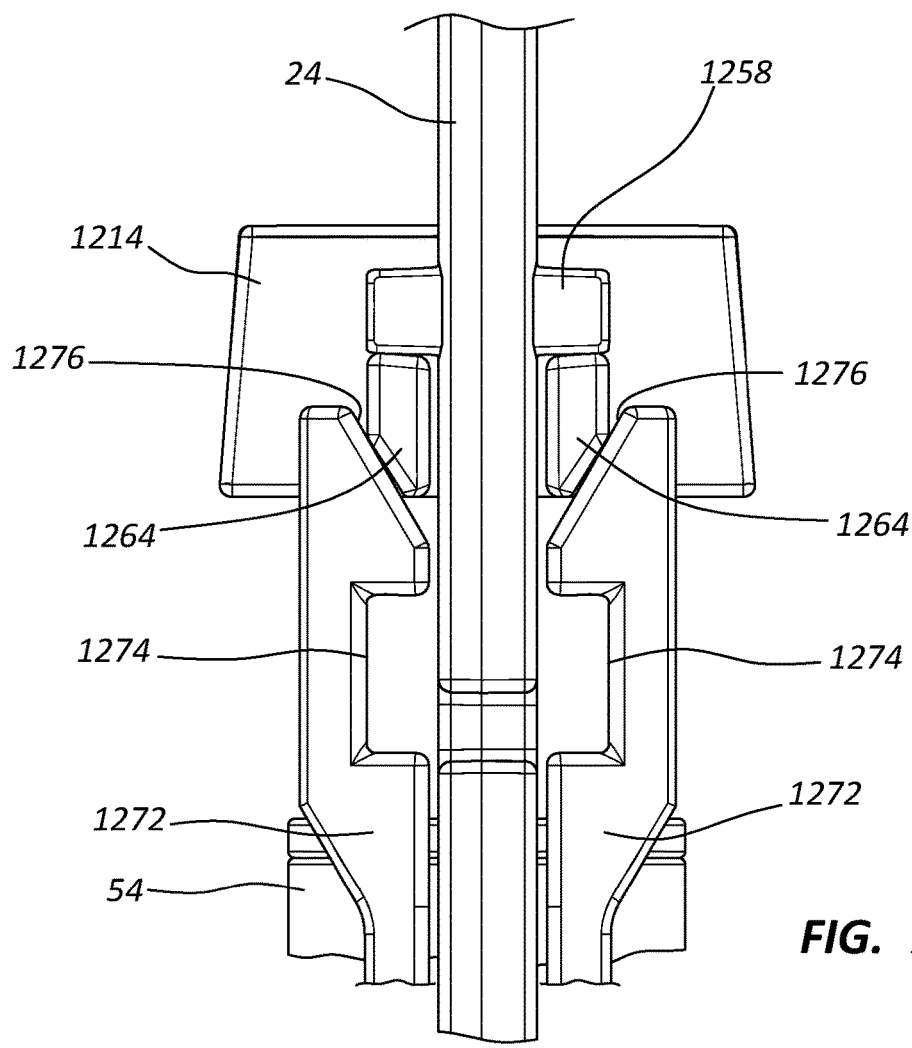

FIGS. 74-75C show that, in accordance with the present embodiment, the insertion tool 10 as presently described further includes locking of catheter movement prior to the distal advancement of the guidewire 22 as described above. In detail, FIGS. 74 and 75A show the guidewire advancement assembly 20 and the tail portion 1224 of the handle assembly 1220 of the catheter advancement assembly 40 in their initial positions within the insertion tool housing 12, that is, prior to distal guidewire advancement and catheter distal advancement. In this position, two spring arms 1272 of the tail portion 1224 are positioned such that both guide posts 1264 of the needle hub 1214 are seated within respective notches 1274 of the spring arms, best seen in FIG. 75A. In this position, the tail portion 1224 is prevented from movement. Given the attachment of the tail portion 1224 to the hub 46 of the catheter 42, this also prevents distal advancement of the catheter or any other portion of the catheter advancement assembly 40.

As seen in FIGS. 75A and 75B, distal advancement of the guidewire lever 24 causes its actuation block 1258 to engage slanted surfaces 1276 of each spring arm 1272. As best seen in FIG. 75B, continued distal movement of the guidewire lever 24 causes the actuation block 1258 to spread open the spring arms 1272, which disengages the guide posts 1264 from spring arm notches 1274. The actuation block 1258 impacts the guide posts 1264, as seen in FIG. 75B, at the point of full distal advancement of the guidewire 22 and the positioning of the free end of the spring arm 1260 of the guidewire lever 24 just above the pocket 1266 of the needle hub 1214, as was described above in connection with FIGS. 71-73. At this point, the spring arms 1272 of the tail portion 1224 are disengaged from the guide posts 1264 of the needle hub 1214, and distal catheter advancement is thus enabled such as by user movement of the handle assembly 1220, as shown by the distal movement of the spring arms in FIG. 75C. Also, and as was described above in connection with FIGS. 71-73, this distal catheter advancement correspondingly distally moves the safety housing 54, which is attached to the catheter 42. Movement of the safety housing causes the free end of the spring arm 1260 of the distally advanced guidewire lever 24 fall into the pocket 1266 of the needle hub 1214, locking further movement of the guidewire 22 barring return of the safety housing to its initial position adjacent the needle hub.

Thus, it is seen that the configuration of the insertion tool 10 of the present embodiment prevents distal movement of the catheter 42 until full distal extension of the guidewire 22 has occurred. Further subsequent movement of the guidewire 22 is prevented while the catheter 42 has been distally advanced at least incrementally from its original proximal position. In another embodiment, an incremental amount of guidewire distal advancement could enable catheter advancement.

In yet another embodiment, locking of guidewire movement is made permanent after full distal advancement. This could be achieved, in one embodiment, by configuring the spring arm 1260 of the guidewire lever 24 and the pocket 1266 of the needle hub 1214 to not interact with the safety housing 54; as such, once the free end of the spring arm 1260 seats within the needle hub pocket 1266, it remains seated permanently. In another embodiment, locking of catheter movement is made after full distal catheter advancement. In still another embodiment, guidewire and/or catheter advancement can be achieved via a ratcheting mechanism.

In another embodiment, the ability to advance the catheter is unrelated to guidewire advancement. In yet another embodiment, the spring arm 1260 of the guidewire lever 24 can be removed such that no locking of the guidewire advancement assembly 20 occurs. In turn, this enables locking of catheter advancement until full distal guidewire advancement has occurred. These and other variations are therefore contemplated.

Figure 76:
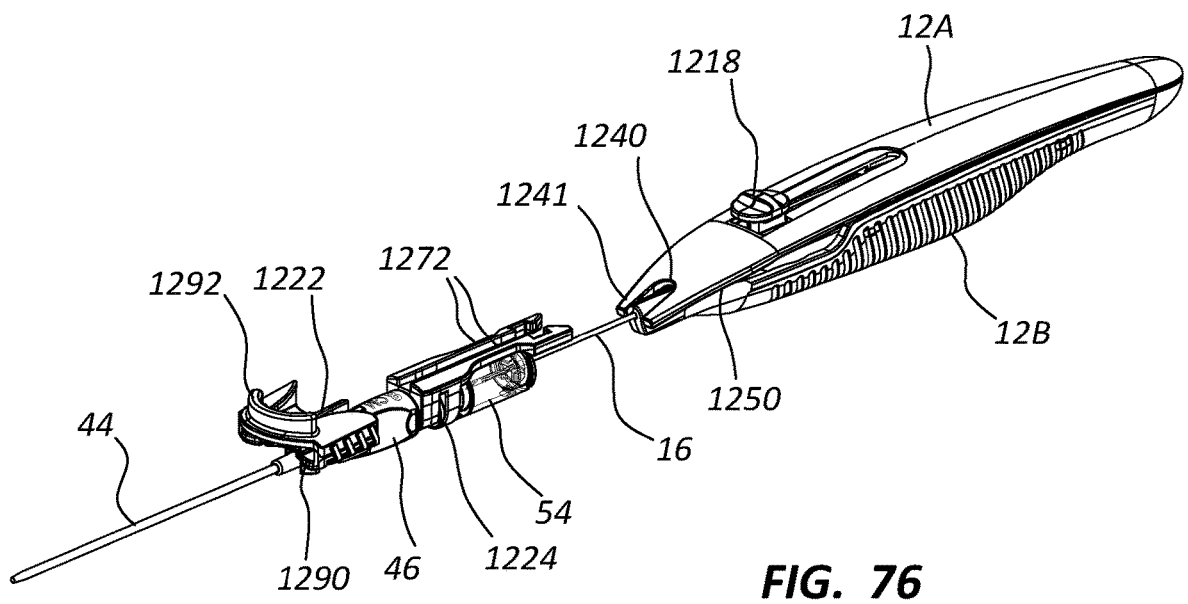
FIG. 76 shows the catheter advancement assembly of the insertion tool of FIGS. 67A-67F.

FIG. 76 depicts various details regarding the distal advancement of the catheter 42 from the insertion tool 10. Once the guidewire advancement assembly 20 has distally advanced the guidewire 22 such that it extends past the distal end 16B of the needle 16, the catheter advancement assembly 40 is free (as described above in connection with FIGS. 74-75C) to be employed in distally advancing the catheter 42 out the distal end of the insertion tool housing 12. The catheter 42 is advanced by a user engaging the finger pad portion 1290 of the head portion 1222 of the handle assembly 1220 and moving it distally. Note that ridges 1282 (FIGS. 69A, 69B) are included to assist the user in gripping the finger pad portion 1290. The finger pad portion 1290 slides distally in the gap 1250 defined between the top and bottom housing portions. As part of the head portion 1222, which in turn is attached to the hub 46 of the catheter 42, distal sliding of the finger pad portion 1290 distally advances the catheter.

As the catheter 42 is distally advanced, the distal movement of the finger pad portion 1290 causes the finger pad portion to impinge on and push upwards the top housing portion 12A as a portion of the head portion 1222 slides through the gap 1250. This in turn lifts the distal portion of the top housing portion 12A, including the slot 1240 and the fork 1241 of the stability structure 70. Lifting of the slot 1240 and fork 1241 causes the arms 1248 of the bottom housing portion 12B to disengage from the slot, thus enabling them to spread apart. Two posts 1286 disposed on the head portion 1222 of the handle assembly 1220 (see also FIG. 77) push against each of the arms 1248 as the catheter distally advances, which causes the arms to separate. This separation of the arms 1248, together with the lifting by the finger pad portion 1290 of the top housing portion, enables the catheter 42 to pass through the distal end of the housing 12.

FIG. 76 shows removal of the catheter 42 and catheter advancement assembly 40 from the insertion tool housing 12, wherein continued distal advancement of the head portion 1222 of the handle assembly 1220 via the user engaging and advancing the finger pad portion 1290 causes the catheter 42, the handle assembly 1220 (including the head portion 1222 and the tail portion 1224), and the safety housing 54 removably attached to the catheter hub 46 to slide distally along the needle 16 and out of the housing 12. This action is performed, for instance, to advance the catheter tube 44 into the vessel of the patient after the needle 16 and the guidewire 22 have cooperated to transcutaneously provide a pathway into the vessel.

Further separation of the catheter 42 and handle assembly 1220 from the housing 12 causes the safety housing 54 to arrive at the distal end 16B of the needle 16, at which point the needle safety component disposed in the safety housing engages the needle distal tip to shield the distal tip and prevent accidental needle sticks for the user, wherein the safety housing laterally detaches from the catheter hub 46 and remains with the needle.

Figure 77:
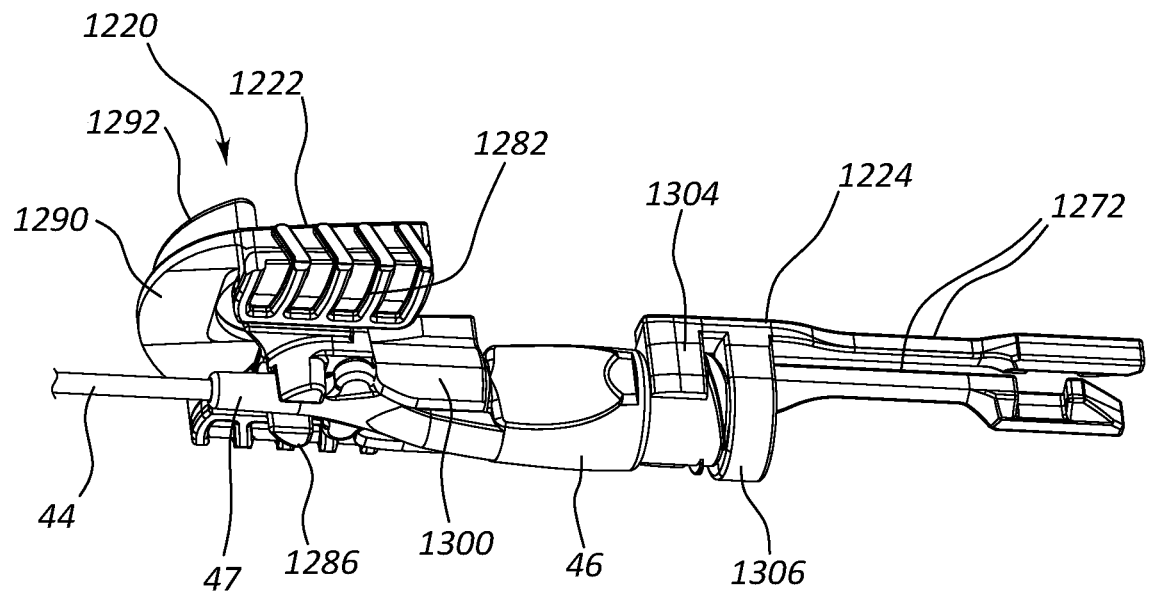
FIG. 77 is a perspective view of the catheter advancement assembly of the insertion tool of FIGS. 67A-67F.

FIG. 77 shows various features of the handle assembly 1220, which includes the head portion 1222 and the tail portion 1224. After the above separation of the safety housing 54 and needle 16 from the catheter 42 and handle assembly 1220, the head portion 1222 and the tail portion 1224 remain attached to the needle hub 46 and its corresponding strain relief 47 via clip arms 1300 and 1304, respectively.

At this point, the head portion 1222 can be removed from the catheter hub 46/strain relief 47 by the hand of the user to overcome the friction fit of the clip arms 1300. The tail portion 1224, which includes a loop 1306 disposed about the valve 52, can also be removed via pulling and twisting by the user to overcome the friction fit of the clip arms 1304 and avoid the threads of the catheter hub 46. This action will remove the valve 52 (see FIG. 68), which is attached to the tail portion 1224. In another embodiment, the tail portion loop 1306 is configured so that the valve 52 is exposed after removal of the tail portion 1224 so as to enable removal of the valve by the user when desired. Once the head portion 1222 and the tail portion 1224 of the handle assembly 1220 have been removed from the catheter 42, the catheter can be dressed and used as desired. The handle assembly 1220 can be configured in other ways, in addition to what has been shown and described above.

Figure 78A:
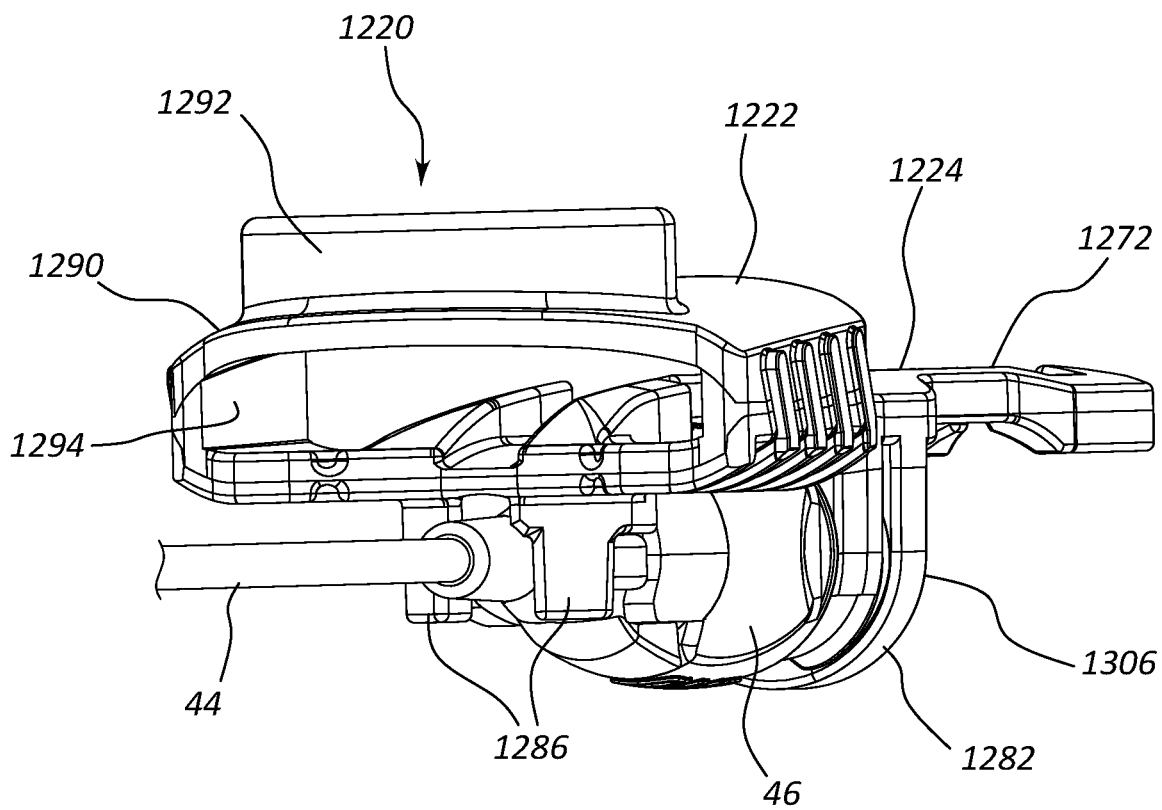
FIGS. 78A and 78B are various views of the catheter advancement assembly of the insertion tool of FIGS. 67A-67F.
Figure 78B:
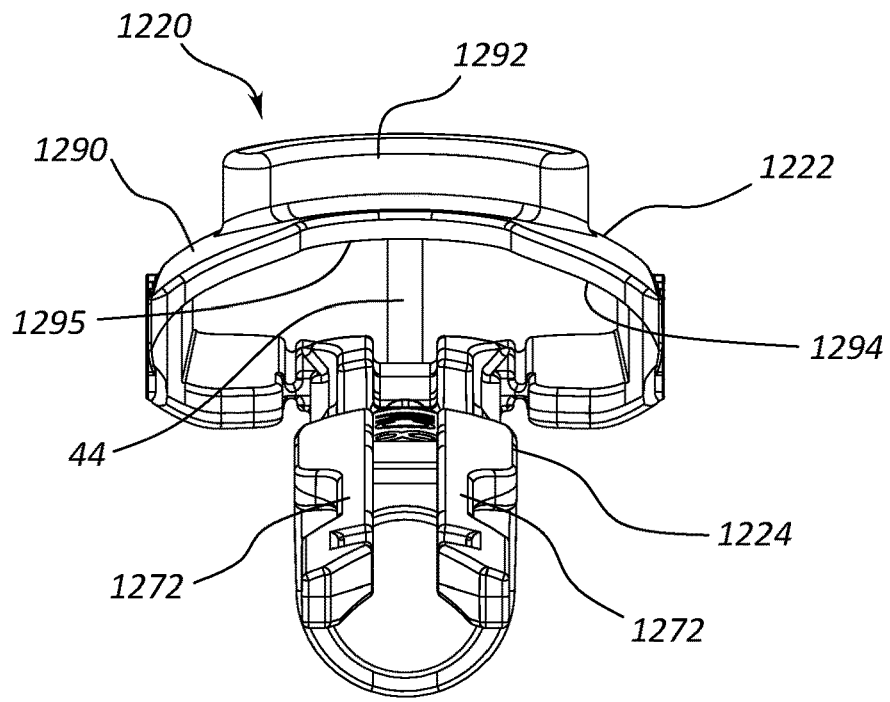

FIGS. 78A and 78B depict various details regarding the handle assembly 1220, including the head portion 1222 and the tail portion 1224, as part of the catheter advancement assembly 40. As shown, the head portion 1222 includes the finger pad portion 1290 that is configured to enable a user's thumb and/or finger(s) to advance the catheter 42 distally out of the insertion tool 10, as shown in FIG. 76. The ridges 1292 are included on the finger pad portion 1290 to assist user gripping thereof. The rounded, raised surface 1292 is included on a top surface of the finger pad portion 1290 and provides a surface against which the user can apply force to distally push the head portion 1222.

The head portion 1222 defines a cavity 1294 inside of which a portion of the distal portion of the top housing portion 12A of the insertion tool housing 12 is disposed, such that the head portion can slide over the distal portion of the top housing portion 12A, as seen in FIG. 76, for example. Such an engagement enables the head portion to be distally slid over the distal portion of the top housing portion 12A, via user engagement with the finger pad portion 1290, so as to distally advance the catheter 42 out the distal end of the insertion tool housing 12. As a result of such advancement (which separates the catheter 42 from the housing 12), it is seen that the cavity 1294 of the head portion 1222 separates from the top housing portion 12A.

Figure 70:
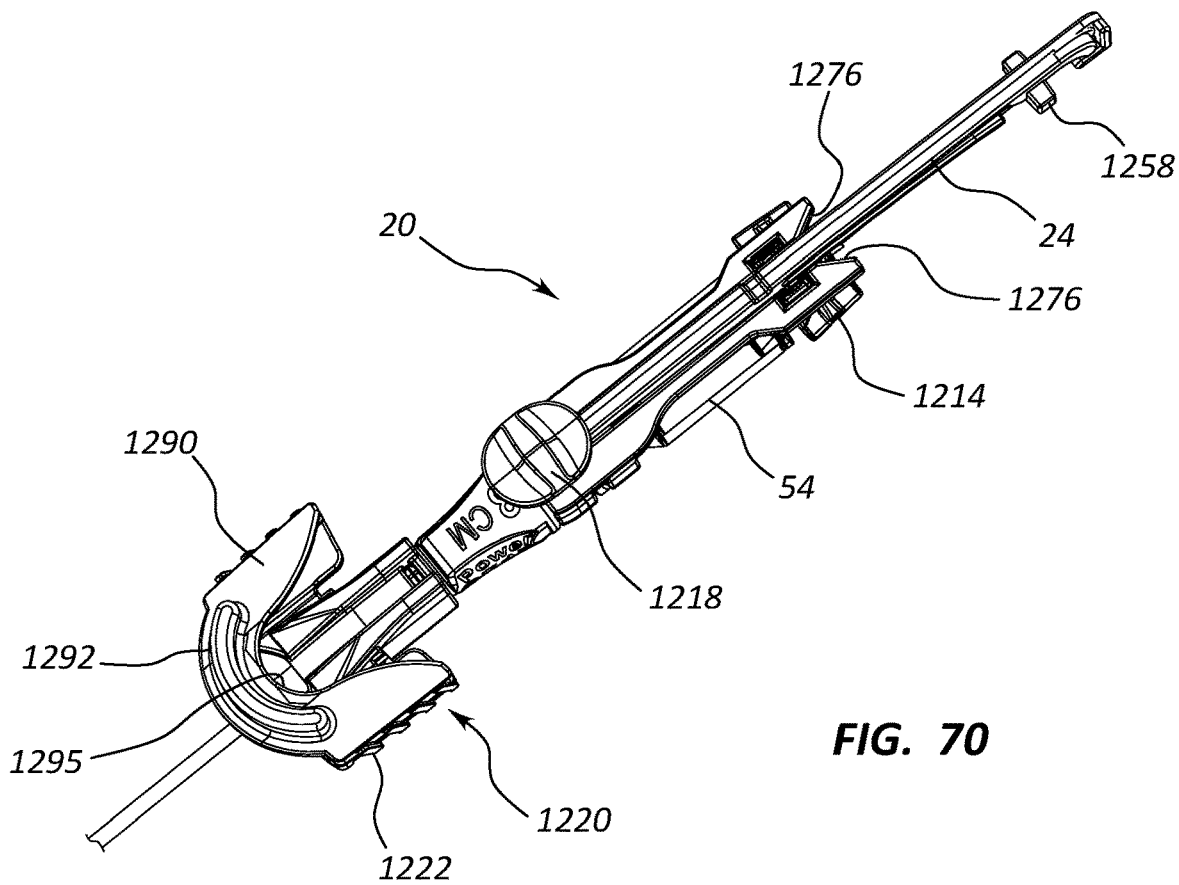
FIG. 70 is a top view of a guidewire advancement assembly and a catheter advancement assembly of FIGS. 67A-67F.

Note that FIGS. 67E, 70, and 78B show that the finger pad portion 1290 of the handle assembly 1220 further includes a cove 1295 into which the finger pad 1218 of the guidewire lever 24 seats when the finger pad 1218 is slid distally by the user to distally advance the guidewire 22. Thus, it is seen that the finger pad 1218 of the guidewire advancement assembly 20 and the finger pad portion 1290 of the head portion 1222 of the catheter advancement assembly 40 cooperate to provide for one-handed advancement of the guidewire 22 and the catheter 42.

In particular, the finger pad 1218 slides distally atop the housing 12 to advance the guidewire 22 until the finger pad 1218 seats in the cove 1295 of the finger pad portion 1290 of the head portion 1222. The user can then transition the thumb and/or finger(s) from the finger pad 1218 to the finger pad portion 1290 of the head portion 1222 adjacent to the curved raised surface 1292 thereof without substantial repositioning of the thumb and/or finger(s), at which point continued distal pressure can be applied to distally slide the finger pad portion 1290 and correspondingly distally advance the catheter 42 out the distal end of the insertion tool housing 12, as desired. Thus, the distal termination point of the sliding finger pad 1218 of the guidewire advancement assembly 20 closely corresponds in position with the proximal commencement point of the finger pad portion 1290 of the catheter advancement assembly 40. It is appreciated that the finger pad 1218, finger pad portion 1290, ridges 1282, raised surface 1292, etc. can be configured in other ways as well.

Figure 80:
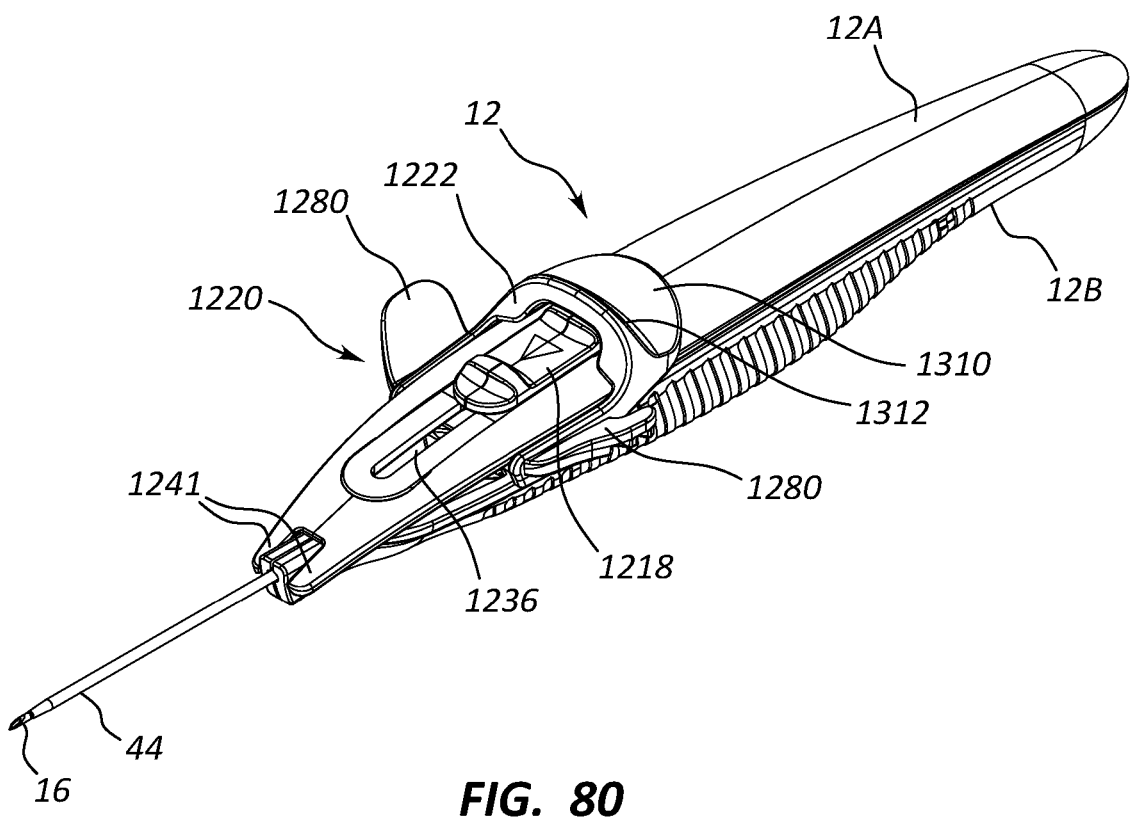
FIG. 80 is a perspective view of a catheter insertion tool according to one embodiment.
Figure 81:
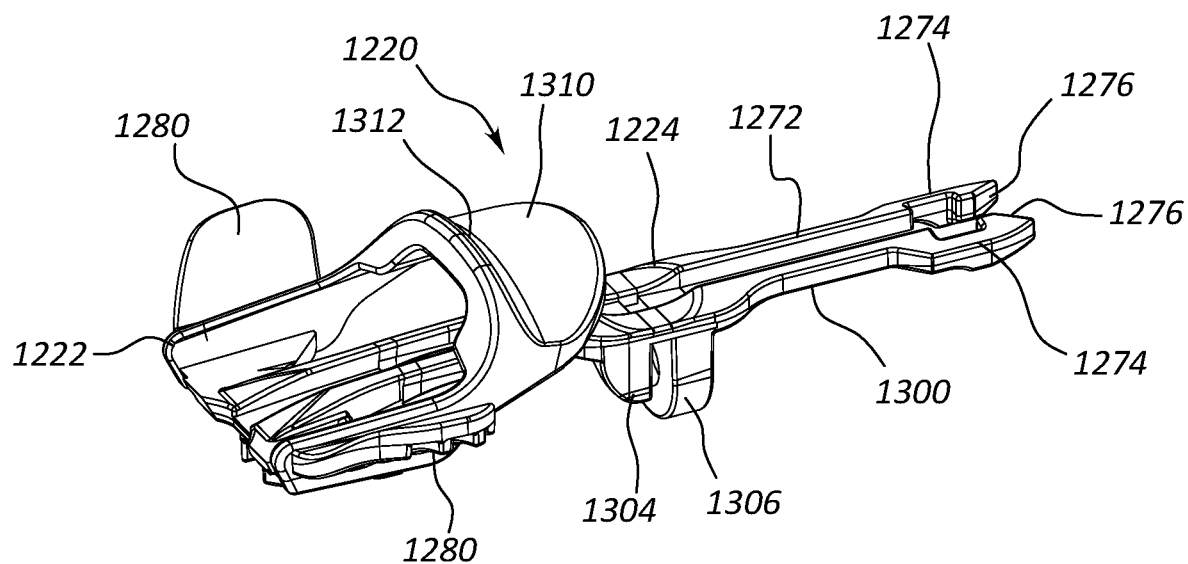
FIG. 81 is a perspective view of a catheter advancement assembly of the catheter insertion tool of FIG. 80.

FIGS. 80 and 81 depict details of the catheter insertion tool 10 according to one embodiment, wherein the finger pad 1218 of the guidewire advancement assembly 20 is elongated in shape and includes a pair of ridges to assist with engagement therewith by a thumb and/or finger(s) of the user. Further, the handle assembly 1220 of the catheter advancement assembly 40 includes the head portion 1222 and the tail portion formed as an integral component, as shown. The head portion 1220 includes two wings 1280 similar to those described above in connection with FIGS. 48A-49 for enabling distal advancement of the catheter 42 out of the housing 12. The head portion 1220 further includes a cover portion 1310 that arches over the top housing portion 12A, extending between and connecting with each of the wings 1280, as shown in FIG. 80. So disposed, the cover portion 1310 is disposed over a portion of the finger pad 1218. A ridge, or contour 1310, is included on a top surface of the cover portion 1310 to assist the user in engaging the cover portion with a thumb and/or finger(s). It is thus seen that the catheter advancement assembly 40 can be used to distally advance the catheter 42 via sliding movement by the user manually engaging either or both of the wings 1280 and/or the cover portion 1310.

Figure 82A:
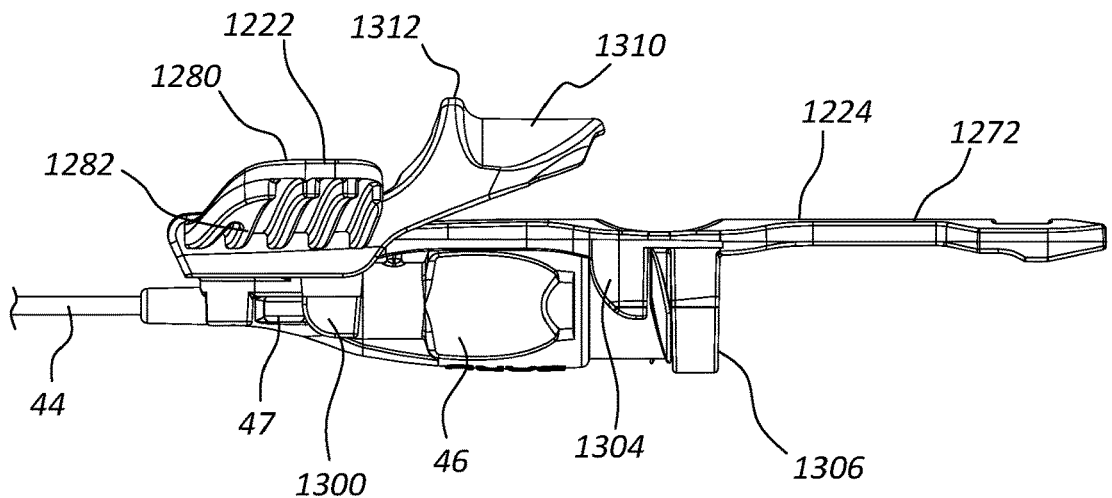
FIGS. 82A and 82B are side views of the guidewire advancement assembly and catheter assembly of FIG. 80.
Figure 82B:
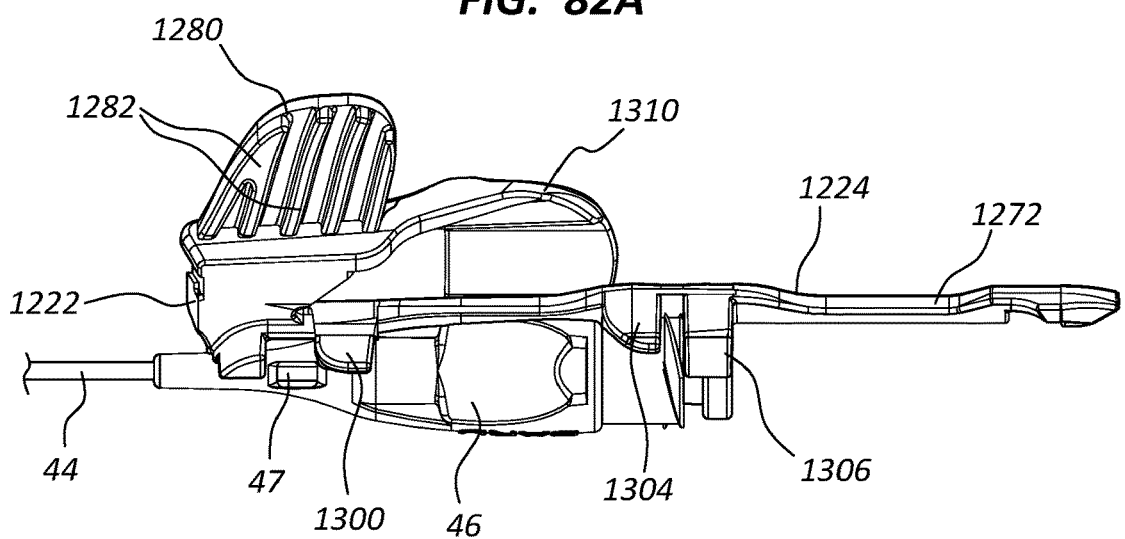

FIG. 81 shows that the head portion 1220 and the tail portion 1224 of the handle assembly 1220 are integrally formed in the present embodiment. FIGS. 82A and 82B show that, once it has been removed from the catheter insertion tool 10 as in previous embodiments, the handle assembly 1220 can be removed from the catheter 42 (as would occur after the catheter tube 44 thereof has been inserted into the vessel of a patient) by first bending the head portion of the handle assembly upward and proximally, as in FIG. 82B, so as to disengage the clip arms 1300 and 1304 from the strain relief 47 and the catheter hub 46, respectively. The handle assembly 1220 can then be pulled proximally with respect to the catheter 42 to release engagement therebetween.

Figure 83:
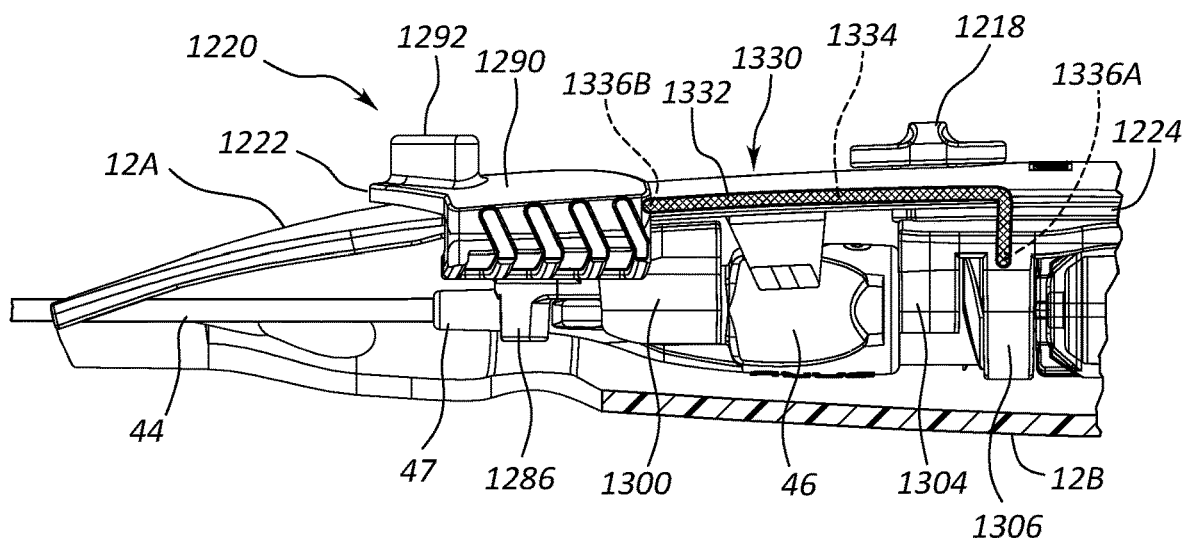
FIG. 83 is a partial cross-sectional side view of a catheter insertion tool including a blood flash indicator according to one embodiment.
Figure 84:
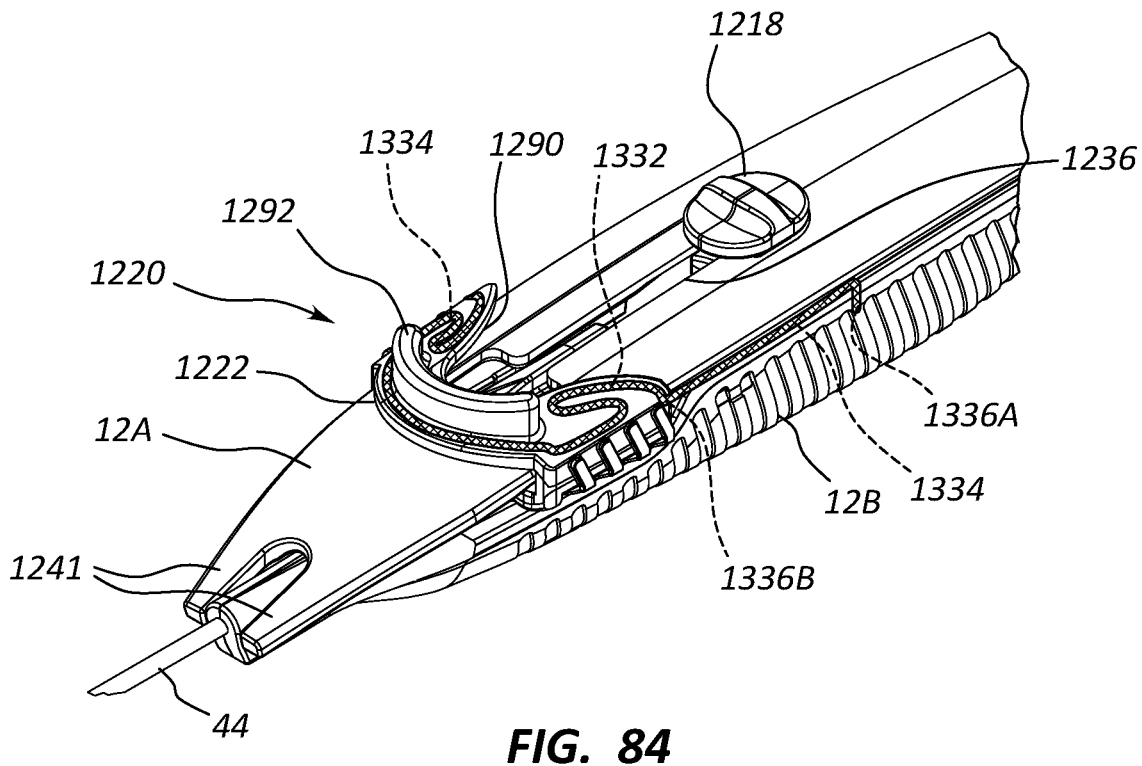
FIG. 84 is a perspective view of a catheter insertion tool including a blood flash indicator according to one embodiment.
Figure 85:
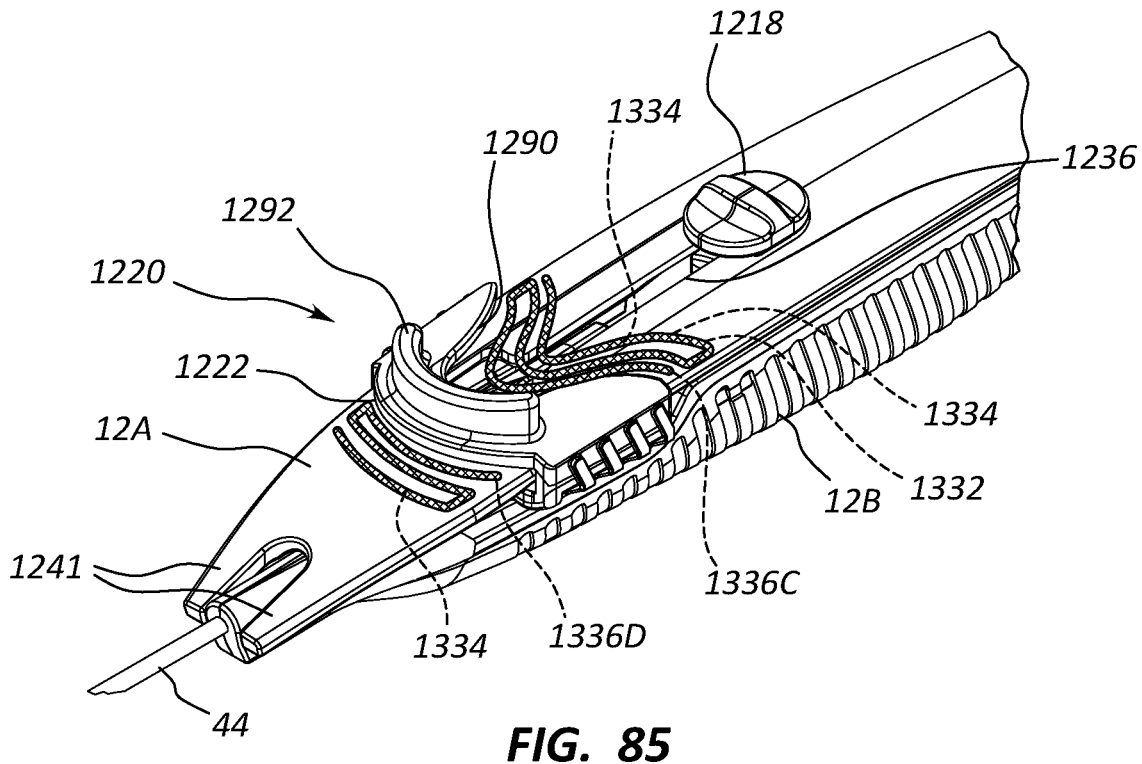
FIG. 85 is a perspective view of a catheter insertion tool including a blood flash indicator according to one embodiment.

FIGS. 83-85 depict various details regarding a continuous blood flash indicator 1330 for enabling the user to ensure that blood or other fluid is present in the lumen of the needle 16 of the catheter insertion tool 10, thus ensuring that the needle distal tip 16B is disposed in the vein or vessel of the patient during use of the insertion tool to place the catheter 42. In FIG. 83, the flash indicator 1330 includes an elongate channel 1332 that is in fluid communication with the lumen of the needle 16 of the insertion device 10. The channel 1332 is shaped as to define a pathway 1334, such as a tortuous pathway for instance, along which blood present in the lumen of the needle 16 can travel after exiting the needle and entering the channel.

In greater detail, FIG. 83 shows that the channel 1332 establishes fluid communication with the lumen of the needle 16 via a conduit, or access point 1336A, defined through the loop 1306 of the tail portion 1224 of the handle assembly 1220, wherein the conduit fluidly connects with the needle 16 via a notch defined in the needle, or by other suitable mode. In one embodiment, the access point 1336A is defined through the valve plug 52 (FIG. 68), the valve plug defining a hole that fluidly connects the valve plug with the catheter hub lumen. In another embodiment, the access point 1336A is defined at a point proximal to the safety housing 54 but distal to the needle hub 1214. These and other possible locations are contemplated.

The channel 1332 extends distally from the conduit, the channel being defined by a portion of the handle assembly 1220, as shown in FIG. 83. The channel 1332 here is covered by the portion of the top housing portion 12A. The thermoplastic or other material of the top housing portion 12A that covers the channel 1332 is translucent in the present embodiment so as to enable the user to see blood present in the channel. In another embodiment, the housing itself can define at least a portion of the channel 1332.

FIGS. 83 and 84 show that, in one embodiment of the blood flash indicator 1330, the channel 1332 defined by the handle assembly 1220 fluidly connects to the finger pad portion 1290 of the head portion 1222 of the catheter advancement assembly 40 via an access point 1336B such that the pathway 1334 is also defined on the finger pad portion. Again, the portion of the finger pad portion 1290 defining the channel 1332 is translucent in the present embodiment so as to enable the user to view the blood flowing therein.

In one embodiment of the blood flash indicator 1330, the pathway 1334 formed by the channel 1332 can be defined at multiple locations. FIG. 85 depicts an example of this, wherein a portion of the pathway 1334 is included on the top housing portion 12A in a location proximal to the finger pad portion 1290 (with fluid access thereto being provided via an access point 1336C), and another portion of the pathway 1334 is included on the top housing portion in a location distal to the finger pad portion (with fluid access thereto being provided via an access point 1336D). The access points 1336C and 1336D are in fluid communication with another portion of the channel 1332 that extends to fluidly connect with a portion of the needle 16 (via an access point such as the access point 1336A as is seen in FIG. 83) or other fluid-carrying portion of the insertion device 10.

The pathways 1334 shown in FIGS. 84 and 85 form elongated, tortuously shaped pathways along which blood present in the lumen of the needle 16 can travel after exiting the needle. The pathway 1334 shown in FIG. 84 defines a circuitous pattern that travels along the form of the finger pad portion 1290, while the pathway of FIG. 85 defines a back-and-forth pattern along the top surface of the top housing portion 12A. It is appreciated, though, that a variety of different pathway designs and locations on/in the insertion device 10 can be employed. In the present embodiment, the pathways 1334 defined on the top housing portion 12A are formed by clear tubing that is attached (via pressing, for instance) to the top housing portion in the patterns shown. In one embodiment, upon distal extension of the handle assembly 1220 of the catheter advancement assembly 40, the clear tubing separates from the top housing portion as the handle assembly 1220 is extended and detaches from the housing 12. In another embodiment, the channel 1332 is integrally formed with the housing 12.

A user can observe the blood within the pathway 1334 defined by the channel 1332 to confirm that the distal tip of the needle 16 is disposed in the vein or other desired blood-carrying vessel of the patient. As the pathway 1334 is relatively lengthy, the progress of the blood as it proceeds in the channel 1332 enables the flash indicator 1330 to function as a continuous flash indicator wherein blood is present in and progressing along the route defined by the pathway 1334 as long as the needle distal tip 16B is disposed in the blood-carrying vessel (or other fluid-carrying vessel in other embodiments). It is appreciated that the channel and pathway can be formed with one of a variety of processes, including molding, machining, etc. Note that the channel 1332 can be included on other structures in addition to what is shown and described herein, including the hub 46 or other portion of the catheter 42, a valve assembly, other portions of the housing 12, etc.

Various pathway designs are contemplated, a trunk-and-branch pattern, a back-and-forth pattern, a periodic tooth-like pattern about a circumference of a component, a zig-zag pattern, a converging back-and-forth pattern, circular, helix patterns, etc.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description.

All changes that come within the meaning and range of equivalency of the claims are to be embraced within their scope.

What is claimed is:

1. An insertion device for inserting a catheter into a body of a patient, comprising:
   a housing in which at least a portion of the catheter is initially disposed;
   a needle distally extending from the housing, the needle having a proximal end coupled to a needle hub, the needle hub fixed to the housing, wherein at least the portion of the catheter is pre-disposed over the needle;
   a guidewire;
   a guidewire advancement assembly including a first user engagement component configured to selectively advance a distal end of the guidewire out a distal opening of the needle in preparation for distal advancement of the catheter;
   a catheter advancement assembly including:
      a second user engagement component configured to selectively advance the catheter in a distal direction, the first user engagement component distally slidable to a distal termination point that is proximate a proximal commencement point of the second user engagement component; and
      a locking portion releasably engaged with the needle hub, the guidewire advancement assembly including a disengagement portion configured to release the locking portion of the catheter advancement assembly from the needle hub when the guidewire is distally advanced; and
   a flash indicator configured to indicate a presence of a fluid within a needle lumen, the flash indicator including an elongate channel in fluid communication with the needle lumen, the channel defining a pathway through which the fluid present in the needle lumen is configured to pass, the fluid in the pathway observable by a user of the insertion device,
   wherein the catheter advancement assembly further comprises a tail portion extending proximally in the housing, the tail portion comprising a first spring arm and a second spring arm, the locking portion of the catheter assembly comprising a first notch on the first spring arm and a second notch on the second spring arm, wherein the first notch is engaged with a first guide post of the needle hub and the second notch is engaged with a second guide post of the needle hub.

2. The insertion device according to claim 1, wherein the fluid includes blood, the blood present within the needle lumen when a distal end of the needle is disposed within a blood-carrying vessel of the patient.

3. The insertion device according to claim 2, wherein the blood proceeds along the pathway while the distal end of the needle is disposed in the blood-carrying vessel of the patient.

4. The insertion device according to claim 1, wherein the elongate channel is in fluid communication with the needle via an access point defined by a portion of the catheter advancement assembly.

5. The insertion device according to claim 4, wherein the elongate channel extends from the catheter advancement assembly to a portion of the housing.

6. The insertion device according to claim 4, wherein a portion of the pathway is included on a finger pad portion of the catheter advancement assembly and is in communication with the portion of the pathway included with the housing.

7. The insertion device according to claim 1, wherein the pathway defines a tortuous path.

8. The insertion device according to 1, wherein the elongate channel is defined in a translucent portion of the insertion device so as to be observable by the user.

9. The insertion device according to 1, wherein the first user engagement component includes a slide member coupled to the guidewire, the guidewire having a distal end of the needle in a slide member first position, the guidewire moving distal of the distal end of the needle in a slide member second position, the slide member second position being distal of the slide member first position.

10. The insertion device according to claim 1, wherein the second user engagement component includes engagement ridges on opposing sides.

11. The insertion device according to claim 1, wherein a proximal end of the guidewire is secured to the housing, and wherein an intermediate portion of the guidewire includes a U-shaped bend.

12. The insertion device according to claim 1, wherein the catheter includes a catheter hub, the catheter advancement assembly removably attached to the catheter hub, wherein a valve is removably included in the catheter hub, and wherein a safety housing is removably disposed in the valve.

13. The insertion device according to claim 1, wherein the guidewire advancement assembly includes a spring arm designed to engage with a pocket in the housing to prevent proximal retraction of the guidewire after full distal advancement of the guidewire.

14. The insertion device according to claim 13, wherein the spring arm is disposed on a guidewire lever attached to the first user engagement component, and wherein the pocket is included in the needle hub in the housing, the proximal end of the needle mounted to the needle hub.

15. The insertion device according to claim 14, wherein the catheter advancement assembly includes a safety housing, a needle safety component disposed within the safety housing, and wherein distal movement of the safety housing enables a free end of the spring arm to seat in the pocket of the needle hub after full distal advancement of the guidewire.

16. The insertion device according to claim 15, wherein the catheter advancement assembly is configured such that proximal movement of the safety housing to a position adjacent the needle hub pushes the free end of the spring arm out of the pocket of the needle hub to enable guidewire advancement and retraction.

17. The insertion device according to claim 14, wherein the guidewire lever includes an actuation block designed to engage a portion of the catheter advancement assembly after full distal advancement of the guidewire, and wherein engagement of the actuation block with the portion of the catheter advancement assembly enables the catheter to be distally advanced.

18. The insertion device according to claim 1, wherein the disengagement portion of the guidewire advancement assembly comprises an actuation block configured to contact the first spring arm and the second spring arm to move the first notch out of engagement with the first guide post and to move the second notch out of engagement with the second guide post.

19. The insertion device according to claim 18, wherein the first spring arm and the second spring arm each include a slanted surface configured for contact with the actuation block to release the locking portion of the catheter advancement assembly from the needle hub.

* * * * *